United States Patent
Banka et al.

(10) Patent No.: US 8,324,221 B2
(45) Date of Patent: Dec. 4, 2012

(54) PYRIMIDYL CYCLOPENTANES AS AKT PROTEIN KINASE INHIBITORS

(75) Inventors: Anna L. Banka, Raleigh, NC (US); James F. Blake, Boulder, CO (US); Josef R. Bencsik, Boulder, CO (US); Kin Chiu Fong, Longmont, CO (US); Martin F. Hentemann, Carlisle, MA (US); Douglas M. Sammond, Boulder, CO (US); Ian S. Mitchell, Boulder, CO (US); Rui Xu, Boulder, CO (US); Eli M. Wallace, Boulder, CO (US); Tony Tang, Boulder, CO (US)

(73) Assignee: Array Biopharma Inc., Boulder, CO (US)

( * ) Notice: Subject to any disclaimer, the term of this patent is extended or adjusted under 35 U.S.C. 154(b) by 203 days.

(21) Appl. No.: 12/812,384

(22) PCT Filed: Jan. 9, 2009

(86) PCT No.: PCT/US2009/030603
§ 371 (c)(1),
(2), (4) Date: Nov. 11, 2010

(87) PCT Pub. No.: WO2009/089454
PCT Pub. Date: Jul. 16, 2009

(65) Prior Publication Data
US 2011/0053959 A1 Mar. 3, 2011

Related U.S. Application Data

(60) Provisional application No. 61/020,125, filed on Jan. 9, 2008.

(51) Int. Cl.
*A01N 43/54* (2006.01)
*A01N 43/90* (2006.01)
*A61K 31/517* (2006.01)
*A61K 31/519* (2006.01)
*C07D 239/70* (2006.01)

(52) U.S. Cl. .................... 514/258.1; 544/253
(58) Field of Classification Search .............. 514/258.1; 544/253
See application file for complete search history.

(56) References Cited

U.S. PATENT DOCUMENTS

| | | | |
|---|---|---|---|
| 7,495,007 B2 | 2/2009 | Chen et al. | |
| 8,003,651 B2 | 8/2011 | Mitchell et al. | |
| 8,063,050 B2 | 11/2011 | Mitchell et al. | |
| 2005/0130954 A1 | 6/2005 | Mitchell et al. | |
| 2008/0051399 A1 | 2/2008 | Mitchell et al. | |
| 2008/0051419 A1 | 2/2008 | Corbett et al. | |
| 2008/0058327 A1 | 3/2008 | Mitchell et al. | |
| 2009/0111805 A1 | 4/2009 | Morris et al. | |
| 2010/0168123 A1 | 7/2010 | Mitchell et al. | |
| 2011/0015204 A1 | 1/2011 | Bencsik et al. | |
| 2011/0034499 A1 | 2/2011 | Budzik et al. | |

FOREIGN PATENT DOCUMENTS

| WO | WO 02/22604 A1 | 3/2002 |
|---|---|---|
| WO | WO 2005/051304 A2 | 6/2005 |
| WO | WO 2005/113762 A1 | 12/2005 |
| WO | WO 2006/090261 A1 | 8/2006 |
| WO | WO 2006090261 A1 * | 8/2006 |
| WO | WO 2008/006032 A1 | 1/2008 |
| WO | WO 2008/006040 A1 | 1/2008 |

OTHER PUBLICATIONS

Alessi et al., "Characterization of a 3-phosphoinositide-dependent protein kinase which phosphorylates and activates protein kinase Bα", *Curr. Biol.*, 7, 261-269 (1997).

Balendran et al., "PDK1 acquires PDK2 activity in the presence of a synthetic peptide derived from the carboxyl terminus of PRK2", *Curr. Biol.*, 9, 393-404 (1999).

Bellacosa et al., "Molecular Alterations of the *AKT2* Oncogene in Ovarian and Breast Carcinomas", *Int. J. Cancer, (Pred. Oncol.)* 64, 280-285 (1995).

Brodbeck et al., "A Human Protein Kinase Bγ with Regulatory Phosphorylation Sites in the Activation Loop and in the C-terminal Hydrophobic Domain", *J. Biol. Chem.*, 274, No. 14, 9133-9136 (1999). Brognard et al., "Akt/Protein Kinase B is Constitutively Active in Non-Small Cell Lung Cancer Cells and Promotes Cellular Survival and Resistance to Chemotherapy and Radiation", *Cancer Res.*, 61, 3986-3997 (2001).

Cheng et al., "*AKT2*, a putative oncogene encoding a member of a subfamily of protein-serine/threonine kinases, is amplified in human ovarian carcinomas", *Proc. Natl. Acad. Sci. USA*, vol. 89, 9267-9271 (1992).

Cheng et al., "Amplification of *AKT2* in human pancreatic cancer cells and inhibition of *AKT2* expression and tumorigenicity by antisense RNA", *Proc. Natl. Acad. Sci.*, USA, vol. 93, 3636-3641 (1996).

Coffer et al., "Molecular cloning and characterization of a novel putative protein-serine kinase related to the cAMP-dependent and protein kinase C families", *Eur. J. Biochem.*, 201, 475-481 (1991).

(Continued)

*Primary Examiner* — Sreeni Padmanabhan
*Assistant Examiner* — Jason A Deck
(74) *Attorney, Agent, or Firm* — Viksnins Harris & Padys PLLP

(57) ABSTRACT

The present invention provides compounds of Formula (I) including tautomers, resolved enantiomers, resolved diastereomers, solvates, metabolites, salts and pharmaceutically acceptable prodrugs thereof. Also provided are methods of using the compounds of this invention as Akt protein kinase inhibitors and for the treatment of Akt-mediated diseases, for example, hyperproliferative diseases such as cancer.

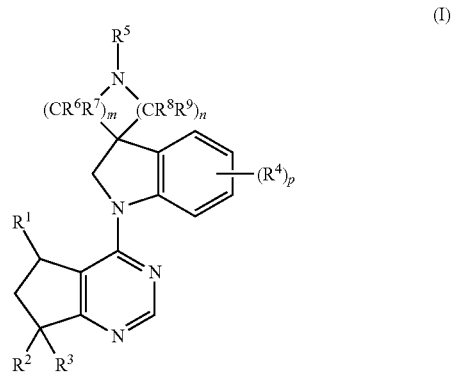

(I)

60 Claims, No Drawings

OTHER PUBLICATIONS

Cohen, "Protein kinases—the major drug targets of the twenty-first century?" *Nature Rev. Drug Discovery,* vol. 1, 309-315 (2002).

Delcommenne et al., "Phosphoinositide-3-OH kinase-dependent regulation of glycogen synthase kinase 3 and protein kinase B/AKT by the integrin-linked kinase", *Proc. Natl. Acad. Sci. USA,* vol. 95, 11211-11216 (1998).

Graff et al., "Increased AKT Activity Contributes to Prostate Cancer Progression by Dramatically Accelerating Prostate Tumor Growth and Diminishing p27$^{Kip1}$ Expression", *J. Biol. Chem.,* vol. 275, No. 32, 24500-24505 (2000).

Hardie et al., "The Protein Kinase Facts Book. I and II", *Academic Press,* San Diego, CA., 48-56 (1995).

Hass-Kogan et al., "Protein kinase B (PKB/Akt) activity is elevated in glioblastoma cells due to mutation of the tumor suppressor *PTEN/MMAC*", *Current Biology,* 8, 1195-1198 and Supp. page (1998).

Hay, "The Akt-mTOR tango and its relevance to cancer", *Cancer Cell,* vol. 8, 179-183 (2005).

Hemmings, "Akt Signaling: Linking Membrane Events to Life and Death Decisions", *Science,* vol. 275, 628-630 (1997).

Li et al., "Targeting Serine/Threonine Protein Kinase B/Akt and Cell-cycle Checkpoint Kinases for Treating Cancer", *Current Topics in Med. Chem.,* 2, 939-971 (2002).

Lippa et al., "Synthesis and structure based optimization of novel Akt inhibitors", *Bioorganic & Medicinal Chemistry Letters 18,* 3359-3363 (2008).

Nakatani et al., "Identification of a Human Akt3 (Protein Kinase B γ) Which Contains the Regulatory Serine Phosphorylation Site", *Biochem. Biophys. Res. Commun.,* 257, 906-910 (1999).

Patent Cooperation Treaty, International Search Report for PCT/US2009/030603, 14 pages, dated Mar. 30, 2009.

Staal, "Molecular cloning of the *akt* oncogene and its human homologues *AKT1* and *AKT2* : Amplification of *AKT1* in a primary human gastric adenocarcinoma", *Proc. Natl. Acad. Sci.,* USA, vol. 84, 5034-5037 (1987).

Toker et al., "Akt/Protein Kinase B is Regulated by Autophosphorylation at the Hypothetical PDK-2 Site", *J. Biol. Chem.,* vol. 275, No. 12, 8271-8274 (2000).

Toker et al., "Akt Signaling and Cancer: Surviving but not Moving On", *Cancer Res.* 66 (8), 3963-3966 (2006).

Zinda et al., "AKT-1, -2, -3 are Expressed in Both Normal and Tumor Tissues of the Lung, Breast, Prostate, and Colon,", *Clin. Cancer Res.,* vol. 7, 2475-2479 (2001).

\* cited by examiner

PYRIMIDYL CYCLOPENTANES AS AKT PROTEIN KINASE INHIBITORS

Related Applications

This application claims priority to United States Provisional Application No. 61/020,125 that was filed on Jan. 9, 2008.

BACKGROUND OF THE INVENTION

1. Field of the Invention

This invention relates to novel inhibitors of serine/threonine protein kinases (e.g., Akt and related kinases), pharmaceutical compositions containing the inhibitors, methods for preparing these inhibitors and their use as therapeutics. The inhibitors are useful, for example, for the treatment of hyperproliferative diseases, such as cancer and inflammation, in mammals.

2. Description of the State of the Art

Protein kinases (PK) are enzymes that catalyze the phosphorylation of hydroxy groups on tyrosine, serine and threonine residues of proteins by transfer of the terminal (gamma) phosphate from ATP. Through signal transduction pathways, these enzymes modulate cell growth, differentiation and proliferation, i.e., virtually all aspects of cell life in one way or another depend on PK activity (Hardie, G. and Hanks, S. (1995) *The Protein Kinase Facts Book I and II*, Academic Press, San Diego, Calif.). Furthermore, abnormal PK activity has been related to a host of disorders, ranging from relatively non-life threatening diseases such as psoriasis to extremely virulent diseases such as glioblastoma (brain cancer). Protein kinases are an important target class for therapeutic modulation (Cohen, P. (2002) Nature Rev. Drug Discovery 1:309).

Protein kinases include two classes; protein tyrosine kinases (PTK) and serine-threonine kinases (STK). The Protein Kinase B/Akt enzymes are a group of serine/threonine kinases that are overexpressed in a variety of human tumors. One of the best-characterized targets of the PI3K lipid products is the 57 KD serine/threonine protein kinase Akt, downstream of PI3K in the signal transduction pathway (Hemmings, B. A. (1997) Science 275:628; Hay N. (2005) Cancer Cell 8:179-183). Akt is the human homologue of the protooncogene v-akt of the acutely transforming retrovirus Akt8. Due to its high sequence homology to protein kinases A and C, Akt is also called Protein Kinase B (PKB) and Related to A and C(RAC). Three isoforms of Akt are known to exist, namely Akt1, Akt2 and Akt3, which exhibit an overall homology of 80% (Staal, S. P. (1987) Proc. Natl. Acad. Sci. 84:5034; Nakatani, K. (1999) Biochem. Biophys. Res. Commun. 257: 906; Li et al (2002) Current Topics in Med. Chem. 2:939-971; WO 2005/113762). The Akt isoforms share a common domain organization that consists of a pleckstrin homology domain at the N-terminus, a kinase catalytic domain, and a short regulatory region at the C-terminus. In addition, both Akt2 and Akt3 exhibit splice variants. Upon recruitment to the cell membrane by PtdInd(3,4,5)P$_3$, Akt is phosphorylated (activated) by PDK1 at T308, T309 and T305 for isoforms Akt1 (PKBα), Akt2 (PKBβ) and Akt3 (PKBγ), respectively, and at S473, S474 and S472 for isoforms Akt1, Akt2 and Akt3, respectively. Such phosphorylation occurs by an as yet unknown kinase (putatively named PDK2), although PDK1 (Balendran, A., (1999) Curr. Biol. 9:393), autophosphorylation (Toker, A. (2000) J. Biol. Chem. 275:8271) and integrin-linked kinase (ILK) (Delcommenne, M. (1998) Proc. Natl. Acad. Sci. USA, 95:11211) have been implicated in this process. Akt activation requires its phosphorylation on residue Ser 473 in the C-terminal hydrophobic motif (Brodbeck et al (1999) J. Biol. Chem. 274:9133-9136; Coffer et al (1991) Eur. J. Biochem. 201:475-481; Alessi et al (1997) Curr. Biol. 7:261-269). Although monophosphorylation of Akt activates the kinase, bis(phosphorylation) is required for maximal kinase activity.

Akt is believed to assert its effect on cancer by suppressing apoptosis and enhancing both angiogenesis and proliferation (Toker et al. (2006) Cancer Res. 66(8):3963-3966). Akt is overexpressed in many forms of human cancer including, but not limited to, colon (Zinda et al (2001) Clin. Cancer Res. 7:2475), ovarian (Cheng et al (1992) Proc. Natl. Acad. Sci. USA 89:9267), brain (Haas Kogan et al (1998) Curr. Biol. 8:1195), lung (Brognard et al (2001) Cancer Res. 61:3986), pancreatic (Bellacosa et al (1995) Int. J. Cancer 64:280-285; Cheng et al (1996) Proc. Natl. Acad. Sci. 93:3636-3641), prostate (Graff et al (2000) J. Biol. Chem. 275:24500) and gastric carcinomas (Staal et al (1987) Proc. Natl. Acad. Sci. USA 84:5034-5037).

The development of kinase inhibitors that target abnormally regulated pathways and ultimately result in disease is of enormous ethical and commercial interest to the medical and pharmaceutical community. A compound that inhibits (1) recruitment of Akt to the cell membrane, (2) activation by PDK1 or PDK2, (3) substrate phosphorylation, or (4) one of the downstream targets of Akt could be a valuable anticancer agent, either as a stand-alone therapy or in conjunction with other accepted procedures.

Inhibitors of Akt are known, see for example, United States Patent Application Publication 2005/0130954, United States Patent Application Publication 2008/0058327, United States Patent Application Publication 2008/0051399, and International Patent Application Publication WO 2006/090261.

SUMMARY OF THE INVENTION

The present invention includes novel compounds and compositions that inhibit protein kinases. The compounds and compositions of the present invention have utility as therapeutic agents for diseases and conditions that can be treated by the inhibition of protein kinases.

One aspect includes compounds having the general Formula I:

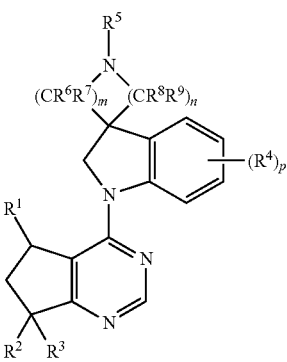

and tautomers, resolved enantiomers, resolved diastereomers, solvates, metabolites, salts and pharmaceutically acceptable prodrugs thereof, wherein $R^1$-$R^9$, m, n and p are defined herein.

Another aspect includes pharmaceutical compositions comprising a compound of Formula I and a pharmaceutically acceptable carrier, adjuvant or vehicle.

Another aspect includes a method of treating or lessening the severity of a disease or condition susceptible to the inhibition of an Akt protein kinase activity in a patient, comprising administering to said patient a therapeutically effective amount of a compound of Formula I. Exemplary Akt protein kinase mediated conditions that can be treated include, but are not limited to, inflammatory, hyperproliferative, cardiovascular, neurodegenerative, gynecological, and dermatological diseases and disorders.

Another aspect includes a method of inhibiting the production of Akt protein kinases in a mammal, which comprises administering to said mammal a compound of Formula I, or an enantiomer, solvate, metabolite, or pharmaceutically acceptable salt or prodrug thereof in an amount effective to inhibit production of an Akt protein kinase.

Another aspect includes methods of inhibiting the activity of Akt protein kinases, comprising contacting said kinase with a compound of Formula I.

Compounds of Formula I can be used advantageously in combination with other known therapeutic agents. Accordingly, another aspect includes pharmaceutical compositions comprising a compound of Formula I or an enantiomer, solvate, metabolite, or pharmaceutically acceptable salt or prodrug thereof, in combination with a second therapeutic agent.

An additional aspect includes the use of a compound of Formula I, or an enantiomer, solvate, metabolite, or pharmaceutically acceptable salt or prodrug thereof, for therapy. In one embodiment, the therapy comprises the treatment of an Akt protein kinase-mediated condition.

Another aspect includes kits for the treatment of an Akt protein kinase-mediated disease or disorder, said kit comprising a first pharmaceutical composition comprising a compound of Formula I, or an enantiomer, solvate, metabolite, or pharmaceutically acceptable salt or prodrug thereof, a container, and optionally a package insert or label indicating a treatment. The kits can further comprise a second compound or formulation comprising a second pharmaceutical agent useful for treating said disease or disorder.

Additional advantages and novel features of this invention shall be set forth in part in the description that follows, and in part will become apparent to those skilled in the art upon examination of the following specification, or can be learned by the practice of the invention. The advantages of the invention can be realized and attained by means of the instrumentalities, combinations, compositions, and methods particularly pointed out in the appended claims.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which can be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this specification controls.

Definitions

The term "alkyl" as used herein refers to a saturated linear or branched-chain monovalent hydrocarbon radical of one to twelve carbon atoms (i.e. $C_1$-$C_{12}$), wherein the alkyl radical can be optionally substituted independently with one or more substituents described below. Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (1-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "cycloalkyl," refers to saturated or partially unsaturated cyclic hydrocarbon radical having from three to twelve carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl ring fused to a saturated, partially unsaturated or aromatic cycloalkyl or heterocyclic ring. Examples of cycloalkyl groups include, but are not limited to, cyclopropyl, cyclobutyl, cyclopentyl, cyclohexyl, cycloheptyl, and the like. Bicyclic cycloalkyl includes those cycloalkyls having 7 to 12 ring atoms arranged, for example, as a bicyclo[4,5], [5,5], [5,6] or [6,6] system, or as bridged systems such as bicyclo[2.2.1]heptane, bicyclo[2.2.2]octane, and bicyclo[3.2.2]nonane. The cycloalkyl can be optionally substituted independently with one or more substituents described herein.

"Aryl" as used herein means a monovalent aromatic hydrocarbon radical of 6-20 carbon atoms derived by the removal of one hydrogen atom from a single carbon atom of a parent aromatic ring system. Aryl includes bicyclic radicals comprising an aromatic ring fused to a saturated, partially unsaturated ring, or aromatic carbocyclic or heterocyclic ring. Exemplary aryl groups include, but are not limited to, radicals derived from benzene, naphthalene, anthracene, biphenyl, indene, indane, 1,2-dihydronapthalene, 1,2,3,4-tetrahydronapthalene, and the like. Aryl groups can be optionally substituted independently with one or more substituents described herein.

The terms "heterocycle", "heterocyclyl" and "heterocyclic ring" as used herein are used interchangeably and refer to a saturated or partially unsaturated carbocyclic radical of 3 to 8 ring atoms in which at least one ring atom is a heteroatom independently selected from nitrogen, oxygen and sulfur, the remaining ring atoms being C, where one or more ring atoms can be optionally substituted independently with one or more substituents described below. The radical can be a carbon radical or heteroatom radical. "Heterocyclyl" also includes radicals where heterocycle radicals are fused with a saturated, partially unsaturated, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxepanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. The heterocycle can be C-attached or N-attached where such is possible. For instance, a group derived from pyrrole can be pyrrol-1-yl (N-attached) or pyrrol-3-yl (C-attached). Further, a group derived from imidazole can be imidazol-1-yl (N-attached) or imidazol-4-yl (C-attached). Examples of heterocyclic groups wherein 2 ring carbon atoms are substituted with oxo (=O) moieties are isoindoline-1,3-dionyl and 1,1-dioxo-thiomorpholinyl. The heterocycle groups herein are optionally substituted independently with one or more substituents described herein.

The term "heteroaryl" as used herein refers to a monovalent aromatic radical of a 5-, 6-, or 7-membered ring and includes fused ring systems (at least one of which is aromatic) of 5-10 atoms containing at least one heteroatom independently selected from nitrogen, oxygen, and sulfur. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups can be optionally substituted independently with one or more substituents described herein.

By way of example and not limitation, carbon bonded heterocycles and heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Further examples of carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles and heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of an isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

The term "a" as used herein means one or more.

As used herein, the terms "compound of this invention," "compounds of the present invention" and "compounds of Formula I" includes compounds of Formula I and tautomers, resolved enantiomers, resolved diastereomers, racemic mixtures, solvates, metabolites, salts (including pharmaceutically acceptable salts) and pharmaceutically acceptable prodrugs thereof.

It is to be understood that in instances where two or more radicals are used in succession to define a substituent attached to a structure, the first named radical is considered to be terminal and the last named radical is considered to be attached to the structure in question. Thus, for example, an arylalkyl radical is attached to the structure in question by the alkyl group.

Groups may be used recursevly and may appear in the same structure more than one time. It is to be understood that the recursive groups can have independent and distinct values. As one example, in certain embodiments, the group $R^{10}$ may appear recursively, such as in the structure

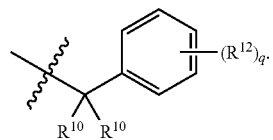

It is understood that one $R^{10}$ can have an independent and distinct value from the other $R^{10}$ in the same structure. As an example, in certain embodiments, both $R^{10}$ in the above structure can be hydrogen, or, in certain embodiments, the two $R^{10}$ in the above structure can have different values, for example, one $R^{10}$ is hydrogen and the other $R^{10}$ is OH.

AKT Inhibitors

Compounds of Formula I are useful for inhibiting protein kinases, for example, Akt protein kinases. Such compounds have utility as therapeutic agents for diseases that can be treated by the inhibition of the Akt protein kinase signaling pathway and tyrosine and serine/threonine kinase receptor pathways.

In particular, certain compounds of Formula I wherein $R^2$ is OH were found to be at least 50-fold more selective for Akt versus protein kinase A (PKA). For example, at least 100-fold, and as a further example, at least 150-fold more selective for Akt versus PKA. Selectivity over PKA is desirable, since PKA is involved in many cellular processes important for the normal function and physiology of many cell types. Additionally, inhibition of PKA is not believed to contribute to the anti-proliferative and pro-apoptotic effects of Akt inhibition. Thus, inhibition of PKA could lead to adverse events not associated with Akt inhibition without contributing to the disease modifying benefits of Akt inhibition.

The compounds of Formula I can also be useful as inhibitors of tyrosine kinases as well as serine and threonine kinases in addition to Akt.

In general, one aspect of the invention includes compounds of Formula I:

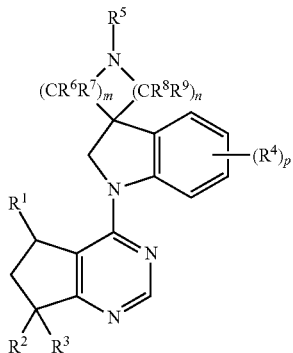

and tautomers, resolved enantiomers, resolved diastereomers, solvates, metabolites, salts and pharmaceutically acceptable prodrugs thereof, wherein:

$R^1$ is H, $CH_3$, $CH_2CH_3$, $CH(CH_3)_2$, $CH=CH_2$, $CH_2OH$, $CF_3$, $CHF_2$, $CH_2F$, or $C_3-C_6$ cycloalkyl;

$R^2$ is H, OH, $OCH_3$ or F;

$R^3$ is H, F or $CH_3$;

each $R^4$ is independently selected from H, F, Cl, Br, I, CN, $(CH_2)_tNR^{10}R^{10}$, $(CH_2)_tOR^{10}$, $(CH_2)_tC(O)R^{10}$, $(CH_2)_tC(O)OR^{16}$, $(CH_2)_tC(O)NR^{10}R^{10}$, $(CH_2)_tNR^{10}C(O)R^{10}$, $(CH_2)_tNR^{10}C(O)OR^{16}$, $(CH_2)_tNR^{10}C(O)NR^{10}R^{10}$, $C_1-C_6$ alkyl, $(CR^{10}R^{10})_tC_3-C_8$ cycloalkyl, $(CR^{10}R^{10})_tC_3-C_6$ heterocyclyl, $(CR^{10}R^{10})_tC_6-C_8$ aryl, $O(CR^{10}R^{10})_tC_6-C_8$ aryl, $(CR^{10}R^{10})_tC_3-C_6$ heteroaryl, wherein said alkyl, cycloalkyl, heterocyclyl, aryl and heteroaryl are optionally substituted by one or more F, Cl, Br, I, CN, $C_1-C_3$ alkyl, $CF_3$, OH or $O(C_1-C_3$ alkyl);

$R^5$ is H, $C_1-C_6$ alkyl, $(CR^{10}R^{10})_tOR^{10}$, $(CR^{10}R^{10})_tNR^{10}R^{10}$, $(CH_2)_tC_3-C_8$ cycloalkyl, $(CH_2)_tC_6-C_8$ aryl, wherein said aryl is optionally substituted by F, Cl, Br or I;

$R^6$, $R^7$, $R^8$ and $R^9$ are independently selected from H, $C_1-C_6$ alkyl, $(CR^{10}R^{10})_tOR^{10}$, $(CR^{10}R^{10})_tC_6-C_8$ aryl; wherein said aryl is optionally substituted by F, Cl, Br or I;

$R^{10}$ is independently selected from H, OH, $O(C_1-C_3$ alkyl), $(CH_2)_tNR^{11}R^{11}$, $(CH_2)_tC(O)NR^{11}R^{11}$, $(CH_2)_tS(O)NR^{11}R^{11}$, $(CH_2)_tS(O)_2NR^{11}R^{11}$, $C_1-C_6$ alkyl, $(CH_2)_tC_3-C_8$ cycloalkyl, $(CH_2)_tC_3-C_6$ heterocyclyl, $(CH_2)_tC_6-C_8$ aryl and $(CH_2)_tC_3-C_6$ heteroaryl, wherein said alkyl, cycloalkyl, heterocyclyl, aryl and heteroaryl are optionally substituted by one or more F, Cl, Br, I, CN, $C_1-C_3$ alkyl, $CF_3$, OH, $O(C_1-C_3$ alkyl); or two $R^{10}$ are taken together to form oxo or a $C_3-C_6$ heterocyclyl;

$R^{11}$ is independently selected from H, $C_1-C_3$ alkyl, OH, $OC_1-C_3$ alkyl, $NH_2$, $N(C_1-C_3$ alkyl)$_2$; or two $R^{11}$ are taken together to form a $C_3-C_6$ heterocyclyl, optionally substituted by methyl or ethyl;

m and n are independently 1, 2 or 3, provided that m and n taken together are 3, 4 or 5;

p is 0, 1, 2 or 3; and each t is independently 0, 1, 2, 3 or 4.

Compounds of Formula I include compounds wherein $R^1$ is H, $CH_3$, $CH_2CH_3$, $CH=CH_2$, $CH_2OH$, $CF_3$, $CHF_2$ or $CH_2F$.

In one embodiment, the invention includes compounds of Formula I and tautomers, resolved enantiomers, resolved diastereomers and pharmaceutically acceptable salts thereof.

In one embodiment, m is 2 and n is 1.

In one embodiment, m is 2 and n is 2.

In one embodiment, m is 3 and n is 1.

In one embodiment, m is 3 and n is 2.

In one embodiment, m is 4 and n is 1.

In one embodiment, m and n are independently 1 or 2, provided that m and n taken together are 3.

In one embodiment, m and n are independently 1, 2 or 3, provided that m and n taken together are 4.

In one embodiment, Formula I includes compounds wherein p is 1 or 2 and $R^4$ is F, Cl, Br, I, CN, $(CH_2)_tNR^{10}R^{10}$ or $(CH_2)_tOR^{10}$.

In one embodiment, Formula I includes compounds wherein p is 1 or 2 and $R^4$ is F, Cl, Br, I, CN, $(CH_2)_nNR^7R^7$ or $(CH_2)_nOR^7$.

Referring to the residue of Formula I having the structure:

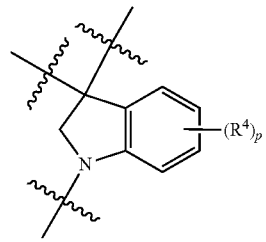

example embodiments include residues selected from:

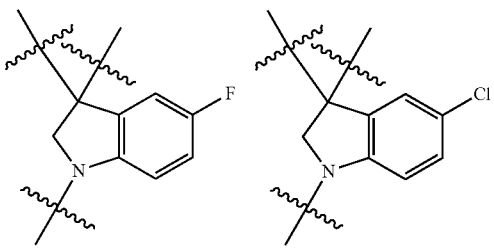

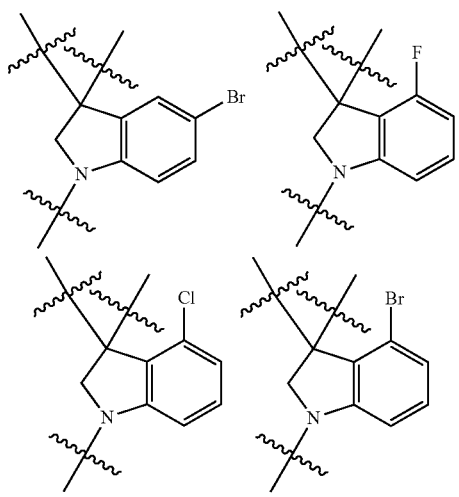

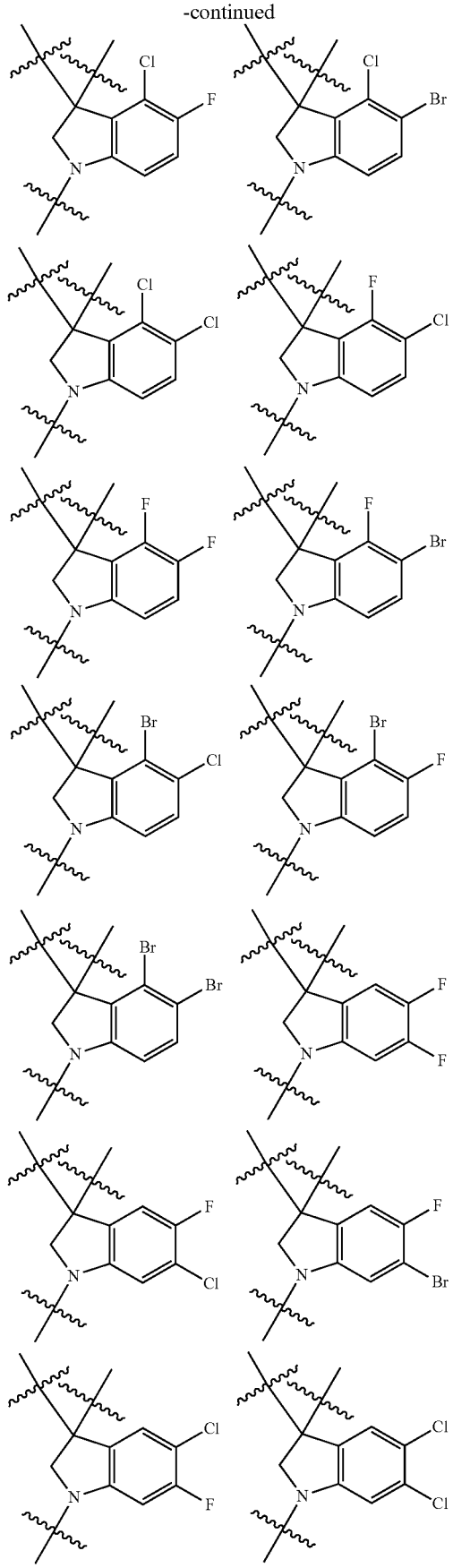
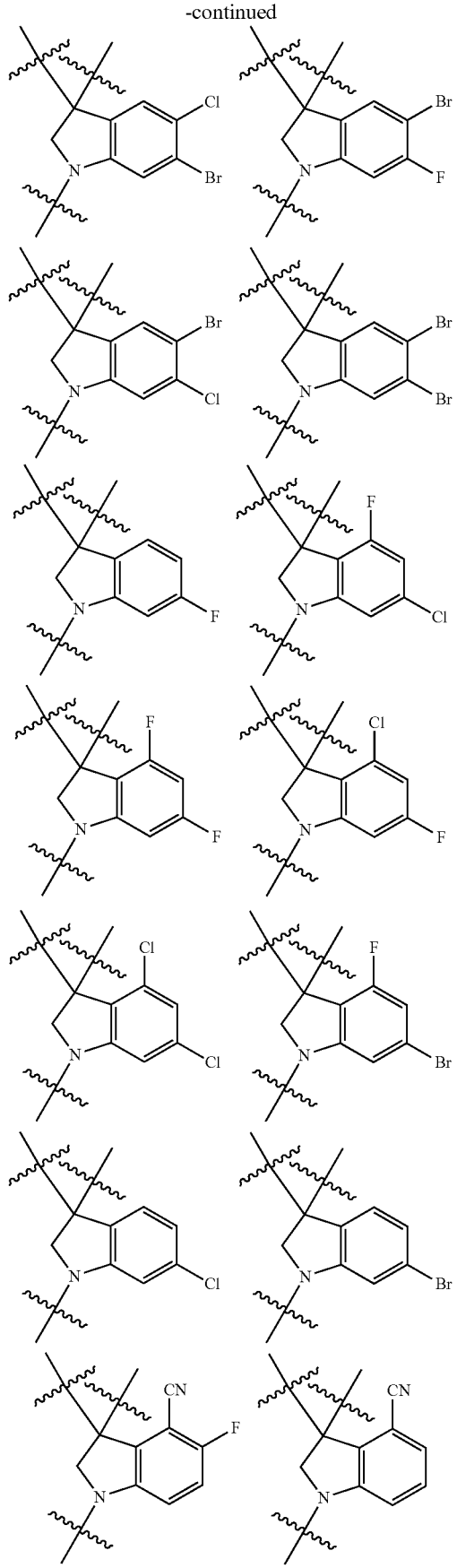

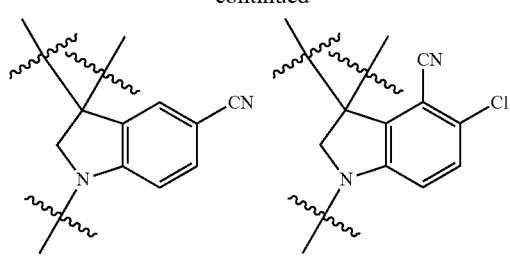
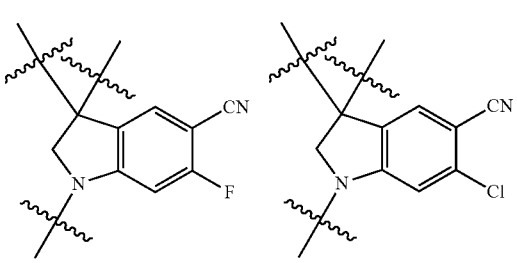
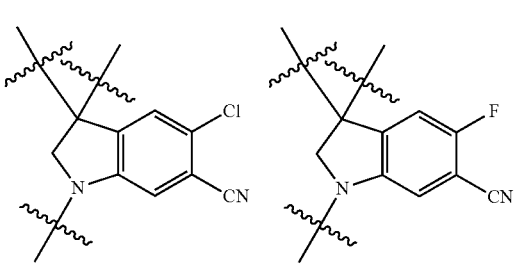
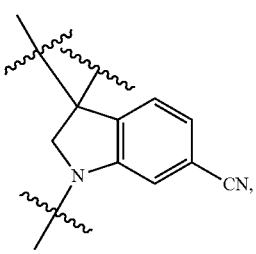
wherein the wavy lines represent points of attachment of the residue in Formula I.
Referring to the residue of Formula I having the structure:
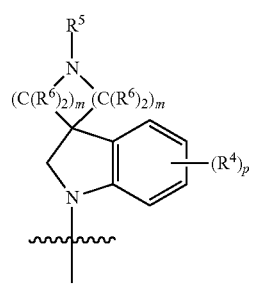
example embodiments include residues selected from:
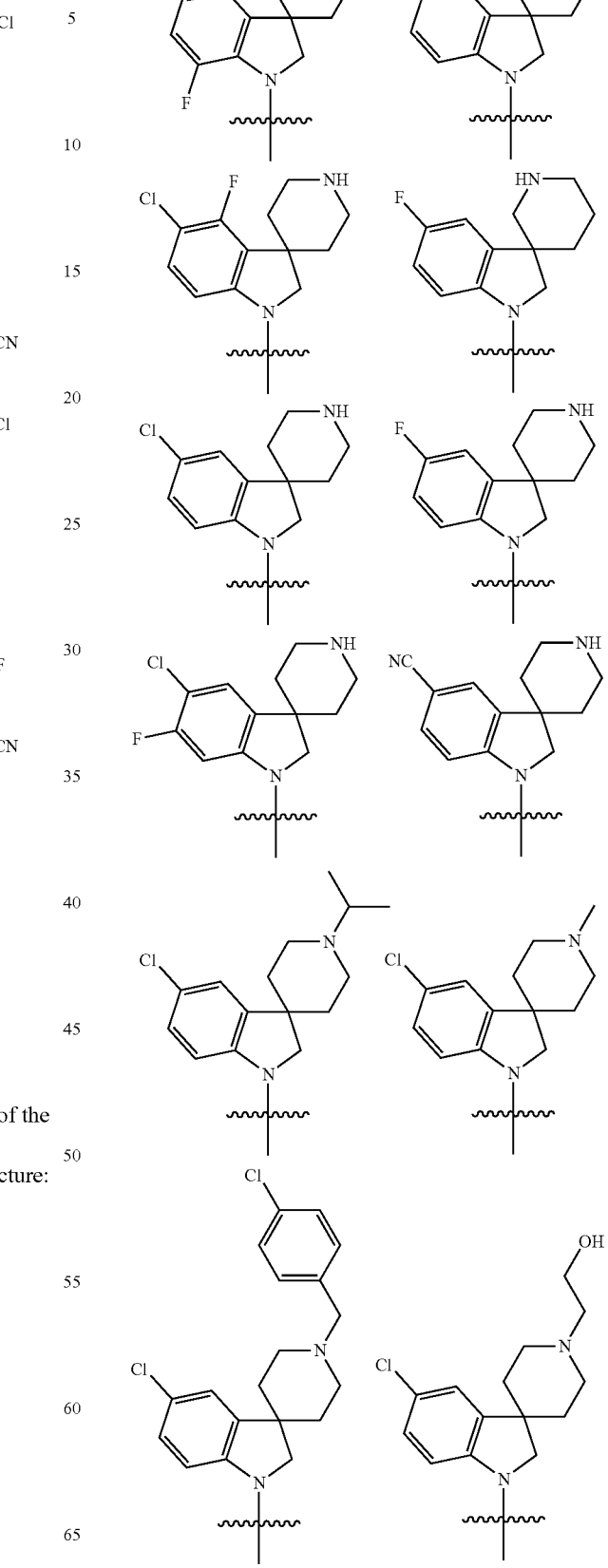

-continued
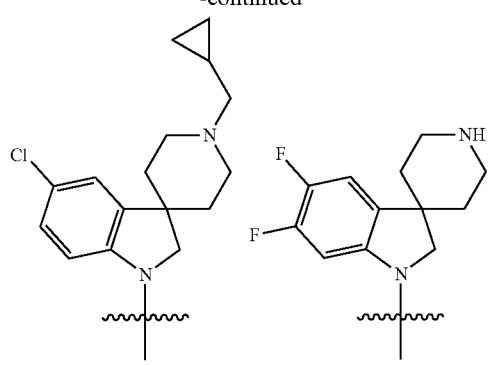
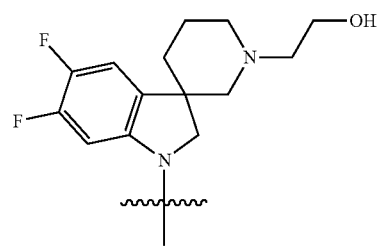
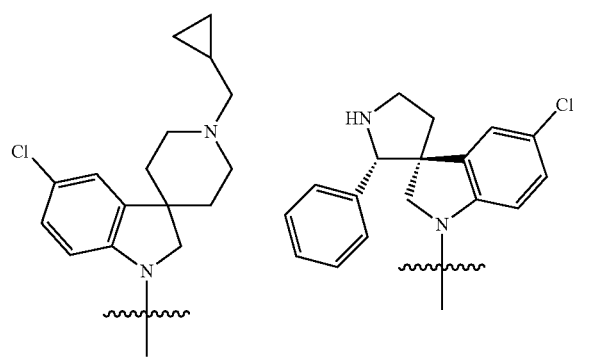
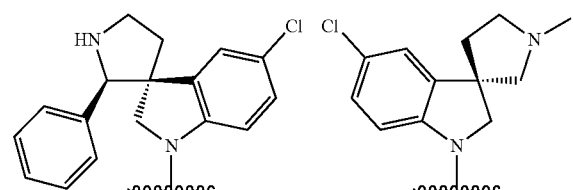
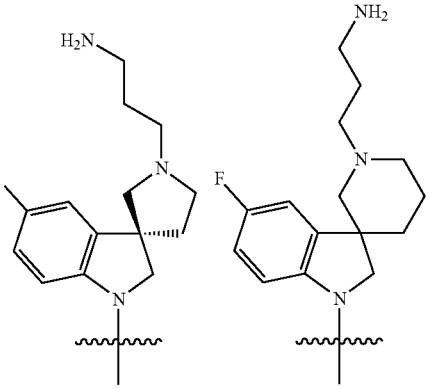
-continued
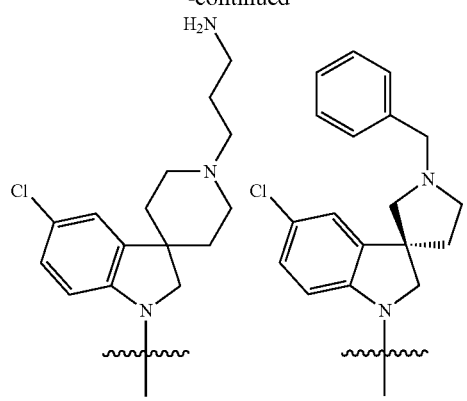
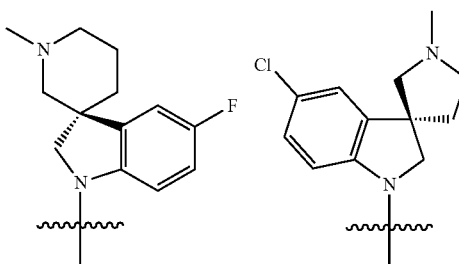
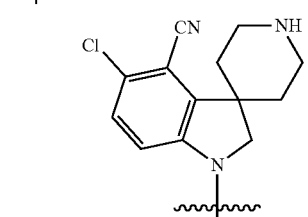
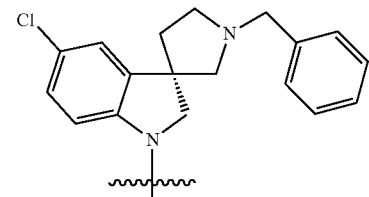
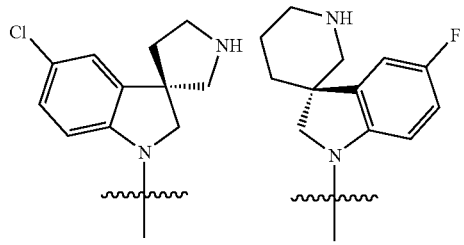
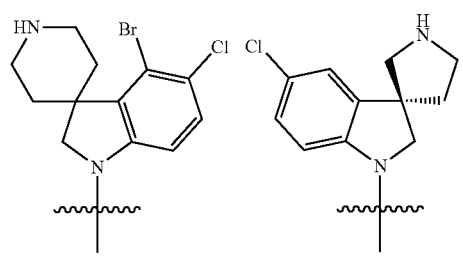

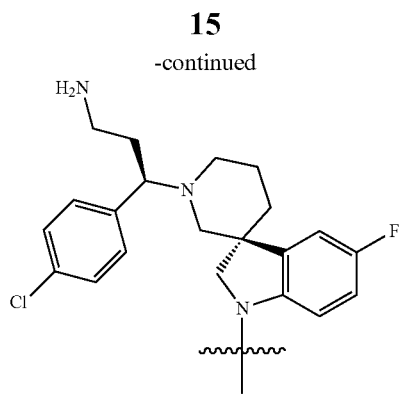
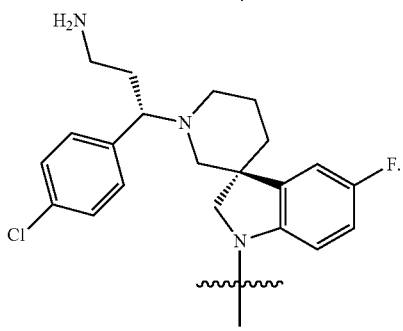
wherein the wavy line represents points of attachment for the residue in Formula I.
Again, referring to the residue of Formula I having the structure:
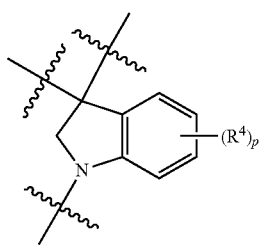
example embodiments include residues selected from:
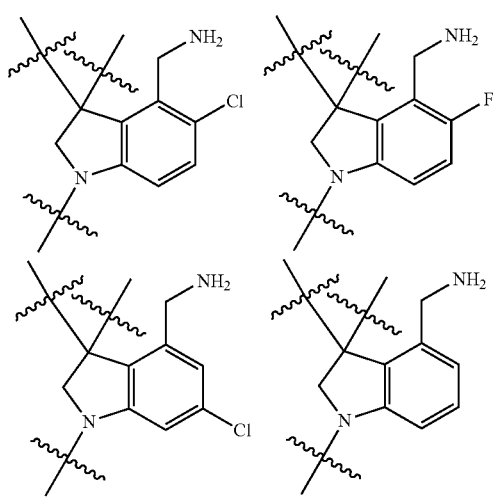
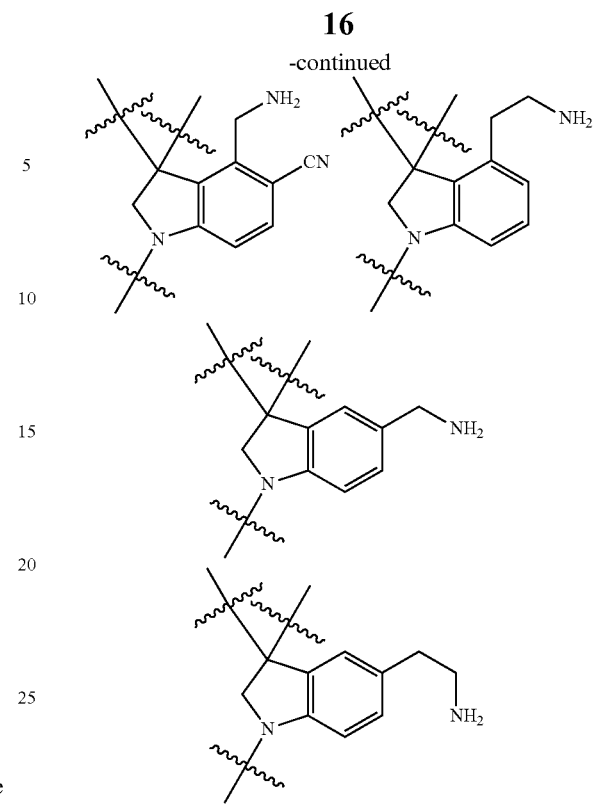
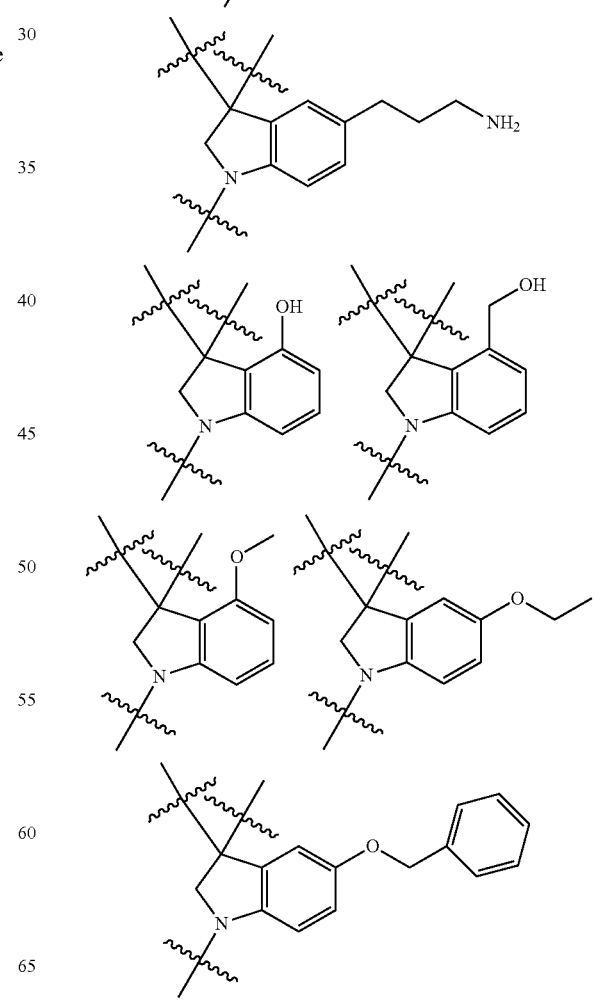

17
-continued
18
-continued
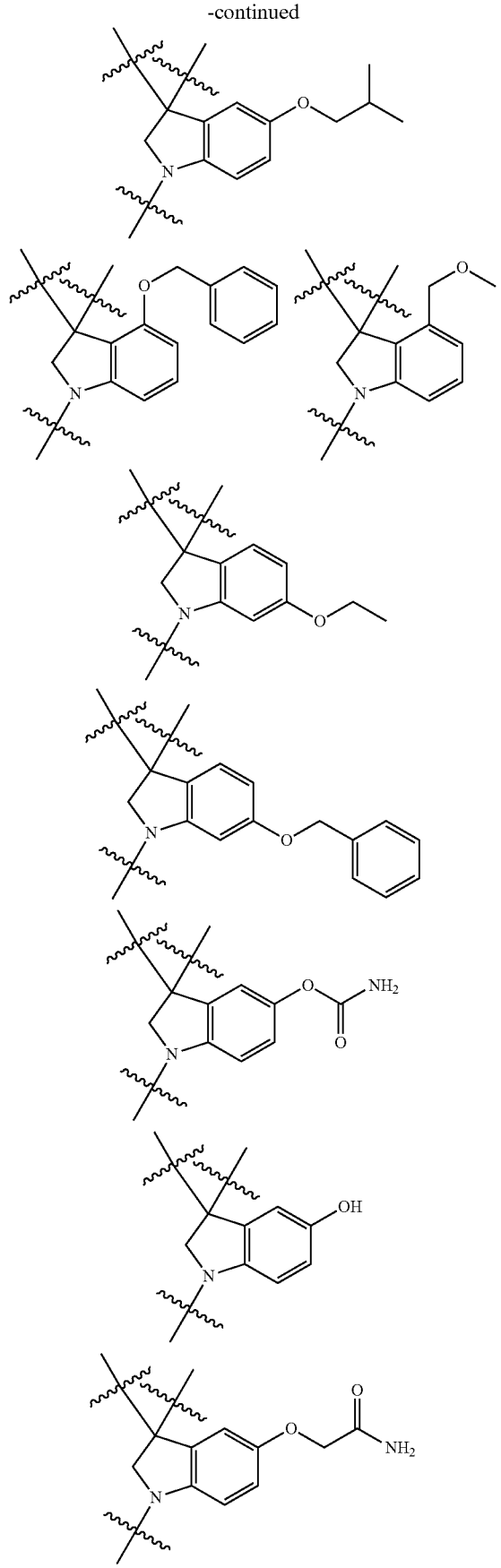
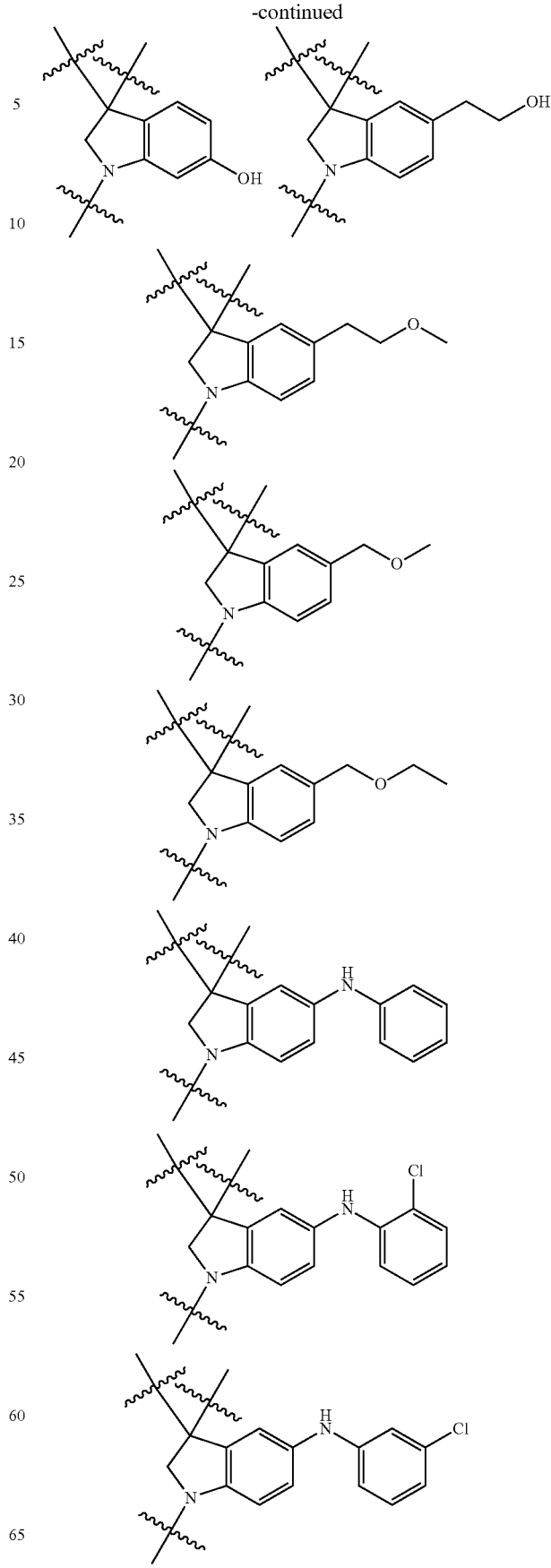

-continued
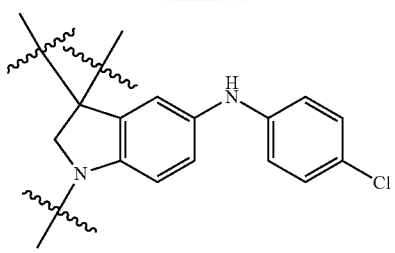
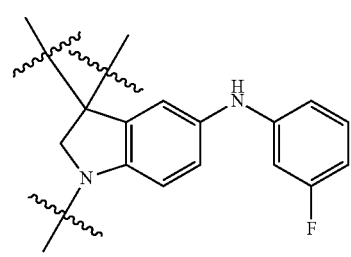
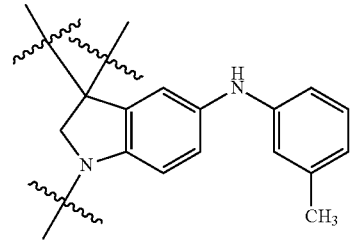
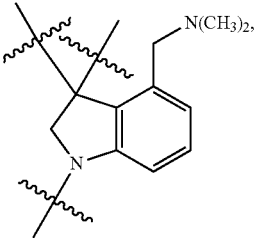
wherein the wavy lines represent points of attachment of the residue in Formula I.
Again, referring to the residue of Formula I having the structure:
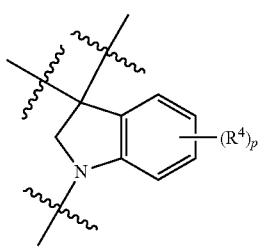
example embodiments include residues selected from:
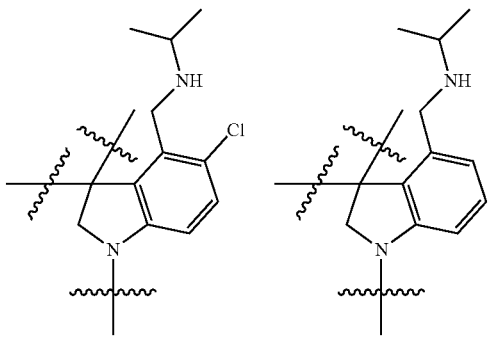
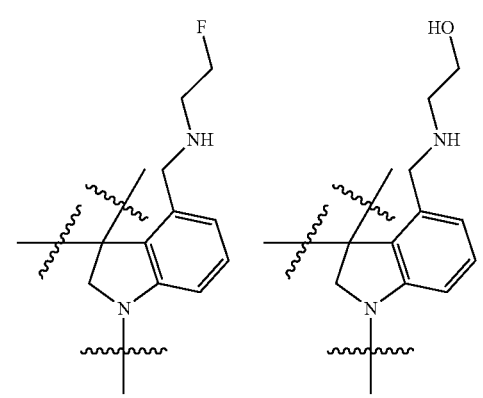
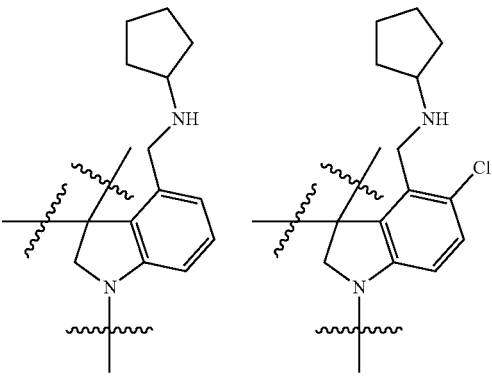
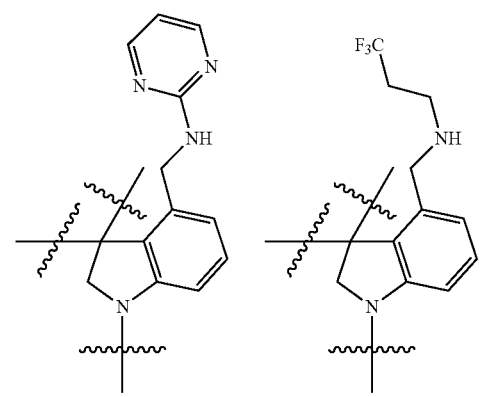

-continued
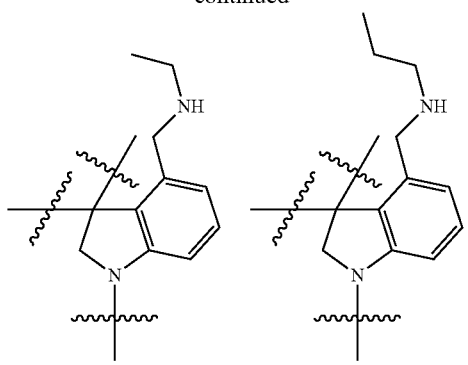
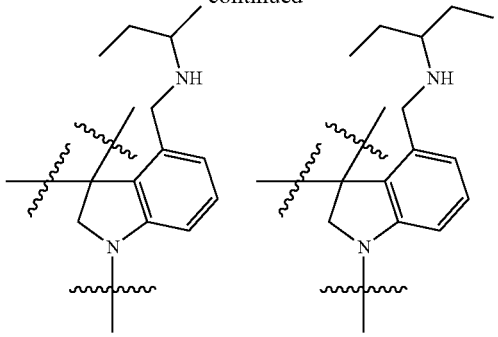
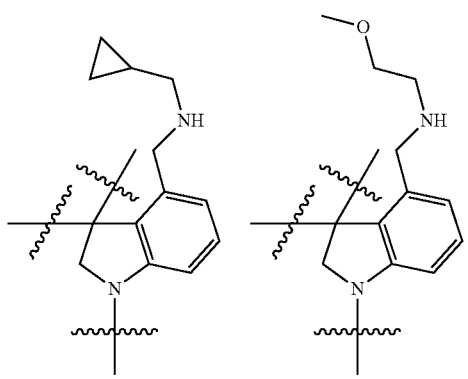
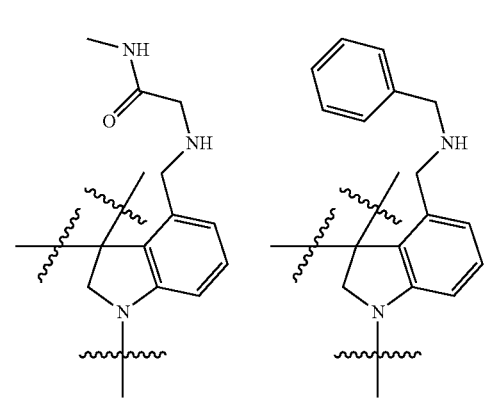
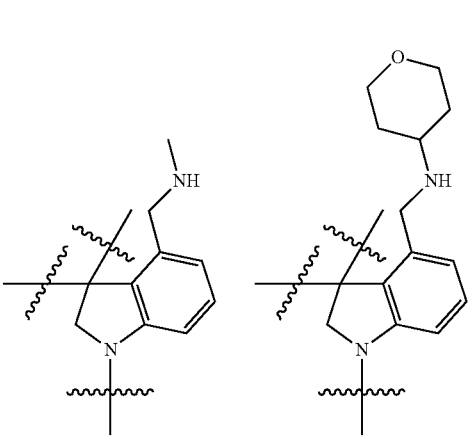
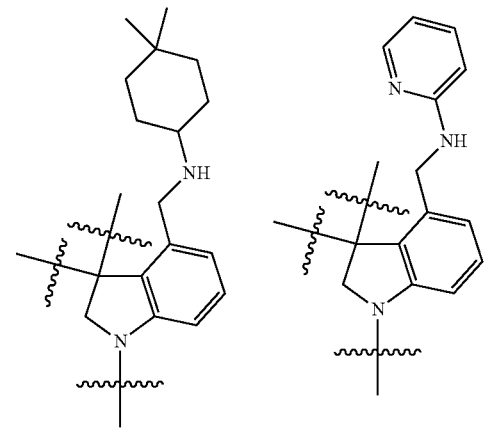
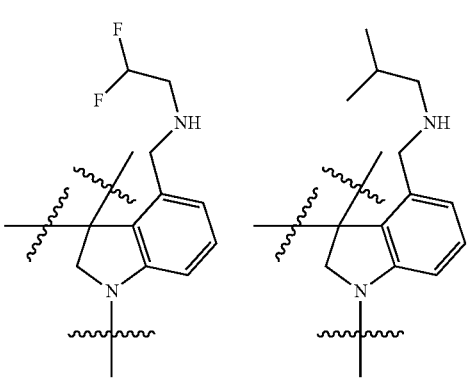
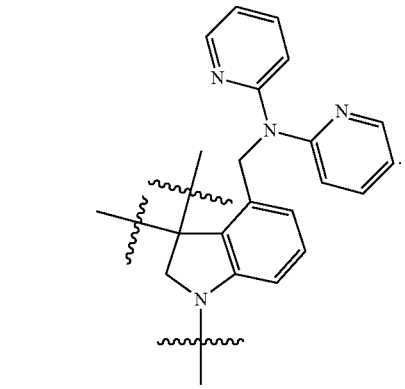

Again, referring to the residue of Formula I having the structure:

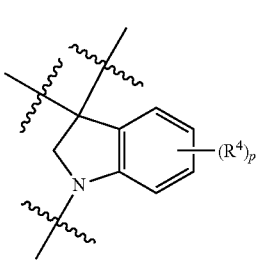

example embodiments include residues selected from:

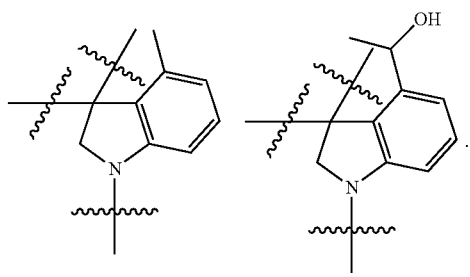

Again, referring to the residue of Formula I having the structure:

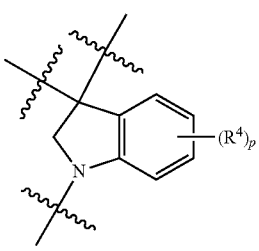

example embodiments include the residue:

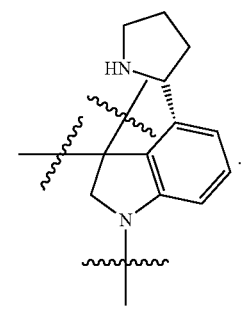

In one embodiment, Formula I includes compounds in which $R^4$ is $(CR^{10}R^{10})_tC_6$-$C_8$ aryl, wherein said aryl is optionally substituted by F, Cl, Br or I.

In certain embodiments, $R^4$ is selected from:

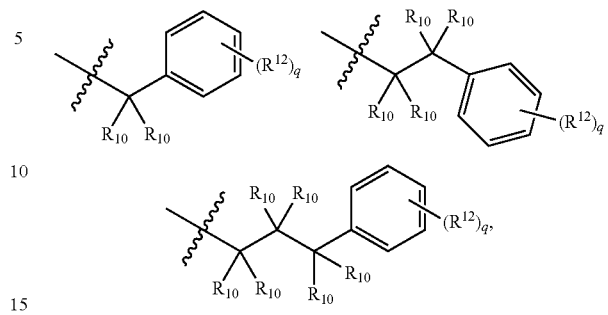

wherein the wavy line represents the point of attachment of $R^4$ in Formula I;

$R^{12}$ is F, Cl, Br or I;

q is 0, 1, 2, 3, 4 or 5; and $R^{10}$ is independently selected from H, OH, O($C_1$-$C_3$ alkyl), $(CH_2)_rNR^{11}R^{11}$, $C_1$-$C_6$ alkyl, $(CH_2)_rC_3$-$C_8$ cycloalkyl or $(CH_2)_rC_3$-$C_6$ heterocyclyl, wherein said cycloalkyl and heterocyclyl are optionally substituted by one or more $C_1$-$C_3$ alkyl, or two $R^{10}$ are taken together to form oxo.

In certain embodiments, $R^4$ is selected from:

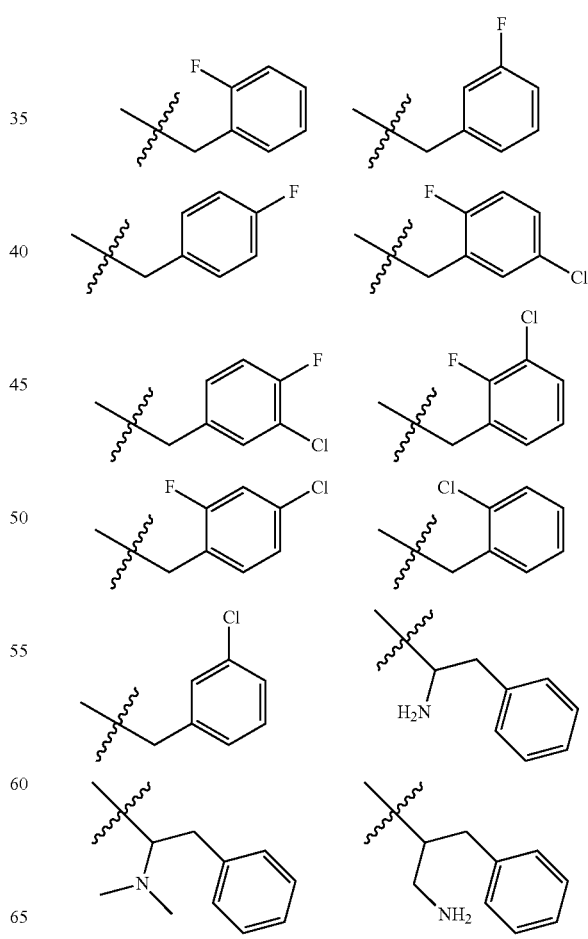

-continued

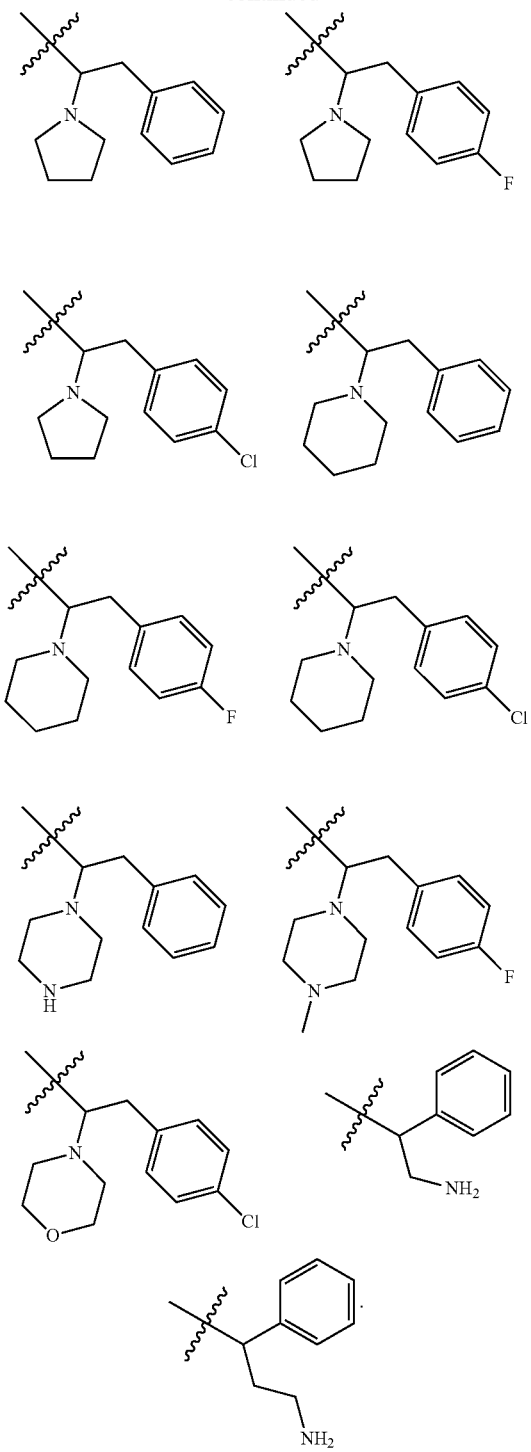

In certain embodiments, R⁴ is O(CR¹⁰R¹⁰)ₜC₆-C₈ aryl, wherein said aryl is optionally substituted by F, Cl, Br or I.

In certain embodiments, Formula I includes compounds wherein t is 0, 1, 2 or 3; R¹⁰ is independently selected from H, OH, O(C₁-C₃ alkyl) or (CH₂)NR¹¹R¹¹, or two R¹⁰ are taken together to form oxo; and R¹¹ is independently selected from H or C₁-C₃ alkyl, or two R¹¹ are taken together to form a C₃-C₆ heterocyclyl, optionally substituted by methyl or ethyl.

In certain embodiments, R⁴ is selected from:

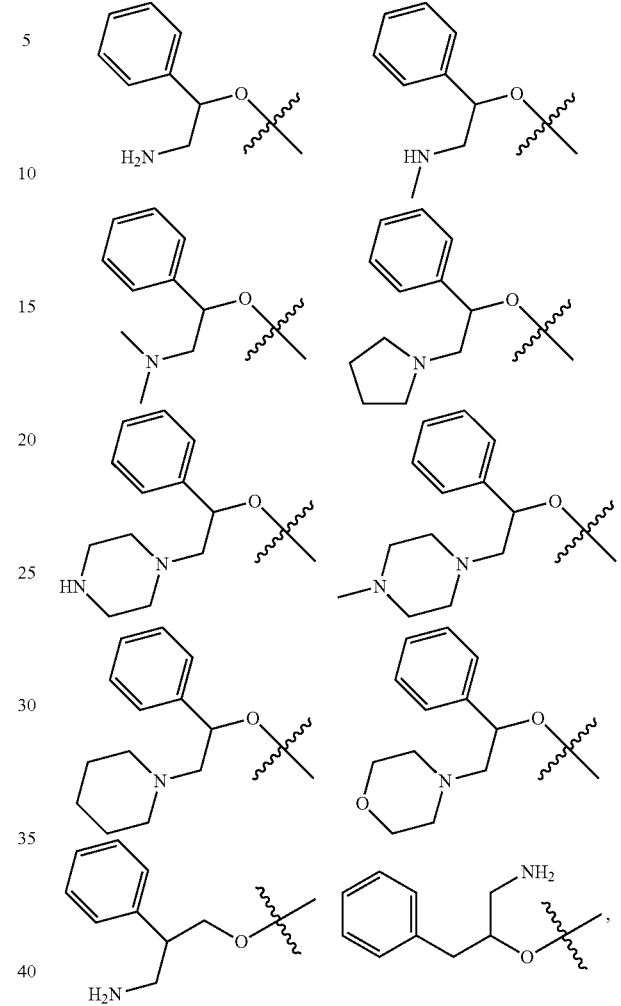

wherein the wavy line represents the point of attachment of R⁴ in Formula I.

In certain embodiments, R⁴ is C₁-C₆ alkyl or (CR¹⁰R¹⁰)ₜ C₃-C₈ cycloalkyl, wherein said alkyl and cycloalkyl are optionally substituted by F.

In certain embodiments, R⁴ is methyl, ethyl, n-propyl, isopropyl, cyclopropyl, cyclobutyl, cyclopentyl, methylcyclopropyl or ethylcyclopropyl.

In certain embodiments, R⁴ is CH(OH)CH₃.

In certain embodiments, R⁴ is (CH₂)ₜC(O)NR¹⁰R¹⁰ or (CH₂)ₜNR¹⁰C(O)R¹⁰.

In one embodiment, R⁴ is selected from:

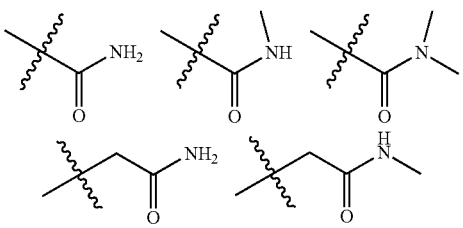

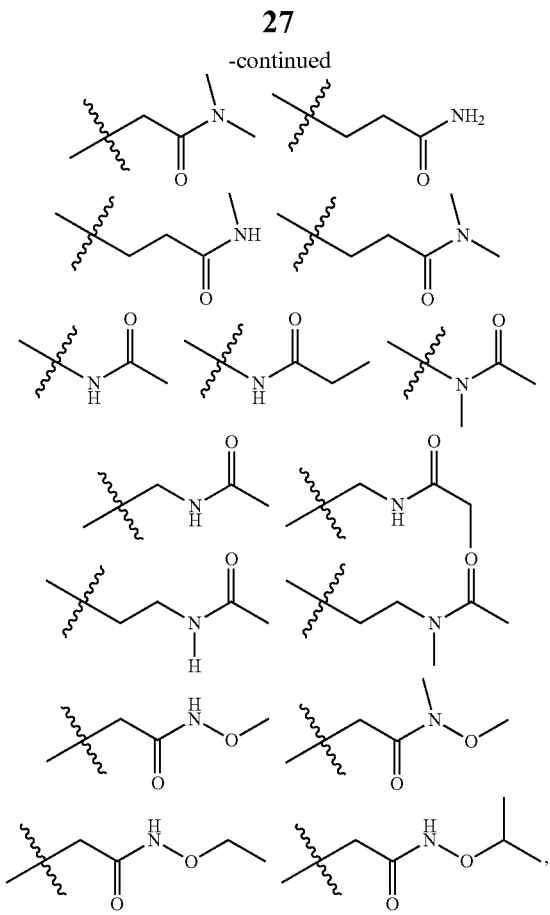

wherein the wavy line represents the point of attachment of $R^4$ in Formula I.

In certain embodiments, $R^4$ is $(CH_2)_tNR^{10}R^{10}$.

In one embodiment, $R^4$ is selected from:

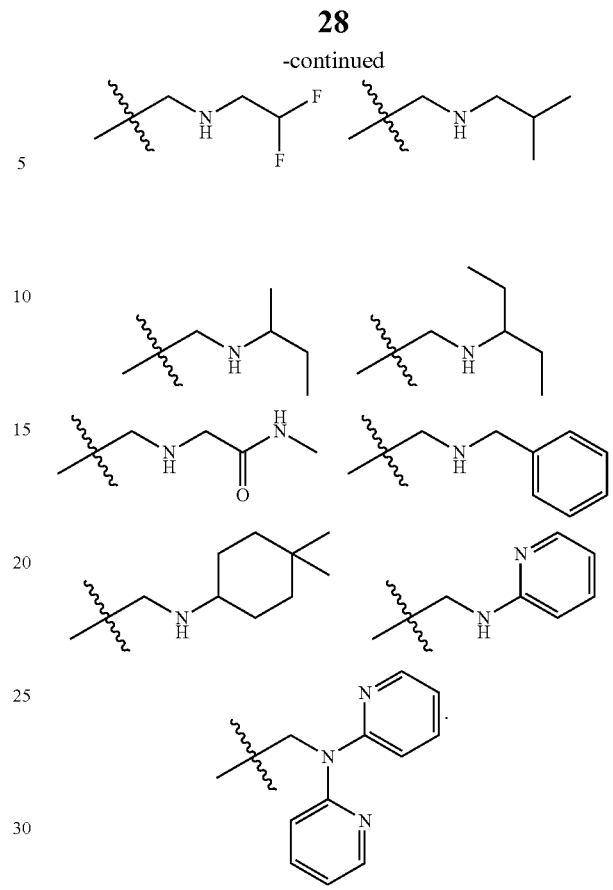

In certain embodiments, $R^4$ is $(CR^{10}R^{10})_tC_3$-$C_6$ heterocyclyl.

In one embodiment, $R^4$ is pyrrolidine.

In one embodiment, $R^1$ is H, $CH_3$, $CH_2CH_3$, $CH(CH_3)_2$, $CH{=}CH_2$, $CH_2OH$, $CF_3$, $CHF_2$, $CH_2F$, or $C_3$-$C_6$ cycloalkyl.

In one embodiment, $R^1$ is H, $CH_3$, $CH_2CH_3$, $CH(CH_3)_2$, $CF_3$, or cyclopentyl; $R^2$ is H, F, OH or $OCH_3$; and $R^3$ is H, $CH_3$ or F.

In one embodiment, $R^1$ is H, $CH_3$, $CH_2CH_3$ or $CF_3$; $R^2$ is H, F, OH or $OCH_3$; and $R^3$ is H, $CH_3$ or F.

In one embodiment, $R^1$ is H or $CH_3$.

In one embodiment, le is $C_3$-$C_6$ cycloalkyl. In certain embodiments, le is cyclopentyl.

In one embodiment, $R^2$ is H, F or OH.

In one embodiment, $R^3$ is H or F.

In one embodiment, the residue of Formula I having the structure:

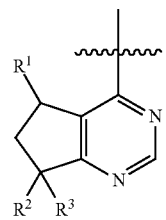

is selected from:

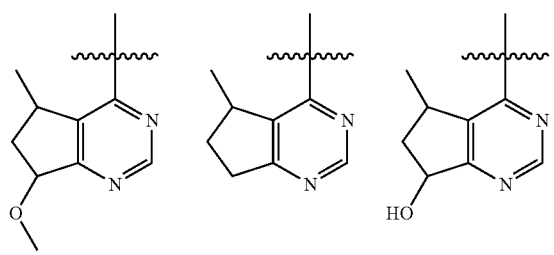

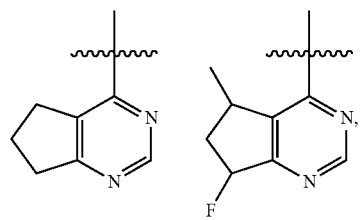

and wherein the wavy line represents the point of attachment of the residue in Formula I.

In one embodiment, the residue of Formula I is selected from:

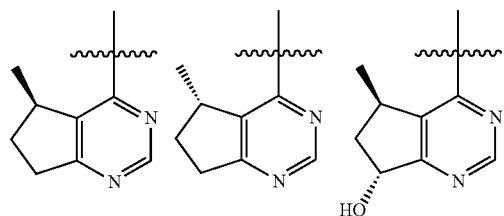

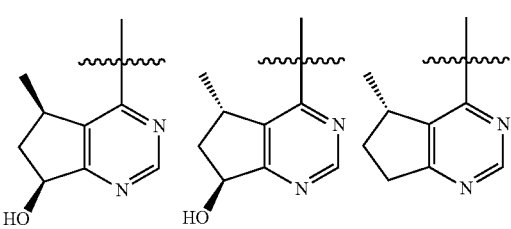

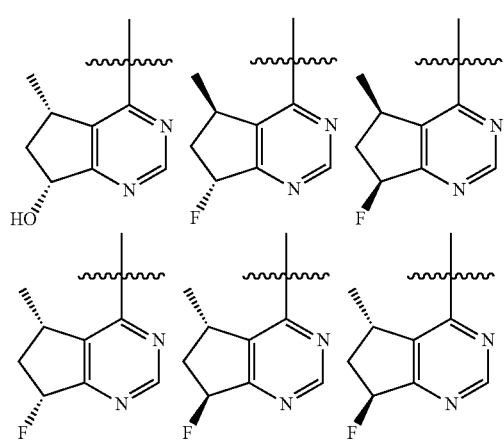

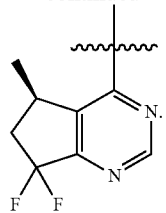

In one embodiment, the residue of Formula I having the structure:

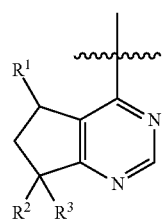

is selected from:

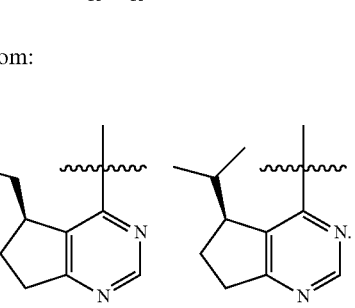

In one embodiment, wherein $R^5$ is H.

In one embodiment, $R^5$ is methyl, ethyl, n-propyl, iso-propyl.

In one embodiment, $R^5$ is $(CR^{10}R^{10})_t OR^{10}$ or $(CR^{10}R^{10})_t NR^{10}R^{10}$.

In one embodiment, $(CR^{10}R^{10})_t OR^{10}$ is $(CR^{10}R^{10})_t OH$; and $(CR^{10}R^{10})_t NR^{10}R^{10}$ is $(CR^{10}R^{10})_t NH_2$ or $(CR^{10}R^{10})_t NHR^{10}$.

In one embodiment, $R^5$ is selected from:

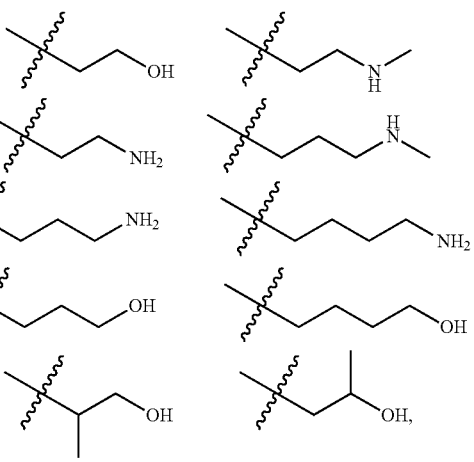

wherein the wavy line represents the point of attachment of $R^5$ in Formula I.

In one embodiment, $R^5$ is selected from:

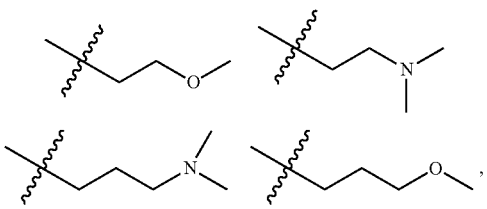

wherein the wavy line represents the point of attachment of $R^5$ in Formula I.

In one embodiment, $R^5$ is $(CH_2)_t C_3$-$C_8$ cycloalkyl or $(CH_2)_t C_6$-$C_8$ aryl, wherein said aryl is optionally substituted by F or Cl.

In one embodiment, $R^5$ is selected from:

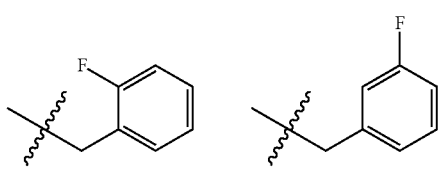

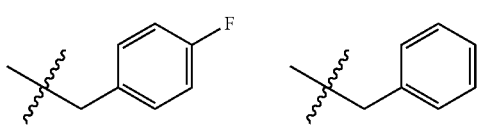

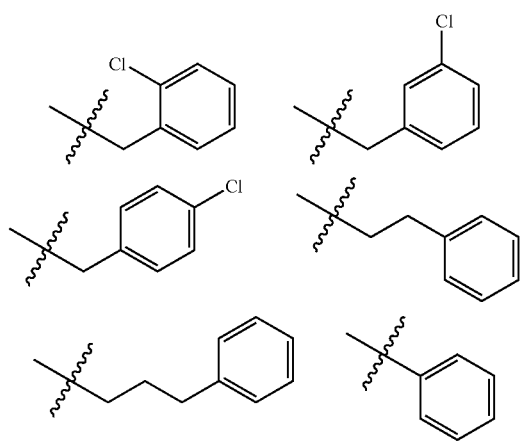

wherein the wavy line represents the point of attachment of $R^5$ in Formula I;

In certain embodiments, one of $R^6$, $R^7$, $R^8$ and $R^9$ is $(CR^{10}R^{10})_t C_6$-$C_8$ aryl, wherein said aryl is optionally substituted by F, Cl, Br or I.

In one embodiment, $(CR^{10}R^{10})_t C_6$-$C_s$ aryl is $(CR^{10}R^{10})_t$ phenyl optionally substituted by F, Cl, Br or I.

In one embodiment, t is 0.

In certain embodiment, one of $R^6$, $R^7$, $R^8$ and $R^9$ is selected from:

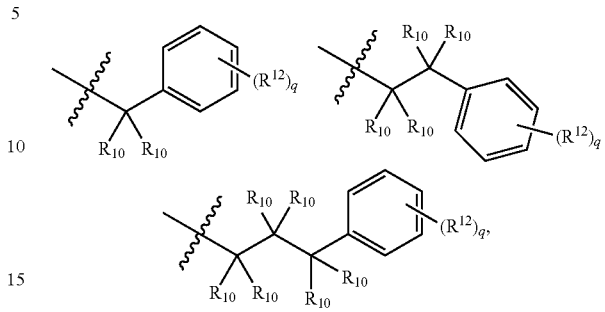

and the remaining $R^6$, $R^7$, $R^8$ and $R^9$ are H, wherein the wavy line represents the point of attachment in Formula I;

$R^{12}$ is F, Cl, Br or I;

q is 0, 1, 2, 3, 4 or 5; and $R^{10}$ is independently selected from H, OH, $O(C_1$-$C_3$ alkyl), $(CH_2)NR^{11}R^{11}$, $C_1$-$C_6$ alkyl, $(CH_2)_t C_3$-$C_8$ cycloalkyl, $(CH_2)_t C_3$-$C_6$ heterocyclyl.

In one embodiment, one of $R^6$, $R^7$, $R^8$ and $R^9$ is selected from:

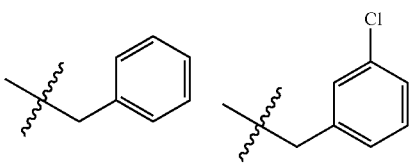

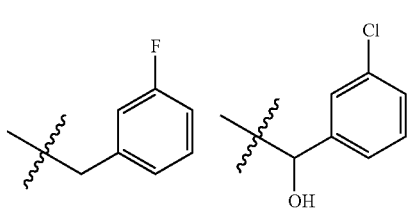

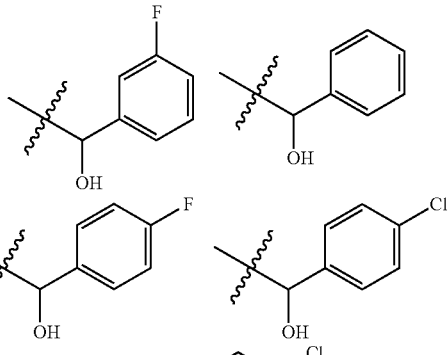

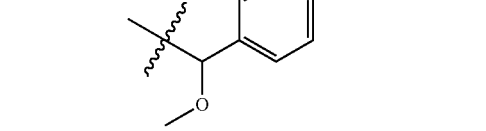

In one embodiment, one of $R^6$, $R^7$, $R^8$ and $R^9$ is selected from:

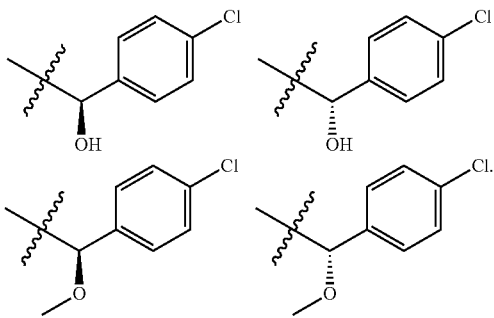

In one embodiment, one of $R^6$, $R^7$, $R^8$ and $R^9$ is $(CR^{10}R^{10})_tOR^{10}$, and the remaining $R^6$, $R^7$, $R^8$ and $R^9$ are H.

In one embodiment, $(CR^{10}R^{10})_tOR^{10}$ is $(CR^{10}R^{10})_tOH$.

In one embodiment $(CR^{10}R^{10})_tOH$ is selected from

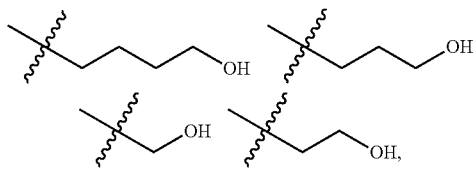

wherein the wavy line represents the point of attachment in Formula I.

As exemplary embodiments, Formula I includes the following compounds:
(R)-5-chloro-1-(5-methyl-6,7-dihydro-5H-cyclopenta[d]pyrimidin-4-yl)spiro[indoline-3,4'-piperidine];
(R)-5-bromo-1-(5-methyl-6,7-dihydro-5H-cyclopenta[d]pyrimidin-4-yl)spiro[indoline-3,4'-piperidine];
5-chloro-1-((5R,7S)-7-fluoro-5-methyl-6,7-dihydro-5H-cyclopenta[d]pyrimidin-4-yl)spiro[indoline-3,4'-piperidine];
5-chloro-1-((5R,7R)-7-fluoro-5-methyl-6,7-dihydro-5H-cyclopenta[d]pyrimidin-4-yl)spiro[indoline-3,4'-piperidine];
(5R,7R)-4-(5-chlorospiro[indoline-3,4'-piperidine]-1-yl)-5-methyl-6,7-dihydro-5H-cyclopenta[d]pyrimidin-7-ol;
(5R,7S)-4-(5-chlorospiro[indoline-3,4'-piperidine]-1-yl)-5-methyl-6,7-dihydro-5H-cyclopenta[d]pyrimidin-7-ol;
(R)-5-cyclopropyl-1-(5-methyl-6,7-dihydro-5H-cyclopenta[d]pyrimidin-4-yl)spiro[indoline-3,4'-piperidine];
(R)-5-chloro-1-(5-methyl-6,7-dihydro-5H-cyclopenta[d]pyrimidin-4-yl)spiro[indoline-3,4'-piperidine]-4-carbonitrile;
(R)-N-(3-chlorophenyl)-1-(5-methyl-6,7-dihydro-5H-cyclopenta[d]pyrimidin-4-yl)spiro[indoline-3,4'-piperidin]-5-amine;
(R)-2-(1-(5-methyl-6,7-dihydro-5H-cyclopenta[d]pyrimidin-4-yl)spiro[indoline-3,4'-piperidine]-5-yl)acetamide;
(R)-5-(3-fluorobenzyl)-1-(5-methyl-6,7-dihydro-5H-cyclopenta[d]pyrimidin-4-yl)spiro[indoline-3,4'-piperidine];
2-(1-((R)-5-methyl-6,7-dihydro-5H-cyclopenta[d]pyrimidin-4-yl)spiro[indoline-3,4'-piperidine]-5-yloxy)-2-phenylethanamine;
(R)-(1-(5-methyl-6,7-dihydro-5H-cyclopenta[d]pyrimidin-4-yl)spiro[indoline-3,4'-piperidine]-5-yl)methanamine;
(R)-2-(1-(5-methyl-6,7-dihydro-5H-cyclopenta[d]pyrimidin-4-yl)spiro[indoline-3,4'-piperidine]-5-yl)ethanamine;
(S)-5-chloro-1-((R)-5-methyl-6,7-dihydro-5H-cyclopenta[d]pyrimidin-4-yl)spiro[indoline-3,3'-pyrrolidine];
(R)-5-chloro-1-((R)-5-methyl-6,7-dihydro-5H-cyclopenta[d]pyrimidin-4-yl)spiro[indoline-3,3'-pyrrolidine];
(R)-4-((R)-5-fluorospiro[indoline-3,3'-piperidine]-1-yl)-5-methyl-6,7-dihydro-5H-cyclopenta[d]pyrimidine;
(R)-4-((S)-5-fluorospiro[indoline-3,3'-piperidine]-1-yl)-5-methyl-6,7-dihydro-5H-cyclopenta[d]pyrimidine;
(5R,7R)-4-(5-chloro-1'-methylspiro[indoline-3,4'-piperidine]-1-yl)-5-methyl-6,7-dihydro-5H-cyclopenta[d]pyrimidin-7-ol;
(R)-3-(4-chlorophenyl)-3-((R)-5-fluoro-1-((R)-5-methyl-6,7-dihydro-5H-cyclopenta[d]pyrimidin-4-yl)spiro[indoline-3,3'-piperidine]-1'-yl)propan-1-amine;
(S)-3-(4-chlorophenyl)-3-((R)-5-fluoro-1-((R)-5-methyl-6,7-dihydro-5H-cyclopenta[d]pyrimidin-4-yl)spiro[indoline-3,3'-piperidine]-1'-yl)propan-1-amine;
(R)-3-(5-chloro-1-(5-methyl-6,7-dihydro-5H-cyclopenta[d]pyrimidin-4-yl)spiro[indoline-3,4'-piperidine]-1'-yl)propan-1-amine;
(5R,7R)-4-(5-chlorospiro[indoline-3,3'-pyrrolidine]-1-yl)-5-methyl-6,7-dihydro-5H-cyclopenta[d]pyrimidin-7-ol;
(2'R,3S)-5-chloro-1-((R)-5-methyl-6,7-dihydro-5H-cyclopenta[d]pyrimidin-4-yl)-2'-phenylspiro[indoline-3,3'-pyrrolidine];
(2'S,3S)-5-chloro-1-((R)-5-methyl-6,7-dihydro-5H-cyclopenta[d]pyrimidin-4-yl)-2'-phenylspiro[indoline-3,3'-pyrrolidine];
(5R,7R)-4-((3S,5'S)-5'-(hydroxymethyl)spiro[indoline-3,3'-pyrrolidine]-1-yl)-5-methyl-6,7-dihydro-5,4-cyclopenta[d]pyrimidin-7-ol;
(5R,7R)-4-((3S,5'S)-5'-((R)-(4-chlorophenyl)(hydroxy)methyl)spiro[indoline-3,3'-pyrrolidine]-1-yl)-5-methyl-6,7-dihydro-5H-cyclopenta[d]pyrimidin-7-ol;
(5R,7R)-4-((3S,5'S)-5'-((S)-(4-chlorophenyl)(hydroxy)methyl)spiro[indoline-3,3'pyrrolidine]-1-yl)-5-methyl-6,7-dihydro-5H-cyclopenta[d]pyrimidin-7-ol;
(5R,7R)-4-(2'-benzyl-5-chlorospiro[indoline-3,4'-piperidine]-1-yl)-5-methyl-6,7-dihydro-5H-cyclopenta[d]pyrimidin-7-ol;
N-((1-((5R,7R)-7-hydroxy-5-methyl-6,7-dihydro-5H-cyclopenta[d]pyrimidin-4-yl)spiro[indoline-3,4'-piperidine]-4-yl)methyl)acetamide;
(5R,7R)-4-(4-((isopropylamino)methyl)spiro[indoline-3,4'-piperidine]-1-yl)-5-methyl-6,7-dihydro-5H-cyclopenta[d]pyrimidin-7-ol;
(5R,7R)-4-(4-(aminomethyl)-5-chlorospiro[indoline-3,4'-piperidine]-1-yl)-5-methyl-6,7-dihydro-5H-cyclopenta[d]pyrimidin-7-ol;
5-chloro-1-(6,7-dihydro-5H-cyclopenta[d]pyrimidin-4-yl)spiro[indoline-3,4'-piperidine];
(R)-5-ethoxy-1-(5-methyl-6,7-dihydro-5H-cyclopenta[d]pyrimidin-4-yl)spiro[indoline-3,4'-piperidine];
(R)-5-fluoro-1-(5-methyl-6,7-dihydro-5H-cyclopenta[d]pyrimidin-4-yl)spiro[indoline-3,4'-piperidine];
(R)-5-chloro-7-fluoro-1-(5-methyl-6,7-dihydro-5H-cyclopenta[d]pyrimidin-4-yl)spiro[indoline-3,4'-piperidine];
(R)-5-chloro-6-fluoro-1-(5-methyl-6,7-dihydro-5H-cyclopenta[d]pyrimidin-4-yl)spiro[indoline-3,4'-piperidine];
(R)-5-chloro-4-fluoro-1-(5-methyl-6,7-dihydro-5H-cyclopenta[d]pyrimidin-4-yl)spiro[indoline-3,4'-piperidine];
(R)-4,5-difluoro-1-(5-methyl-6,7-dihydro-5H-cyclopenta[d]pyrimidin-4-yl)spiro[indoline-3,4'-piperidine];
(R)-5,6-difluoro-1-(5-methyl-6,7-dihydro-5H-cyclopenta[d]pyrimidin-4-yl)spiro[indoline-3,4'-piperidine];

(R)-4-bromo-5-chloro-1-(5-methyl-6,7-dihydro-5H-cyclopenta[d]pyrimidin-4-yl)spiro[indoline-3,4'-piperidine];
(R)-1-(5-methyl-6,7-dihydro-5H-cyclopenta[d]pyrimidin-4-yl)spiro[indoline-3,4'-piperidine]-5-carbonitrile;
(R)-1-(5-methyl-6,7-dihydro-5H-cyclopenta[d]pyrimidin-4-yl)spiro[indoline-3,4'-piperidine]-4-carbonitrile;
(R)-(1-(5-methyl-6,7-dihydro-5H-cyclopenta[d]pyrimidin-4-yl)spiro[indoline-3,4'-piperidine]-4-yl)methanamine;
(R)-(5-chloro-1-(5-methyl-6,7-dihydro-5H-cyclopenta[d]pyrimidin-4-yl)spiro[indoline-3,4'-piperidine]-4-yl)methanamine;
(R)-2-(5-chloro-1-(5-methyl-6,7-dihydro-5H-cyclopenta[d]pyrimidin-4-yl)spiro[indoline-3,4'-piperidine]-1'-yl)ethanol;
(R)-5-chloro-1'-(4-chlorobenzyl)-1-(5-methyl-6,7-dihydro-5H-cyclopenta[d]pyrimidin-4-yl)spiro[indoline-3,4'-piperidine];
(R)-5-chloro-1'-methyl-1-(5-methyl-6,7-dihydro-5H-cyclopenta[d]pyrimidin-4-yl)spiro[indoline-3,4'-piperidine];
(R)-5-chloro-1'-isopropyl-1-(5-methyl-6,7-dihydro-5H-cyclopenta[d]pyrimidin-4-yl)spiro[indoline-3,4'-piperidine];
(R)-5-chloro-1'-(cyclopropylmethyl)-1-(5-methyl-6,7-dihydro-5H-cyclopenta[d]pyrimidin-4-yl)spiro[indoline-3,4'-piperidine];
(R)-N-methoxy-2-(1-(5-methyl-6,7-dihydro-5H-cyclopenta[d]pyrimidin-4-yl)spiro[indoline-3,4'-piperidine]-5-yl)acetamide;
(R)-N-methyl-2-(1-(5-methyl-6,7-dihydro-5H-cyclopenta[d]pyrimidin-4-yl)spiro[indoline-3,4'-piperidine]-5-yl)acetamide;
(R)-N-((1-(5-methyl-6,7-dihydro-5H-cyclopenta[d]pyrimidin-4-yl)spiro[indoline-3,4'-piperidine]-5-yl)methyl)acetamide;
(R)-2-(1-(5-methyl-6,7-dihydro-5H-cyclopenta[d]pyrimidin-4-yl)spiro[indoline-3,4'-piperidine]-5-yl)ethanol;
(R)-1-(5-methyl-6,7-dihydro-5H-cyclopenta[d]pyrimidin-4-yl)spiro[indoline-3,4'-piperidine]-5-carboxamide;
(R)-5-(benzyloxy)-1-(5-methyl-6,7-dihydro-5H-cyclopenta[d]pyrimidin-4-yl)spiro[indoline-3,4'-piperidine];
(R)-1-(5-methyl-6,7-dihydro-5H-cyclopenta[d]pyrimidin-4-yl)spiro[indoline-3,4'-piperidin]-5-ol;
(R)-2-(1-(5-methyl-6,7-dihydro-5H-cyclopenta[d]pyrimidin-4-yl)spiro[indoline-3,4'-piperidine]-5-yloxy)acetamide;
2-((R)-5-fluoro-1-((R)-5-methyl-6,7-dihydro-5H-cyclopenta[d]pyrimidin-4-yl)spiro[indoline-3,3'-piperidine]-1'-yl)ethanol;
(R)-4-((R)-5-fluoro-1'-methylspiro[indoline-3,3'-piperidine]-1-yl)-5-methyl-6,7-dihydro-5H-cyclopenta[d]pyrimidine;
(5R,7R)-4-(5-chloro-1'-(cyclopropylmethyl)spiro[indoline-3,4'-piperidine]-1-yl)-5-methyl-6,7-dihydro-5H-cyclopenta[d]pyrimidin-7-ol;
(5R,7R)-4-(5-(benzyloxy)spiro[indoline-3,4'-piperidine]-1-yl)-5-methyl-6,7-dihydro-5H-cyclopenta[d]pyrimidin-7-ol;
(S)-1'-benzyl-5-chloro-1-((R)-5-methyl-6,7-dihydro-5H-cyclopenta[d]pyrimidin-4-yl)spiro[indoline-3,3'-pyrrolidine];
(R)-1'-benzyl-5-chloro-1-((R)-5-methyl-6,7-dihydro-5H-cyclopenta[d]pyrimidin-4-yl)spiro[indoline-3,3'-pyrrolidine];
3-(5-fluoro-1-((R)-5-methyl-6,7-dihydro-5H-cyclopenta[d]pyrimidin-4-yl)spiro[indoline-3,3'-piperidine]-1'-yl)propan-1-amine;
(S)-5-chloro-1'-methyl-1-((R)-5-methyl-6,7-dihydro-5H-cyclopenta[d]pyrimidin-4-yl)spiro[indoline-3,3'-pyrrolidine];
3-((S)-5-chloro-1-((R)-5-methyl-6,7-dihydro-5H-cyclopenta[d]pyrimidin-4-yl)spiro[indoline-3,3'-pyrrolidine]-1'-yl)propan-1-amine;
(R)-5-chloro-1'-methyl-1-((R)-5-methyl-6,7-dihydro-5H-cyclopenta[d]pyrimidin-4-yl)spiro[indoline-3,3'-pyrrolidine]; and
(5R,7R)-4-(4-((dimethylamino)methyl)spiro[indoline-3,4'-piperidine]-1-yl)-5-methyl-6,7-dihydro-5H-cyclopenta[d]pyrimidin-7-ol;
and pharmaceutically acceptable salts thereof.

As exemplary embodiments, Formula I also includes the following compounds:
(5R,7R)-4-(5-chloro-4-((isopropylamino)methyl)spiro[indoline-3,4'-piperidine]-1-yl)-5-methyl-6,7-dihydro-5H-cyclopenta[d]pyrimidin-7-ol;
(R)-N-((1-(5-methyl-6,7-dihydro-5H-cyclopenta[d]pyrimidin-4-yl)spiro[indoline-3,4'-piperidine]-4-yl)methyl)propan-2-amine;
N-((1-((5R,7S)-7-fluoro-5-methyl-6,7-dihydro-5H-cyclopenta[d]pyrimidin-4-yl)spiro[indoline-3,4'-piperidine]-4-yl)methyl)propan-2-amine;
(R)-2-fluoro-N-((1-(5-methyl-6,7-dihydro-5H-cyclopenta[d]pyrimidin-4-yl)spiro[indoline-3,4'-piperidine]-4-yl)methyl)ethanamine;
(R)-2-((1-(5-methyl-6,7-dihydro-5H-cyclopenta[d]pyrimidin-4-yl)spiro[indoline-3,4'-piperidine]-4-yl)methylamino)ethanol;
(R)-N-((1-(5-methyl-6,7-dihydro-5H-cyclopenta[d]pyrimidin-4-yl)spiro[indoline-3,4'-piperidine]-4-yl)methyl)cyclopentanamine;
(R)-N-((5-chloro-1-(5-methyl-6,7-dihydro-5H-cyclopenta[d]pyrimidin-4-yl)spiro[indoline-3,4'-piperidine]-4-yl)methyl)propan-2-amine;
(R)-N-((5-chloro-1-(5-methyl-6,7-dihydro-5H-cyclopenta[d]pyrimidin-4-yl)spiro[indoline-3,4'-piperidine]-4-yl)methyl)cyclopentanamine;
(5R,7R)-4-((S)-4-((isopropylamino)methyl)spiro[indoline-3,3'-pyrrolidine]-1-yl)-5-methyl-6,7-dihydro-5H-cyclopenta[d]pyrimidin-7-ol;
(5R,7R)-4-((R)-4-((isopropylamino)methyl)spiro[indoline-3,3'-pyrrolidine]-1-yl)-5-methyl-6,7-dihydro-5H-cyclopenta[d]pyrimidin-7-ol;
(5R,7R)-5-methyl-4-((R)-4-methylspiro[indoline-3,3'-pyrrolidine]-1-yl)-6,7-dihydro-5H-cyclopenta[d]pyrimidin-7-ol;
(R)-N-((1-(5-methyl-6,7-dihydro-5H-cyclopenta[d]pyrimidin-4-yl)spiro[indoline-3,4'-piperidine]-4-yl)methyl)pyrimidin-2-amine;
1-((R)-5-methyl-6,7-dihydro-5H-cyclopenta[d]pyrimidin-4-yl)-4-((R)-pyrrolidin-2-yl)spiro[indoline-3,4'-piperidine];
(R)-N-((1-(5-ethyl-6,7-dihydro-5H-cyclopenta[d]pyrimidin-4-yl)spiro[indoline-3,4'-piperidine]-4-yl)methyl)propan-2-amine;
(S)-N-((1-(5-cyclopentyl-6,7-dihydro-5H-cyclopenta[d]pyrimidin-4-yl)spiro[indoline-3,4'-piperidine]-4-yl)methyl)propan-2-amine;
(S)-N-((1-(5-isopropyl-6,7-dihydro-5H-cyclopenta[d]pyrimidin-4-yl)spiro[indoline-3,4'-piperidine]-4-yl)methyl)propan-2-amine;
(S)-N-((1-(5-isopropyl-6,7-dihydro-5H-cyclopenta[d]pyrimidin-4-yl)spiro[indoline-3,4'-piperidine]-4-yl)methyl)cyclopentanamine;
1-(1-((R)-5-methyl-6,7-dihydro-5H-cyclopenta[d]pyrimidin-4-yl)spiro[indoline-3,4'-piperidine]-4-yl)ethanol;

(5R,7R)-4-(4-((isopropylamino)methyl)spiro[indoline-3,4'-piperidine]-1-yl)-5-methyl-6,7-dihydro-5H-cyclopenta[d]pyrimidin-7-ol;
(R)-3,3,3-trifluoro-N-((1-(5-methyl-6,7-dihydro-5H-cyclopenta[d]pyrimidin-4-yl)spiro[indoline-3,4'-piperidine]-4-yl)methyl)propan-1-amine;
(R)-N-((1-(5-methyl-6,7-dihydro-5H-cyclopenta[d]pyrimidin-4-yl)spiro[indoline-3,4'-piperidine]-4-yl) methyl) ethanamine;
(R)-N-((1-(5-methyl-6,7-dihydro-5H-cyclopenta[d]pyrimidin-4-yl)spiro[indoline-3,4'-piperidine]-4-yl)methyl)propan-1-amine;
(R)-1-cyclopropyl-N-((1-(5-methyl-6,7-dihydro-5H-cyclopenta[d]pyrimidin-4-yl)spiro[indoline-3,4'-piperidine]-4-yl)methyl)methanamine;
(R)-2-methoxy-N-((1-(5-methyl-6,7-dihydro-5H-cyclopenta[d]pyrimidin-4-yl)spiro[indoline-3,4'-piperidine]-4-yl)methyl)ethanamine;
(R)-N-((1'-methyl-1-(5-methyl-6,7-dihydro-5H-cyclopenta[d]pyrimidin-4-yl)spiro[indoline-3,4'-piperidine]-4-yl)methyl)propan-2-amine;
(R)-N-methyl-1-(1-(5-methyl-6,7-dihydro-5H-cyclopenta[d]pyrimidin-4-yl)spiro[indoline-3,4'-piperidine]-4-yl)methanamine;
(R)-N-((1-(5-methyl-6,7-dihydro-5H-cyclopenta[d]pyrimidin-4-yl)spiro[indoline-3,4'-piperidine]-4-yl)methyl)tetrahydro-2H-pyran-4-amine;
(R)-2,2-difluoro-N-((1-(5-methyl-6,7-dihydro-5H-cyclopenta[d]pyrimidin-4-yl)spiro[indoline-3,4'-piperidine]-4-yl)methyl)ethanamine;
(R)-2-methyl-N-((1-(5-methyl-6,7-dihydro-5H-cyclopenta[d]pyrimidin-4-yl)spiro[indoline-3,4'-piperidine]-4-yl)methyl)propan-1-amine;
N-((1-((R)-5-methyl-6,7-dihydro-5H-cyclopenta[d]pyrimidin-4-yl)spiro[indoline-3,4'-piperidine]-4-yl)methyl)butan-2-amine;
(R)-N-((1-(5-methyl-6,7-dihydro-5H-cyclopenta[d]pyrimidin-4-yl)spiro[indoline-3,4'-piperidine]-4-yl)methyl)pentan-3-amine;
(R)-N-methyl-2-((1-(5-methyl-6,7-dihydro-5H-cyclopenta[d]pyrimidin-4-yl)spiro[indoline-3,4'-piperidine]-4-yl)methylamino)acetamide;
(R)-N-benzyl-1-(1-(5-methyl-6,7-dihydro-5H-cyclopenta[d]pyrimidin-4-yl)spiro[indoline-3,4'-piperidine]-4-yl)methanamine;
(R)-4,4-dimethyl-N-((1-(5-methyl-6,7-dihydro-5H-cyclopenta[d]pyrimidin-4-yl)spiro[indoline-3,4'-piperidine]-4-yl)methyl)cyclohexanamine;
(R)-N-((1-(5-methyl-6,7-dihydro-5H-cyclopenta[d]pyrimidin-4-yl)spiro[indoline-3,4'-piperidine]-4-yl) methyl)pyridin-2-amine; and
(R)-N-((1-(5-methyl-6,7-dihydro-5H-cyclopenta[d]pyrimidin-4-yl)spiro[indoline-3,4'-piperidine]-4-yl)methyl)-N-(pyridin-2-yl)pyridin-2-amine
and pharmaceutically acceptable salts thereof.

The compounds of this invention can possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and diastereomers, and mixtures, racemic or otherwise, thereof. Accordingly, this invention also includes all such isomers, including diastereomeric mixtures, pure diastereomers and pure enantiomers of the compounds of this invention. The term "enantiomer" refers to two stereoisomers of a compound which are non-superimposable mirror images of one another.

The term "diastereomer" refers to a pair of optical isomers which are not mirror images of one another. Diastereomers have different physical properties, e.g. melting points, boiling points, spectral properties, and reactivities.

The compounds of the present invention can also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of Formula I include solvates, pharmaceutically acceptable prodrugs and salts (including pharmaceutically acceptable salts) of such compounds.

The phrase "pharmaceutically acceptable" indicates that the substance or composition is compatible chemically and/or toxicologically with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" can also be used to refer to a complex wherein the solvent molecule is water.

A "prodrug" is a compound that can be converted under physiological conditions or by solvolysis to the specified compound or to a salt of such compound. Prodrugs include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, cirtulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of Formula I can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in *Advanced Drug Delivery Reviews*, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in *J. Med. Chem.*, 1996, 39, 10. More specific examples include replacement of the hydrogen atom of the alcohol group with a group such as $(C_1-C_6)$alkanoyloxymethyl, 1-(($C_1-C_6$)alkanoyloxy)ethyl, 1-methyl-1-(($C_1$-$C_6$)alkanoyloxy)ethyl, $(C_1-C_6)$alkoxycarbonyloxymethyl, N-$(C_1-C_6)$alkoxy-carbonylaminomethyl, succinoyl, $(C_1-C_6)$ alkanoyl, $\alpha$-amino$(C_1-C_4)$alkanoyl, arylacyl and $\alpha$-aminoacyl, or $\alpha$-aminoacyl-$\alpha$-aminoacyl, where each $\alpha$-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate).

Free amines of compounds of Formula I can also be derivatized as amides, sulfonamides or phosphonamides. All of these moieties can incorporate groups including, but not limited to, ether, amine and carboxylic acid functionalities. For example, a prodrug can be formed by the replacement of a hydrogen atom in the amine group with a group such as R-carbonyl, RO-carbonyl, NRR'-carbonyl, wherein R and R' are each independently $(C_1-C_{10})$alkyl, $(C_3-C_7)$cycloalkyl, or benzyl, or R-carbonyl is a natural $\alpha$-aminoacyl or natural $\alpha$-aminoacyl-natural $\alpha$-aminoacyl, —C(OH)C(O)OY whereinY is H, $(C_1-C_6)$alkyl or benzyl, —C$(OY_0)Y_1$ wherein $Y_0$ is $(C_1-C_4)$ alkyl and $Y_1$ is $(C_1-C_6)$alkyl, carboxy$(C_1-C_6)$ alkyl, amino$(C_1-C_4)$alkyl or mono-N- or di-N,N-$(C_1-C_6)$ alkylaminoalkyl, or —C$(Y_2)Y_3$ wherein $Y_2$ is H or methyl and $Y_3$ is mono-N- or di-N,N-$(C_1-C_6)$alkylamino, morpholino, piperidin-1-yl or pyrrolidin-1-yl.

For additional examples of prodrug derivatives, see, for example, a) *Design of Prodrugs*, edited by H. Bundgaard, (Elsevier, 1985) and *Methods in Enzymology*, Vol. 42, p. 309-396, edited by K. Widder, et al. (Academic Press, 1985); b) *A Textbook of Drug Design and Development*, edited by Krogsgaard-Larsen and H. Bundgaard, Chapter 5 "Design and Application of Prodrugs," by H. Bundgaard p. 113-191 (1991); c) H. Bundgaard, *Advanced Drug Delivery Reviews*, 8:1-38 (1992); d) H. Bundgaard, et al., *Journal of Pharmaceutical Sciences*, 77:285 (1988); and e) N. Kakeya, et al., *Chem. Pharm. Bull.*, 32:692 (1984), each of which is specifically incorporated herein by reference.

Alternatively or additionally, compound of the invention can possess a sufficiently acidic group, a sufficiently basic group, or both functional groups, and accordingly react with any of a number of inorganic or organic bases or acids to form a salt. Examples of salts include those salts prepared by reaction of the compounds of the present invention with a mineral or organic acid or an inorganic base, such salts including, but not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, $\gamma$-hydroxybutyrates, glycollates, tartrates, methanesulfonates, propanesulfonates, naphthalene-1-sulfonates, naphthalene-2-sulfonates, and mandelates. Since a single compound of the present invention can include more than one acidic or basic moiety, the compounds of the present invention can include mono, di or tri-salts in a single compound.

In one example, in the case where the compound has basic properties, the desired salt can be prepared by any method available in the art, for example, by treatment of the free base with an acidic compound, for example an inorganic acid such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid such as glucuronic acid or galacturonic acid, an alpha hydroxy acid such as citric acid or tartaric acid, an amino acid such as aspartic acid or glutamic acid, an aromatic acid such as benzoic acid or cinnamic acid, a sulfonic acid such as p-toluenesulfonic acid or ethanesulfonic acid, or the like.

In another example, in the case where the compound has acidic properties, the desired salt can be prepared by any method known to one of ordinary skill in the art, for example, by treatment of the free acid with an inorganic or organic base. Examples of inorganic salts include those formed with alkali and alkaline earth metals such as lithium, sodium, potassium, barium and calcium. Examples of organic base salts for use include, for example, ammonium, dibenzylammonium, benzylammonium, 2-hydroxyethylammonium, bis (2-hydroxyethyl)ammonium, phenylethylbenzylamine, dibenzylethylenediamine, and the like salts. Other salts of acidic moieties can include, for example, those salts formed with procaine, quinine and N-methylglucosamine, plus salts formed with basic amino acids such as glycine, ornithine, histidine, phenylglycine, lysine and arginine.

In certain embodiments, the salt is a "pharmaceutically acceptable salt" which, unless otherwise indicated, includes salts that retain the biological effectiveness of the corresponding free acid or base of the specified compound and are not biologically or otherwise undesirable.

The compounds of Formula I also include other salts of such compounds which are not necessarily pharmaceutically acceptable salts, and which can be useful as intermediates for preparing and/or purifying compounds of Formula I and/or for separating enantiomers of compounds of Formula I.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically-labeled compounds of the present invention (e.g., those labeled with $^3$H and $^{14}$C) are useful in compound and/or substrate tissue distribution assays. Tritiated (i.e., $^3$H) and carbon-14 (i.e., $^{14}$C) isotopes are useful for their ease of preparation and detectability. Further, substitution with heavier isotopes such as deuterium (i.e., $^2$H) can afford certain therapeutic advantages resulting from greater metabolic stability (e.g., increased in vivo half-life or reduced dosage requirements). Positron emitting isotopes such as $^{15}$O, $^{13}$N, $^{11}$C and $^{18}$F are useful for positron emission tomography (PET) studies to examine substrate receptor occupancy. Isotopically labeled compounds of the present invention can generally be prepared by following procedures analogous to those disclosed in the Schemes and/ or in the Examples herein below, by substituting an isotopically labeled reagent for a non-isotopically labeled reagent.

Metabolites of Compounds of Formula I

Also falling within the scope of this invention are the in vivo metabolic products of compounds of Formula I described herein. A "metabolite" is a pharmacologically active product produced through metabolism in the body of a specified compound or salt thereof. Such products can result, for example, from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolites are identified, for example, by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolites, so long as they are not otherwise found in vivo, are useful in diagnostic assays for therapeutic dosing of the compounds of the invention.

Synthesis of Compounds of Formula I

Compounds of this invention can be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements).

Compounds of Formula I can be prepared singly or as compound libraries comprising at least 2, for example 5 to 1,000 compounds, or 10 to 100 compounds. Libraries of compounds of Formula I can be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds of Formula I, or salts thereof.

For illustrative purposes, Schemes 1 to 15 show general methods for preparing the compounds of the present invention, as well as key intermediates. For a more detailed description of the individual reaction steps, see the Examples section below. Those skilled in the art will appreciate that other synthetic routes can be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

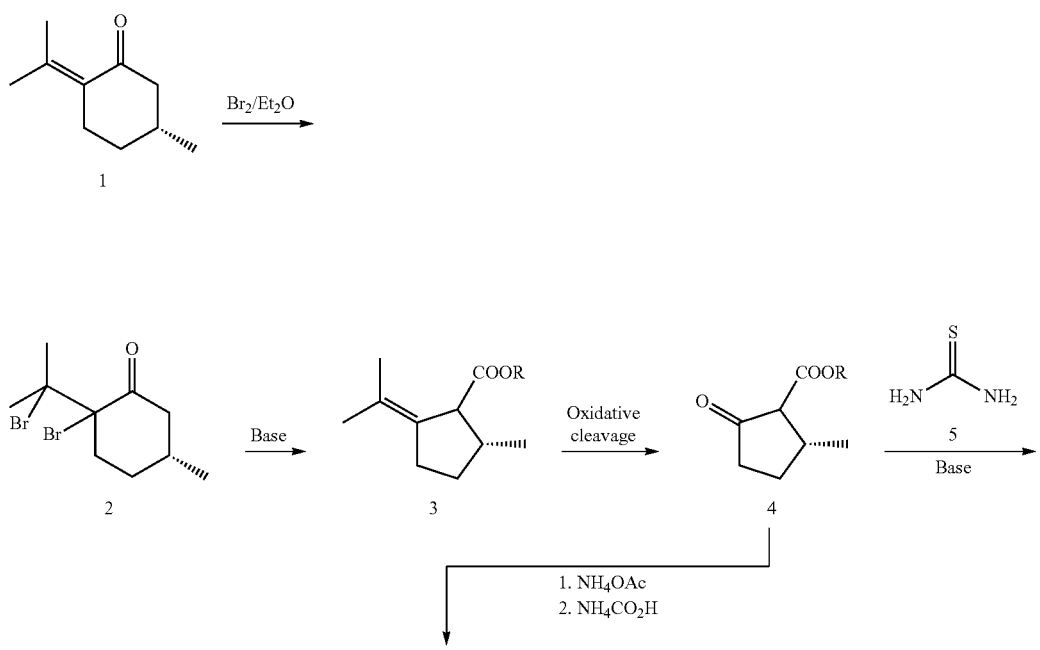

Scheme 1

-continued

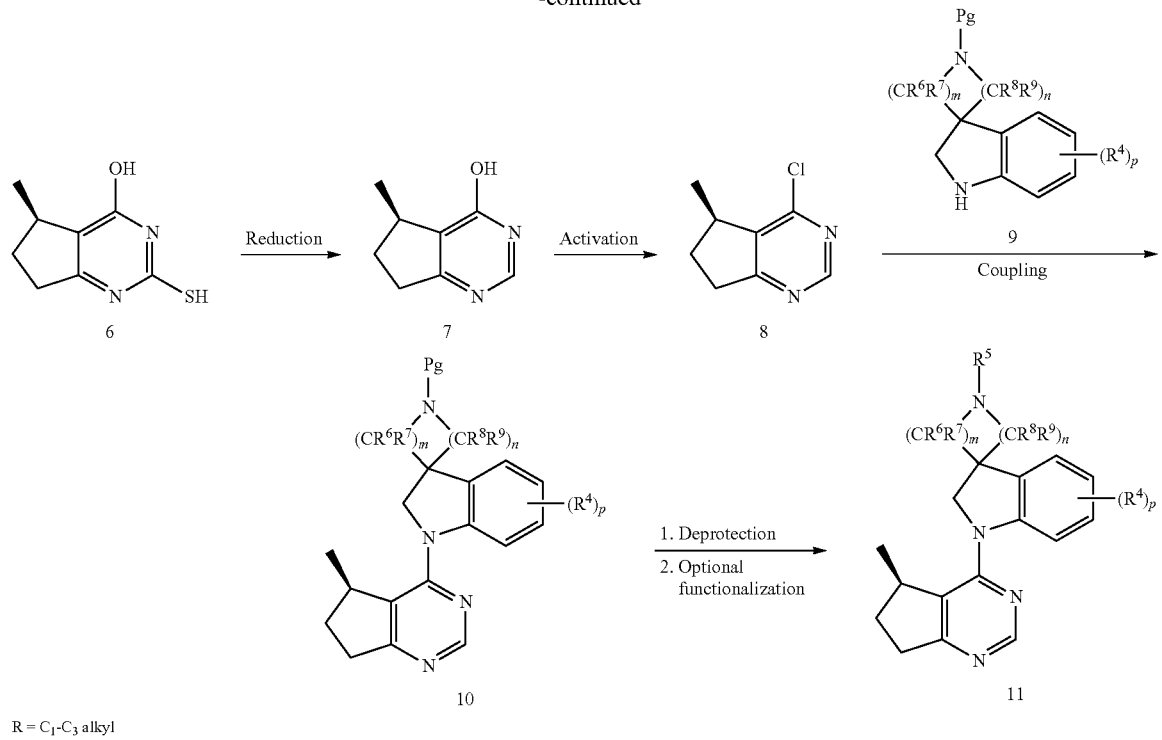

R = $C_1$-$C_3$ alkyl

Scheme 1 shows a method of preparing compound II of Formula I wherein $R^2$ and $R^3$ are hydrogen and $R^1$ is methyl. According to Scheme 1, intermediate 3 can be prepared by brominating (+)-pulegone 1 to provide the di-bromide 2, followed by treatment of the di-bromide 2 with a base such as sodium ethoxide. Oxidative cleavage (for example, ozonolysis at about –80° C. to –50° C.) of the pulegenate 3 gives the ketoester 4. The pyrimidine ring 6 is constructed by reaction of the ketoester 4 with thiourea in the presence of base such as KOH. The mercapto group at 2-position of compound 6 is eliminated by reduction (for example, Raney Ni in ammonia) to give compound 7. Alternatively, the ketoester 4 can be converted to the same hydroxypyrimidine 7 by treatment with (for example) an ammonia synthon such as $NH_4OAc$, followed by pyrimidine formation using, for example, ammonium formate in the presence of formamide at 50° C. to 250° C. and/or at high pressure and/or microwave assistance. Activation of the hydroxypyrimidine 7 (for example, $POCl_3$) provides the 4-chloropyrimidine 8. Compounds of formula 10 can be synthesized by coupling of the chloropyrimidine 8 with optionally substituted spiroindolines of formula 9 where Pg is an amine protecting group (for example, Boc, Cbz or benzyl group) via metal-mediated reactions, typically using a Pd catalyst such as $Pd(OAc)_2$, a phosphine ligand, such as Xantphos (9,9-dimethyl-4,5-bis(diphenylphosphino)xanthene available from Strem Chemicals, Inc., Newburyport, Mass.), a base such as $Cs_2CO_3$, in an organic solvent such as toluene or THF at a temperature of between about 25° C. to 120° C. The amine protecting group in 10 can be removed using conventional procedures to produce the free amine. The addition and removal of numerous protecting groups is discussed by T. W. Greene and G. M. Wults in *Protective Groups in Organic Synthesis*, Second Edition, Wiley, New York, 1991. For example, Boc protecting group can be removed by treating with a strong acid such as trifluoroacetic acid (TFA) or hydrochloric acid in the presence of an inert solvent such as dichloromethane or methanol. Removal of Cbz group can be carried out by catalytic hydrogenation with hydrogen in the presence of a palladium catalyst or by transfer hydrogenation. Benzyl group can be removed by catalytic hydrogenation, transfer hydrogenation or by treatment with 1-chloroethyl chloroformate. After deprotection, the unprotected amines can be optionally functionalized (for example, alkylation or reductive amination to introduce new substituents) to give rise to the final compound 11. If need be, these analogues can then be subject to separation techniques to give the single enantiomers.

Scheme 2

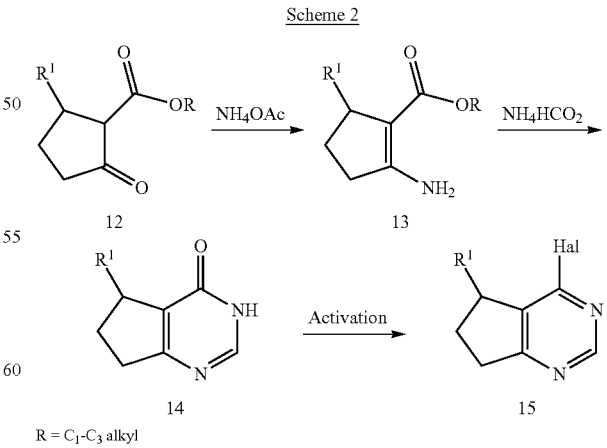

R = $C_1$-$C_3$ alkyl
Hal = Br, Cl, I

Scheme 2 shows a method of preparing compound 15, optionally substituted with various $R^1$ groups. According to Scheme 2, amination of compound 12 using an ammonia synthon (eg. NH₄OAc) gives compound 13. Pyrimidine formation using, for example, ammonium formate in the presence of formamide at about 50° to 250° C. and/or at high pressure and/or microwave assistance gives the bicyclic unit 14. Activation of compound 14 using, for example, POCl₃ or SOCl₂ gives the activated pyrimidine 15.

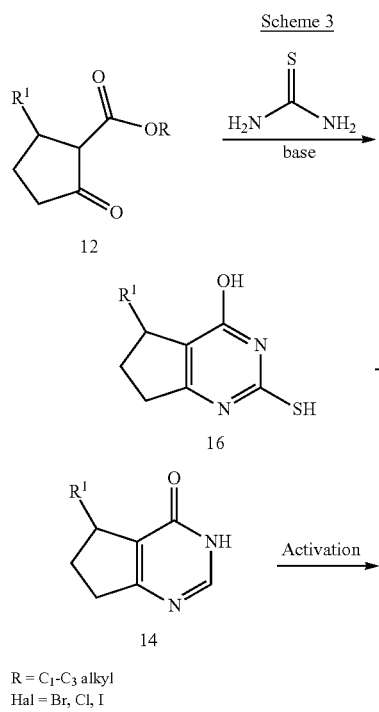

R = C₁-C₃ alkyl
Hal = Br, Cl, I

Scheme 3 shows an alternative method of preparing compound 15, optionally substituted with various R¹ groups. According to Scheme 3, the pyrimidine ring is constructed by reacting the ketoester 12 with thiourea in the presence of a base such as KOH. The mercapto group at 2-position of compound 16 is eliminated by reduction (eg. Raney Ni in ammonia) to give 14. Activation of compound 14 using, for example, POCl₃ or SOCl₂ gives the activated pyrimidine 15.

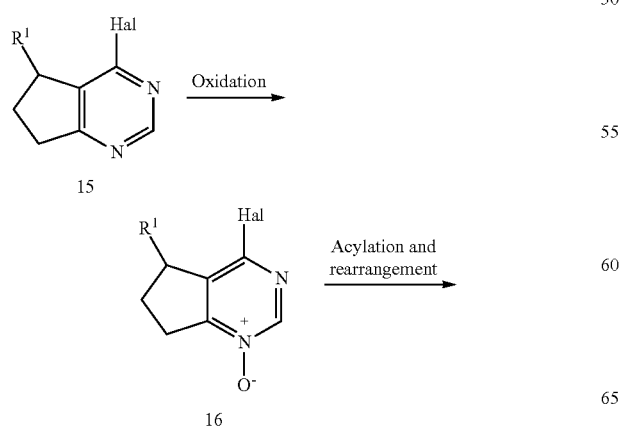

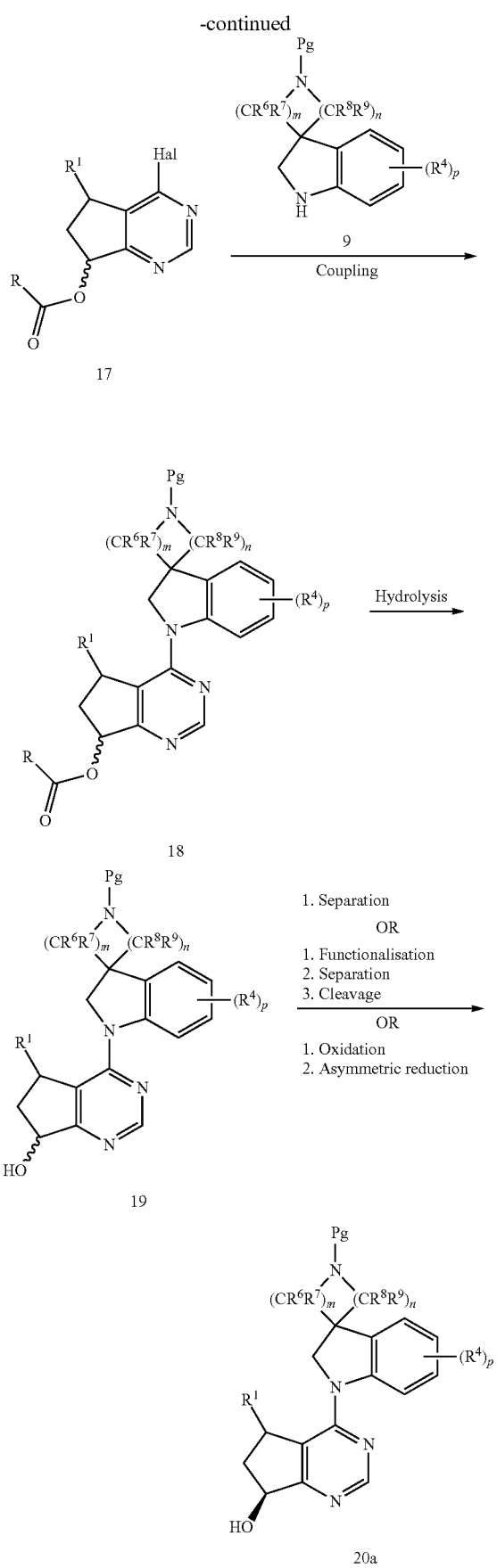

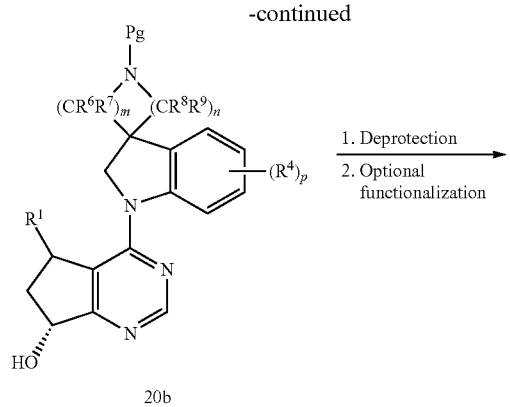

20b

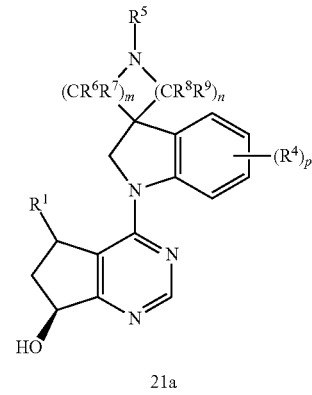

21a

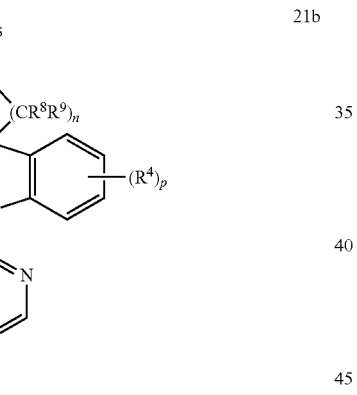

21b

Hal = Br, Cl, I

Scheme 4 illustrates a method for preparing compounds 21a and 21b. According to Scheme 4, oxidation of the 4-halopyrimidine 15 with an oxidizing agent such as m-CPBA (meta-chloroperbenzoic acid), Oxone® (E. I. du Pont de Nemours and Company), or hydrogen peroxide at a temperature of about 0° C. to about room temperature in a solvent, for example, DCM or chloroform, provides the N-oxide 16. Treatment of 16 with an acylating agent, such as acetic anhydride, and followed by heating (about 40° C. to 200° C.) causes rearrangement to furnish esters 17 (R=Me if acetic anhydride is used). Metal-catalyzed coupling reaction between 17 and spiroindolines 9 leads to compound 18. Ester hydrolysis using an aqueous base, such as NaOH or LiOH, at about 0° C. to 80° C. gives the alcohol 19. Compound 19 is then either: 1) Subjected to separation (e.g. chromatography with a chiral or achiral stationary phase); 2) Functionalized (eg. acylation with 4-nitrobenzoyl chloride) to facilitate separation, separated (eg. chromatography or recrystallization) and then hydrolyzed upon treatment with a base such as lithium hydroxide in an aqueous/organic solvent mixture at about 0° C. to 80° C.; or 3) Oxidized (eg. Swern conditions, MnO$_4$ or pyridine-SO$_3$ complex, see Larock's *Comprehensive Organic Transformations* for examples of the oxidation of alcohols to ketones) followed by an asymmetric reduction (for example, a catalytic chiral catalyst in the presence of hydrogen, the Corey-Bakshi-Shibata catalyst ("CBS catalyst") or a borohydride reducing agent in the presence of a chiral ligand). All alternatives provide a route into the separate diastereomers 20a and 20b, wherein R$^2$ is hydroxy.

Removal of the protecting group followed by additional optional functionalization affords compounds 21a and 21b.

Scheme 5

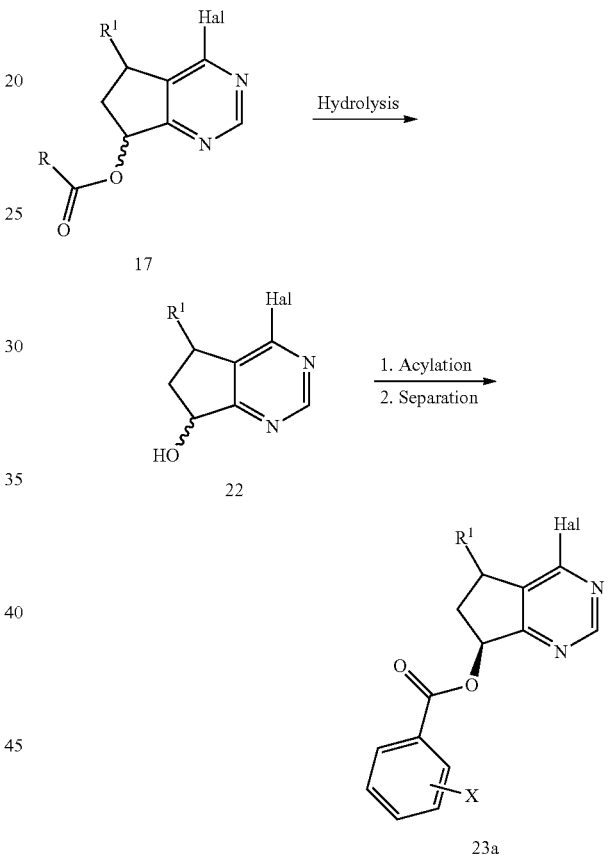

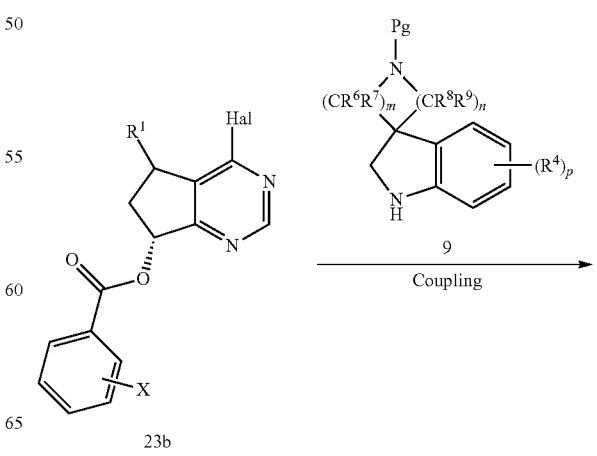

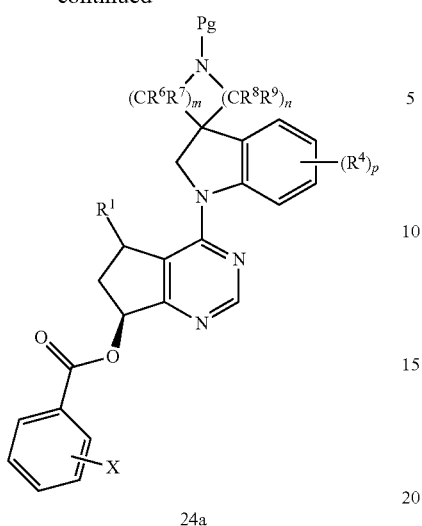

24a

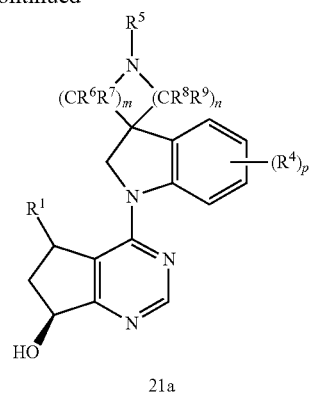

21a

21b

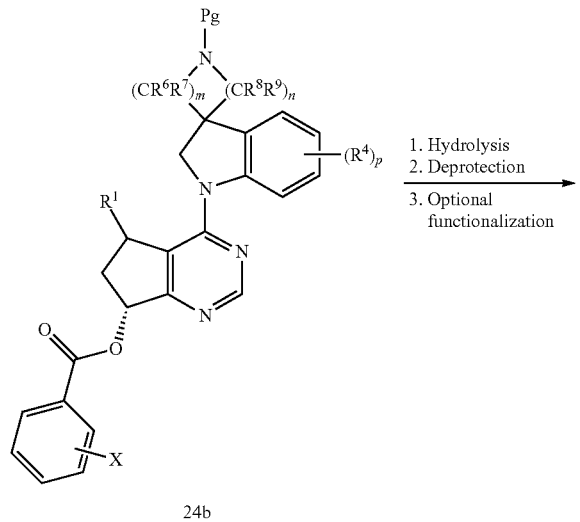

X = 4-Br or 4-NO₂

Scheme 5 shows an alternative method of preparing compounds 21a and 21b. According to Scheme 5, hydrolysis of compound 17 (prepared according to the method of Scheme 4) using an aqueous base, such as NaOH or LiOH, at about 0° C. to 80° C. gives secondary alcohols 22. Compound 22 is then functionalised (eg. 4-nitrobenzoyl chloride or 4-bromobenzoyl chloride in the presence of NEt₃ at about −20° C. to 50° C.) and separated (eg. chromatography or recrystallisation) to provide a route into the separate, protected diastereomers 23a and 23b. 23a and 23b can then be transformed to final compounds 21a and 21b, respectively, by a sequence of metal-catalyzed coupling reaction, ester hydrolysis, removal of the amine protecting group, and additional optional functionalization of the unprotected free amines.

24b

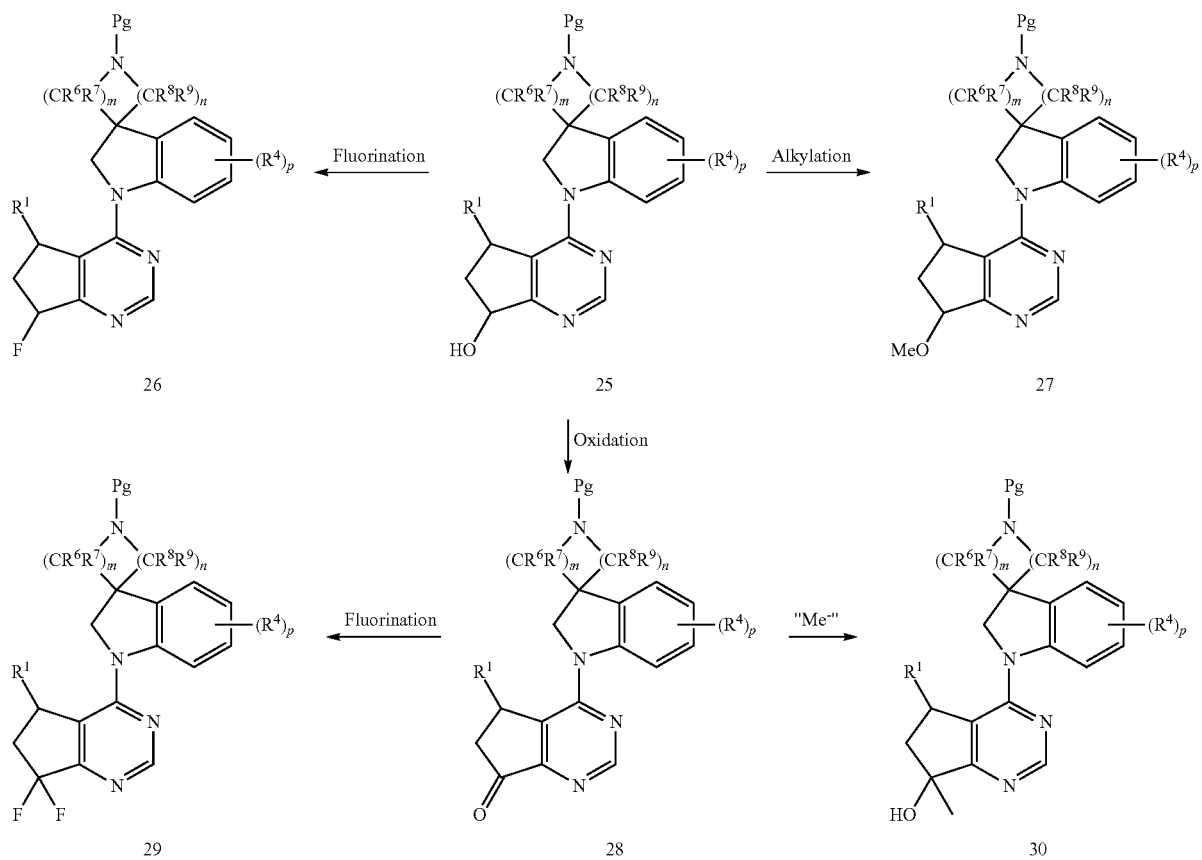

Scheme 6 shows a general method for the functionalization of the hydroxyl group of compound 25 of Formula I, permitting entry into alternate $R^2$ and $R^3$ groups. For example, the alcohol 25 can be converted to a fluoro-group 26 by treatment with a fluorinating agent such as DAST (diethylaminosulfurtrifluoride). Alternatively, the alcohol 25 can be alkylated (eg. a methylating agent such as MeI and a strong base, such as NaH) to give the methoxy analog 27 ($R^3$=H). Alternatively 25 can be oxidized (for example, Swern conditions, $MnO_4$ or pyridine-$SO_3$ complex) to provide the ketone 28, which in turn could be treated with a fluorinating agent such as DAST or Deoxo-Fluor™ (Air Products), in a solvent, such as DCM or chloroform, to give the gem-difluoride analogue 29. This ketone could also be treated with an organometallic nucleophile, for example MeMgBr or MeLi, to generate the tertiary alcohol 30.

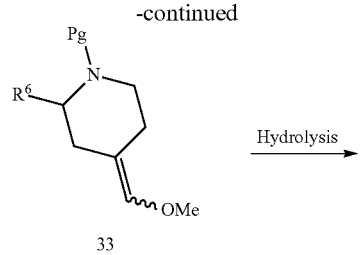

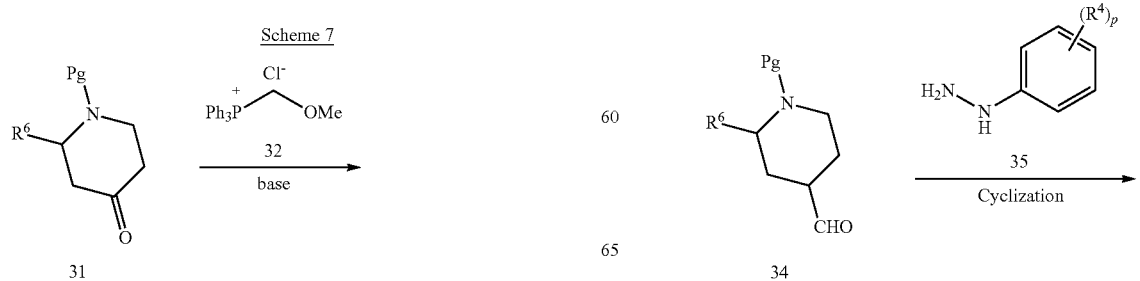

-continued

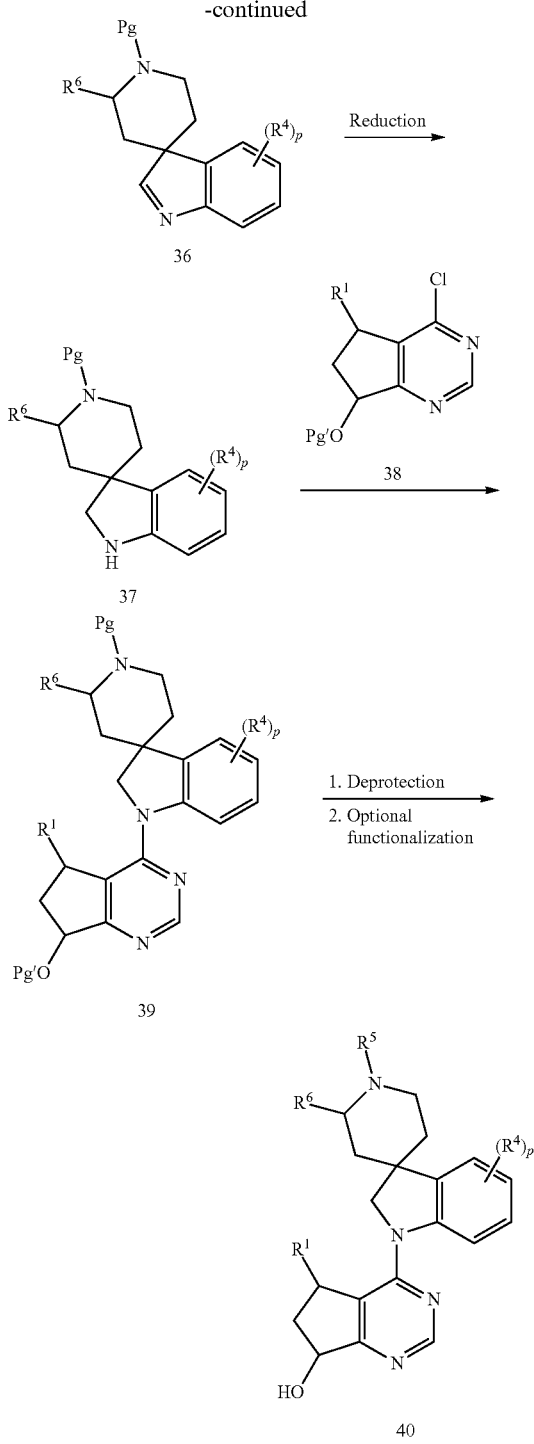

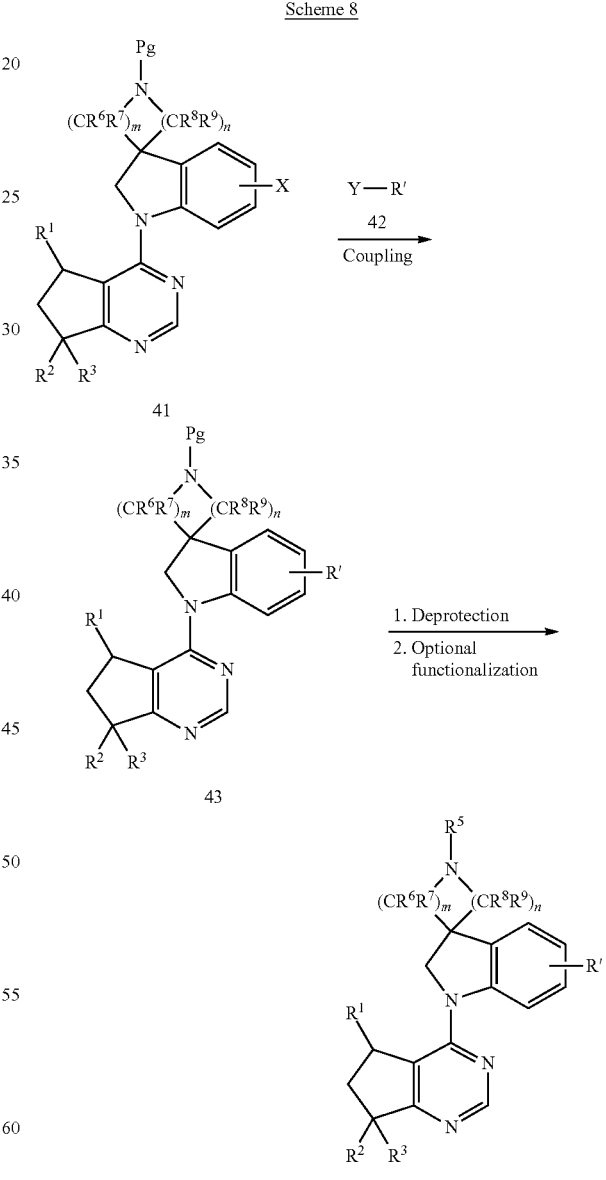

example, KOBu$^t$ or NaN(SiMe$_3$)$_2$) followed by acidic hydrolysis of the resulting intermediate 33. Compound 33 can also be subject to the reaction with phenylhydrazine 35 and be hydrolyzed to form the aldehyde 34 in situ under the acidic reaction condition. Reduction of the imine 36 using a reducing agent (for example, sodium borohydride, sodium triacetoxy borohydride, or triethylsilane) affords the indoline 37. Metal-catalyzed coupling reaction between 37 and chloropyrimidine 38 where Pg' is a hydroxyl protecting group (for example, an ester) leads to compound 39. Removal of protecting groups followed by final functionalization of the unprotected free amine (e.g. alkylation or reductive amination introduce new substituents) gives rise to the final compounds 40. These analogues can then be subject to separation techniques to give the single diastereomers.

Scheme 7 shows a method of preparing compound 40. According to Scheme 7, imine 36 can be synthesized by the reaction of an N-protected aldehyde 34 and a substituted phenylhydrazine 35 in the presence of an acid (for example, trifluoroacetic acid) in an organic solvent (for example, chloroform, dichloromethane, or toluene) at about 20° C. to 120° C. Aldehyde 34 can be purchased commercially or produced by methods known in the art. For example, aldehyde 34 can be synthesized from ketone 31 by reaction with methoxymethyl (triphenyl)phosphonium chloride or methoxymethyl(triphenyl)phosphonium bromide in the presence of a base (for Scheme 8 illustrates a method for preparing compounds 44. Intermediate 41 where X is Br or I can be prepared by methods disclosed above. 41 can react with various coupling components 42 via metal-mediated reactions to furnish product 43. For example, compounds bearing an N-linked substituent can be prepared by a Pd or Cu mediated coupling between intermediate 41 and amines (Buchwald et al. (2000), *J. Org. Chem.*, 65, 1144; Hartwig et al. (1998) *Angew. Chem. Int. Ed. Eng.* 37, 2046). Compounds bearing an alkyl or an aryl substituent can be prepared by Suzuki coupling (Miyaura, N. Suzuki A. (1995), *Chem. Rev.* 95, 2457; *Org. React.* (1997), 50, 1) between intermediates 41 and 42, wherein Y is a boronic acid or boronic ester, in the presence of a base (for example, $Na_2CO_3$ and $Et_3N$), a catalytic Pd(0) species (for example, $Pd(PPh_3)_4$, $Pd(PPh_3)_2Cl_2$, $Pd_2(dba)_3$ and $Pd(OAc)_2$) and a ligand, for example $PPh_3$ and $AsPh_3$. Alternatively, alkyl and aryl substituted indolines 43 can also be prepared by Nigeshi or Kumada couplings between 41 and 42, wherein Y—R' is an organo zinc reagent, in the presence of a Pd (for example, $Pd(PPh_3)_4$) or Ni (for example $Ni(acac)_2$) catalyst. Alternatively, alkyl and aryl substituted compounds 43 can also be prepared by Stille coupling between 41 and 42, wherein Y—R' is an organo stanane reagent, in the presence of a Pd catalyst. Compounds bearing an O- or S-linked substituent can be prepared by reactions between intermediate 41 and alcohols or thiols in the presence of a base (for example, $Cs_2CO_3$) and a Cu catalyst (for example, CuCl, CuI, or the like) under modified Ullman coupling conditions (Wolter, M. et. al. *Org. Lett.* 2002, 4, 973-976). Removal of protecting groups followed by final functionalization of the unprotected free amine (e.g. alkylation or reductive amination to introduce new substituents) gives rise to the final compounds 44. These analogues can then be subject to separation techniques to give the single diastereomers.

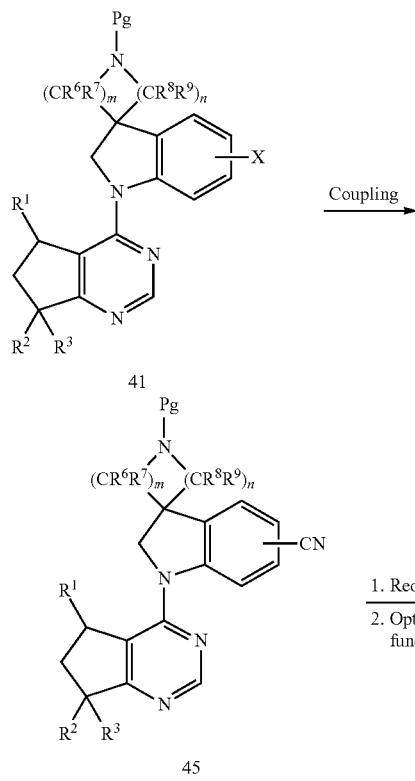

Scheme 9

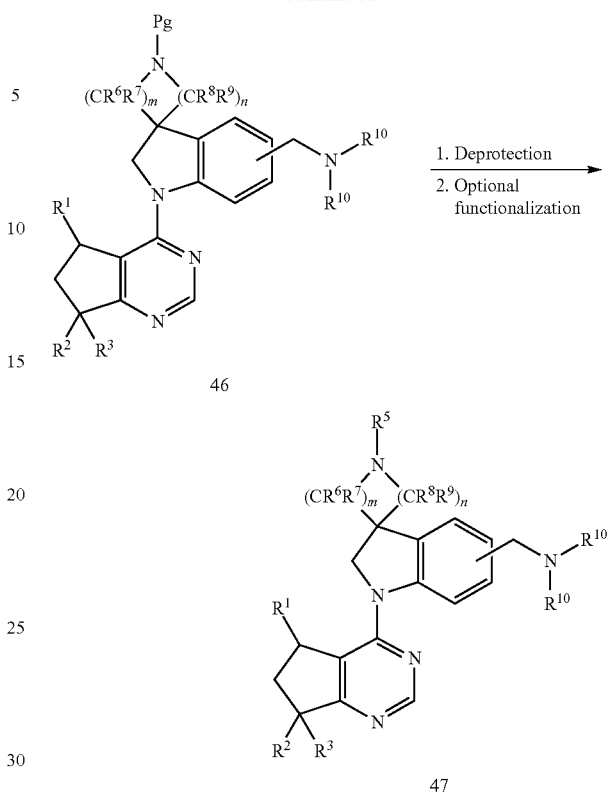

Scheme 9 illustrates a method for preparing compounds 47. Compounds bearing a CN group on the phenyl ring can be prepared by a Pd or Cu mediated coupling between 41 and a cyano source, such as zinc cyanide. The CN group in the resulting product 45 can be further reduced to a primary amine by methods known in the art (for example, catalytic hydrogenation in the presence of Raney Ni or Pd/C, lithium aluminum hydride or similar hydrides or alkoxyhydrides, sodium borohydride/$CoCl_2$ complex and the like). The resulting amine can be optionally functionalized (for example, alkylation, reductive amination or acylation to introduce new substituents) to afford compound 46. Removal of protecting groups followed by final functionalization of the unprotected free amine gives rise to the final compounds 47. These analogues can then be subject to separation techniques to give the single diastereomers.

Scheme 10

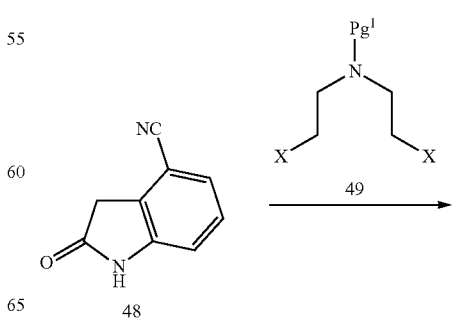

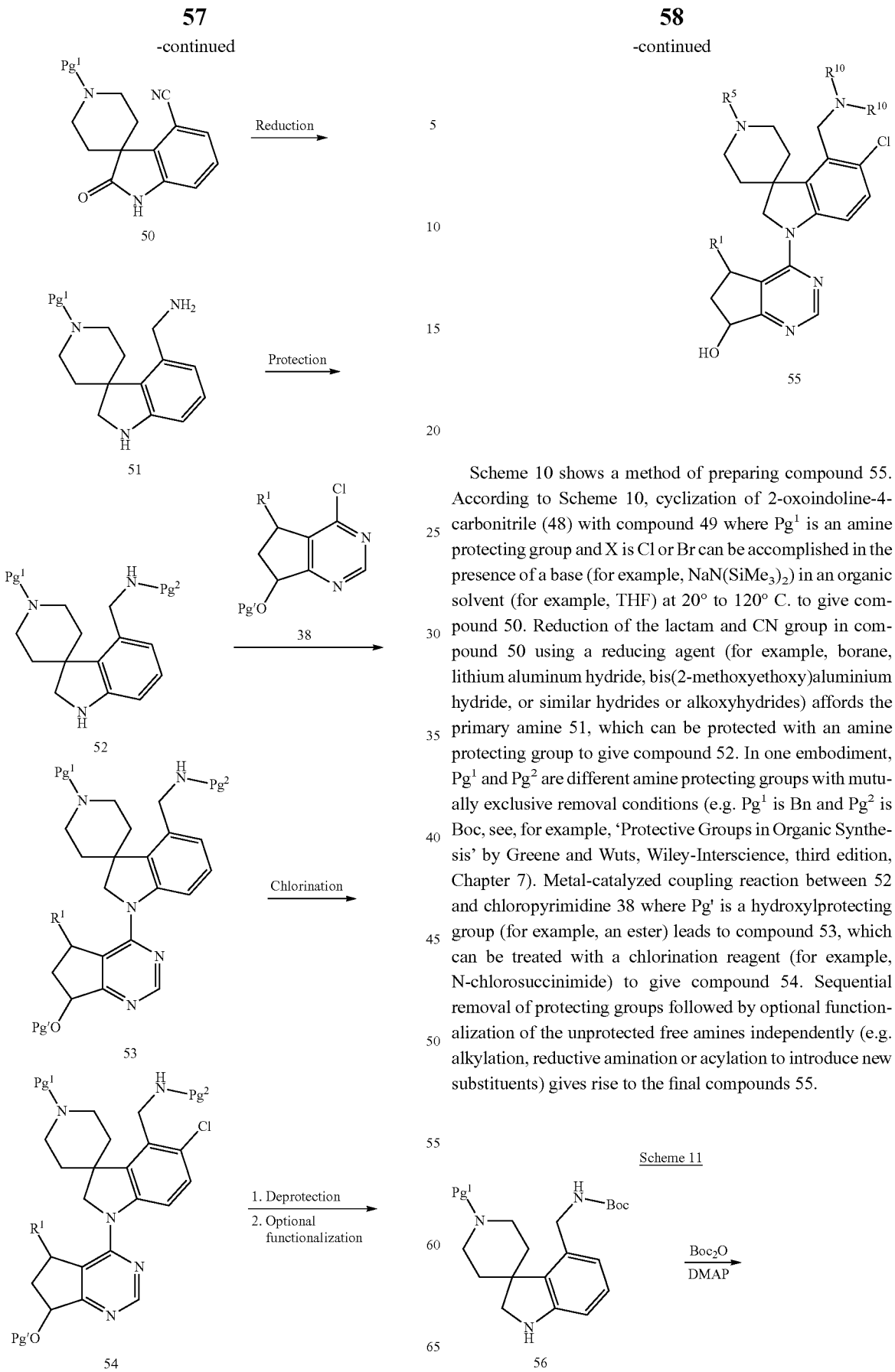

Scheme 10 shows a method of preparing compound 55. According to Scheme 10, cyclization of 2-oxoindoline-4-carbonitrile (48) with compound 49 where $Pg^1$ is an amine protecting group and X is Cl or Br can be accomplished in the presence of a base (for example, $NaN(SiMe_3)_2$) in an organic solvent (for example, THF) at 20° to 120° C. to give compound 50. Reduction of the lactam and CN group in compound 50 using a reducing agent (for example, borane, lithium aluminum hydride, bis(2-methoxyethoxy)aluminium hydride, or similar hydrides or alkoxyhydrides) affords the primary amine 51, which can be protected with an amine protecting group to give compound 52. In one embodiment, $Pg^1$ and $Pg^2$ are different amine protecting groups with mutually exclusive removal conditions (e.g. $Pg^1$ is Bn and $Pg^2$ is Boc, see, for example, 'Protective Groups in Organic Synthesis' by Greene and Wuts, Wiley-Interscience, third edition, Chapter 7). Metal-catalyzed coupling reaction between 52 and chloropyrimidine 38 where Pg' is a hydroxylprotecting group (for example, an ester) leads to compound 53, which can be treated with a chlorination reagent (for example, N-chlorosuccinimide) to give compound 54. Sequential removal of protecting groups followed by optional functionalization of the unprotected free amines independently (e.g. alkylation, reductive amination or acylation to introduce new substituents) gives rise to the final compounds 55.

Scheme 11

59
-continued

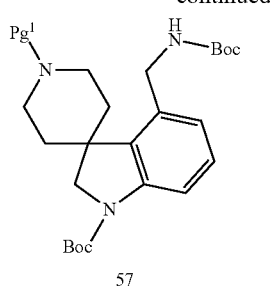
57

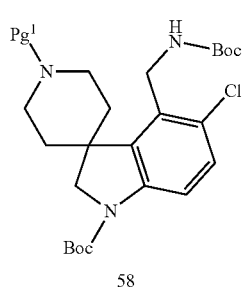
58

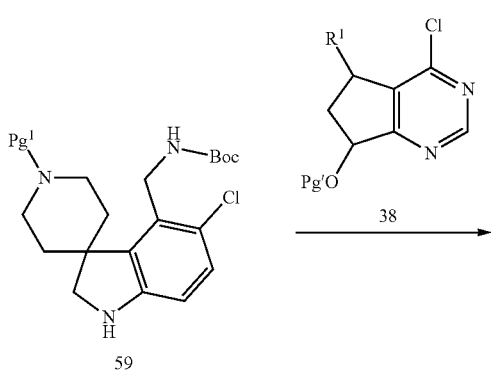
59

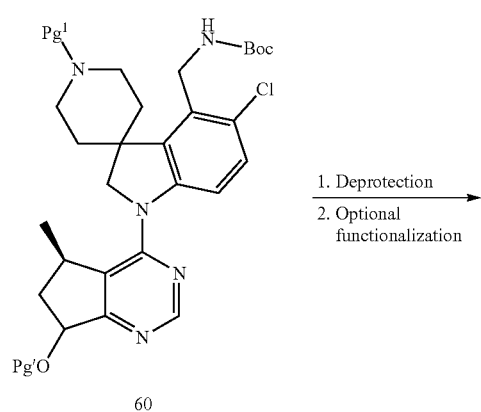
60

60
-continued

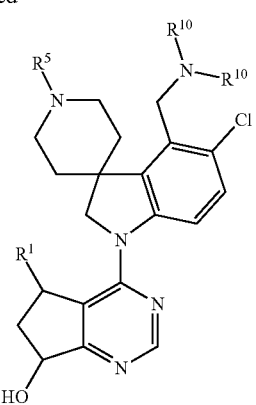
55

Scheme 11 shows an alternative synthesis of compound 55. According to Scheme 11, the indoline nitrogen in compound 56 is protected by Boc group to give compound 57, which can be treated with a chlorination reagent (for example, N-chlorosuccinimide) to give compound 58. Removal of both Boc protecting groups using HCl in dioxane followed by selective protection of the primary amine by Boc affords compound 59. Compound 60 can be prepared by metal-catalyzed coupling reaction between 59 and chloropyrimidine 38 where, for example, Pg' is a hydroxylprotecting group (such as an ester). Sequential removal of protecting groups followed by optional functionalization of the unprotected free amines independently (e.g. alkylation, reductive amination or acylation to introduce new substituents) gives rise to the final compounds 55.

Scheme 12

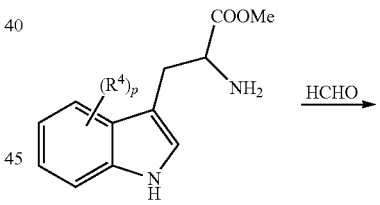
61

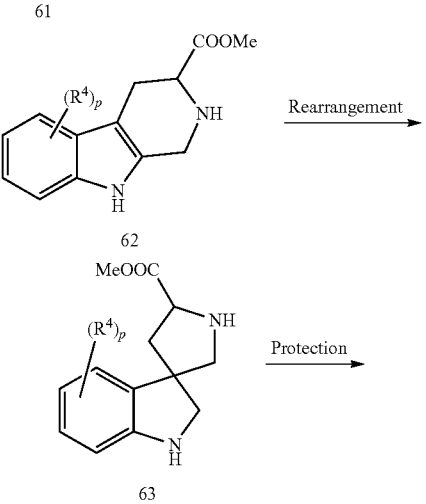
62

63

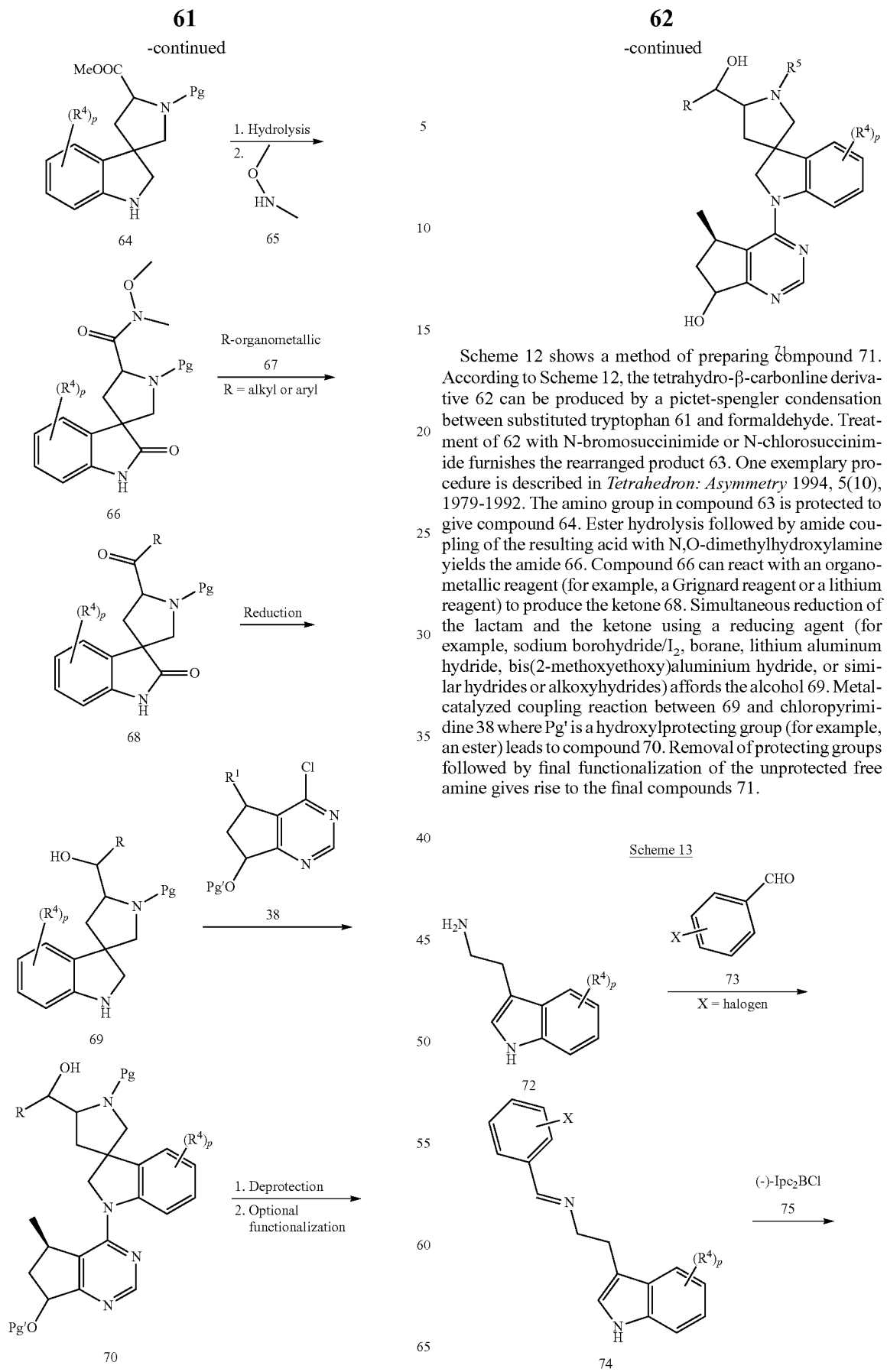

Scheme 12 shows a method of preparing compound 71. According to Scheme 12, the tetrahydro-β-carbonline derivative 62 can be produced by a pictet-spengler condensation between substituted tryptophan 61 and formaldehyde. Treatment of 62 with N-bromosuccinimide or N-chlorosuccinimide furnishes the rearranged product 63. One exemplary procedure is described in *Tetrahedron: Asymmetry* 1994, 5(10), 1979-1992. The amino group in compound 63 is protected to give compound 64. Ester hydrolysis followed by amide coupling of the resulting acid with N,O-dimethylhydroxylamine yields the amide 66. Compound 66 can react with an organometallic reagent (for example, a Grignard reagent or a lithium reagent) to produce the ketone 68. Simultaneous reduction of the lactam and the ketone using a reducing agent (for example, sodium borohydride/$I_2$, borane, lithium aluminum hydride, bis(2-methoxyethoxy)aluminium hydride, or similar hydrides or alkoxyhydrides) affords the alcohol 69. Metal-catalyzed coupling reaction between 69 and chloropyrimidine 38 where Pg' is a hydroxylprotecting group (for example, an ester) leads to compound 70. Removal of protecting groups followed by final functionalization of the unprotected free amine gives rise to the final compounds 71.

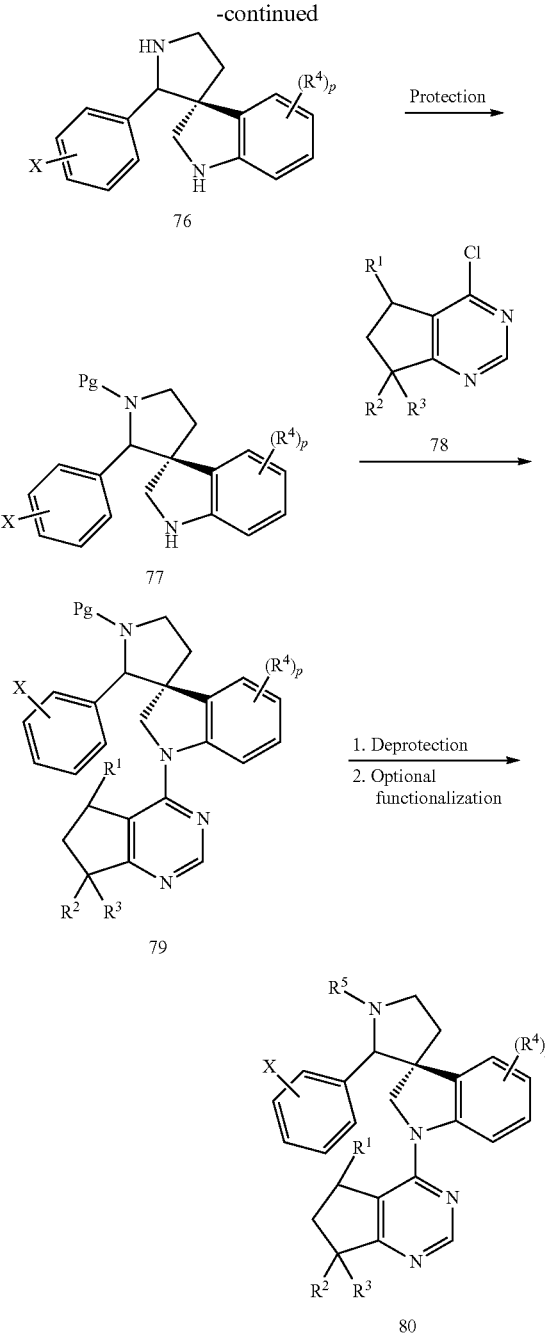

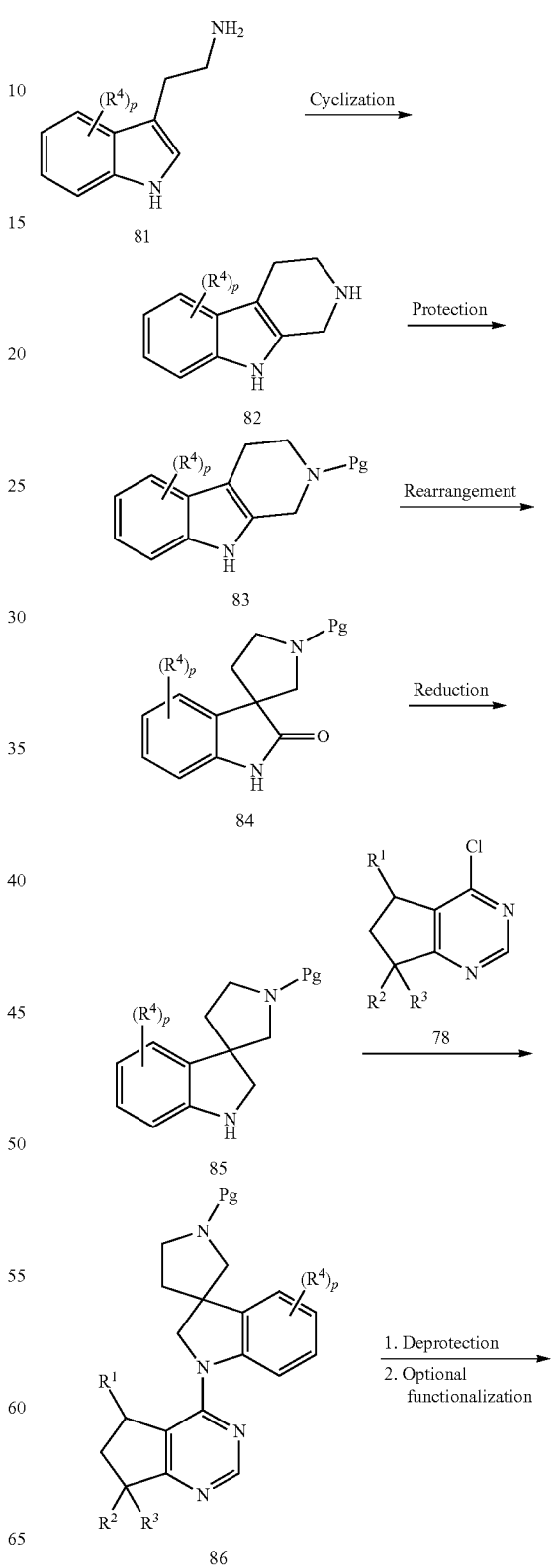

alization of the unprotected free amine (e.g. alkylation or reductive amination to introduce new substituents) gives rise to the final compounds 80.

Scheme 13 shows a method of preparing compound 80. According to Scheme 13, the imine 74 can be synthesized by condensation between substituted tryptamine 72 and benzaldehyde 73 in the presence of a dehydrating reagent (for example, molecular sieves). Treatment of 74 with chloro (–)-diisopinocamphenylborane, (–)-Ipc₂BCl, in an organic solvent (for example, dichloromethane) gives compound 76 as a mixture of two diastereomers, which can be separated by well known separation techniques, such as chromatography. One exemplary procedure is described in *Heterocycles* 1992, 33(2), 801-811. The amino group in compound 76 is protected to give compound 77. Metal-catalyzed coupling reaction between 77 and chloropyrimidine 78 leads to compound 79. Removal of protecting groups followed by final function- -continued

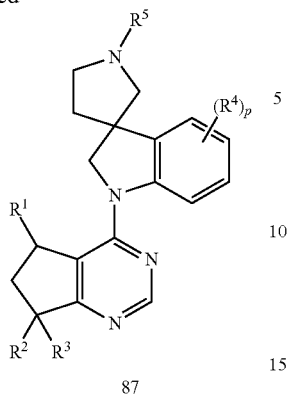

87

Scheme 14 shows a method of preparing compound 87. According to Scheme 14, 1,2,3,4-tetrahydro-β-carboline 82 can be synthesized by Pictet-Spengler condensation of substituted tryptamine 81 with formaldehyde. Alternatively, tryptamine 81 can first react with glyoxylic acid to give a 1-carboxylic acid intermediate, which is then decarboxylated by treatment with an acid (for example, concentrated HCl) to afford compound 82. One exemplary procedure is described in Organic Syntheses, 1971, 51, 136. The amino group in compound 82 is protected with an amine protecting group (for example, Boc) to give compound 83. Treatment of 83 with N-bromosuccinimide or N-chlorosuccinimide furnishes the rearranged product 84. Reduction of the lactam using a reducing agent (for example, borane, NaBH$_4$/I$_2$, lithium aluminum hydride, bis(2-methoxyethoxy)aluminium hydride, or similar hydrides or alkoxyhydrides) affords intermediate 85, which can be converted to the final compound 87 by a sequence of metal-catalyzed coupling reaction, deprotection and optional functionalization of the unprotected free amine.

Scheme 15

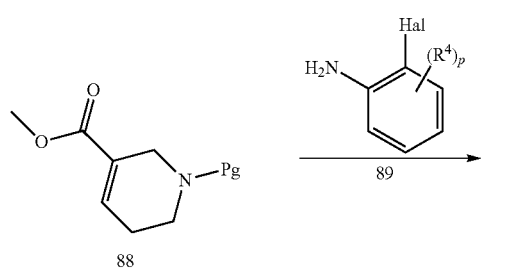

88

89

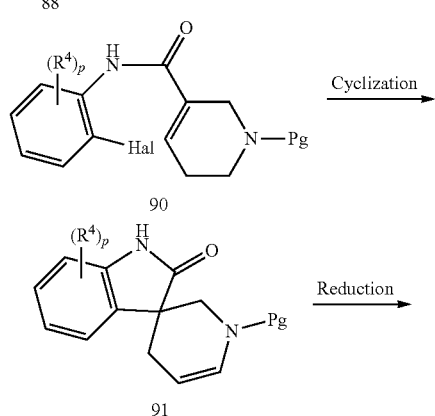

90

91

-continued

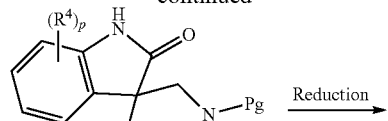

92

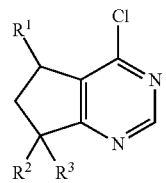

78

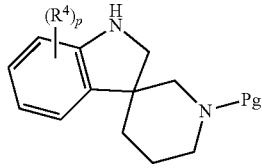

93

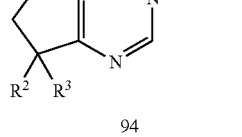

94

1. Deprotection
2. Optional functionalization

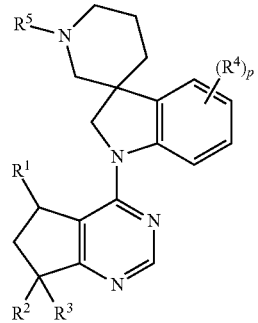

95

Scheme 15 shows a method of preparing compound 95. According to Scheme 15, the amide 90 can be synthesized by reaction between the ester 88 and an ortho-halogen (for example, Br or I) substituted aniline 89 in the presence of trimethylaluminium. Cyclization is accomplished under Heck conditions in the presence of a Pd catalyst (for example, Pd(OAc)$_2$ or Pd$_2$ dba$_3$), a phosphine ligand such as triphenylphosphine or an additive (for example, tetrabutylammonium bromide), a base such as Et$_3$N, in an organic solvent such as DMF at a temperature of between about 25° C. to 120° C. to give the olefin 91, which is reduced (for example, by hydrogenation or transfer hydrogenation) to produce compound 92. Reduction of the lactam using a reducing agent (for example, borane, NaBH$_4$/I$_2$, lithium aluminum hydride, bis (2-methoxyethoxy)aluminium hydride, or similar hydrides or alkoxyhydrides) affords intermediate 93. Metal-catalyzed coupling reaction between 93 and chloropyrimidine 78 leads to compound 94. Removal of protecting groups followed by final functionalization of the unprotected free amine (e.g. alkylation or reductive amination to introduce new substituents) gives rise to the final compounds 95.

Methods of Separation

In any of the synthetic methods for preparing compounds of Formula I, it can be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a reaction mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of the method for separation depends on the nature of the materials involved. For example, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an optically active compound (for example, a chiral auxiliary such as a chiral alcohol or Mosher's acid chloride), separating the diastereomers and converting (e.g., hydrolyzing) the individual diastereoisomers to the corresponding pure enantiomers. Enantiomers can be separated by use of a chiral HPLC column, as known to one of ordinary skill in the art. Crystallization is another exemplary method for separating enantiomers. In another embodiment, compounds of Formula I can include atropisomers (e.g., substituted biaryls), which can be separated using, for example, chromatographic methods of separation.

A single stereoisomer, e.g., an enantiomer, substantially free of its stereoisomer can be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., *J. Chromatogr.*, (1975) 113(3):283-302). Racemic mixtures of chiral compounds of the invention can be separated and isolated by any method known to one skilled in the art, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts can be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−)menthyl chloroformate in the presence of base, or Mosher ester, α-methoxy-α-(trifluoromethyl)phenyl acetate (Jacob III. *J. Org. Chem.*, (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, *J. of Chromatogr.*, (1990) 513: 375-378). Enriched or purified enantiomers can be distinguished by methods used to distinguish other chiral molecules with asymmetric carbon atoms, such as optical rotation and circular dichroism.

Methods of Treatment with Compounds of Formula I

In another embodiment, the present invention relates to a method of treating or lessening the severity of a disease or condition susceptible to the inhibition of an Akt protein kinase activity in a patient, comprising administering to said patient a therapeutically effective amount of a compound of Formula I.

In one embodiment, the Akt kinase is Akt-1, Akt-2 or Akt-3 kinase.

In one embodiment, the Akt kinase is any combination of all three Akt-1, Akt-2 and Akt-3 kinase.

In another embodiment, the Akt kinase is any combination of Akt-1 and one of Akt-2 and Akt-3 kinase. Alternatively, the Akt kinase is a combination of Akt-2 and Akt-3 kinase.

The compounds of the present invention can be used as prophylactics or therapeutic agents for treating diseases, disorders or conditions mediated by modulation or regulation of Akt protein kinases, tyrosine kinases, additional serine/threonine kinases, and/or dual specificity kinases. Akt protein kinase mediated conditions that can be treated according to the methods of this invention include, but are not limited to, inflammatory, hyperproliferative cardiovascular, neurodegenerative, gynecological, and dermatological diseases and disorders.

In one embodiment, said pharmaceutical composition is for the treatment of a hyperproliferative disease or condition. In one embodiment, the hyperproliferative disease or condition is cancer. In another embodiment, the disease or condition is a sarcoma. In another embodiment, the disease or condition is a carcinoma. In another embodiment, the disease or condition is squamous cell carcinoma. In another embodiment, the disease or condition is an adenoma or adenocarcinoma.

In an embodiment, the hyperproliferative disease or condition includes, but is not limited to, cancers of the following categories: (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell lung, small cell lung; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), cholangiocarcinoma, hepatoblastoma, angiosarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); (9) Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; (10) Skin: advanced melanoma, malignant melanoma, basal cell carcinoma, squamous cell carcinoma, Karposi's sarcoma, moles dysplastic nevi, lipoma, angioma, dermatofibroma, keloids, psoriasis; (11) Adrenal glands: neuroblastoma; (12) Breast: metastatic breast; breast adenocarcinoma; (13) Colon; (14) Oral cavity; (15) Hairy cell leukemia; (16) Head and neck; (17) and others including refractory metastatic disease; Kaposi's sarcoma; Bannayan-Zonana syndrome; and Cowden disease or Lhermitte-Duclos disease, among other kinds of hyperproliferative disorders.

Compounds and methods of this invention can be also used to treat diseases and conditions such as rheumatoid arthritis, osteoarthritis, Chron's disease, angiofibroma, ocular diseases (e.g., retinal vascularisation, diabetic retinopathy, age-related macular degeneration, macular degeneration, etc.), multiple sclerosis, obesity, Alzheimer's disease, restenosis, autoimmune diseases, allergy, asthma, endometriosis, atherosclerosis, vein graft stenosis, peri-anastomatic prothetic graft stenosis, prostate hyperplasia, chronic obstructive pulmonary disease, psoriasis, inhibition of neurological damage due to tissue repair, scar tissue formation (and can aid in wound healing), multiple sclerosis, inflammatory bowel disease, infections, particularly bacterial, viral, retroviral or parasitic infections (by increasing apoptosis), pulmonary disease, neoplasm, Parkinson's disease, transplant rejection (as an immunosupressant), septic shock, etc.

Accordingly, another aspect of this invention provides a method of treating diseases or medical conditions in a mammal mediated by Akt protein kinases, comprising administering to said mammal one or more compounds of Formula I or a pharmaceutically acceptable salt or prodrug thereof in an amount effective to treat or prevent said disorder.

The phrase "effective amount" means an amount of compound that, when administered to a mammal in need of such treatment, is sufficient to (i) treat or prevent a particular disease, condition, or disorder mediated by the activity of one or more Akt protein kinases, tyrosine kinases, additional serine/threonine kinases, and/or dual specificity kinases, (ii) attenuate, ameliorate, or eliminate one or more symptoms of the particular disease, condition, or disorder, or (iii) prevent or delay the onset of one or more symptoms of the particular disease, condition, or disorder described herein. In the case of cancer, an effective amount of the drug can reduce the number of cancer cells; reduce the tumor size; inhibit (i.e., slow to some extent and in some cases stop) cancer cell infiltration into peripheral organs; inhibit (i.e., slow to some extent and in some cases stop) tumor metastasis; inhibit, to some extent, tumor growth; and/or relieve to some extent one or more of the symptoms associated with the cancer. To the extent the drug can prevent growth and/or kill existing cancer cells, it can be cytostatic and/or cytotoxic. For cancer therapy, efficacy can be measured, for example, by assessing the time to disease progression (TTP) and/or determining the response rate (RR).

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

"Treating" is intended to mean at least the mitigation of a disease condition in a mammal, such as a human, that is affected, at least in part, by the activity of one or more Akt protein kinases, tyrosine kinases, additional serine/threonine kinases, and/or dual specificity kinases. The terms "treat" and "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those found to be predisposed to having the disease condition but have not yet been diagnosed as having it; modulating and/or inhibiting the disease condition. The terms "treating", "treat", or "treatment" embrace both preventative, i.e., prophylactic, and palliative treatment.

As used herein, the term "patient" includes all mammals. The term "mammal" refers to a warm-blooded animal that has or is at risk of developing a disease described herein and includes, but is not limited to, guinea pigs, dogs, cats, rats, mice, hamsters, and primates, including humans.

This invention also provides compounds of Formula I for use in the treatment of Akt protein kinase-mediated conditions.

An additional aspect of the invention is the use of a compound of Formula I in the preparation of a medicament for therapy, such as for the treatment or prevention of Akt protein kinase-mediated conditions.

Combination Therapy

The compounds of the present invention can be used in combination with one or more additional drugs such as described below. The dose of the second drug can be selected based on a clinically employed dose. The proportion of the compound of the present invention and the second drug can be determined according to the administration subject, the administration route, the target disease, the clinical condition, the combination, and other factors. In cases where the administration subject is a human, for instance, the second drug can be used in an amount of 0.01 to 100 parts by weight per part by weight of the compound of the present invention.

In one embodiment, the second compound of the pharmaceutical combination formulation or dosing regimen has complementary activities in relation to the compound of Formula I, such that they do not adversely affect each other. Such drugs can be present in combination in amounts that are effective for the purpose intended. Accordingly, another aspect of the present invention provides a composition comprising a compound of Formula I in combination with a second drug described herein.

A compound of Formula I and the additional pharmaceutically active drug(s) can be administered together in a unitary pharmaceutical composition or separately and, when administered separately this can occur simultaneously or sequentially in any order. Such sequential administration can be close in time or remote in time. The amounts of the compound of this invention and the second drug(s) and the relative timings of administration will be selected in order to achieve the desired combined therapeutic effect.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

A "chemotherapeutic agent" is a chemical compound useful in the treatment of cancer, regardless of mechanism of action. Chemotherapeutic agents include compounds used in "targeted therapy" and conventional chemotherapy.

Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), Irinotecan (CAMPTOSAR®, Pfizer) and Gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE™ (Cremophor-free), albumin-engineered nanoparticle formulations of paclitaxel (American Pharmaceutical Partners, Schaumberg, Ill.), and TAXOTERE® (doxetaxel; Rhône-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifene citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the PI3K inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Routes of Administration

The compounds of the invention can be administered by any route known to one skilled in the art. Exemplary routes include, but are not limited to, oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. Where the compound is administered orally, it can be formulated as a pill, capsule, tablet, etc. with a pharmaceutically acceptable carrier or excipient. Where the compound is administered parenterally, it can be formulated with a pharmaceutically acceptable parenteral vehicle and in a unit dosage injectable form, as detailed below.

Pharmaceutical Formulations

In order to use a compound of this invention for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of this invention. In certain embodiments, the pharmaceutical composition comprises a compound of Formula I in association with a pharmaceutically acceptable carrier, adjuvant, vehicle or diluent.

The pharmaceutical compositions of the invention are formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The therapeutically effective amount of the compound to be administered will be governed by such considerations, and is the minimum amount necessary to prevent, ameliorate, or treat the disorder. The compound of the present invention is typically formulated into pharmaceutical dosage forms to provide an easily controllable dosage of the drug and to enable patient compliance with the prescribed regimen.

In certain embodiments, the composition for use herein is sterile. In particular, formulations to be used for in vivo administration must be sterile. Such sterilization is readily accomplished, for example, by filtration through sterile filtration membranes. The compound ordinarily can be stored as a solid composition, a lyophilized formulation or as an aqueous solution.

Pharmaceutical formulations of the compounds of the present invention can be prepared for various routes and types of administration. For example, a compound of this invention having the desired degree of purity can optionally be mixed with pharmaceutically acceptable diluents, carriers, excipients or stabilizers (Remington The Science and Practice of Pharmacy (2005) 21st edition, Hendrickson, R. Ed.), in the form of a lyophilized formulation, a milled powder, or an aqueous solution. Formulations can be conducted by mixing at ambient temperature and a given pH, and at the desired degree of purity, with physiologically acceptable carriers (for example, carriers that are non-toxic to recipients at the dosages and concentrations employed). The pH of the formulation depends mainly on the particular use and the concentration of compound, but can range from about 3 to about 8. Formulation in an acetate buffer at about pH 5 is one exemplary embodiment. The formulations can be prepared using conventional dissolution and mixing procedures. For example, the bulk drug substance (i.e., compound of the present invention or stabilized form of the compound (e.g., complex with a cyclodextrin derivative or other known complexation agent) is dissolved in a solvent, for example, water or ethanol, in the presence of one or more excipients.

The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Exemplary aqueous solvents include, but are not limited to water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The formulations can also include one or more stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament). The active pharmaceutical ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences 16th edition, Osol, A. Ed. (1980). A "liposome" is a small vesicle composed of various types of lipids, phospholipids and/or surfactant which is useful for delivery of a drug (such as a compound of Formula I and, optionally, an additional therapeutic agent) to a mammal. The components of the liposome are commonly arranged in a bilayer formation, similar to the lipid arrangement of biological membranes.

Sustained-release preparations of compounds of this invention can be prepared. Examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

Pharmaceutical compositions comprising compounds of Formula I can be in the form of a sterile injectable preparation, such as a sterile injectable aqueous or oleaginous suspension. This suspension can be formulated according to the known art using dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

Exemplary formulations for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

In another embodiment, compositions comprising a compound of Formula I can also be in a form for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder).

Exemplary pharmaceutically-acceptable excipients for a tablet formulation include, but are not limited to, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations can be uncoated or coated either to modify their disintegration and the subsequent absorption of the active ingredient within the gastrointestinal tract, or to improve their stability and/or appearance, in either case, using conventional coating agents and procedures known in the art.

Compositions for oral use can be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions can be formulated by suspending the active ingredient in a vegetable oil (such as arachis oil, olive oil, sesame oil or coconut oil) or in a mineral oil (such as liquid paraffin). The oily suspensions can also contain a thickening agent such as beeswax, hard paraffin or cetyl alcohol. Sweetening agents such as those set out above, and flavoring agents can be added to provide a palatable oral preparation. These compositions can be preserved by the addition of an anti-oxidant such as ascorbic acid.

Dispersible powders and granules for preparation of an aqueous suspension by the addition of water generally contain the active ingredient together with a dispersing or wetting agent, suspending agent and one or more preservatives. Dispersing or wetting agents and suspending agents are exemplified by those already mentioned above. Additional excipients such as sweetening, flavoring and coloring agents, can also be present.

The pharmaceutical compositions of the invention can also be in the form of oil-in-water emulsions. The oily phase can be a vegetable oil, such as olive oil or arachis oil, or a mineral oil, such as for example liquid paraffin or a mixture of any of these. Emulsifying agents can be, for example, naturally-occurring gums such as gum acacia or gum tragacanth, naturally-occurring phosphatides such as soya bean, lecithin, esters or partial esters derived from fatty acids and hexitol anhydrides (for example sorbitan monooleate) and condensation products of the said partial esters with ethylene oxide such as polyoxyethylene sorbitan monooleate. The emulsions can also contain sweetening, flavoring and preservative agents.

Syrups and elixirs can be formulated with sweetening agents such as glycerol, propylene glycol, sorbitol, aspartame or sucrose, and can also contain a demulcent, preservative, flavoring and/or coloring agent.

Suppository formulations can be prepared by mixing the active ingredient with a non-irritating excipient that is solid at ordinary temperatures but liquid at the rectal temperature and will therefore melt in the rectum to release the drug. Exemplary excipients include, but are not limited to, cocoa butter and polyethylene glycols. Formulations for vaginal administration can be presented as pessaries, tampons, creams, gels, pastes, foams or spray formulations containing in addition to the active ingredient such carriers as are known in the art.

Topical formulations, such as creams, ointments, gels and aqueous or oily solutions or suspensions, can generally be obtained by formulating an active ingredient with a conventional, topically acceptable, vehicle or diluent using conventional procedures well known in the art.

Compositions for transdermal administration can be in the form of those transdermal skin patches that are well known to those of ordinary skill in the art.

Formulations for intrapulmonary or nasal administration have a particle size for example in the range of about 0.1 to 500 microns (including particle sizes in a range between about 0.1 and 500 microns in increments microns such as about 0.5, 1, 30 microns, 35 microns, etc.), which is administered by rapid inhalation through the nasal passage or by inhalation through the mouth so as to reach the alveolar sacs. Exemplary formulations include aqueous or oily solutions of the active ingredient. Formulations for aerosol or dry powder administration can be prepared according to conventional methods and can be delivered with other therapeutic agents such as compounds heretofore used in the treatment or prophylaxis disorders as described below.

The pharmaceutical composition (or formulation) for application can be packaged in a variety of ways depending upon the method used for administering the drug. For example, an article for distribution can include a container having deposited therein the pharmaceutical formulation. Containers for use include those that are well known to one of ordinary skill in the art, and include materials such as bottles (plastic and glass), sachets, ampoules, plastic bags, metal cylinders, and the like. The container can also include a tamper-proof assemblage to prevent indiscreet access to the contents of the package. In addition, the container has deposited thereon a label that describes the contents of the container. The label can also include warnings. The formulations can also be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. In certain embodiments, unit dosage formulations comprise a daily dose or unit daily sub-dose, as herein above recited, or a fraction thereof, of the active ingredient.

The invention further provides veterinary compositions comprising at least one active ingredient as above defined together with a veterinary carrier therefore. Veterinary carriers are materials useful for the purpose of administering the composition and can be solid, liquid or gaseous materials which are otherwise inert or acceptable in the veterinary art and are compatible with the active ingredient. These veterinary compositions can be administered parenterally, orally or by any other desired route.

The amount of a compound of this invention that is combined with one or more excipients to produce a single dosage form will necessarily vary depending upon the subject treated, the severity of the disorder or condition, the rate of administration, the disposition of the compound and the discretion of the prescribing physician. In one embodiment, about an effective amount of a compound of Formula I is administered to a mammal in need thereof. Administration in one embodiment occurs in an amount between about 0.001 mg/kg of body weight to about 60 mg/kg of body weight per day. In another embodiment, administration occurs in an amount between about 0.5 mg/kg of body weight to about 40 mg/kg of body weight per day. In some instances, dosage levels below the lower limit of the aforesaid range can be more than adequate, while in other cases still larger doses can be employed without causing any harmful side effect, provided that such larger doses are first divided into several small doses for administration throughout the day. For further information on routes of administration and dosage regimes, see Chapter 25.3 in Volume 5 of *Comprehensive Medicinal Chemistry* (Corwin Hansch; Chairman of Editorial Board), Pergamon Press 1990, which is specifically incorporated herein by reference.

Articles of Manufacture

In another embodiment of the invention, an article of manufacture, or "kit", containing materials useful for the treatment of the disorders described above is provided. In one embodiment, the kit comprises a container comprising a composition comprising a compound of Formula I. Exemplary containers include, but are not limited to, bottles, vials, syringes, blister pack, etc. The container can be formed from a variety of materials such as glass or plastic. The container can hold a compound of this invention or a formulation thereof which is effective for treating the condition and can have a sterile access port (for example, the container can be an intravenous solution bag or a vial having a stopper pierceable by a hypodermic injection needle).

The kit can further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. In one embodiment, the label or package inserts indicates that the composition comprising a compound of this invention can be used to treat a disorder mediated, for example, by Akt kinase. The label or package insert can also indicate that the composition can be used to treat other disorders.

In certain embodiments, the kits are used for the delivery of solid oral forms of a compound of this invention, such as tablets or capsules. In an embodiment, a kit includes a number of unit dosages, in one example any number from about 1 to about 1,000. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to another embodiment, a kit comprises (a) a first container comprising a first pharmaceutical composition comprising a compound of Formula I contained therein; and (b) a second container comprising a second pharmaceutical composition contained therein, wherein the second pharmaceutical formulation comprises a second compound useful for treating a disorder mediated by Akt kinase. Alternatively, or additionally, the kit further comprises a third container comprising a pharmaceutically-acceptable buffer, such as bacteriostatic water for injection (BWFI), phosphate-buffered saline, Ringer's solution and dextrose solution. It can further include other materials desirable from a commercial and user standpoint, including other buffers, diluents, filters, needles, and syringes.

The kit can further comprise directions for the administration of the compound of this invention and, if present, the second pharmaceutical formulation. For example, if the kit comprises a first composition comprising a compound of this invention and a second pharmaceutical formulation, the kit can further comprise directions for the simultaneous, sequential or separate administration of the first and second pharmaceutical compositions to a patient in need thereof.

In certain other embodiments wherein the kit comprises a composition of this invention and a second therapeutic agent, the kit can comprise a container for containing the separate compositions such as a divided bottle or a divided foil packet, however, the separate compositions can also be contained within a single, undivided container. In certain embodiments, the kit comprises directions for the administration of the separate components. The kit form is particularly advantageous when the separate components are administered in different dosage forms (e.g., oral and parenteral), are administered at different dosage intervals, or when titration of the individual components of the combination is desired by the prescribing physician.

Accordingly, a further aspect of this invention provides a kit for treating a disorder or disease mediated by Akt kinase, wherein said kit comprises a) a first pharmaceutical composition comprising a compound of this invention or a pharmaceutically acceptable salt thereof; and b) instructions for use.

In certain embodiments, the kit further comprises (c) a second pharmaceutical composition, wherein the second pharmaceutical composition comprises a second compound for treating a disorder or disease mediated by Akt kinase. In certain embodiment comprising a second pharmaceutical composition, the kit further comprises instructions for the simultaneous, sequential or separate administration of said first and second pharmaceutical compositions to a patient in need thereof. In certain embodiments, said first and second pharmaceutical compositions are contained in separate containers. In other embodiments, said first and second pharmaceutical compositions are contained in the same container.

Although the compounds of Formula I are primarily of value as therapeutic agents for use in mammals, they are also useful whenever it is required to control Akt protein kinases, tyrosine kinases, additional serine/threonine kinases, and/or dual specificity kinases. Thus, they are useful as pharmacological standards for use in the development of new biological tests and in the search for new pharmacological agents.

The activity of the compounds of this invention can be assayed for Akt protein kinases, tyrosine kinases, additional serine/threonine kinases, and/or dual specificity kinases in vitro, in vivo, or in a cell line. In vitro assays include assays that determine inhibition of the kinase activity. Alternate in vitro assays quantitate the ability of the inhibitor to bind to kinases and can be measured either by radiolabelling the inhibitor prior to binding, isolating the inhibitor/kinase complex and determining the amount of radiolabel bound, or by running a competition experiment where new inhibitors are incubated with known radioligands. These and other useful in vitro and cell culture assays are well known to those of skill in the art.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed.

BIOLOGICAL EXAMPLES

AKT-1 Kinase Assay

The activity of the compounds described in the present invention can be determined by the following kinase assay, which measures the phosphorylation of a fluorescently-labeled peptide by full-length human recombinant active Akt-1 by fluorescent polarization using a commercially available IMAP kit.

The assay materials are obtained from an IMAP Akt Assay Bulk Kit, product #R8059, from Molecular Devices, Sunnyvale, Calif. The kit materials include an IMAP Reaction Buffer (5×). The diluted 1×IMAP Reaction Buffer contained 10 mM Tris-HCl, pH 7.2, 10 mM $MgCl_2$, 0.1% BSA, 0.05% $NaN_3$. DTT is routinely added to a final concentration of 1 mM immediately prior to use. Also included is IMAP Binding Buffer (5×), and IMAP Binding Reagent. The Binding Solution is prepared as a 1:400 dilution of IMAP Binding Reagent into 1×IMAP Binding Buffer.

The fluorescein-labeled Akt Substrate (Crosstide) has the sequence (F1)-GRPRTSSFAEG. A stock solution of 20 µM is made up in 1×IMAP Reaction Buffer.

The plates used include a Costar 3657 (382-well made of polypropylene and having a white, v-bottom) that is used for compound dilution and for preparing the compound-ATP mixture. The assay plate is a Packard ProxyPlate™-384 F.

The Akt-1 used is made from full-length, human recombinant Akt-1 that is activated with PDK1 and MAP kinase 2.

To perform the assay, stock solutions of compounds at 10 mM in DMSO are prepared. The stock solutions and the control compound are serially diluted 1:2 nine times into DMSO (10 µL of compound+10 µL of DMSO) to give 50× dilution series over the desired dosing range. Next, 2.1-µL aliquots of the compounds in DMSO are transferred to a Costar 3657 plate containing 50 µL of 10.4 µM ATP in 1×IMAP Reaction Buffer containing 1 mM DTT. After thorough mixing, 2.5-µL aliquots are transferred to a ProxyPlate™-384 F plate.

The assay is initiated by the addition of 2.5-µL aliquots of a solution containing 200 nM of fluorescently-labeled peptide substrate and 4 nM Akt-1. The plate is centrifuged for 1 minute at 1000 g and incubated for 60 minute at ambient temperature. The reaction is then quenched by the addition of 15 µL of Binding Solution, centrifuged again and incubated for an additional 30 minutes at ambient temperature prior to reading on a Victor 1420 Multilabel HTS Counter configured to measure fluorescence polarization.

The compounds of Examples 1-66 were tested in the above assay and found to have an $IC_{50}$ of less than about 10 µM. The compounds of Examples 1-101 were tested in the above assay and found to have an $IC_{50}$ of less than about 10 µM. Many of the compounds have an $IC_{50}$ of less than about 1 µM.

PREPARATIVE EXAMPLES

In order to illustrate the invention, the following examples are included. However, it is to be understood that these examples do not limit the invention and are only meant to suggest a method of practicing the invention. Persons skilled in the art will recognize that the chemical reactions described can be readily adapted to prepare a number of other compounds of Formula I, and alternative methods for preparing the compounds of this invention are deemed to be within the scope of this invention. For example, the synthesis of non-exemplified compounds according to the invention can be successfully performed by modifications apparent to those skilled in the art, e.g., by protecting interfering groups, by utilizing reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), dichloromethane (DCM), toluene, and dioxane were purchased from Sigma-Aldrich Co. (St. Louis, Mo.) in Sure/Seal™ bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

$^1$H NMR spectra were recorded on a Varian, Inc. (Palo Alto, Calif.) instrument operating at 400 MHz. $^1$H-NMR spectra were obtained as $CDCl_3$, $CD_3OD$, $D_2O$ or $d_6$-DMSO solutions (reported in ppm), using tetramethylsilane (0.00 ppm) or residual solvent ($CDCl_3$: 7.25 ppm; $CD_3OD$: 3.31 ppm; $D_2O$: 4.79 ppm; $d_6$-DMSO: 2.50 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Unless otherwise noted, LCMS retention times (Rt) were measured using an Agilent 1100 Series HPLC instrument (column: YMC, ODS-AQ 4.6×150 mm, 3 um, PN AQ12S030546WT; gradient: 5-95% acetonitrile (1% isopropanol, 10 mM ammonium acetate)/water (1% isopropanol, 10 mM ammonium acetate) at 2 mL/min over 5.5 min). APCI+ means positive atmospheric pressure chemical ionization.

Example 1

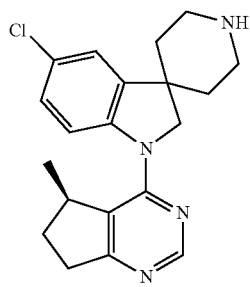

(R)-5-chloro-1-(5-methyl-6,7-dihydro-5H-cyclopenta[d]pyrimidin-4-yl)spiro[indoline-3,4'-piperidine]

Step 1: TFA (2.2 ml, 28 mmol) was added to a stirred solution of tert-butyl 4-formylpiperidine-1-carboxylate (2.00 g, 9.38 mmol), 1-(4-chlorophenyl)hydrazine hydrochloride (1.68 g, 9.38 mmol) and ethanol (0.2 mL) in CHCl$_3$ (200 mL) at about 0° C. The reaction mixture was then stirred at about 50° C. overnight. After cooling, the reaction was quenched by the addition of 10% NH$_4$OH (20 mL) and ice (60 mL). The organic layer was separated. The aqueous layer was extracted with DCM. The combined organic layers were washed with brine, dried over MgSO$_4$, filtered and concentrated to yield tert-butyl 5-chlorospiro[indole-3,4'-piperidine]-1'-carboxylate which was used in the next step without further purification (2.57 g, 85%). LCMS (APCI+) m/z 221, 223 [M+H-Boc]$^+$; Rt=3.67 min.

Step 2: NaBH$_4$ (1.29 g, 34.0 mmol) was added to a stirred solution of tert-butyl 5-chlorospiro[indole-3,4'-piperidine]-1'-carboxylate (2.57 g, 8.01 mmol) in absolute EtOH (100 mL) portionwise. The reaction was stirred at about room temperature overnight. The reaction was concentrated. The crude residue was taken up in DCM, washed with water and brine, dried over MgSO$_4$, filtered, and concentrated. The crude residue was purified by column chromatography (25-35% EtOAc/Hexane) to yield tert-butyl 5-chlorospiro[indoline-3,4'-piperidine]-1'-carboxylate. LCMS (APCI+) m/z 223, 225 [M+H-Boc]$^+$; Rt=3.86 min.

Step 3: (R)-(+)-Pulegone (76.12 g, 0.5 mmol), anhydrous NaHCO$_3$ (12.5 g) and anhydrous ether (500 mL) were added to a 1 L round-bottom flask. The reaction mixture was cooled with an ice-bath under nitrogen. Bromine (25.62 mL, 0.5 mmol) was added dropwise over about 30 minutes. The mixture was filtered and added to NaOEt (21%, 412 mL, 1.11 mmol) in an ice-cooled bath. The mixture was stirred at about room temperature overnight, and then 5% HCl (1 L) and ether (300 mL) were added. The aqueous phase was extracted with ether (2×300 mL). The combined organic phase was washed with water, dried and concentrated. The residue was added to a warmed solution of semicarbazide hydrochloride (37.5 g) and NaOAc (37.5 g) in water (300 mL). Then boiling ethanol (300 mL) was added to give a clear solution. The mixture was refluxed for 2.5 hours and then stirred at about room temperature overnight. The mixture was treated with water (1 L) and ether (300 mL). The aqueous phase was extracted with ether (2×300 mL). The combined organic phase was washed with water, dried and concentrated. The residue was purified by vacuum distillation (73-76° C. at 0.8 mm Hg) to give (2R)-ethyl 2-methyl-5-(propan-2-ylidene)cyclopentanecarboxylate (63 g, 64%). $^1$H NMR (CDCl$_3$, 400 MHz) δ 4.13 (m, 2H), 3.38 (d, J=16 Hz, 0.5H), 2.93 (m, 0.5H), 2.50-2.17 (m, 2H), 1.98 (m, 1H), 1.76 (m, 1H), 1.23 (m, 6H), 1.05 (m, 6H).

Step 4: (2R)-Ethyl 2-methyl-5-(propan-2-ylidene)cyclopentanecarboxylate (24 g, 0.122 mol) in ethyl acetate (100 mL) was cooled to −68° C. with dry ice/isopropanol. Ozonized oxygen (5-7 ft$^3$h$^{-1}$ of O$_2$) was bubbled through the solution for 3.5 hours. The reaction mixture was flushed with nitrogen at about room temperature until the color about disappeared. The ethyl acetate was removed under vacuum, and the residue was dissolved in acetic acid (150 mL) and cooled by ice water. Zinc powder (45 g) was then added. The solution was stirred for about 30 minutes and then filtered. The filtrate was neutralized with 2N NaOH (1.3 L) and NaHCO$_3$. The aqueous phase was extracted with ether (3×200 mL) The organic phase was combined, washed with water, dried and concentrated to afford (2R)-ethyl 2-methyl-5-oxocyclopentanecarboxylate (20 g, 96%). $^1$H NMR (CDCl$_3$, 400 MHz) δ 4.21 (m, 2H), 2.77 (d, J=11.2 Hz, 1H), 2.60 (m, 1H), 2.50-2.10 (m, 3H), 1.42 (m, 1H), 1.33 (m, 3H), 1.23 (m, 3H).

Step 5: KOH (8.3 g, 147.9 mmol) in water (60 mL) was added to a solution of a mixture of (2R)-ethyl 2-methyl-5-oxocyclopentanecarboxylate (20 g, 117.5 mmol) and thiourea (9.2 g, 120.9 mmol) in ethanol (100 mL). The mixture was refluxed for 10 hours. After cooling, the solvent was removed, and the residue was neutralized with concentrated HCl (12 mL) at 0° C. The mixture was then extracted with DCM (3×150 mL). The solvent was removed, and the residue was purified by silica gel chromatography, eluting with hexane/ethyl acetate (2:1) to give (R)-2-mercapto-5-methyl-6,7-dihydro-5H-cyclopenta[d]pyrimidin-4-ol (12 g, 56%). MS (APCI+) [M+H]$^+$ 183.

Step 6: Raney Nickel (15 g) and NH$_4$OH (20 mL) were added to a suspension of (R)-2-mercapto-5-methyl-6,7-dihydro-5H-cyclopenta[d]pyrimidin-4-ol (12 g, 65.8 mmol) in distilled water (100 mL). The mixture was refluxed for 3 hours and then filtered. The filtrate was concentrated to afford (R)-5-methyl-6,7-dihydro-5H-cyclopenta[d]pyrimidin-4-ol (9.89 g, 99%). MS (APCI+) [M+H]$^+$151.

Step 7: A mixture of (R)-5-methyl-6,7-dihydro-5H-cyclopenta[d]pyrimidin-4-ol (5.8 g, 38.62 mmol) in POCl$_3$ (20 mL) was refluxed for about 5 minutes. Excess POCl$_3$ was removed under vacuum, and the residue was dissolved in DCM (50 mL). The mixture was then added to saturated NaHCO$_3$ (200 mL) The aqueous phase was extracted with DCM (3×100 mL), and the combined organic phases were dried and concentrated. The residue was purified by silica gel chromatography, eluting with ethyl acetate to give (R)-4-chloro-5-methyl-6,7-dihydro-5H-cyclopenta[d]pyrimidine (3.18 g, 49%). $^1$H NMR (CDCl$_3$, 400 MHz) δ 8.81 (s, 1H), 3.47 (m, 1H), 3.20 (m, 1H), 3.05 (m, 1H), 2.41 (m, 1H), 1.86 (m, 3H), 1.47 (m, 3H).

Step 8: A pear-shaped flask was charged with Pd(OAc)$_2$ (2.1 mg, 0.0093 mmol) and 9,9-dimethyl-4,5-bis(diphenylphosphino)xanthene (8.1 mg, 0.014 mmol) and purged with nitrogen. To the flask was added (R)-4-chloro-5-methyl-6,7-dihydro-5H-cyclopenta[d]pyrimidine (19 mg, 0.11 mmol), tert-butyl 5-chlorospiro[indoline-3,4'-piperidine]-1'-carboxylate (30 mg, 0.093 mmol), Cs$_2$CO$_3$ (45 mg, 0.14 mmol) and toluene (0.9 mL). The mixture was heated at about 100° C. for 4 hours. After cooling to about room temperature, the reaction was diluted with EtOAc, filtered through CELITE® (Celite Corp., Santa Barbara, Calif.), and concentrated. The crude product was purified by column chromatography (hexanes:EtOAc, 5:1 to 3:1) to give (R)-tert-butyl 5-chloro-1-(5-methyl-6,7-dihydro-5H-cyclopenta[d]pyrimidin-4-yl)spiro[indoline-3,4'-piperidine]-1'-carboxylate as an oil (30 mg, 71%). LCMS (APCI+) m/z 455, 457 [M+H]$^+$; Rt=4.14 min.

Step 9: A solution of (R)-tert-butyl 5-chloro-1-(5-methyl-6,7-dihydro-5H-cyclopenta[d]pyrimidin-4-yl)spiro[indoline-3,4'-piperidine]-1'-carboxylate (30 mg, 0.066 mmol) in DCM was treated with 4N HCl in dioxane (0.5 mL) The reaction was stirred at about room temperature overnight. The reaction was concentrated and triturated with ether (×2) to yield (R)-5-chloro-1-(5-methyl-6,7-dihydro-5H-cyclopenta

[d]pyrimidin-4-yl)spiro[indoline-3,4'-piperidine]dihydrochloride (21 mg, 73%). LCMS (APCI+) m/z 355, 357 [M+H]+; Rt=2.09 min.

Example 2

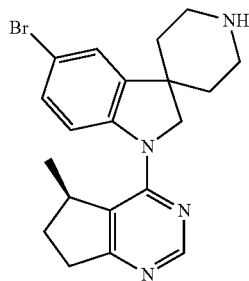

(R)-5-bromo-1-(5-methyl-6,7-dihydro-5H-cyclopenta[d]pyrimidin-4-yl)spiro[indoline-3,4'-piperidine]

Step 1: Tert-butyl 5-bromospiro[indole-3,4'-piperidine]-1'-carboxylate was prepared by the procedures described in Example 1, Step 1, substituting 1-(4-chlorophenyl)hydrazine hydrochloride with 1-(4-bromophenyl)hydrazine hydrochloride. LCMS (APCI+) m/z 265, 267 [M+H-Boc]+; Rt=3.73 min.

Step 2: Tert-butyl 5-bromospiro[indoline-3,4'-piperidine]-1'-carboxylate was prepared by the procedures described in Example 1, Step 2, substituting tert-butyl 5-chlorospiro[indole-3,4'-piperidine]-1'-carboxylate with tert-butyl 5-bromospiro[indole-3,4'-piperidine]-1'-carboxylate. LCMS (APCI+) m/z 267, 269 [M+H-Boc]+; Rt=3.89 min.

Step 3: (R)-tert-butyl 5-bromo-1-(5-methyl-6,7-dihydro-5H-cyclopenta[d]pyrimidin-4-yl)spiro[indoline-3,4'-piperidine]-1'-carboxylate was prepared by the procedures described in Example 1, Step 8, substituting tert-butyl 5-chlorospiro[indoline-3,4'-piperidine]-1'-carboxylate with tert-butyl 5-bromospiro[indoline-3,4'-piperidine]-1'-carboxylate. LCMS (APCI+) m/z 499, 501 [M+H]+; Rt=4.57 min.

Step 4: (R)-5-bromo-1-(5-methyl-6,7-dihydro-5H-cyclopenta[d]pyrimidin-4-yl)spiro[indoline-3,4'-piperidine]dihydrochloride was prepared by the procedures described in Example 1, Step 9, substituting (R)-tert-butyl 5-chloro-1-(5-methyl-6,7-dihydro-5H-cyclopenta[d]pyrimidin-4-yl)spiro[indoline-3,4'-piperidine]-1'-carboxylate with (R)-tert-butyl 5-bromo-1-(5-methyl-6,7-dihydro-5H-cyclopenta[d]pyrimidin-4-yl)spiro[indoline-3,4'-piperidine]-1'-carboxylate. LCMS (APCI+) m/z 399, 401 [M+H]+; Rt=2.14 min.

Example 3

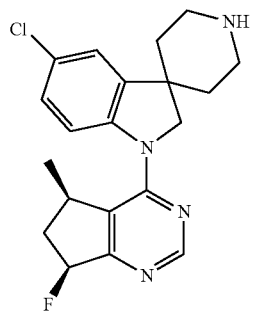

5-chloro-1-((5R,7S)-7-fluoro-5-methyl-6,7-dihydro-5H-cyclopenta[d]pyrimidin-4-yl)spiro[indoline-3,4'-piperidine]

Step 1 to Step 3 describes an alternative synthesis of (R)-4-chloro-5-methyl-6,7-dihydro-5H-cyclopenta[d]pyrimidine Step 1: Ammonium acetate (240.03 g, 3113.9 mmol) was added to a solution of (R)-ethyl 2-methyl-5-oxocyclopentanecarboxylate (106.0 g, 622.78 mmol) in MeOH (1.2 L). The reaction mixture was stirred at about room temperature under nitrogen for 20 hours, after which it was complete as judged by TLC and HPLC. The reaction mixture was concentrated to remove MeOH. The resulting residue was dissolved in DCM, washed twice with H₂O, once with brine, dried (Na₂SO₄), filtered, and concentrated to give (R)-ethyl 2-amino-5-methylcyclopent-1-enecarboxylate (102 g, 97% yield) as an orange oil. LC/MS (APCI+) m/z 170 [M+H]+.

Step 2: A solution containing (R)-ethyl 2-amino-5-methylcyclopent-1-enecarboxylate (161.61 g, 955.024 mmol) and ammonium formate (90.3298 g, 1432.54 mmol) in formamide (303.456 mL, 7640.19 mmol) was heated to an internal temperature of 150° C. and stirred for 17 hours. The reaction mixture was cooled, and transferred to a 2 L single extracted flask. Then excess formamidine was removed by high vacuum distillation. Once formamidine stopped coming over, the remaining oil in the still pot was dissolved in DCM and washed with brine (3×200 mL). The combined aqueous washes were extracted with DCM. The combined organic extracts were dried (Na₂SO₄), filtered, and concentrated. The resulting oil was dissolved in minimal DCM, and this solution was added using a separatory funnel to a stirred solution of ether (about 5 volumes of ether vs. DCM solution), causing some precipitate to form. This precipitate was removed by filtration through a medium fit funnel which was rinsed with ether and disposed. The filtrate was concentrated, the trituration from ether repeated two more times and then dried on high vacuum line to give (R)-5-methyl-6,7-dihydro-5H-cyclopenta[d]pyrimidin-4-ol (93.225 g, 65.00% yield) as a pasty solid. LC/MS (APCI−) m/z 149.2.

Step 3: Neat POCl₃ (463.9 mL, 5067 mmol) was added slowly by addition funnel to a 0° C. solution of (R)-5-methyl-6,7-dihydro-5H-cyclopenta[d]pyrimidin-4-ol (152.2 g, 1013 mmol) in DCE (1.2 L). After the addition was complete, the reaction mixture was warmed to about room temperature, then heated to reflux and stirred for about 70 minutes. The reaction was complete as determined by HPLC. The reaction mixture was cooled to about room temperature, and the excess POCl₃ was quenched in 4 portions as follows: Reaction mixture transferred to separatory funnel and dripped into a beaker containing ice and saturated NaHCO₃ solution cooled in an ice bath. Once the addition of each portion of the reaction mixture was completed, the quenched mixture was stirred about 30 minutes to ensure complete destruction of POCl₃ prior to transfer to separatory funnel. The mixture was transferred to the separatory funnel and extracted twice with DCM. The combined extracts were dried (Na₂SO₄), filtered, and concentrated. The crude was purified on silica gel as follows: silica gel (1 kg) was slurried in 9:1 hexane:ethyl acetate onto a 3 L fitted funnel, silica settled under vacuum, topped with sand. The crude was loaded with a DCM/hexane mixture, and the compound was eluted using 1 L sidearm flasks under vacuum. High Rf byproducts eluted first, then (R)-4-chloro-5-methyl-6,7-dihydro-5H-cyclopenta[d]pyrimidine (104.4 g, 61.09% yield) as an oil. ¹H NMR (CDCl₃, 400 MHz) δ 8.81 (s, 1H), 3.47 (m, 1H), 3.20 (m, 1H), 3.05 (m, 1H), 2.41 (m, 1H), 1.86 (m, 3H), 1.47 (m, 3H).

Step 4: A solution of (R)-4-chloro-5-methyl-6,7-dihydro-5H-cyclopenta[d]pyrimidine (5.0 g, 30 mmol) in CHCl$_3$ (80 mL) at 0° C. was treated with m-CPBA (12 g, 53 mmol) in portions. The reaction was stirred at about room temperature overnight. The reaction was cooled to 0° C. and to this was added Na$_2$SO$_3$ (25 g, 200 mmol) in water (100 mL) (slurry), followed by dropwise addition of Na$_2$CO$_3$ (14 g, 130 mmol) in water (100 mL). The mixture was stirred for about 30 minutes. The aqueous phase was extracted with CHCl$_3$. The organic phase was dried with MgSO$_4$ and concentrated under reduced pressure at low temperature (<25° C.) to afford the crude (R)-4-chloro-5-methyl-6,7-dihydro-5H-cyclopenta[d]pyrimidine 1-oxide (5.5 g, 100%) which was not purified further. $^1$H NMR (CDCl$_3$, 400 MHz) δ 8.66 (s, 1H), 3.50 (m, 1H), 3.20 (m, 2H), 2.44 (m, 1H), 1.90 (m, 1H), 1.37 (d, J=7.2 Hz, 3H).

Step 5: A solution of (R)-4-chloro-5-methyl-6,7-dihydro-5H-cyclopenta[d]pyrimidine 1-oxide (5.5 g, 30 mmol) in Ac$_2$O (40 ml) was heated to 110° C. for 3 hours. After cooling, the acetic anhydride was evaporated under vacuum. The residue was taken up in DCM and added to a stirring cold solution of saturated NaHCO$_3$ solution. The layers were extracted with DCM, dried over MgSO$_4$, filtered, and concentrated. The crude black/dark brown oil was chromatographed (Biotage) eluting with 20% EtOAc/Hexane to give (5R)-4-chloro-5-methyl-6,7-dihydro-5H-cyclopenta[d]pyrimidin-7-yl acetate (3.0 g, 44%). $^1$H NMR (CDCl$_3$, 400 MHz) δ 8.92 (m, 1H), 6.30-6.03 (m, 1H), 3.60-3.30 (m, 1H), 2.84 (m, 1H), 2.40-2.20 (m, 1H), 2.15 (d, J=6 Hz, 2H), 1.75 (m, 2H), 1.47 (d, J=6.8, 2H), 1.38 (d, J=7.2, 1H). MS (APCI+) [M+H]$^+$227.

Step 6: tert-butyl 1-((5R)-7-acetoxy-5-methyl-6,7-dihydro-5H-cyclopenta[d]pyrimidin-4-yl)-5-chlorospiro[indoline-3,4'-piperidine]-1'-carboxylate was prepared by the procedures described in Example 1, Step 8, substituting (R)-4-chloro-5-methyl-6,7-dihydro-5H-cyclopenta[d]pyrimidine with (5R)-4-chloro-5-methyl-6,7-dihydro-5H-cyclopenta[d]pyrimidin-7-yl acetate. LCMS (APCI+) m/z 513.2 [M+H]$^+$; Rt=4.14 min.

Step 7: A solution of tert-butyl 1-((5R)-7-acetoxy-5-methyl-6,7-dihydro-5H-cyclopenta[d]pyrimidin-4-yl)-5-chlorospiro[indoline-3,4'-piperidine]-1'-carboxylate (0.170 g, 0.331 mmol) in 2:1 THF:H$_2$O (1.8 mL) was cooled to about 0° C. LiOH—H$_2$O (0.034 g, 0.83 mmol) was added and the reaction was stirred at about room temperature for 4 hours. The reaction was quenched by the addition of 1N HCl to pH 6. The aqueous phase was extracted with EtOAc. The combined organics were washed with brine, dried over MgSO$_4$, filtered and concentrated. The crude residue was purified by column chromatography (30-70% EtOAc/Hexane) to yield tert-butyl 5-chloro-1-45R)-7-hydroxy-5-methyl-6,7-dihydro-5H-cyclopenta[d]pyrimidin-4-yl)spiro[indoline-3,4'-piperidine]-1'-carboxylate (0.065 g, 42%). LCMS (APCI+) m/z 471, 473 [M+H]$^+$; Rt=3.82 min.

Step 8: A solution of tert-butyl 5-chloro-1-((5R)-7-hydroxy-5-methyl-6,7-dihydro-5H-cyclopenta[d]pyrimidin-4-yl)spiro[indoline-3,4'-piperidine]-1'-carboxylate (0.065 g, 0.14 mmol) and TEA (0.038 ml, 0.28 mmol) in DCM was cooled to about 0° C. To the mixture was added 4-nitrobenzoyl chloride (0.031 g, 0.17 mmol). The reaction was stirred at about 0° C. for about 5 minutes, then warmed to about room temperature and stirred for 1.5 hours. The reaction was diluted with DCM and saturated NaHCO$_3$. The combined extracts were washed with brine, dried over MgSO$_4$, filtered and concentrated. The crude residue was purified by column chromatography (30-50% EtOAc/Hexane) to yield tert-butyl 5-chloro-1-((5R,7R)-5-methyl-7-(4-nitrobenzoyloxy)-6,7-dihydro-5H-cyclopenta[d]pyrimidin-4-yl)spiro[indoline-3,4'-piperidine]-1'-carboxylate (0.020 g, 23%). LCMS (APCI+) m/z 620, 622 [M+H]$^+$; Rt=4.65 min, and to yield tert-butyl 5-chloro-1-((5R,7S)-5-methyl-7-(4-nitrobenzoyloxy)-6,7-dihydro-5H-cyclopenta[d]pyrimidin-4-yl)spiro[indoline-3,4'-piperidine]-1'-carboxylate (0.029 g, 29%). LCMS (APCI+) m/z 620, 622 [M+H]$^+$; Rt=4.66 min.

Step 9 to Step 11 describes an alternative synthesis of tert-butyl 5-chloro-1-((5R,7R)-5-methyl-7-(4-nitrobenzoyloxy)-6,7-dihydro-5H-cyclopenta[d]pyrimidin-4-yl)spiro[indoline-3,4'-piperidine]-1'-carboxylate.

Step 9: (5R)-4-chloro-5-methyl-6,7-dihydro-5H-cyclopenta[d]pyrimidin-7-ol was prepared by the procedures described in Example 3, Step 7, substituting tert-butyl 1-((5R)-7-acetoxy-5-methyl-6,7-dihydro-5H-cyclopenta[d]pyrimidin-4-yl)-5-chloro spiro[indoline-3,4'-piperidine]-1'-carboxylate with (5R)-4-chloro-5-methyl-6,7-dihydro-5H-cyclopenta[d]pyrimidin-7-yl acetate. LCMS (APCI+) m/z 185, 187 [M+H]$^+$; Rt=2.09 min.

Step 10: (5R)-4-chloro-5-methyl-6,7-dihydro-5H-cyclopenta[d]pyrimidin-7-yl 4-nitrobenzoate was prepared by the procedures described in Example 3, Step 8, substituting tert-butyl 5-chloro-1-((5R)-7-hydroxy-5-methyl-6,7-dihydro-5H-cyclopenta[d]pyrimidin-4-spiro[indoline-3,4'-piperidine]-1'-carboxylate with (5R)-4-chloro-5-methyl-6,7-dihydro-5H-cyclopenta[d]pyrimidin-7-ol. The two diastereomers were separated by column chromatography on silica gel. Elution with 11% EtOAc/Hexane gave the less polar diastereomer (5R,7R)-4-chloro-5-methyl-6,7-dihydro-5H-cyclopenta[d]pyrimidin-7-yl 4-nitrobenzoate. LCMS (APCI+) m/z 334, 336 [M+H]$^+$; Rt=3.86 min. Further elution with 14% EtOAc/Hexane gave the second diastereomer (5R,7S)-4-chloro-5-methyl-6,7-dihydro-5H-cyclopenta[d]pyrimidin-7-yl 4-nitrobenzoate. LCMS (APCI+) m/z 334, 336 [M+H]$^+$; Rt=3.86 min Step 11: tert-butyl 5-chloro-1-((5R,7R)-5-methyl-7-(4-nitrobenzoyloxy)-6,7-dihydro-5H-cyclopenta[d]pyrimidin-4-yl) spiro[indoline-3,4'-piperidine]-1'-carboxylate was prepared by the procedures described in Example 1, Step 8, substituting (R)-4-chloro-5-methyl-6,7-dihydro-5H-cyclopenta[d]pyrimidine with (5R,7R)-4-chloro-5-methyl-6,7-dihydro-5H-cyclopenta[d]pyrimidin-7-yl 4-nitrobenzoate. LCMS (APCI+) m/z 620, 622 [M+H]$^+$; Rt=4.66 min.

Step 12: A solution of tert-butyl 5-chloro-1-((5R,7R)-5-methyl-7-(4-nitrobenzoyloxy)-6,7-dihydro-5H-cyclopenta[d]pyrimidin-4-yl)spiro[indoline-3,4'-piperidine]-1'-carboxylate (0.020 g, 0.032 mmol) in THF:H$_2$O (2:1, 0.3 mL) was cooled to about 0° C. and treated with LiOH—H$_2$O (0.0027 g, 0.065 mmol). The reaction was stirred at about 0° C. for about 5 minutes, followed by about room temperature for 1.5 hours. The reaction was concentrated and diluted with saturated NaHCO$_3$ and extracted with EtOAc. The combined extracts were washed with brine, dried over MgSO$_4$, filtered and concentrated. Crude residue was purified by preparative HPLC to yield tert-butyl 5-chloro-1-((5R,7R)-7-hydroxy-5-methyl-6,7-dihydro-5H-cyclopenta[d]pyrimidin-4-yl)spiro[indoline-3,4'-piperidine]-1'-carboxylate (0.005 g, 36%). LCMS (APCI+) m/z 471, 473 [M+H]$^+$; Rt=4.11 min.

Step 13: A solution of tert-butyl 5-chloro-1-((5R,7R)-7-hydroxy-5-methyl-6,7-dihydro-5H-cyclopenta[d]pyrimidin-4-yl)spiro[indoline-3,4'-piperidine]-1'-carboxylate (0.010 g, 0.021 mmol) in DCM (0.3 mL) was cooled to about −20° C. The solution was treated with DAST (0.0084 ml, 0.064 mmol) and stirred at about −20° C. for 1.5 hours. The reaction was quenched with ice then warmed to ambient temperature. The mixture was diluted with saturated aqueous NH$_4$Cl solution. The organic layer was separated. The aqueous phase was extracted with DCM. The combined organics were dried over MgSO₄, filtered and concentrated. The crude residue was purified by column chromatography (30-50% EtOAc/Hexane) to yield tert-butyl 5-chloro-1-((5R,7S)-7-fluoro-5-methyl-6,7-dihydro-5H-cyclopenta[d]pyrimidin-4-yl)spiro[indoline-3,4'-piperidine]-1'-carboxylate (0.004 g, 40%). LCMS (APCI+) m/z 473, 475 [M+H]⁺; Rt=3.98 min.

Step 14: 5-chloro-1-((5R,7S)-7-fluoro-5-methyl-6,7-dihydro-5H-cyclopenta[d]pyrimidin-4-yl)spiro[indoline-3,4'-piperidine]dihydrochloride was prepared by the procedures described in Example 1, Step 9, substituting (R)-tert-butyl 5-chloro-1-(5-methyl-6,7-dihydro-5H-cyclopenta[d]pyrimidin-4-yl)spiro[indoline-3,4'-piperidine]-1'-carboxylate with tert-butyl 5-chloro-1-((5R,7S)-7-fluoro-5-methyl-6,7-dihydro-5H-cyclopenta[d]pyrimidin-4-yl)spiro[indoline-3,4'-piperidine]-1'-carboxylate. LCMS (APCI+) m/z 373, 375 [M+H]⁺; Rt=2.14 min.

Example 4

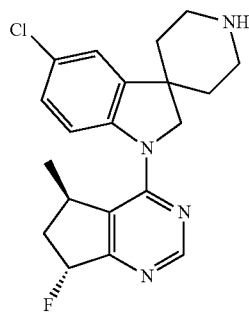

5-chloro-1-((5R,7R)-7-fluoro-5-methyl-6,7-dihydro-5H-cyclopenta[d]pyrimidin-4-yl)spiro[indoline-3,4'-piperidine]

Step 1: tert-butyl 5-chloro-1-((5R,7S)-7-hydroxy-5-methyl-6,7-dihydro-5H-cyclopenta[d]pyrimidin-4-yl)spiro[indoline-3,4'-piperidine]-1'-carboxylate was prepared by the procedures described in Example 3, Step 12, substituting (tert-butyl 5-chloro-1-((5R,7R)-5-methyl-7-(4-nitrobenzoyloxy)-6,7-dihydro-5H-cyclopenta[d]pyrimidin-4-yl)spiro[indoline-3,4'-piperidine]-1'-carboxylate with tert-butyl 5-chloro-1-((5R,7S)-5-methyl-7-(4-nitrobenzoyloxy)-6,7-dihydro-5H-cyclopenta[d]pyrimidin-4-yl)spiro[indoline-3,4'-piperidine]-1'-carboxylate. LCMS (APCI+) m/z 471, 473 [M+H]⁺; Rt=4.05 min.

Step 2: tert-butyl 5-chloro-1-45R,7R)-7-fluoro-5-methyl-6,7-dihydro-5H-cyclopenta[d]pyrimidin-4-yl)spiro[indoline-3,4'-piperidine]-1'-carboxylate was prepared by the procedures described in Example 3, Step 13, substituting tert-butyl 5-chloro-1-((5R,7R)-7-hydroxy-5-methyl-6,7-dihydro-5H-cyclopenta[d]pyrimidin-4-yl)spiro[indoline-3,4'-piperidine]-1'-carboxylate with tert-butyl 5-chloro-1-((5R,7S)-7-hydroxy-5-methyl-6,7-dihydro-5H-cyclopenta[d]pyrimidin-4-yl)spiro[indoline-3,4'-piperidine]-1'-carboxylate. LCMS (APCI+) m/z 473, 475 [M+H]⁺; Rt=3.95 min.

Step 3: 5-chloro-1-((5R,7R)-7-fluoro-5-methyl-6,7-dihydro-5H-cyclopenta[d]pyrimidin-4-yl)spiro[indoline-3,4'-piperidine]dihydrochloride was prepared by the procedures described in Example 1, Step 9, substituting (R)-tert-butyl 5-chloro-1-(5-methyl-6,7-dihydro-5H-cyclopenta[d]pyrimidin-4-yl)spiro[indoline-3,4'-piperidine]-1'-carboxylate with tert-butyl 5-chloro-1-((5R,7R)-7-fluoro-5-methyl-6,7-dihydro-5H-cyclopenta[d]pyrimidin-4-yl)spiro[indoline-3,4'-piperidine]-1'-carboxylate. LCMS (APCI+) m/z 373, 375 [M+H]⁺; Rt=2.40 min.

Example 5

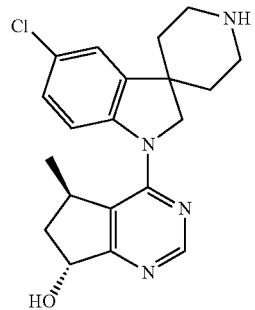

(5R,7R)-4-(5-chlorospiro[indoline-3,4'-piperidine]-1-yl)-5-methyl-6,7-dihydro-5H-cyclopenta[d]pyrimidin-7-ol (5R,7R)-4-(5-chlorospiro[indoline-3,4'-piperidine]-1-yl)-5-methyl-6,7-dihydro-5H-cyclopenta[d]pyrimidin-7-ol dihydrochloride was prepared by the procedures described in Example 1, Step 9, substituting (R)-tert-butyl 5-chloro-1-(5-methyl-6,7-dihydro-5H-cyclopenta[d]pyrimidin-4-yl)spiro[indoline-3,4'-piperidine]-1'-carboxylate with tert-butyl 5-chloro-1-((5R,7R)-7-hydroxy-5-methyl-6,7-dihydro-5H-cyclopenta[d]pyrimidin-4-yl)spiro[indoline-3,4'-piperidine]-1'-carboxylate. LCMS (APCI+) m/z 371, 373 [M+H]⁺; Rt=1.92 min.

Example 6

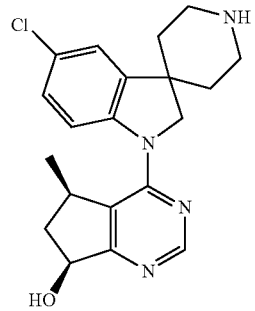

(5R,7S)-4-(5-chlorospiro[indoline-3,4'-piperidine]-1-yl)-5-methyl-6,7-dihydro-5H-cyclopenta[d]pyrimidin-7-ol (5R,7S)-4-(5-chlorospiro[indoline-3,4'-piperidine]-1-yl)-5-methyl-6,7-dihydro-5H-cyclopenta[d]pyrimidin-7-ol dihydrochloride was prepared by the procedures described in Example 1, Step 9, substituting (R)-tert-butyl 5-chloro-1-(5-methyl-6,7-dihydro-5H-cyclopenta[d]pyrimidin-4-yl)spiro[indoline-3,4'-piperidine]-1'-carboxylate with tert-butyl 5-chloro-1-((5R,7S)-7-hydroxy-5-methyl-6,7-dihydro-5H- cyclopenta[d]pyrimidin-4-yl)spiro[indoline-3,4'-piperidine]-1'-carboxylate. LCMS (APCI+) m/z 371, 373 [M+H]+; Rt=1.82 min.

Example 7

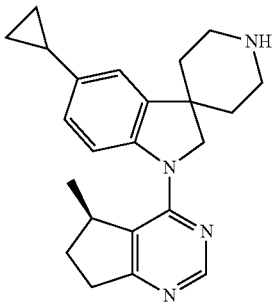

(R)-5-cyclopropyl-1-(5-methyl-6,7-dihydro-5H-cyclopenta[d]pyrimidin-4-yl)spiro[indoline-3,4'-piperidine]

Step 1: To a stirred suspension of ZnBr₂ (41 mg, 0.18 mmol) in THF (0.5 mL) was added dropwise a 0.5 M solution of cyclopropylmagnesium bromide in THF (0.36 mL, 0.18 mmol) at about −78° C. under nitrogen. After being stirred at about −78° C. for about 30 min, the resulting solution was allowed to warm to about 0° C. A solution of (R)-tert-butyl 5-bromo-1-(5-methyl-6,7-dihydro-5H-cyclopenta[d]pyrimidin-4-yl)spiro[indoline-3,4'-piperidine]-1'-carboxylate (38 mg, 0.076 mmol) and Pd(PPh₃)₄ (4.4 mg, 0.0038 mmol) in THF (0.3 mL) was added. The resulting mixture was heated to about 60° C. overnight. After cooling, the mixture was diluted with EtOAc, washed with water and brine, dried and concentrated. The residue was purified by reverse phase preparative HPLC to give (R)-tert-butyl 5-cyclopropyl-1-(5-methyl-6,7-dihydro-5H-cyclopenta[d]pyrimidin-4-yl)spiro[indoline-3,4'-piperidine]-1'-carboxylate (20 mg, 57%). LCMS (APCI+) m/z 461 [M+H]+; Rt=3.24 min.

Step 2: (R)-5-cyclopropyl-1-(5-methyl-6,7-dihydro-5H-cyclopenta[d]pyrimidin-4-yl)spiro[indoline-3,4'-piperidine] dihydrochloride was prepared by the procedures described in Example 1, Step 9, substituting (R)-tert-butyl 5-chloro-1-(5-methyl-6,7-dihydro-5H-cyclopenta[d]pyrimidin-4-yl)spiro[indoline-3,4'-piperidine]-1'-carboxylate with (R)-tert-butyl 5-cyclopropyl-1-(5-methyl-6,7-dihydro-5H-cyclopenta[d]pyrimidin-4-yl)spiro[indoline-3,4'-piperidine]-1'-carboxylate. LCMS (APCI+) m/z 361 [M+H]+; Rt=2.23 min.

Example 8

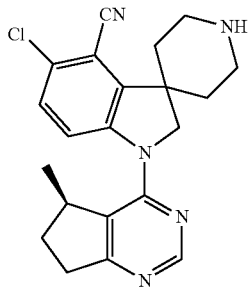

(R)-5-chloro-1-(5-methyl-6,7-dihydro-5H-cyclopenta[d]pyrimidin-4-yl)spiro[indoline-3,4'-piperidine]-4-carbonitrile Step 1: tert-butyl 4-bromo-5-chlorospiro[indoline-3,4'-piperidine]-1'-carboxylate was prepared as a major isomer by the procedures described in Example 1, Step 1-2, substituting 1-(4-chlorophenyl)hydrazine hydrochloride with (3-bromo-4-chlorophenyl)hydrazine hydrochloride. LCMS (APCI+) m/z 401, 403 [M+H-Boc]+; Rt=4.16 min.

Step 2: (R)-tert-butyl 4-bromo-5-chloro-1-(5-methyl-6,7-dihydro-5H-cyclopenta[d]pyrimidin-4-yl)spiro[indoline-3,4'-piperidine]-1'-carboxylate was prepared by the procedures described in Example 1, Step 8, substituting tert-butyl 5-chlorospiro[indoline-3,4'-piperidine]-1'-carboxylate with tert-butyl 4-bromo-5-chlorospiro[indoline-3,4'-piperidine]-1'-carboxylate. LCMS (APCI+) m/z 533, 535 [M+H]+; Rt=4.99 min.

Step 3: To a solution (R)-tert-butyl 4-bromo-5-chloro-1-(5-methyl-6,7-dihydro-5H-cyclopenta[d]pyrimidin-4-yl) spiro[indoline-3,4'-piperidine]-1'-carboxylate (0.200 g, 0.375 mmol) in DMF (2 mL) was added zinc cyanide (0.088 g, 0.75 mmol) and tetrakis(triphenylphosphine)palladium (0) (0.022 g, 0.019 mmol). The mixture was heated at about 95° C. for 2 days. After cooling, the mixture was diluted with water and extracted with EtOAc. The combined organic layers were washed with saturated aqueous NaHCO₃ solution and brine, dried and concentrated. The residue was purified by flash chromatography on silica gel (EtOAc hexanes, 1:1) to give (R)-tert-butyl 5-chloro-4-cyano-1-(5-methyl-6,7-dihydro-5H-cyclopenta[d]pyrimidin-4-yl)spiro[indoline-3,4'-piperidine]-1'-carboxylate (0.060 g, 33%) as a oil. LCMS (APCI+) m/z 480, 482 [M+H]+; Rt=4.51 min.

Step 4: (R)-5-chloro-1-(5-methyl-6,7-dihydro-5H-cyclopenta[d]pyrimidin-4-yl)spiro[indoline-3,4'-piperidine]-4-carbonitrile dihydrochloride was prepared by the procedures described in Example 1, Step 9, substituting (R)-tert-butyl 5-chloro-1-(5-methyl-6,7-dihydro-5H-cyclopenta[d]pyrimidin-4-yl)spiro[indoline-3,4'-piperidine]-1'-carboxylate with (R)-tert-butyl 5-chloro-4-cyano-1-(5-methyl-6,7-dihydro-5H-cyclopenta[d]pyrimidin-4-yl)spiro[indoline-3,4'-piperidine]-1'-carboxylate. LCMS (APCI+) m/z 380, 382 [M+H]+; Rt=2.76 min.

Example 9

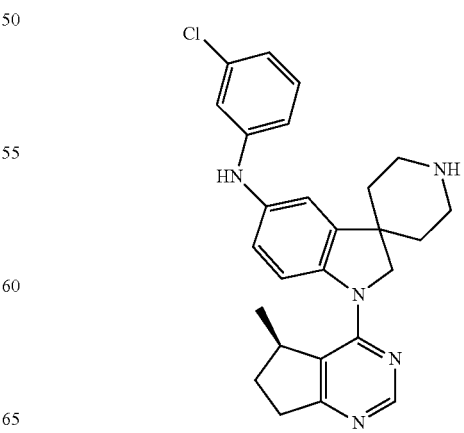

(R)-N-(3-chlorophenyl)-1-(5-methyl-6,7-dihydro-5H-cyclopenta[d]pyrimidin-4-yl)spiro[indoline-3,4'-piperidin]-5-amine Step 1: A pear-shaped flask was charged with Pd(OAc)$_2$ (0.9 mg, 0.004 mmol) and rac-BINAP (81 mg, 0.13 mmol) and purged with N$_2$. To the flask was added (R)-tert-butyl 5-bromo-1-(5-methyl-6,7-dihydro-5H-cyclopenta[d]pyrimidin-4-yl)spiro[indoline-3,4'-piperidine]-1'-carboxylate (20 mg, 0.040 mmol), 3-chlorobenzenamine (10 mg, 0.080 mmol), NaOBu$^t$ (7.7 mg, 0.080 mmol) and toluene (0.5 mL) The mixture was heated at about 95° C. for 2 days. After cooling to about room temperature, the reaction was diluted with EtOAc, filtered through Celite, and concentrated. The crude product was purified by column chromatography (DCM:MeOH, 80:1) to give (R)-tert-butyl 5-(3-chlorophenylamino)-1-(5-methyl-6,7-dihydro-5H-cyclopenta[d]pyrimidin-4-yl)spiro[indoline-3,4'-piperidine]-1'-carboxylate (13 mg, 59%) as a yellow oil. LCMS (APCI+) m/z 546 [M+H]$^+$; Rt=4.24 min.

Step 2: (R)-N-(3-chlorophenyl)-1-(5-methyl-6,7-dihydro-5H-cyclopenta[d]pyrimidin-4-yl)spiro[indoline-3,4'-piperidin]-5-amine dihydrochloride was prepared by the procedures described in Example 1, Step 9, substituting (R)-tert-butyl 5-chloro-1-(5-methyl-6,7-dihydro-5H-cyclopenta[d]pyrimidin-4-yl)spiro[indoline-3,4'-piperidine]-1'-carboxylate with (R)-tert-butyl 5-(3-chlorophenylamino)-1-(5-methyl-6,7-dihydro-5H-cyclopenta[d]pyrimidin-4-yl)spiro[indoline-3,4'-piperidine]-1'-carboxylate. LCMS (APCI+) m/z 446 [M+H]$^+$; Rt=2.76 min.

Example 10

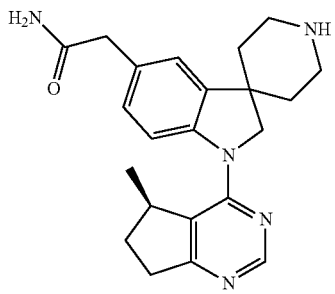

(R)-2-(1-(5-methyl-6,7-dihydro-5H-cyclopenta[d]pyrimidin-4-yl)spiro[indoline-3,4'-piperidine]-5-yl)acetamide Step 1: tert-butyl 5-(2-ethoxy-2-oxoethyl)spiro[indole-3,4'-piperidine]-1'-carboxylate was prepared by the procedures described in Example 1, Step 1, substituting 1-(4-chlorophenyl)hydrazine hydrochloride with ethyl 2-(4-hydrazinylphenyl)acetate. LCMS (APCI+) m/z 273.1 [M+H-Boc]$^+$; Rt=3.40 min.

Step 2: tert-butyl 5-(2-ethoxy-2-oxoethyl)spiro[indoline-3,4'-piperidine]-1'-carboxylate was prepared by the procedures described in Example 1, Step 2, substituting tert-butyl 5-chlorospiro[indole-3,4'-piperidine]-1'-carboxylate with butyl 5-(2-ethoxy-2-oxoethyl)spiro[indole-3,4'-piperidine]-1'-carboxylate. LCMS (APCI+) m/z 275.2 [M+H-Boc]$^+$; Rt=3.58 min.

Step 3: (R)-tert-butyl 5-(2-ethoxy-2-oxoethyl)-1-(5-methyl-6,7-dihydro-5H-cyclopenta[d]pyrimidin-4-yl)spiro[indoline-3,4'-piperidine]-1'-carboxyl ate was prepared by the procedures described in Example 1, Step 8, substituting tert-butyl 5-chlorospiro[indoline-3,4'-piperidine]-1'-carboxylate with tert-butyl 5-(2-ethoxy-2-oxoethyl)spiro[indoline-3,4'-piperidine]-1'-carboxylate. LCMS (APCI+) m/z 507.3 [M+H]$^+$; Rt=3.19 min.

Step 4: A solution of (R)-tert-butyl 5-(2-ethoxy-2-oxoethyl)-1-(5-methyl-6,7-dihydro-5H-cyclopenta[d]pyrimidin-4-yl)spiro[indoline-3,4'-piperidine]-1'-carboxylate (0.325 g, 0.641 mmol) in THF:H$_2$O (2:1, 3 mL) was treated with LiOH—H$_2$O (0.067 g, 1.6 mmol) at about 0° C. The reaction was stirred with warming to about room temperature overnight. The reaction was concentrated and diluted with EtOAc. The organic was washed with saturated NaHCO$_3$, acidified with 1N HCl, and extracted with EtOAc. The combined organics were washed with brine, dried over MgSO$_4$, filtered and concentrated to yield (R)-2-(1'-(tert-butoxycarbonyl)-1-(5-methyl-6,7-dihydro-5H-cyclopenta[d]pyrimidin-4-yl)spiro[indoline-3,4'-piperidine]-5-yl)acetic acid. LCMS (APCI+) m/z 479.3 [M+H]$^+$; Rt=2.82 min.

Step 5: To a stirred solution of (R)-2-(1'-(tert-butoxycarbonyl)-1-(5-methyl-6,7-dihydro-5H-cyclopenta[d]pyrimidin-4-yl)spiro[indoline-3,4'-piperidine]-5-yl)acetic acid (0.020 g, 0.042 mmol), DIEA (0.023 ml, 0.13 mmol), and HBTU (0.017 g, 0.046 mmol) in 1:1 mixture of DCM/DMF (0.2 mL) was added NH$_4$Cl (0.0067 g, 0.13 mmol). The reaction was stirred at about room temperature overnight. An additional equivalent of DIEA and NH$_4$Cl were added and the reaction stirred at about room temperature overnight. The reaction was diluted with DCM, washed with saturated NaHCO$_3$ and brine, dried over MgSO$_4$, filtered, and concentrated. The crude residue was purified by column chromatography (3-5% MeOH/DCM) to yield (R)-tert-butyl 5-(2-amino-2-oxoethyl)-1-(5-methyl-6,7-dihydro-5H-cyclopenta[d]pyrimidin-4-yl)spiro[indoline-3,4'-piperidine]-1'-carboxylate (0.012 g, 60%). LCMS (APCI+) m/z 478.3 [M+H]$^+$; Rt=3.05 min.

Step 6: ((R)-2-(1-(5-methyl-6,7-dihydro-5H-cyclopenta[d]pyrimidin-4-yl)spiro[indoline-3,4'-piperidine]-5-yl)acetamide dihydrochloride was prepared by the procedures described in Example 1, Step 9, substituting (R)-tert-butyl 5-chloro-1-(5-methyl-6,7-dihydro-5H-cyclopenta[d]pyrimidin-4-yl)spiro[indoline-3,4'-piperidine]-1'-carboxylate with (R)-tert-butyl 5-(2-amino-2-oxoethyl)-1-(5-methyl-6,7-dihydro-5H-cyclopenta[d]pyrimidin-4-yl)spiro[indoline-3,4'-piperidine]-1'-carboxylate. LCMS (APCI+) m/z 378.4 [M+H]$^+$; Rt=1.78 min.

Example 11

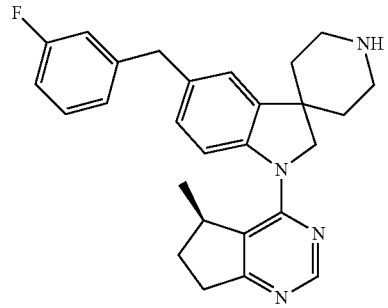

(R)-5-(3-fluorobenzyl)-1-(5-methyl-6,7-dihydro-5H-cyclopenta[d]pyrimidin-4-yl)spiro[indoline-3,4'-piperidine]

Step 1: 1'-tert-butyl 5-ethyl Spiro[indole-3,4'-piperidine]-1',5-dicarboxylate was prepared by the procedures described in Example 1, Step 1, substituting 1-(4-chlorophenyl)hydrazine hydrochloride with ethyl 4-hydrazinylbenzoate hydrochloride. LCMS (APCI+) m/z 259.2 [M+H-Boc]+; Rt=3.27 min.

Step 2: 1'-tert-butyl 5-ethyl Spiro[indoline-3,4'-piperidine]-1',5-dicarboxylate was prepared by the procedures described in Example 1, Step 2, substituting tert-butyl 5-chloro spiro[indole-3,4'-piperidine]-1'-carboxylate with 1'-tert-butyl 5-ethyl spiro[indole-3,4'-piperidine]-1',5-dicarboxylate. LCMS (APCI+) m/z 261.3 [M+H-Boc]+; Rt=3.76 min.

Step 3: (R)-1'-tert-butyl 5-ethyl 1-(5-methyl-6,7-dihydro-5H-cyclopenta[d]pyrimidin-4-yl)spiro[indoline-3,4'-piperidine]-1',5-dicarboxylate was prepared by the procedures described in Example 1, Step 8, substituting tert-butyl 5-chloro spiro[indoline-3,4'-piperidine]-1'-carboxylate with 1'-tert-butyl 5-ethyl spiro[indoline-3,4'-piperidine]-1',5-dicarboxylate. LCMS (APCI+) m/z 493.3 [M+H]+; Rt=4.33 min.

Step 4: (R)-1'-(tert-butoxycarbonyl)-1-(5-methyl-6,7-dihydro-5H-cyclopenta[d]pyrimidin-4-yl)spiro[indoline-3,4'-piperidine]-5-carboxylic acid was prepared by the procedures described in Example 10, Step 4, substituting (R)-tert-butyl 5-(2-ethoxy-2-oxoethyl)-1-(5-methyl-6,7-dihydro-5H-cyclopenta[d]pyrimidin-4-yl)spiro[indoline-3,4'-piperidine]-1'-carboxylate with (R)-1'-tert-butyl 5-ethyl 1-(5-methyl-6,7-dihydro-5H-cyclopenta[d]pyrimidin-4-yl)spiro[indoline-3,4'-piperidine]-1',5-dicarboxylate. LCMS (APCI+) m/z 465.3 [M+H]+; Rt=2.86 min Step 5: (R)-tert-butyl 5-(methoxy(methyl)carbamoyl)-1-(5-methyl-6,7-dihydro-5H-cyclopenta[d]pyrimidin-4-yl)spiro[indoline-3,4'-piperidine]-1'-carboxylate was prepared by the procedures described in Example 10, Step 5, substituting (R)-2-(1'-(tert-butoxycarbonyl)-1-(5-methyl-6,7-dihydro-5H-cyclopenta[d]pyrimidin-4-yl)spiro[indoline-3,4'-piperidine]-5-yl)acetic acid with (R)-1'-(tert-butoxycarbonyl)-1-(5-methyl-6,7-dihydro-5H-cyclopenta[d]pyrimidin-4-yl)spiro[indoline-3,4'-piperidine]-5-carboxylic acid, and substituting NH4Cl with N,O-dimethylhydroxylamine hydrochloride. LCMS (APCI+) m/z 508.3 [M+H]+; Rt=3.56 min.

Step 6: To a solution of 1-bromo-3-fluorobenzene (0.066 ml, 0.59 mmol) in THF (0.3 mL) was added dropwise n-BuLi in hexane (0.23 ml, 0.52 mmol) at about −78° C. under nitrogen. After being stirred at about −78° C. for about 20 minutes, a solution of (R)-tert-butyl 5-(methoxy(methyl)carbamoyl)-1-(5-methyl-6,7-dihydro-5H-cyclopenta[d]pyrimidin-4-yl)spiro[indoline-3,4'-piperidine]-1'-carboxylate (0.050 g, 0.099 mmol) in THF (0.2 mL) was added dropwise to the reaction mixture at about −78° C. After 2 hours, i-PrOH (0.090 ml, 1.2 mmol) and water (2.0 mL) were added to the mixture, and the cold bath was removed. The mixture was stirred at about room temperature for about 20 minutes. The mixture was extracted with EtOAc. The combined organic layers were washed with water and brine, dried over MgSO4, and concentrated. The crude residue was purified by column chromatography (1-3% MeOH/DCM) to yield (R)-tert-butyl 5-(3-fluorobenzoyl)-1-(5-methyl-6,7-dihydro-5H-cyclopenta[d]pyrimidin-4-yl)spiro[indoline-3,4'-piperidine]-1'-carboxylate (0.023 g, 43%). LCMS (APCI+) m/z 543.3 [M+H]+; Rt=4.49 min.

Step 7: To a stirred solution of (R)-tert-butyl 5-(3-fluorobenzoyl)-1-(5-methyl-6,7-dihydro-5H-cyclopenta[d]pyrimidin-4-yl)spiro[indoline-3,4'-piperidine]-1'-carboxylate (0.047 g, 0.087 mmol) in MeOH (0.5 mL) was added NaBH4 (0.0036 g, 0.095 mmol) at about 0° C. The reaction was stirred for 1.5 hours and quenched by the addition of saturated NH4Cl solution. The solvent was evaporated under reduced pressure. The solid was dissolved in water and extracted with EtOAc. The combined extracts were washed with brine, dried MgSO4, filtered and concentrated. The crude residue was purified by column chromatography (1-3% MeOH/DCM) to yield tert-butyl 5-((3-fluorophenyl)(hydroxy)methyl)-1-((R)-5-methyl-6,7-dihydro-5H-cyclopenta[d]pyrimidin-4-yl)spiro[indoline-3,4'-piperidine]-1'-carboxylate (0.035 g, 74%). LCMS (APCI+) m/z 545.3 [M+H]+; Rt=4.02 min.

Step 8: A flask charged with TFA (0.294 ml, 3.82 mmol) was cooled to about 0° C. and treated with NaBH4 (0.0133 g, 0.353 mmol) in small portions. The mixture was stirred for 1 hour. A solution of tert-butyl 5-((3-fluorophenyl)(hydroxy)methyl)-1-((R)-5-methyl-6,7-dihydro-5H-cyclopenta[d]pyrimidin-4-yl)spiro[indoline-3,4'-piperidine]-1'-carboxylate (0.032 g, 0.0588 mmol) in DCM (0.18 mL) was added slowly over about 15 minutes. The mixture was allowed to warm to about room temperature and stirred overnight. An additional 3 equivalents of NaBH4 was added the reaction was stirred at about room temperature overnight. The reaction was diluted with water, basified with 2N NaOH, and extracted with EtOAc. The combined organics were washed with water, dried over MgSO4, filtered, and concentrated. The crude residue was purified by column chromatography (4% 7 N ammonia in MeOH/DCM) to yield the free base, which was taken up in DCM and acidified with 2N HCl in Et2O. Removal of the solvents afforded ((R)-5-(3-fluorobenzyl)-1-(5-methyl-6,7-dihydro-5H-cyclopenta[d]pyrimidin-4-yl)spiro[indoline-3,4'-piperidine]dihydrochloride (0.001 g, 6%). LCMS (APCI+) m/z 429.4 [M+H]+; Rt=3.15 min.

Example 12

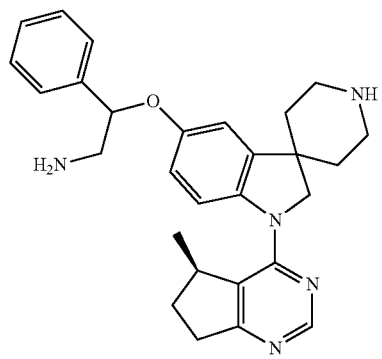

2-(1-((R)-5-methyl-6,7-dihydro-5H-cyclopenta[d]pyrimidin-4-yl)spiro[indoline-3,4'-piperidine]-5-yloxy)-2-phenylethanamine Step 1: tert-butyl 5-(benzyloxy)spiro[indole-3,4'-piperidine]-1'-carboxylate was prepared by the procedures described in Example 1, Step 1, substituting 1-(4-chlorophenyl) hydrazine hydrochloride with 4-(benzyloxy)phenyl)hydrazine hydrochloride. LCMS (APCI+) m/z 393 [M+H]+; Rt=3.95 min.

Step 2: tert-butyl 5-(benzyloxy)spiro[indoline-3,4'-piperidine]-1'-carboxylate was prepared by the procedures described in Example 1, Step 2, substituting tert-butyl 5-chloro spiro[indole-3,4'-piperidine]-1'-carboxylate with tert-butyl 5-(benzyloxy)spiro[indole-3,4'-piperidine]-F-carboxylate. LCMS (APCI+) m/z 395 [M+H]+; Rt=3.98 min Step 3: (R)-tert-butyl 5-(benzyloxy)-1-(5-methyl-6,7-dihydro-5H-cyclopenta[d]pyrimidin-4-yl)spiro[indoline-3,4'-piperidine]-1'-carboxyl ate was prepared by the procedures described in Example 1, Step 8, substituting tert-butyl 5-chlorospiro[indoline-3,4'-piperidine]-1'-carboxylate with tert-butyl 5-(benzyloxy)spiro[indoline-3,4'-piperidine]-1'-carboxylate. LCMS (APCI+) m/z 527 [M+H]+; Rt=4.79 min.

Step 4: To a stirred solution of (R)-tert-butyl 5-(benzyloxy)-1-(5-methyl-6,7-dihydro-5H-cyclopenta[d]pyrimidin-4-yl)spiro[indoline-3,4'-piperidine]-1'-carboxylate (0.80 g, 1.5 mmol) in MeOH (20 mL) under $N_2$ was added 10% Pd/C (0.20 g). The reaction vessel was evacuated under vacuum and hydrogenated under $H_2$ (50 psi) for 48 hours. The hydrogen gas was evacuated and the catalyst was removed by filtration. The filtrate was concentrated. The residue was purified by flash chromatography (DCM:MeOH, 30:1) to give (R)-tert-butyl 5-hydroxy-1-(5-methyl-6,7-dihydro-5H-cyclopenta[d]pyrimidin-4-yl)spiro[indoline-3,4'-piperidine]-1'-carboxylate (0.40 g, 60%) as an oil. LCMS (APCI+) m/z 437 [M+H]+; Rt=3.42 min.

Step 5: To a stirred solution of tert-butyl 2-hydroxy-2-phenylethylcarbamate (0.082 g, 0.34 mmol) and (R)-tert-butyl 5-hydroxy-1-(5-methyl-6,7-dihydro-5H-cyclopenta[d]pyrimidin-4-yl)spiro[indoline-3,4'-piperidine]carboxyl ate (0.100 g, 0.230 mmol) in THF (0.4 mL) was added $PPh_3$ (0.090 g, 0.34 mmol) under nitrogen. The reaction was cooled in an ice bath. After about 20 minutes, DEAD (0.054 ml, 0.34 mmol) was added dropwise to the reaction mixture. The reaction was allowed to stir with warming to about room temperature overnight. The salts were removed by filtration and the solvent was evaporated under reduced pressure. The crude product was used in the next step without further purification. LCMS (APCI+) m/z 656.5 [M+H]+; Rt=4.39 min Step 6: A solution of tert-butyl 5-(2-(tert-butoxycarbonylamino)-1-phenylethoxy)-1-(R)-5-methyl-6,7-dihydro-5H-cyclopenta[d]pyrimidin-4-yl)spiro[indoline-3,4'-piperidine]-1'-carboxylate (0.235 g, 0.358 mmol) in DCM (4 mL) was treated with 4N HCl in dioxane (1 mL). The reaction was stirred at about room temperature overnight. The solvents were removed and the crude residue was partitioned between DCM and 1N HCl. The aqueous phase was extracted with DCM (×3), and then basified with 1N NaOH. The free base was extracted with DCM. The combined organics were washed with brine, dried over $MgSO_4$, filtered and concentrated. The crude residue was purified by reverse phase column chromatography (0-60% ACN/$H_2O$) to give the free base, which was taken up in DCM and acidified with 2N HCl in ether. Removal of the solvents under reduced pressure afforded 2-(1-((R)-5-methyl-6,7-dihydro cyclopenta[d]pyrimidin-4-yl)spiro[indoline-3,4'-piperidine]-5-yloxy)-2-phenylethanamine trihydrochloride (0.008 g, 5%). LCMS (APCI+) m/z 456.2 [M+H]+; Rt=2.49 min.

Example 13

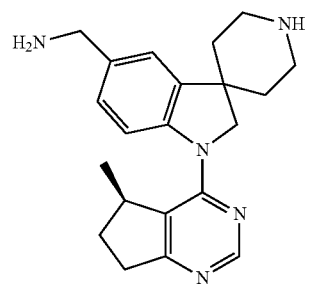

(R)-(1-(5-methyl-6,7-dihydro-5H-cyclopenta[d]pyrimidin-4-yl)spiro[indoline-3,4'-piperidine]-5-yl) methanamine Step 1: (R)-tert-butyl 5-cyano-1-(5-methyl-6,7-dihydro cyclopenta[d]pyrimidin-4-yl)spiro[indoline-3,4'-piperidine]-1'-carboxylate was prepared by the procedures described in Example 8, Step 3, substituting (R)-tert-butyl 4-bromo-5-chloro-1-(5-methyl-6,7-dihydro-5H-cyclopenta[d]pyrimidin-4-yl)spiro[indoline-3,4'-piperidine]-1'-carboxylate with (R)-tert-butyl 5-bromo-1-(5-methyl-6,7-dihydro-5H-cyclopenta[d]pyrimidin-4-yl)spiro[indoline-3,4'-piperidine]-1'-carboxylate. LCMS (APCI+) m/z 446 [M+H]+; Rt=3.41 min.

Step 2: (R)-tert-butyl 5-cyano-1-(5-methyl-6,7-dihydro-5H-cyclopenta[d]pyrimidin-4-yl)spiro[indoline-3,4'-piperidine]-1'-carboxylate (0.182 g, 0.409 mmol) in a mixture of THF (6 mL) and $NH_4OH$ (513 pt) was hydrogenated over Raney Nickel (0.0012 g, 0.014 mmol) under of $H_2$ (1 atm.) at about room temperature for 2 days. The reaction mixture was filtered through glass filter paper and the filtrate was concentrated. The crude product was taken up in DCM (0.2 mL) TEA (0.010 ml, 0.070 mmol) was added to the reaction followed by a solution of $Boc_2O$ (0.011 g, 0.052 mmol) in DCM (0.2 mL). The reaction was stirred at about room temperature overnight. The reaction was diluted with DCM and washed with saturated $NaHCO_3$. The combined organics were washed with brine, dried over $MgSO_4$, filtered, and concentrated. The crude residue was purified by column chromatography (1-5% MeOH/DCM) to yield (R)-tert-butyl 5-((tert-butoxycarbonylamino)methyl)-1-(5-methyl-6,7-dihydro cyclopenta[d]pyrimidin-4-yl)spiro[indoline-3,4'-piperidine]-1'-carboxylate (0.009 g). LCMS (APCI+) m/z 550 [M+H]+; Rt=4.07 min.

Step 3: (R)-(1-(5-methyl-6,7-dihydro-5H-cyclopenta[d] pyrimidin-4-yl)spiro[indoline-3,4'-piperidine]-5-yl)methanamine trihydrochloride was prepared by the procedures described in Example 1, Step 9, substituting (R)-tert-butyl 5-chloro-1-(5-methyl-6,7-dihydro-5H-cyclopenta[d]pyrimidin-4-yl)spiro[indoline-3,4'-piperidine]-1'-carboxylate with (R)-tert-butyl 5-((tert-butoxycarbonylamino)methyl)-1-(5-methyl-6,7-dihydro-5H-cyclopenta[d]pyrimidin-4-yl)spiro

[indoline-3,4'-piperidine]-1'-carboxylate. LCMS (APCI+) m/z 350 [M+H]+; Rt=1.80 min.

Example 14

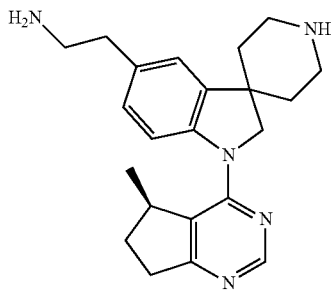

(R)-2-(1-(5-methyl-6,7-dihydro-5H-cyclopenta[d]pyrimidin-4-yl)spiro[indoline-3,4'-piperidine]-5-yl)ethanamine Step 1: To a stirred solution of (R)-tert-butyl 5-(2-ethoxy-2-oxoethyl)-1-(5-methyl-6,7-dihydro-5H-cyclopenta[d]pyrimidin-4-yl)spiro[indoline-3,4'-piperidine]-1'-carboxylate (0.039 g, 0.0770 mmol) in THF (0.4 mL) was added dropwise DIBAL-H (0.308 ml, 0.308 mmol) (1M in THF) at 0° C. under nitrogen. The reaction was stirred with warming to about room temperature for 1 hour. The reaction mixture was added dropwise to a saturated solution of Rochelle's salt (6 mL) and stirred overnight. The reaction was extracted with EtOAc (×3). The combined organics were washed with brine, dried over MgSO4, filtered and concentrated to yield (R)-tert-butyl 5-(2-hydroxyethyl)-1-(5-methyl-6,7-dihydro-5H-cyclopenta[d]pyrimidin-4-yl)spiro[indoline-3,4'-piperidine]-1'-carboxylate (0.021 g, 59%). LCMS (APCI+) m/z 465 [M+H]+; Rt=3.39 min.

Step 2: To a solution of (R)-tert-butyl 5-(2-hydroxyethyl)-1-(5-methyl-6,7-dihydro-5H-cyclopenta[d]pyrimidin-4-yl)spiro[indoline-3,4'-piperidine]-1'-carboxylate (0.021 g, 0.045 mmol) in THF (0.2 mL) was added isoindoline-1,3-dione (0.020 g, 0.14 mmol) and PS—PPh3 (0.081 g, 0.14 mmol). The solution was cooled to 0° C. and DEAD (0.021 ml, 0.14 mmol) was added dropwise. The reaction was allowed to stir with warming to about room temperature for 2 hours. The reaction was filtered and the solvent was evaporated. The crude residue was purified by column chromatography (1-3% MeOH/DCM) to yield (R)-tert-butyl 5-(2-(1,3-dioxoisoindolin-2-yl)ethyl)-1-(5-methyl-6,7-dihydro-5H-cyclopenta[d]pyrimidin-4-yl)spiro[indoline-3,4'-piperidine]-1'-carboxylate (0.014 g, 52%). LCMS (APCI+) m/z 594 [M+H]+; Rt=4.15 min.

Step 3: To a solution of (R)-tert-butyl 5-(2-(1,3-dioxoisoindolin-2-yl)ethyl)-1-(5-methyl-6,7-dihydro-5H-cyclopenta[d]pyrimidin-4-yl)spiro[indoline-3,4'-piperidine]-1'-carboxylate (0.014 g, 0.023 mmol) in EtOH (0.2 mL) was added hydrazine monohydrate (0.012 ml, 0.26 mmol). The solution was heated at 40° C. for 4 hours. After cooling, the solid was filtered and rinsed with EtOH. The filtrate was concentrated to dryness. The crude product was purified by column chromatography (10% MeOH/DCM then 10% MeOH/DCM+1% NH4OH) to yield (R)-tert-butyl 5-(2-aminoethyl)-1-(5-methyl-6,7-dihydro-5H-cyclopenta[d]pyrimidin-4-yl)spiro[indoline-3,4'-piperidine]-1'-carboxylate (0.009 g, 82%). LCMS (APCI+) m/z 464 [M+H]+; Rt=3.22 min.

Step 4: (R)-2-(1-(5-methyl-6,7-dihydro-5H-cyclopenta[d]pyrimidin-4-yl)spiro[indoline-3,4'-piperidine]-5-yl)ethanamine trihydrochloride was prepared by the procedures described in Example 1, Step 9, substituting (R)-tert-butyl 5-chloro-1-(5-methyl-6,7-dihydro-5H-cyclopenta[d]pyrimidin-4-yl)spiro[indoline-3,4'-piperidine]-1'-carboxylate with (R)-tert-butyl 5-(2-aminoethyl)-1-(5-methyl-6,7-dihydro-5H-cyclopenta[d]pyrimidin-4-yl)spiro[indoline-3,4'-piperidine]-1'-carboxylate. LCMS (APCI+) m/z 350 [M+H]+; Rt=1.80 min.

Example 15

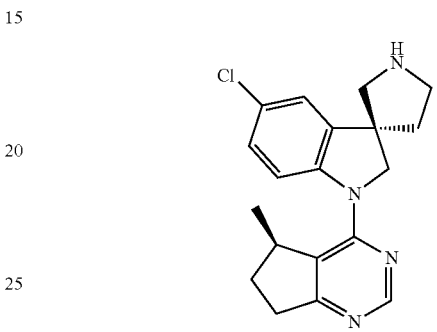

(S)-5-chloro-1-((R)-5-methyl-6,7-dihydro-5H-cyclopenta[d]pyrimidin-4-yl)spiro[indoline-3,3'-pyrrolidine]

Step 1: A stirred suspension of 5-chlorotryptamine hydrochloride (8.00 g, 34.6 mmol) and paraformaldehyde (1.04 g, 34.6 mmol) in water (120 mL) was treated with 3 M acetate buffer (17.5 mL) under nitrogen. The mixture was heated at about 105° C. for 4 hours. The reaction mixture was cooled to about room temperature. The product was isolated by crystallization at about 0° C. The solid was dissolved in MeOH. The solution was basified with 1N NaOH and evaporated to dryness. The residue was washed with cold water and dried to yield 2-(5-chloro-1H-indol-3-yl)ethanamine hydrochloride (5.53 g, 77%). 1H NMR (DMSO-d6, 400 MHz) δ 10.82 (s, 1H), 7.33 (d, J=2.0 Hz, 1H), 7.23 (d, J=8.6 Hz, 1H), 6.94 (dd, J=8.6 Hz, J=2.3 Hz, 1H), 3.80 (s, 1H), 2.92 (t, J=8.4 Hz, 2H), 2.53 (t, J=8.6 Hz, 2H), 2.47-2.46 (m, 2H).

Step 2: To a solution of 2-(5-chloro-1H-indol-3-yl)ethanamine hydrochloride (5.53 g, 26.7 mmol) in 2-propanol/H2O (5/6; 100 mL) was added Boc2O (6.42 g, 29.4 mmol) and K2CO3 (4.06 g, 29.4 mmol). The mixture was allowed to stir at about room temperature overnight. The reaction was diluted with EtOAc and washed with water. The organic layer was dried with MgSO4, filtered and concentrated to yield tert-butyl 6-chloro-3,4-dihydro-1H-pyrido[3,4-b]indole-2(9H)-carboxylate (7.90 g, 96.3%). LCMS (APCI+) m/z 207, 209 [M+H-Boc]+; Rt=4.03 min.

Step 3: A solution of tert-butyl 6-chloro-3,4-dihydro-1H-pyrido[3,4-b]indole-2(9H)-carboxylate (0.500 g, 1.63 mmol) in 1:1:1 THF/AcOH/H2O (45 mL) at about 0° C. was treated with N-Bromosuccinimide (0.319 g, 1.79 mmol) portionwise over about 20 minutes. The resulting mixture was stirred for about 90 minutes at about 0° C. The mixture was then quenched by the addition of saturated Na2CO3 (100 mL) and extracted with DCM. The combined organics were washed with saturated NaHCO3 (2×) and brine, dried over MgSO4, filtered and concentrated. The crude residue was purified by column chromatography (20% EtOAc/Hexane) to yield tert-butyl 5-chloro-2-oxospiro[indoline-3,3'-pyrrolidine]-1'-carboxylate (0.530 g, 100%). LCMS (APCI+) m/z 223, 225 [M+H-Boc]+; Rt=3.26 min.

Step 4: To a stirred solution of tert-butyl 5-chloro-2-oxospiro[indoline-3,3'-pyrrolidine]-1'-carboxylate (0.530 g, 1.64 mmol) in THF (5 mL) was added NaBH₄ (0.311 g, 8.21 mmol). The reaction was cooled to about −20° C. to −10° C. A solution I₂ (0.833 g, 3.28 mmol) in THF (3 mL) was added to the mixture dropwise. The reaction was stirred with warming to about room temperature overnight. The reaction was cooled to about 0° C. and quenched by the addition of saturated NH₄Cl, and diluted with DCM. The organics were washed with Na₂SO₃ and brine, dried over MgSO₄, filtered and concentrated. The crude residue was purified by column chromatography to yield tert-butyl 5-chlorospiro[indoline-3,3'-pyrrolidine]-1'-carboxylate (0.515 g, 100%). LCMS (APCI+) m/z 209, 211 [M+H-Boc]+; Rt=3.67 min.

Step 5: tert-butyl 5-chloro-1-((R)-5-methyl-6,7-dihydro-5H-cyclopenta[d]pyrimidin-4-yl)spiro[indoline-3,3'-pyrrolidine]-1'-carboxylate was prepared by the procedures described in Example 1, Step 8, substituting tert-butyl 5-chlorospiro[indoline-3,4'-piperidine]-1'-carboxylate with tert-butyl 5-chlorospiro[indoline-3,3'-pyrrolidine]-1'-carboxylate. The two diastereomers were separated by column chromatography. (R)-tert-butyl 5-chloro-1-((R)-5-methyl-6,7-dihydro-5H-cyclopenta[d]pyrimidin-4-yl)spiro[indoline-3,3'-pyrrolidine]-F-carboxylate. LCMS (APCI+) m/z 441, 443 [M+H]+; Rt=4.29 min. (S)-tert-butyl 5-chloro-1-((R)-5-methyl-6,7-dihydro-5H-cyclopenta[d]pyrimidin-4-yl)spiro[indoline-3,3'-pyrrolidine]-1'-carboxylate. LCMS (APCI+) m/z 441, 443 [M+H]+; Rt=4.32 min.

Step 6: To a solution of (R)-tert-butyl 5-chloro-1-((R)-5-methyl-6,7-dihydro-5H-cyclopenta[d]pyrimidin-4-yl)spiro[indoline-3,3'-pyrrolidine]-1'-carboxylate (0.107 g, 0.243 mmol) in DCM (2 mL) was added 4N HCl in dioxane (0.5 mL). The reaction was stirred at about room temperature overnight. The solvents were evaporated under reduced pressure. The crude residue was taken up in a minimal amount of MeOH and the solids were crashed out with ether. 15 mg of the material was taken up in MeOH and basified with 7N ammonia in MeOH. The solids, after concentration, were purified by column chromatography (5% MeOH/DCM then 5% 7N NH₄ in MeOH/DCM) to give the free base, which was taken up in DCM and acidified with 2N HCl in ether to yield (S)-5-chloro-1-((R)-5-methyl-6,7-dihydro-5H-cyclopenta[d]pyrimidin-4-yl)spiro[indoline-3,3'-pyrrolidine]dihydrochloride (0.088 g, 100%). LCMS (APCI+) m/z 341, 343 [M+H]+; Rt=2.34 min.

Example 16

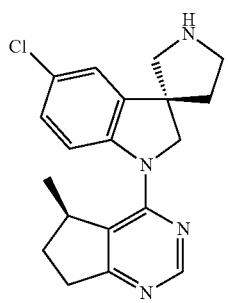

(R)-5-chloro-1-((R)-5-methyl-6,7-dihydro-5H-cyclopenta[d]pyrimidin-4-yl)spiro[indoline-3,3'-pyrrolidine]

(R)-5-chloro-1-((R)-5-methyl-6,7-dihydro-5H-cyclopenta[d]pyrimidin-4-yl)spiro[indoline-3,3'-pyrrolidine]dihydrochloride was prepared by the procedures described in Example 1, Step 9, substituting (R)-tert-butyl 5-chloro-1-(5-methyl-6,7-dihydro-5H-cyclopenta[d]pyrimidin-4-yl)spiro[indoline-3,4'-piperidine]-1'-carboxyl ate with (R)-tert-butyl 5-chloro-1-((R)-5-methyl-6,7-dihydro-5H-cyclopenta[d]pyrimidin-4-yl)spiro[indoline-3,3'-pyrrolidine]-1'-carboxylate. LCMS (APCI+) m/z 341, 343 [M+H]+; Rt=2.31 min.

Example 17

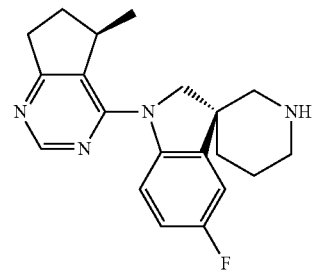

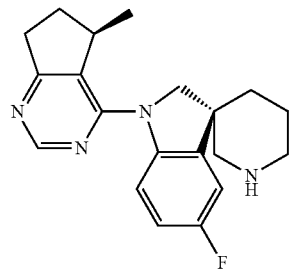

(R)-4-((R)-5-fluorospiro[indoline-3,3'-piperidine]-1-yl)-5-methyl-6,7-dihydro-5H-cyclopenta[d]pyrimidine and (R'-4-((S)-5-fluorospiro[indoline-3,3'-piperidine]-1-yl)-5-methyl-6,7-dihydro-5H-cyclopenta[d]pyrimidine Step 1: Trimethylaluminium (2.0 M in hexanes, 3.98 mL, 7.96 mmol) was added dropwise to a solution of 2-bromo-4-fluoroaniline (1.26 g, 6.63 mmol) in DCM (15 mL) under N₂. After gas evolution ceased, 1-tert-butyl 3-methyl 5,6-dihydropyridine-1,3(2H)-dicarboxylate (1.60 g, 6.63 mmol) in DCM (10 mL) was added and the resulting mixture was refluxed overnight. After cooling to about 0° C., the reaction was quenched by the addition of saturated aqueous NaHCO₃ solution. The organic layer was separated. The aqueous phase was extracted with DCM. The combined organic layers were washed with brine, dried and concentrated. The residue was purified by column chromatography (hexanes:EtOAc, 6:1) to give tert-butyl 3-(2-bromo-4-fluorophenylcarbamoyl)-5,6-dihydropyridine-1(2H)-carboxylate (1.33 g, 50%) as a yellow oil. ¹H NMR (CDCl₃, 400 MHz) δ 8.36 (dd, J=9.2, 6.0

Hz, 1H), 7.87 (br s, 1H), 7.32 (dd, J=7.6, 2.8 Hz, 1H), 7.07 (ddd, J=9.2, 6.0, 2.8 Hz, 1H), 6.82 (br s, 1H), 4.27 (s, 2H), 3.54 (t, J=6.0 Hz, 2H), 2.38 (m, 2H), 1.49 (s, 9H).

Step 2: To a stirred solution of tert-butyl 3-(2-bromo-4-fluorophenylcarbamoyl)-5,6-dihydropyridine-1(2H)-carboxylate (1.30 g, 3.56 mmol) in DMF (18 mL) under N$_2$ was added successively Et$_3$N (1.13 mL, 8.14 mmol), tetrabutylammonium bromide (1.26 g, 3.91 mmol) and Pd(OAc)$_2$ (0.146 g, 0.651 mmol). The resulting mixture was heated at about 100° C. for 3 h. After cooling, the reaction mixture was partitioned between EtOAc and water. The aqueous phase was extracted with EtOAc. The combined organic layers were washed with 1N HCl and brine, dried and concentrated. The residue was purified by column chromatography (hexanes:EtOAc, 4:1) to give tert-butyl 5-fluoro-2-oxo-2',4'-dihydro-1'H-spiro[indoline-3,3'-pyridine]-1'-carboxylate (0.80 g, 77%). LCMS (APCI+) m/z 219 [M+H-Boc]$^+$; Rt=3.41 min.

Step 3: A solution of tert-butyl 5-fluoro-2-oxo-2,4'-dihydro-1'H-spiro[indoline-3,3'-pyridine]-1'-carboxylate (4.0 g, 13 mmol) in THF (50 mL) was hydrogenated at 50 psi in the presence of 5% Pd/C (1.3 g) overnight. The mixture was filtered. Evaporation of the solvent gave tert-butyl 5-fluoro-2-oxospiro[indoline-3,3'-piperidine]-1'-carboxylate (3.9 g, 97%) as an oil. LCMS (APCI+) m/z 221 [M+H-Boc]$^+$; Rt=3.21 min.

Step 4: To a stirred solution of tert-butyl 5-fluoro-2-oxospiro[indoline-3,3'-piperidine]-1'-carboxylate (0.80 g, 2.5 mmol) in toluene (20 mL) was added dropwise a solution of sodium bis(2-methoxyethoxy) aluminium hybrid (Red-Al) in toluene (65% w/w, 1.1 mL, 3.5 mmol) at about 70° C. under N$_2$. The reaction mixture was stirred at about 75° C. for 3 h. After cooling, the reaction mixture was quenched with EtOAc and concentrated in vacuo. The residue was diluted with EtOAc, washed with water and brine, dried and concentrated. The residue was purified by column chromatography (hexane:EtOAc, 3:1) to give tert-butyl 5-fluorospiro[indoline-3,3'-piperidine]-1'-carboxylate (0.18 g, 24%) as an oil. LCMS (APCI+) m/z 307 [M+H]$^+$; Rt=3.66 min.

Step 5: tert-butyl 5-fluoro-1-((R)-5-methyl-6,7-dihydro-5H-cyclopenta[d]pyrimidin-4-yl)spiro[indoline-3,3'-piperidine]-1'-carboxylate was prepared by the procedures described in Example 1, Step 8, substituting tert-butyl 5-chlorospiro[indoline-3,4'-piperidine]-1'-carboxylate with tert-butyl 5-fluorospiro[indoline-3,3'-piperidine]-1'-carboxylate. LCMS (APCI+) m/z 439 [M+H]$^+$; Rt=4.06, 4.35 min.

Step 6: To a solution of tert-butyl 5-fluoro-1-((R)-5-methyl-6,7-dihydro-5H-cyclopenta[d]pyrimidin-4-yl)spiro[indoline-3,3'-piperidine]-1'-carboxylate (0.110 g, 0.251 mmol) in DCM (3 mL) was added 4N HCl in dioxane (0.63 mL). The reaction mixture was stirred overnight and then filtered. Evaporation of the mother liquid gave (R)-4-((S)-5-fluorospiro[indoline-3,3'-piperidine]-1-yl)-5-methyl-6,7-dihydro-5H-cyclopenta[d]pyrimidine dihydrochlorid. LCMS (APCI+) m/z 339 [M+H]$^+$; Rt=2.29 min. The solid collected by filtration was suspended in 5:1 MeCN/MeOH (1 mL) and heated at reflux for about 5 minutes. After cooling, the precipitated solid was filtered and dried in air to give (R)-4-((R)-5-fluorospiro[indoline-3,3'-piperidine]-1-yl)-5-methyl-6,7-dihydro-5H-cyclopenta[d]pyrimidine dihydrochloride. LCMS (APCI+) m/z 339 [M+H]$^+$; Rt=2.31 min.

Example 18

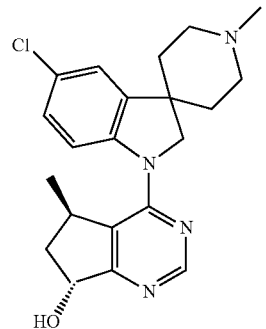

(5R,7R)-4-(5-chloro-1'-methylspiro[indoline-3,4'-piperidine]-1-yl)-5-methyl-6,7-dihydro-5H-cyclopenta[d]pyrimidin-7-ol To a stirred suspension of (5R,7R)-4-(5-chlorospiro[indoline-3,4'-piperidine]-1-yl)-5-methyl-6,7-dihydro-5H-cyclopenta[d]pyrimidin-7-ol dihydrochloride (10 mg, 0.027 mmol) in DCE (0.5 mL) was added DIEA (0.009 mL, 0.05 mmol). The suspension was shaken until dissolved. Formaldehyde (37% w/w in water, 0.022 mL, 0.27 mmol) was added as a solution in THF (0.15 mL) The reaction was allowed to stir at about room temperature for about 15 minutes at which point Na(OAc)$_3$BH was added and the reaction allowed to stir overnight. The reaction mixture was diluted with DCM, washed with saturated aqueous NaHCO$_3$ solution and brine, dried and concentrated. The residue was purified by column chromatography (DCM:MeOH, 8:1) to give the free base, which was taken up in DCM and acidified with 2N HCl in ether. Removal of the solvents under reduced pressure afforded (5R,7R)-4-(5-chloro-1'-methylspiro[indoline-3,41-piperidine]-1-yl)-5-methyl-6,7-dihydro-5H-cyclopenta[d]pyrimidin-7-ol dihydrochloride. LCMS (APCI+) m/z 385, 387 [M+H]$^+$; Rt=2.18 min.

Example 19

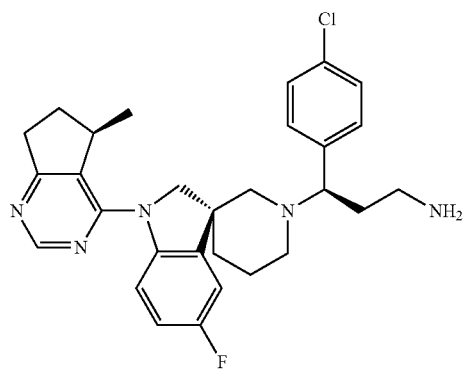

-continued

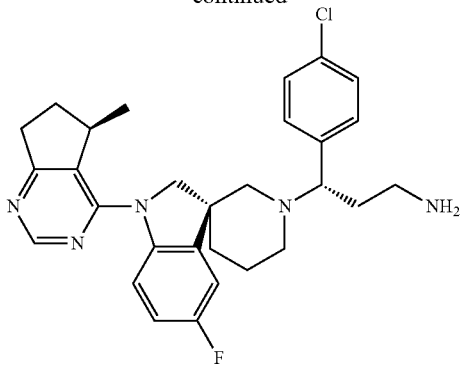

(R)-3-(4-chlorophenyl)-3-((R)-5-fluoro-1-((R)-5-methyl-6,7-dihydro-5H-cyclopenta[d]pyrimidin-4-yl)spiro[indoline-3,3'-piperidine]-1'-yl)propan-1-amine and (S)-3-(4-chlorophenyl)-3-((R)-5-fluoro-1-((R)-5-methyl-6,7-dihydro-5H-cyclopenta[d]pyrimidin-4-yl)spiro[indoline-3,3'-piperidine]-1'-yl)propan-1-amine Step 1: To an ice cooled solution of LAH (1.0 M solution in THF, 54 mL, 54 mmol) was added dropwise a solution of 3-(4-chlorophenyl)-3-oxopropanenitrile (3.20 g, 17.8 mmol) in THF (20 mL). The mixture was allowed to react at about 0° C. for 1 hour followed by reflux overnight. The solution was cooled to about 0° C. and the excess of LAH was quenched with water (2.0 mL) followed by 15% aqueous NaOH solution (2.0 mL) and water (6.0 mL) The mixture was diluted with $Et_2O$ (100 mL) and stirred at about room temperature for about 10 min. The mixture was filtered and the filtrate evaporated in vacuo. The residue was dissolved in DCM (35 mL). $Et_3N$ (3.7 mL, 20 mmol) was added followed by a solution of $Boc_2O$ (2.7 g, 27 mmol) in DCM (10 mL) The reaction was allowed to stir at about room temperature overnight. The mixture was washed with 2N HCl solution, saturated aqueous $NaHCO_3$ solution, water and brine successively, dried and concentrated. The residue was purified by column chromatography (hexanes:EtOAc, 1:1) to give tert-butyl 3-(4-chlorophenyl)-3-hydroxypropylcarbamate (3.0 g, 59%) as a solid. $^1H$ NMR ($CDCl_3$, 400 MHz) δ 7.30 (m, 4H), 4.85 (m, 1H), 4.72 (m, 1H), 3.48 (m, 2H), 1.81 (m, 2H), 1.46 (s, 9H).

Step 2: Triphenylphosphine (1.61 g, 6.12 mmol) was added to a solution of tert-butyl 3-(4-chlorophenyl)-3-hydroxypropylcarbamate (1.40 g, 4.90 mmol) in DCM (30 mL) at about 0° C. NBS (1.05 g, 5.88 mmol) was added portionwise. After 2 h, the reaction mixture was loaded to a short silica gel pad and eluted with EtOAc:hexanes (1:5) to give tert-butyl 3-bromo-3-(4-chlorophenyl)propylcarbamate (0.79 g, 46%) as an oil, which solidified on standing. $^1H$ NMR ($CDCl_3$, 400 MHz) δ 7.35 (m, 4H), 4.96 (m, 1H), 4.63 (br s, 1H), 3.28 (m, 2H), 3.21 (m, 1H), 2.37 (m, 2H), 1.44 (s, 9H).

Step 3: To a stirred solution of (R)-4-(R)-5-fluorospiro[indoline-3,3'-piperidine]-1-yl)-5-methyl-6,7-dihydro-5H-cyclopenta[d]pyrimidine dihydrochloride (85 mg, 0.25 mmol) and $Et_3N$ (0.14 mL, 1.0 mmol) in DMF (1 mL) was added a solution of tert-butyl 3-bromo-3-(4-chlorophenyl)propylcarbamate (96 mg, 0.28 mmol) in DMF (0.5 mL). The reaction mixture was heated at about 80° C. for 5 days. After cooling, the reaction mixture was partitioned between EtOAc and water. The aqueous layer was extracted with EtOAc. The combined organic layers were washed with brine, dried and concentrated to give crude tert-butyl 3-(4-chlorophenyl)-3-((R)-5-fluoro-1-((R)-5-methyl-6,7-dihydro-5H-cyclopenta[d]pyrimidin-4-yl)spiro[indoline-3,3'-piperidine]-1'-yl)propylcarbamate as a mixture of two diastereomers. The residue was purified by column chromatography (hexanes:EtOAc, 2:1) to give the less polar diastereomer D1 (50 mg, 66%). LCMS (APCI+) m/z 606, 608 [M+H]$^+$; Rt=4.76 min. Further elution with 2:1 EtOAc:hexanes gave the second diastereomer D2 (12 mg, 16%). LCMS (APCI+) m/z 606, 608 [M+H]$^+$; Rt=4.61 min.

Step 4: (R)-3-(4-chlorophenyl)-3-(R)-5-fluoro-1-((R)-5-methyl-6,7-dihydro-5H-cyclopenta[d]pyrimidin-4-yl)spiro[indoline-3,3'-piperidine]-1'-yl)propan-1-amine trihydrochloride and (S)-3-(4-chlorophenyl)-3-((R)-5-fluoro-1-((R)-5-methyl-6,7-dihydro-5H-cyclopenta[d]pyrimidin-4-yl)spiro[indoline-3,3'-piperidine]-1'-yl)propan-1-amine trihydrochloride were prepared by the procedures described in Example 1, Step 9, substituting (R)-tert-butyl 5-chloro-1-(5-methyl-6,7-dihydro-5H-cyclopenta[d]pyrimidin-4-yl)spiro[indoline-3,4'-piperidine]-1'-carboxylate with tert-butyl (R)-3-(4-chlorophenyl)-3-((R)-5-fluoro-1-((R)-5-methyl-6,7-dihydro-5H-cyclopenta[d]pyrimidin-4-yl)spiro[indoline-3,3'-piperidine]-1'-yl)propylcarbamate and tert-butyl (S)-3-(4-chlorophenyl)-3-((R)-5-fluoro-1-((R)-5-methyl-6,7-dihydro-5H-cyclopenta[d]pyrimidin-4-yl)spiro[indoline-3,3'-piperidine]-1'-yl)propylcarbamate, respectively. Diastereomer D1: LCMS (APCI+) m/z 506, 508 [M+H]$^+$; Rt=1.66 min. Diastereomer D2: LCMS (APCI+) m/z 506, 508 [M+H]$^+$; Rt=1.63 min.

Example 20

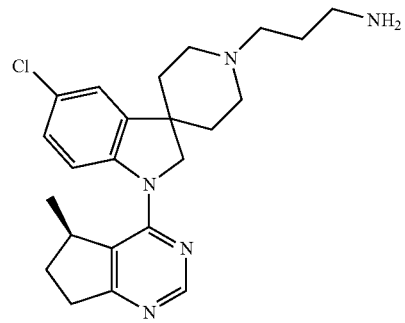

(R)-3-(5-chloro-1-(5-methyl-6,7-dihydro-5H-cyclopenta[d]pyrimidin-4-yl)spiro[indoline-3,4'-piperidine]-1'-yl)propan-1-amine Step 1: A mixture of (R)-5-chloro-1-(5-methyl-6,7-dihydro-5H-cyclopenta[d]pyrimidin-4-yl)spiro[indoline-3,4'-piperidine]dihydrochloride (15 mg, 0.035 mmol), 2-(3-bromopropyl)isoindoline-1,3-dione (13 mg, 0.049 mmol), DIEA (0.018 mL, 0.11 mmol) and DMF (0.5 mL) was heated at about 150° C. in microwave for about 30 min. After cooling, the reaction mixture was partitioned between EtOAc and water. The aqueous phase was extracted with EtOAc. The combined organic layers were washed with water and brine, dried and concentrated. The residue was purified by column chromatography (DCM:MeOH, 20:1) to give (R)-2-(3-(5-chloro-1-(5-methyl-6,7-dihydro-5H-cyclopenta[d]pyrimidin-4-yl)spiro[indoline-3,4'-piperidine]-1'-yl)propyl)isoindoline-1,3-dione (12 mg, 63%). LCMS (APCI+) m/z 542, 544 [M+H]$^+$; Rt=3.79 min.

Step 2: A mixture of (R)-2-(3-(5-chloro-1-(5-methyl-6,7-dihydro-5H-cyclopenta[d]pyrimidin-4-yl)spiro[indoline-3,4'-piperidine]-1'-yl)propyl)isoindoline-1,3-dione (9 mg, 0.02 mmol) and 2M MeNH$_2$ in MeOH (0.5 mL) was stirred at about room temperature overnight. The solvent was evaporated. The residue was purified by column chromatography (DCM:7N ammonia in MeOH, 8:1) to give (R)-3-(5-chloro-1-(5-methyl-6,7-dihydro-5H-cyclopenta[d]pyrimidin-4-yl)spiro[indoline-3,4'-piperidine]-1'-yl)propan-1-amine as a free base, which was taken up in DCM and acidified with 2N HCl in ether. Removal of the solvents under reduced pressure afforded (R)-3-(5-chloro-1-(5-methyl-6,7-dihydro-5H-cyclopenta[d]pyrimidin-4-yl)spiro[indoline-3,4'-piperidine]-1'-yl)propan-1-amine trihydrochloride (5 mg, 74%) as a solid. LCMS (APCI+) m/z 412, 414 [M+H]$^+$; Rt=2.47 min.

Example 21

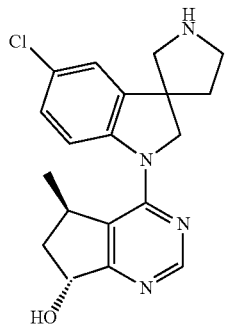

(5R,7R)-4-(5-chlorospiro[indoline-3,3'-pyrrolidine]-1-yl)-5-methyl-6,7-dihydro-5H-cyclopenta[d]pyrimidin-7-ol Step 1: tert-butyl 5-chloro-1-((5R,7R)-5-methyl-7-(4-nitrobenzoyloxy)-6,7-dihydro-5H-cyclopenta[d]pyrimidin-4-yl)spiro[indoline-3,3'-pyrrolidine]-1'-carboxylate was prepared by the procedures described in Example 1, Step 8, substituting (R)-4-chloro-5-methyl-6,7-dihydro-5H-cyclopenta[d]pyrimidine with (5R,7R)-4-chloro-5-methyl-6,7-dihydro-5H-cyclopenta[d]pyrimidin-7-yl 4-nitrobenzoate, and substituting tert-butyl 5-chloro spiro[indoline-3,4'-piperidine]-1'-carboxylate with tert-butyl 5-chlorospiro[indoline-3,3'-pyrrolidine]-1'-carboxylate. LCMS (APCI+) m/z 339.1 [M+H-Boc-pNO$_2$ benzoic acid]$^+$; Rt=4.74 min.

Step 2: tert-butyl 5-chloro-1-((5R,7R)-7-hydroxy-5-methyl-6,7-dihydro-5H-cyclopenta[d]pyrimidin-4-yl)spiro[indoline-3,3'-pyrrolidine]-1'-carboxylate was prepared by the procedures described in Example 3, Step 12, substituting tert-butyl 5-chloro-1-((5R,7R)-5-methyl-7-(4-nitrobenzoyloxy)-6,7-dihydro-5H-cyclopenta[d]pyrimidin-4-yl)spiro[indoline-3,4'-piperidine]-1'-carboxylate with tert-butyl 5-chloro-1-((5R,7R)-5-methyl-7-(4-nitrobenzoyloxy)-6,7-dihydro-5H-cyclopenta[d]pyrimidin-4-yl)spiro[indoline-3,3'-pyrrolidine]-1'-carboxylate. LCMS (APCI+) m/z 357.1 [M+H-Boc]$^+$; Rt=3.86.

Step 3: (5R,7R)-4-(5-chlorospiro[indoline-3,3'-pyrrolidine]-1-yl)-5-methyl-6,7-dihydro-5H-cyclopenta[d]pyrimidin-7-ol dihydrochloride was prepared as a mixture of two diastereomers by the procedures described in Example 1, Step 9, substituting (R)-tert-butyl 5-chloro-1-((5-methyl-6,7-dihydro-5H-cyclopenta[d]pyrimidin-4-yl)spiro[indoline-3,4'-piperidine]-1'-carboxylate with tert-butyl 5-chloro-1-((5R,7R)-7-hydroxy-5-methyl-6,7-dihydro-5H-cyclopenta[d]pyrimidin-4-yl)spiro[indoline-3,3'-pyrrolidine]-1'-carboxylate. LCMS (APCI+) m/z 357.2 [M+H]$^+$; Rt=1.09, 2.09 min.

Example 22

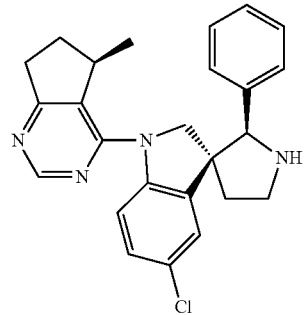

(2'R,3S)-5-chloro-1-((R)-5-methyl-6,7-dihydro-5H-cyclopenta[d]pyrimidin-4-yl)-2'-phenylspiro[indoline-3,3'-pyrrolidine]

Step 1: To a solution of 2-(5-chloro-1H-indol-3-yl)ethanamine (1.67 g, 8.58 mmol) in DCM (43 mL) was added benzaldehyde (0.96 g, 9.0 mmol). The reaction mixture was stirred over molecular sieves 4 Å (4.1 g) overnight. The mixture was filtered through Celite. The filtrate was concentrated in vacuo. The crude product was dissolved in DCM (35 mL) A solution of (−)-Ipc$_2$BCl (12.3 g, 38.2 mmol) in DCM (40 mL) was added to the reaction mixture. The resulting solution was stirred at about room temperature for about 3 days. Aqueous 15% NaOH solution (50 mL) was added and the mixture was stirred for about 15 min. The organic layer was separated. The aqueous layer was extracted with DCM. The combined organic layers were washed with brine, dried and concentrated. The residue was purified by column chromatography (hexane:EtOAc, 1:1) to give the less polar product (2'R,3S)-5-chloro-2'-phenylspiro[indoline-3,3'-pyrrolidine] (0.73 g, 35%). Further elution with EtOAc gave the other diastereomer (2'S,3S)-5-chloro-2'-phenylspiro[indoline-3,3'-pyrrolidine] (0.50 g, 24%). LCMS (APCI+) m/z 285, 287 [M+H]$^+$; Rt=2.35 min.

Step 2: To a stirred solution of (2'R,3S)-5-chloro-2'-phenylspiro[indoline-3,3'-pyrrolidine] (0.73 g, 2.6 mmol) in DCM (15 mL) was added Et$_3$N (0.54 mL). A solution of Boc$_2$O (0.62 g, 2.8 mmol) in DCM (10 mL) was added dropwise. The reaction was stirred at about room temperature overnight. The reaction mixture was washed with saturated aqueous NaHCO$_3$ solution and brine, dried and concentrated. The residue was purified by column chromatography (hexanes:EtOAc, 4:1) to give (2'R,3S)-tert-butyl 5-chloro-2'-phenylspiro[indoline-3,3'-pyrrolidine]-1'-carboxylate (0.75 g, 76%) as a solid. LCMS (APCI+) m/z 385, 387 [M+H]$^+$; Rt=4.34 min.

Step 3: (2'R,3S)-tert-butyl 5-chloro-1-((R)-5-methyl-6,7-dihydro-5H-cyclopenta[d]pyrimidin-4-yl)-2'-phenyl spiro[indoline-3,3'-pyrrolidine]-1'-carboxylate was prepared by the procedures described in Example 1, Step 8, substituting tert-butyl 5-chloro spiro[indoline-3,4'-piperidine]-1'-carboxylate with (2'R,3S)-tert-butyl 5-chloro-2'-phenylspiro[indoline-3,3'-pyrrolidine]-1'-carboxylate. LCMS (APCI+) m/z 417, 419 [M+H-Boc]⁺; Rt=4.92 min.

Step 4: (2'R,3S)-5-chloro-1-((R)-5-methyl-6,7-dihydro-5H-cyclopenta[d]pyrimidin-4-yl)-2'-phenyl spiro[indoline-3,3'-pyrrolidine]dihydrochloride was prepared by the procedures described in Example 1, Step 9, substituting (R)-tert-butyl 5-chloro-1-(5-methyl-6,7-dihydro-5H-cyclopenta[d]pyrimidin-4-yl)spiro[indoline-3,4'-piperidine]-1'-carboxylate with (2'R,3S)-tert-butyl 5-chloro-1-((R)-5-methyl-6,7-dihydro-5H-cyclopenta[d]pyrimidin-4-yl)-2'-phenylspiro[indoline-3,3'-pyrrolidine]-1'-carboxylate. LCMS (APCI+) m/z 417, 419 [M+H]⁺; Rt=3.44 min.

Example 23

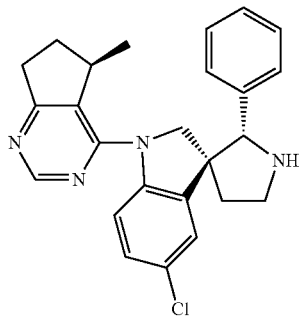

(2'S,3S)-5-chloro-1-((R)-5-methyl-6,7-dihydro-5H-1-cyclopenta[d]pyrimidin-4-yl)-2'-phenylspiro[indoline-3,3'-pyrrolidine]

(2'S,3S)-5-chloro-1-((R)-5-methyl-6,7-dihydro-5H-cyclopenta[d]pyrimidin-4-yl)-2'-phenylspiro[indoline-3,3'-pyrrolidine]dihydrochloride was prepared by the procedures described in Example 22, Step 2 to 4, substituting (2'R,3S)-5-chloro-2'-phenylspiro[indoline-3,3'-pyrrolidine] with (2'S,3S)-5-chloro-2'-phenylspiro[indoline-3,3'-pyrrolidine]. LCMS (APCI+) m/z 417, 419 [M+H]⁺; Rt=3.49 min.

Example 24

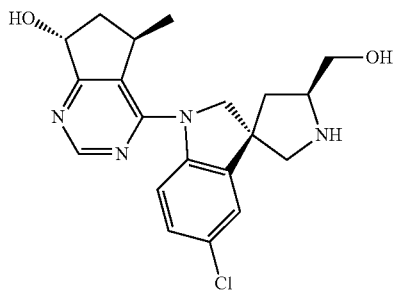

(5R,7R)-4-((3S,5'S)-5'-(hydroxymethyl)spiro[indoline-3,3'-pyrrolidine]-1-yl)-5-methyl-6,7-dihydro-5H-cyclopenta[d]pyrimidin-7-ol Step 1: To a stirred solution of (5'S)-methyl 2-oxospiro[indoline-3,3'-pyrrolidine]-5'-carboxylate (prepared from (S)-methyl 2-amino-3-(1H-indol-3-yl)propanoate hydrochloride according to the literature: Claudio Pellegrini et al. (1994) *Tetrahydron: Asymmetry*, 5, 1979-1992, 4.30 g, 17.5 mmol) in DCM (60 mL) was added Et₃N (3.65 mL, 26.2 mmol). A solution of Boc₂O (4.19 g, 19.2 mmol) in DCM (20 mL) was added dropwise. The reaction mixture was stirred at about room temperature overnight. The organic layer was washed with saturated aqueous NaHCO₃ solution and brine, dried and concentrated. The residue was purified by column chromatography (hexane:EtOAc, 3:1) to give the less polar diastereomer (3S,5'S)-1'-tert-butyl 5'-methyl 2-oxospiro[indoline-3,3'-pyrrolidine]-1',5'-dicarboxylate (1.80 g, 30%) followed the other diastereomer (3R,5'S)-1'-tert-butyl 5'-methyl 2-oxospiro[indoline-3,3'-pyrrolidine]-1',5'-dicarboxylate (1.38 g, 23%). LCMS (APCI+) m/z 347 [M+H]⁺; Rt=3.24 min.

Step 2: (3R,5'S)-tert-butyl 5'-(hydroxymethyl)spiro[indoline-3,3'-pyrrolidine]-1'-carboxylate was prepared by the procedures described in Example 15, Step 4, substituting tert-butyl 5-chloro-2-oxo spiro[indoline-3,3'-pyrrolidine]-1'-carboxylate with (3S,5'S)-1'-tert-butyl 5'-methyl 2-oxospiro[indoline-3,3'-pyrrolidine]-1',5'-dicarboxylate. LCMS (APCI+) m/z 305 [M+H]⁺; Rt=3.12 min.

Step 3: (5R,7R)-4-((3S,5'S)-5'-(hydroxymethyl)spiro[indoline-3,3'-pyrrolidine]-1-yl)-5-methyl-6,7-dihydro-5H-cyclopenta[d]pyrimidin-7-ol dihydro chloride was prepared by the procedures described in Example 21, Step 1 to 3, substituting tert-butyl 5-chlorospiro[indoline-3,3'-pyrrolidine]-1'-carboxylate with (3R,5'S)-tert-butyl 5'-(hydroxymethyl)spiro[indoline-3,3'-pyrrolidine]-1'-carboxylate. LCMS (APCI+) m/z 353 [M+H]⁺; Rt=2.07 min.

Example 25

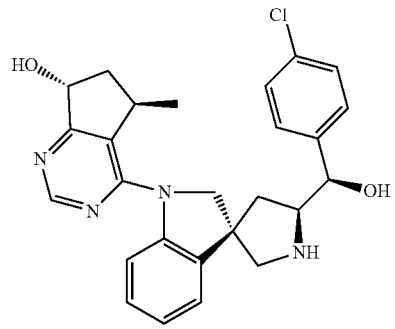

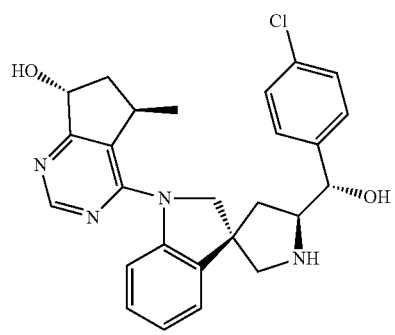

(5R,7R)-4-((3S,5'S)-5'-((R)-(4-chlorophenyl)(hydroxy)methyl)spiro[indoline-3,3'-pyrrolidine]-1-yl)-5-methyl-6,7-dihydro-5H-cyclopenta[d]pyrimidin-7-ol and (5R,7R)-4-((3S,5'S)-5'-((S)-(4-chlorophenyl)(hydroxy)methyl)spiro[indoline-3,3'-pyrrolidine]-1-yl)-5-methyl-6,7-dihydro-5H-cyclopenta[d]pyrimidin-7-ol Step 1: (3S,5'S)-1'-(tert-butoxycarbonyl)-2-oxo spiro[indoline-3,3'-pyrrolidine]-5'-carboxylic acid was prepared by the procedures described in Example 10, Step 4, substituting (R)-tert-butyl 5-(2-ethoxy-2-oxoethyl)-1-(5-methyl-6,7-dihydro-5H-cyclopenta[d]pyrimidin-4-yl)spiro[indoline-3,4'-piperidine]-1'-carboxylate with (3S,5'S)-1'-tert-butyl 5'-methyl 2-oxospiro[indoline-3,3'-pyrrolidine]-1',5'-dicarboxylate. LCMS (APCI+) m/z 333 [M+H]⁺; Rt=1.98 min.

Step 2: (3S,5'S)-tert-butyl 5'-(methoxy(methyl)carbamoyl)-2-oxospiro[indoline-3,3'-pyrrolidine]-1'-carboxylate was prepared by the procedures described in Example 10, Step 5, substituting (R)-2-(1'-(tert-butoxycarbonyl)-1-(5-methyl-6,7-dihydro-5H-cyclopenta[d]pyrimidin-4-yl)spiro[indoline-3,4'-piperidine]-5-yl)acetic acid with (3S,5'S)-1'-(tert-butoxycarbonyl)-2-oxospiro[indoline-3,3'-pyrrolidine]-5'-carboxylic acid, and substituting NH₄Cl with N,O-dimethylhydroxylamine hydrochloride. LCMS (APCI+) m/z 376 [M+H]⁺; Rt=2.88 min.

Step 3: To a stirred solution of (3S,5'S)-tert-butyl 5'-(methoxy(methyl)carbamoyl)-2-oxospiro[indoline-3,3'-pyrrolidine]-1'-carboxylate (310 mg, 0.826 mmol) in THF (4 mL) was added 4-chloro phenylmagnesium bromide (1.0 N in THF, 2.89 mL, 2.89 mmol) at about 0° C. The reaction mixture was warmed to about room temperature and stirred overnight. The reaction was quenched with saturated aqueous NH₄Cl solution and extracted with EtOAc. The combined organic layers were washed with brine, dried and concentrated. The crude product was purified by column chromatography (hexanes:EtOAc, 1:1) to give (3S,5'S)-tert-butyl 5'-(4-chlorobenzoyl)-2-oxospiro[indoline-3,3'-pyrrolidine]-1'-carboxylate (0.240 g, 68%). LCMS (APCI+) m/z 427, 429 [M+H]⁺; Rt=3.94 min.

Step 4: (3R,5'S)-tert-butyl 5'-((4-chlorophenyl)(hydroxy)methyl)spiro[indoline-3,3'-pyrrolidine]-1'-carboxylate was prepared as a mixture of two diastereomers by the procedures described in Example 15, Step 4, substituting tert-butyl 5-chloro-2-oxospiro[indoline-3,3'-pyrrolidine]-1'-carboxylate with (3S,5'S)-tert-butyl 5'-(4-chlorobenzoyl)-2-oxo spiro[indoline-3,3'-pyrrolidine]-1'-carboxylate. The two diastereomers were separated by column chromatography eluting with 25% EtOAc/hexane. LCMS (APCI+) m/z 415, 417 [M+H]⁺; Rt=4.04, 4.08 min.

Step 5: (5R,7R)-4-((3S,5'S)-5'-((R)-(4-chlorophenyl)(hydroxy)methyl)spiro[indoline-3,3'-pyrrolidine]-1-yl)-5-methyl-6,7-dihydro-5H-cyclopenta[d]pyrimidin-7-ol dihydrochloride and (5R,7R)-4-((3S,5'S)-5'-((R)-(4-chlorophenyl)(hydroxy)methyl)spiro[indoline-3,3'-pyrrolidine]-1-yl)-5-methyl-6,7-dihydro-5H-cyclopenta[d]pyrimidin-7-ol dihydrochloride were prepared by the procedures described in Example 21, Step 1 to 3, substituting tert-butyl 5-chlorospiro[indoline-3,3'-pyrrolidine]-1'-carboxylate with (3R,5'S)-tert-butyl 5'-((R)-(4-chlorophenyl)(hydroxy)methyl)spiro[indoline-3,3'-pyrrolidine]-1'-carboxylate and (3R,5'S)-tert-butyl 5'-((R)-(4-chlorophenyl)(hydroxy)methyl)spiro[indoline-3,3'-pyrrolidine]-1'-carboxylate, respectively. The configuration of the hydroxyl groups at the benzylic position was arbitrarily assigned. LCMS (APCI+) m/z 463, 465 [M+H]⁺; Rt=2.68, 2.74 min.

Example 26

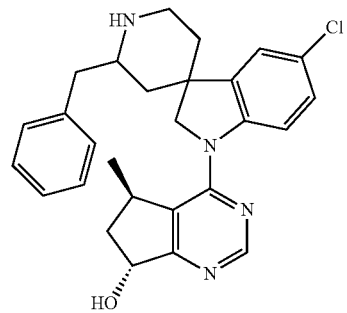

(5R,7R)-4-(2'-benzyl-5-chlorospiro[indoline-3,4'-piperidine]-1-yl)-5-methyl-6,7-dihydro-5H-cyclopenta[d]pyrimidin-7-ol Step 1: Potassium tert-butoxide (4.49 mL, 1M in THF) was added over about 5 minutes to (methoxymethyl) triphenylphosphonium chloride (1.42 g, 4.15 mmol) suspended in anhydrous THF (25 mL) at 0° C. The resulting suspension was stirred at about this temperature for about 45 minutes at which time, tert-butyl 2-benzyl-4-oxopiperidine-1-carboxylate (1.0 g, 3.46 mmol) dissolved in THF (5 mL) was added. The reaction mixture was allowed to warm to ambient and stir for another 6 h. The reaction was quenched by the addition of ammonium chloride solution and then taken up in EtOAc. After washing twice with water and once with brine, the organic portion was dried over magnesium sulfate, filtered and concentrated. The resulting semi-solid residue was purified via silica gel chromatography to give (Z)-tert-butyl 2-benzyl-4-(methoxymethylene)piperidine-1-carboxylate (375 mg, 34%). LCMS (APCI+) m/z 218.1 [M+H]⁺; Rt=4.51 min.

Step 2: Tert-butyl 2-benzyl-4-(methoxymethylene)piperidine-1-carboxylate (274 mg, 0.86 mmol) and (4-chlorophenyl)hydrazine hydrochloride (186 mg, 1.04 mmol) were dissolved in chloroform (10 mL) and then TFA (1.0 mL, 12.98 mmol) was added. The resulting mixture was heated to reflux for 8 h at which time it was cooled to ambient and then quenched by the slow addition of saturated sodium bicarbonate solution. The reaction mixture was dissolved in EtOAc and then washed twice with water and once with brine. The organic portion was dried over magnesium sulfate, filtered and concentrated. The residue was dissolved in dichloromethane (10 mL) and cooled to 0° C. Triethylamine (0.24 mL, 1.73 mmol) was added followed by boc anhydride (189 mg, 0.86 mmol). The resulting solution was warmed ambient and stirred at this temperature for 12 h. At this time, it was taken up in EtOAc and washed twice with water and once with brine. The organic layer was dried over magnesium sulfate, filtered and concentrated. The residue thus obtained was purified via silica gel chromatography to give tert-butyl 2'-benzyl-5-chlorospiro[indole-3,4'-piperidine]-1'-carboxylate as a mixture of diastereomers (220 mg, 62%). LCMS (APCI+) m/z 411.1 [M+H]⁺; Rt=4.56, 4.63 min Step 3: Tert-butyl 2'-benzyl-5-chlorospiro[indole-3,4'-piperidine]-1'-carboxylate (200 mg, 0.49 mmol) was dissolved in dichloromethane (5 mL) and then sodium triacetoxy borohydride (206 mg, 0.97 mmol) was added followed by acetic acid (0.5 mL). The resulting mixture was stirred for 2 h at ambient temperature at which time it was quenched by the addition of saturated sodium bicarbonate solution. The mixture was diluted with EtOAc and then washed twice with water and once with brine. The organic layer was dried over magnesium sulfate, filtered and concentrated to give tert-butyl 2'-benzyl-5-chlorospiro[indoline-3,4'-piperidine]-1'-carboxylate. The material thus obtained was used without further purification (185 mg, 92%). LCMS (APCI+) m/z 311.1; Rt=4.32 min.

Step 4: (5R,7R)-4-(2'-benzyl-5-chlorospiro[indoline-3,4'-piperidine]-1-yl)-5-methyl-6,7-dihydro-5H-cyclopenta[d]pyrimidin-7-ol dihydrochloride was prepared as a mixture of four diastereomers by the procedures described in Example 21, Step 1 to 3, substituting tert-butyl 5-chlorospiro[indoline-3,3'-pyrrolidine]-1'-carboxylate with tert-butyl 2'-benzyl-5-chlorospiro[indoline-3,4'-piperidine]-1'-carboxylate. LCMS (APCI+) m/z 461.3 [M+H]$^+$; Rt=2.42, 2.35, 2.65 and 2.49 min.

Example 27

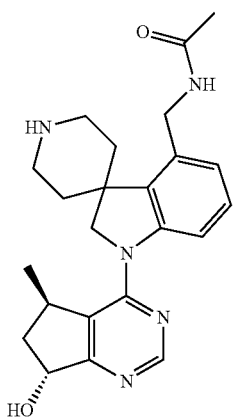

N-((1-((5R,7R)-7-hydroxy-5-methyl-6,7-dihydro-5H-cyclopenta[d]pyrimidin-4-yl)spiro[indoline-3,4'-piperidine]-4-yl)methyl)acetamide Step 1: To a stirred solution of 2-oxoindoline-4-carbonitrile (2.97 g, 18.8 mmol; prepared as described in WO 00/21920) in THF (40 mL) was added dropwise a 1.0 M THF solution of NaHMDS (78.2 mL, 78.2 mmol) at about −78° C. under N$_2$. After stirring at about −78° C. for about 30 min, N-benzylbis(2-chloroethyl)amine hydrochloride (4.20 g, 15.6 mmol) was added as a solid. The reaction mixture was stirred at about −78° C. for about 30 minutes and then allowed to warm to rt. The reaction mixture was then heated at reflux for 2 h. After cooling to about 0° C., the reaction was quenched by the addition of saturated aqueous NH$_4$Cl solution. The reaction mixture was partitioned between EtOAc and water. The aqueous layer was extracted with EtOAc. The combined organic layers were washed with brine, dried and concentrated. The residue was purified by column chromatography (DCM:MeOH, 60:1) to give 1'-benzyl-2-oxo spiro[indoline-3,4'-piperidine]-4-carbonitrile (2.10 g, 42%) as a solid. LCMS (APCI+) m/z 318 [M+H]$^+$; Rt=2.42 min.

Step 2: To a stirred solution of 1'-benzyl-2-oxospiro[indoline-3,4'-piperidine]-4-carbonitrile (0.88 g, 2.8 mmol) in THF (20 mL) was added dropwise a solution of 1N LiAlH$_4$ in THF (11 mL, 11 mmol) at about 0° C. under N$_2$. The reaction mixture was allowed to warm to about room temperature and stirred overnight. The reaction was then heated at reflux for 1 h. After cooling, the reaction was quenched by the dropwise addition of water (0.44 mL), followed by 3N NaOH (0.44 mL) and water (1.3 mL) at about 0° C. The mixture was diluted with Ether and stirred for about 10 min. The reaction mixture was filtered through Celite. The filtrate was concentrated to give crude (1'-benzylspiro[indoline-3,4'-piperidine]-4-yl)methanamine, which was carried forward in the next step without further purification. LCMS (APCI+) m/z 308 [M+H]$^+$; Rt=1.96 min.

Step 3: tert-butyl (1'-benzylspiro[indoline-3,4'-piperidine]-4-yl)methylcarbamate was prepared by the procedures described in Example 24, Step 1, substituting (5'S)-methyl 2-oxospiro[indoline-3,3'-pyrrolidine]-5'-carboxylate with (1'-benzylspiro[indoline-3,4'-piperidine]-4-yl)methanamine. LCMS (APCI+) m/z 408 [M+H]$^+$; Rt=2.98 min.

Step 4: (5R,7R)-4-(1'-benzyl-4-((tert-butoxycarbonylamino)methyl)spiro[indoline-3,4'-piperidine]-1-yl)-5-methyl-6,7-dihydro-5H-cyclopenta[d]pyrimidin-7-yl 4-nitrobenzoate was prepared by the procedures described in Example 1, Step 8, substituting (R)-4-chloro-5-methyl-6,7-dihydro-5H-cyclopenta[d]pyrimidine with (5R,7R)-4-chloro-5-methyl-6,7-dihydro-5H-cyclopenta[d]pyrimidin-7-yl 4-nitrobenzoate, and substituting tert-butyl 5-chlorospiro[indoline-3,4'-piperidine]-1'-carboxylate with tert-butyl (1'-benzylspiro[indoline-3,4'-piperidine]-4-yl)methylcarbamate LCMS (APCI+) m/z 605 [M+H]$^+$; Rt=4.33 min.

Step 5: (5R,7R)-4-(4-(aminomethyl)-1'-benzylspiro[indoline-3,4'-piperidine]-1-yl)-5-methyl-6,7-dihydro-5H-cyclopenta[d]pyrimidin-7-yl 4-nitrobenzoate trihydrochloride was prepared by the procedures described in Example 1, Step 9, substituting (R)-tert-butyl 5-chloro-1-(5-methyl-6,7-dihydro-5H-cyclopenta[d]pyrimidin-4-yl)spiro[indoline-3,4'-piperidine]-1'-carboxylate with (5R,7R)-4-(1'-benzyl-4-((tert-butoxycarbonylamino)methyl)spiro[indoline-3,4'-piperidine]-1-yl)-5-methyl-6,7-dihydro-5H-cyclopenta[d]pyrimidin-7-yl 4-nitrobenzoate. LCMS (APCI+) m/z 605 [M+H]$^+$; Rt=3.26 min.

Step 6: To a stirred solution of (5R,7R)-4-(4-(aminomethyl)-1'-benzylspiro[indoline-3,4'-piperidine]-1-yl)-5-methyl-6,7-dihydro-5H-cyclopenta[d]pyrimidin-7-yl 4-nitrobenzoate trihydrochloride (30 mg, 0.042 mmol) and Et$_3$N (0.034 mL, 0.19 mmol) in DCM (1 mL) was added acetyl chloride (0.0033 mL, 0.046 mmol) at about 0° C. under N$_2$. The reaction was stirred at about 0° C. for about 30 minutes and diluted with DCM. The reaction mixture was washed with saturate aqueous NaHCO$_3$ solution and brine, dried and concentrated. The residue was purified by flash chromatography on silica gel (2% MeOH/DCM) to give (5R,7R)-4-(4-(acetamidomethyl)-1'-benzylspiro[indoline-3,4'-piperidine]-1-yl)-5-methyl-6,7-dihydro-5H-cyclopenta[d]pyrimidin-7-yl 4-nitrobenzoate (28 mg, 68%) as an oil. LCMS (APCI+) m/z 647 [M+H]$^+$; Rt=3.21 min.

Step 7: N-((1'-benzyl-1-((5R,7R)-7-hydroxy-5-methyl-6,7-dihydro-5H-cyclopenta[d]pyrimidin-4-yl)spiro[indoline-3,4'-piperidine]-4-yl)methyl)acetamide was prepared by the procedures described in Example 3, Step 12, substituting (tert-butyl 5-chloro-1-((5R,7R)-5-methyl-7-(4-nitrobenzoyloxy)-6,7-dihydro-5H-cyclopenta[d]pyrimidin-4-yl)spiro[indoline-3,4'-piperidine]-1'-carboxylate with (5R,7R)-4-(4-(acetamidomethyl)-1'-benzylspiro[indoline-3,4'-piperidine]-

1-yl)-5-methyl-6,7-dihydro-5H-cyclopenta[d]pyrimidin-7-yl 4-nitrobenzoate. LCMS (APCI+) m/z 498 [M+H]+; Rt=2.16 min.

Step 8: To a solution of N-((1'-benzyl-1-((5R,7R)-7-hydroxy-5-methyl-6,7-dihydro-5H-cyclopenta[d]pyrimidin-4-yl)spiro[indoline-3,4'-piperidine]-4-yl)methyl)acetamide (19 mg, 0.038 mmol) in MeOH (0.4 mL) was added ammonium formate (24 mg, 0.38 mmol) and 10% Pd/C (4 mg, 20% weight). The mixture was allowed to stir at reflux for 4 h. After cooling, the reaction mixture was filtered through Celite. The filtrate was evaporated in vacuo. The crude residue was purified by column chromatography (4% 7 N ammonia in MeOH/DCM) to yield the free base, which was taken up in DCM and acidified with 2N HCl in Et$_2$O. Removal of the solvents afforded N-((1-((5R,7R)-7-hydroxy-5-methyl-6,7-dihydro-5H-cyclopenta[d]pyrimidin-4-yl)spiro[indoline-3,4'-piperidine]-4-yl)methyl)acetamide dihydrochloride as a solid (12 mg, 77%). LCMS (APCI+) m/z 408 [M+H]+; Rt=1.74 min.

Example 28

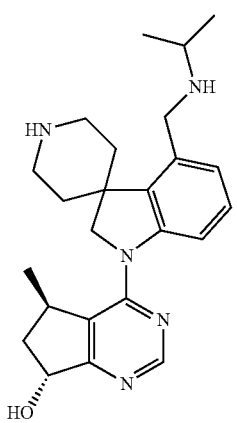

(5R,7R)-4-(4-((isopropylamino)methyl)spiro[indoline-3,4'-piperidine]-1-yl)-5-methyl-6,7-dihydro-5H-cyclopenta[d]pyrimidin-7-ol Step 1: (5R,7R)-4-(1'-benzyl-4-((isopropylamino)methyl)spiro[indoline-3,4'-piperidine]-1-yl)-5-methyl-6,7-dihydro-5H-cyclopenta[d]pyrimidin-7-yl 4-nitrobenzoate was prepared by the procedures described in Example 18, substituting (5R,7R)-4-(5-chlorospiro[indoline-3,4'-piperidine]-1-yl)-5-methyl-6,7-dihydro-5H-cyclopenta[d]pyrimidin-7-ol dihydrochloride with (5R,7R)-4-(4-(aminomethyl)-1'-benzylspiro[indoline-3,4'-piperidine]-1-yl)-5-methyl-6,7-dihydro-5H-cyclopenta[d]pyrimidin-7-yl 4-nitrobenzoate trihydrochloride, and substituting formaldehyde with acetone. LCMS (APCI+) m/z 647 [M+H]+; Rt=3.32 min.

Step 2: (5R,7R)-4-(4-((isopropylamino)methyl)spiro[indoline-3,4'-piperidine]-1-yl)-5-methyl-6,7-dihydro-5H-cyclopenta[d]pyrimidin-7-ol trihydrochloride was prepared by the procedures described in Example 27, Step 7 to 8, substituting (5R,7R)-4-(4-(acetamidomethyl)-1'-benzylspiro[indoline-3,4'-piperidine]-1-yl)-5-methyl-6,7-dihydro-5H-cyclopenta[d]pyrimidin-7-yl 4-nitrobenzoate with (5R,7R)-4-(1'-benzyl-4-((isopropylamino)methyl)spiro[indoline-3,4'-piperidine]-1-yl)-5-methyl-6,7-dihydro-5H-cyclopenta[d]pyrimidin-7-yl 4-nitrobenzoate. LCMS (APCI+) m/z 408 [M+H]+; Rt=1.52 min.

Example 29

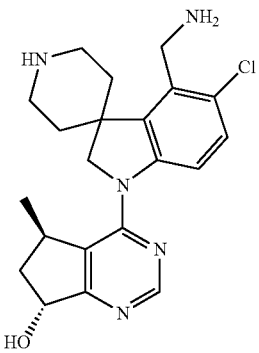

(5R,7R)-4-(4-(aminomethyl)-5-chlorospiro[indoline-3,4'-piperidine]-1-yl)-5-methyl-6,7-dihydro-5H-cyclopenta[d]pyrimidin-7-ol Step 1: To a stirred solution of (5R,7R)-4-(1'-benzyl-4-((tert-butoxycarbonylamino)methyl)spiro[indoline-3,4'-piperidine]-1-yl)-5-methyl-6,7-dihydro-5H-cyclopenta[d]pyrimidin-7-yl 4-nitrobenzoate (30 mg, 0.043 mmol) in toluene (1 mL) was added 1-chloroethyl carbonochloridate (0.009 mL, 0.08 mmol) at about 0° C. The reaction mixture was heated at reflux for 1 h and then evaporated in vacuo. The residue was dissolved in MeOH (1 mL) and the mixture was heated at reflux for 1 h. After cooling, the solvent was evaporated in vacuo to give crude (5R,7R)-4-(4-((tert-butoxycarbonylamino)methyl)spiro[indoline-3,4'-piperidine]-1-yl)-5-methyl-6,7-dihydro-5H-cyclopenta[d]pyrimidin-7-yl 4-nitrobenzoate, which was used in the next step without further purification. LCMS (APCI+) m/z 615 [M+H]+; Rt=3.31 min.

Step 2: tert-butyl 4-((tert-butoxycarbonylamino)methyl)-1-((5R,7R)-5-methyl-7-(4-nitrobenzoyloxy)-6,7-dihydro-5H-cyclopenta[d]pyrimidin-4-yl)spiro[indoline-3,4'-piperidine]-1'-carboxylate was prepared by the procedures described in Example 24, Step 1, substituting (5'S)-methyl 2-oxospiro[indoline-3,3'-pyrrolidine]-5'-carboxylate with (5R,7R)-4-(4-((tert-butoxycarbonylamino)methyl)spiro[indoline-3,4'-piperidine]-1-yl)-5-methyl-6,7-dihydro-5H-cyclopenta[d]pyrimidin-7-yl 4-nitrobenzoate. LCMS (APCI+) m/z 715 [M+H]+; Rt=4.43 min.

Step 3: To a stirred solution of tert-butyl 4-((tert-butoxycarbonylamino)methyl)-1-((5R,7R)-5-methyl-7-(4-nitrobenzoyloxy)-6,7-dihydro-5H-cyclopenta[d]pyrimidin-4-yl)spiro[indoline-3,4'-piperidine]-1'-carboxylate (17 mg, 0.024 mmol) in DCM (0.5 mL) was added 1-chloropyrrolidine-2,5-dione (NCS) (5.7 mg, 0.043 mmol). The reaction mixture was stirred at about room temperature for 48 hours. The reaction mixture was diluted with DCM, washed with saturated aqueous NaHCO$_3$ solution and brine, dried and concentrated. The residue was purified by column chromatography (hexanes:EtOAc, 1:1) to give tert-butyl 4-((tert-butoxycarbonylamino)methyl)-5-chloro-1-((5R,7R)-5-methyl-7-(4-nitrobenzoyloxy)-6,7-dihydro-5H-cyclopenta[d]

pyrimidin-4-yl)spiro[indoline-3,4'-piperidine]-1'-carboxylate (5 mg, 28%). LCMS (APCI+) m/z 749, 751 [M+H]+; Rt=4.66 min.

Step 4 to Step 8 describes an alternative synthesis of tert-butyl 4-((tert-butoxycarbonylamino)methyl)-5-chloro-1-((5R,7R)-5-methyl-7-(4-nitrobenzoyloxy)-6,7-dihydro-5H-cyclopenta[d]pyrimidin-4-yl)spiro[indoline-3,4'-piperidine]-1'-carboxylate.

Step 4: To a stirred solution of tert-butyl (1'-benzylspiro[indoline-3,4'-piperidine]-4-yl)methylcarbamate (0.270 g, 0.662 mmol) in DCM (3 mL) was added Et$_3$N (0.14 mL, 0.99 mmol) and DMAP (0.081 g, 0.66 mmol). A solution of Boc$_2$O (0.174 g, 0.795 mmol) in DCM (1 mL) was added dropwise. The reaction was stirred at about room temperature overnight, and then quenched with saturated aqueous NaHCO$_3$ solution. The aqueous phase was extracted with DCM. The combined extracts were washed with brine and dried. The residue was purified by column chromatography (DCM:MeOH, 80:1) to give tert-butyl 1'-benzyl-4-((tert-butoxycarbonylamino)methyl)spiro[indoline-3,4'-piperidine]-1-carboxylate (0.190 g, 57%). LCMS (APCI+) m/z 508 [M+H]+; Rt=3.92 min.

Step 5: To a stirred solution of tert-butyl 1'-benzyl-4-((tert-butoxycarbonylamino)methyl)spiro[indoline-3,4'-piperidine]-1-carboxylate (115 mg, 0.227 mmol) in DCM (2 mL) was added 1-chloropyrrolidine-2,5-dione (NCS) (66 mg, 0.50 mmol). The reaction mixture was stirred at about room temperature for 48 hours. The reaction mixture was diluted with DCM, washed with saturated aqueous NaHCO$_3$ solution and brine, dried and concentrated. The residue was dissolved in DCM (2 mL) and treated with 4N HCl in dioxane (0.5 mL) overnight. The solvents were evaporated. The residue was taken up in DCM and basidified with saturated aqueous NaHCO$_3$ solution. The aqueous phase was extracted with DCM. The combined organic layers were washed with brine, dried and concentrated to give (1'-benzyl-5-chlorospiro[indoline-3,4'-piperidine]-4-yl)methanamine (40 mg, 52%) as an oil, which was used in the next step without further purification. LCMS (APCI+) m/z 342, 344 [M+H]+; Rt=1.71 min.

Step 6: tert-butyl (1'-benzyl-5-chlorospiro[indoline-3,4'-piperidine]-4-yl)methylcarbamate was prepared by the procedures described in Example 24, Step 1, substituting (5'S)-methyl 2-oxospiro[indoline-3,3'-pyrrolidine]-5'-carboxylate with (1'-benzyl-5-chlorospiro[indoline-3,4'-piperidine]-4-yl)methanamine. LCMS (APCI+) m/z 442, 444 [M+H]+; Rt=3.17 min.

Step 7: (5R,7R)-4-(1'-benzyl-4-((tert-butoxycarbonylamino)methyl)-5-chlorospiro[indoline-3,4'-piperidine]-1-yl)-5-methyl-6,7-dihydro-5H-cyclopenta[d]pyrimidin-7-yl 4-nitrobenzoate was prepared by the procedures described in Example 1, Step 8, substituting (R)-4-chloro-5-methyl-6,7-dihydro-5H-cyclopenta[d]pyrimidine with (5R,7R)-4-chloro-5-methyl-6,7-dihydro-5H-cyclopenta[d]pyrimidin-7-yl 4-nitrobenzoate, and substituting tert-butyl 5-chlorospiro[indoline-3,4'-piperidine]-1'-carboxylate with tert-butyl (1'-benzyl-5-chlorospiro[indoline-3,4'-piperidine]-4-yl)methylcarbamate. LCMS (APCI+) m/z 739, 741 [M+H]+; Rt=4.53 min.

Step 8: To a stirred solution of (5R,7R)-4-(1'-benzyl-4-((tert-butoxycarbonylamino)methyl)-5-chlorospiro[indoline-3,4'-piperidine]-1-yl)-5-methyl-6,7-dihydro-5H-cyclopenta[d]pyrimidin-7-yl 4-nitrobenzoate (41 mg, 0.055 mmol) in dichloroethane (1 mL) was added 1-chloroethyl carbonochloridate (0.012 mL, 0.11 mmol) at about 0° C. The reaction mixture was heated at reflux for 1 hour and then evaporated in vacuo. The residue was redissolved in MeOH (1 mL) was heated at reflux for 1 hour. After cooling, the solvent was evaporated in vacuo. The residue was taken up in DCM (1 mL) Et$_3$N (0.019 mL, 0.14 mmol) and Boc$_2$O (13 mg, 0.061 mmol) were added to the reaction mixture. After being stirred at about room temperature for 2 h, the reaction was quenched with saturated aqueous NaHCO$_3$ solution. The aqueous phase was extracted with DCM. The combined extracts were washed with brine and dried. The residue was purified by column chromatography (hexanes:EtOAc, 1:1) to give tert-butyl 4-((tert-butoxycarbonylamino)methyl)-5-chloro-1-((5R,7R)-5-methyl-7-(4-nitrobenzoyloxy)-6,7-dihydro-5H-cyclopenta[d]pyrimidin-4-yl)spiro[indoline-3,4'-piperidine]-1'-carboxylate (28 mg, 67%). LCMS (APCI+) m/z 749, 751 [M+H]+; Rt=4.66 min.

Step 9: (5R,7R)-4-(4-(aminomethyl)-5-chlorospiro[indoline-3,4'-piperidine]-1-yl)-5-methyl-6,7-dihydro-5H-cyclopenta[d]pyrimidin-7-ol dihydrochloride was prepared by the procedures described in Example 21, Step 2 to 3, substituting tert-butyl 5-chloro-1-((5R,'7R)-5-methyl-7-(4-nitrobenzoyloxy)-6,7-dihydro-5H-cyclopenta[d]pyrimidin-4-yl)spiro[indoline-3,3'-pyrrolidine]-1'-carboxylate with tert-butyl 4-((tert-butoxycarbonylamino)methyl)-5-chloro-1-((5R,7R)-5-methyl-7-(4-nitrobenzoyloxy)-6,7-dihydro-5H-cyclopenta[d]pyrimidin-4-yl)spiro[indoline-3,4'-piperidine]-1'-carboxylate. LCMS (APCI+) m/z 400, 402 [M+H]+; Rt=1.66 min.

Examples 30-66 shown in Table 1 can also be made according to the above described methods.

TABLE 1

| Example | Structure | Name | LCMS |
|---|---|---|---|
| 30 | 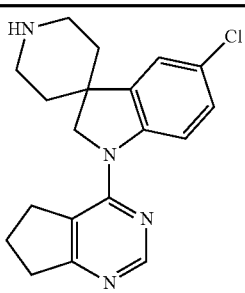 | 5-chloro-1-(6,7-dihydro-5H-cyclopenta[d]pyrimidin-4-yl)spiro[indoline-3,4'-piperidine] | m/z 341, 343 Rt: 2.00 min |

TABLE 1-continued

| Example | Structure | Name | LCMS |
|---|---|---|---|
| 31 | 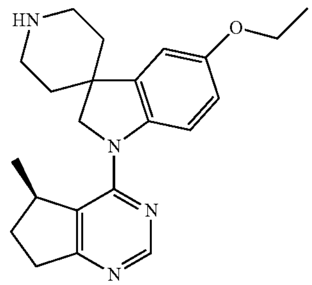 | (R)-5-ethoxy-1-(5-methyl-6,7-dihydro-5H-cyclopenta[d]pyrimidin-4-yl)spiro[indoline-3,4'-piperidine] | m/z 365 Rt: 2.39 min |
| 32 | 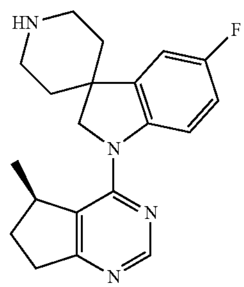 | (R)-5-fluoro-1-(5-methyl-6,7-dihydro-5H-cyclopenta[d]pyrimidin-4-yl)spiro[indoline-3,4'-piperidine] | m/z 339 Rt: 2.33 min |
| 33 | 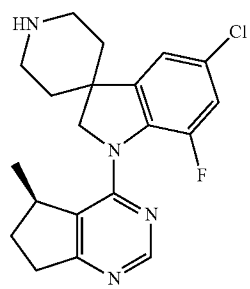 | (R)-5-chloro-7-fluoro-1-(5-methyl-6,7-dihydro-5H-cyclopenta[d]pyrimidin-4-yl)spiro[indoline-3,4'-piperidine] | m/z 373, 375 Rt: 2.24 min |
| 34 | 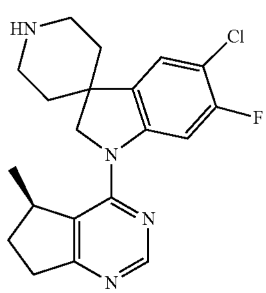 | (R)-5-chloro-6-fluoro-1-(5-methyl-6,7-dihydro-5H-cyclopenta[d]pyrimidin-4-yl)spiro[indoline-3,4'-piperidine] | m/z 373, 375 Rt: 2.21 min |
| 35 | 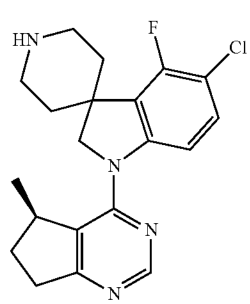 | (R)-5-chloro-4-fluoro-1-(5-methyl-6,7-dihydro-5H-cyclopenta[d]pyrimidin-4-yl)spiro[indoline-3,4'-piperidine] | m/z 373, 375 Rt: 2.19 min |

TABLE 1-continued

| Example | Structure | Name | LCMS |
|---|---|---|---|
| 36 | 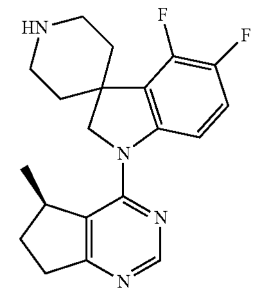 | (R)-4,5-difluoro-1-(5-methyl-6,7-dihydro-5H-cyclopenta[d]pyrimidin-4-yl)spiro[indoline-3,4'-piperidine] | m/z 357 Rt: 2.23 min |
| 37 | 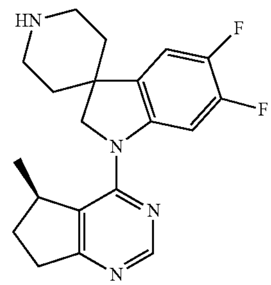 | (R)-5,6-difluoro-1-(5-methyl-6,7-dihydro-5H-cyclopenta[d]pyrimidin-4-yl)spiro[indoline-3,4'-piperidine] | m/z 357 Rt: 2.25 min |
| 38 | 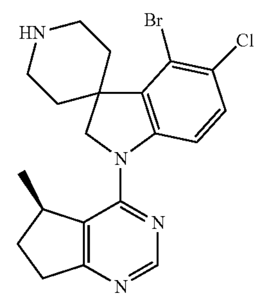 | (R)-4-bromo-5-chloro-1-(5-methyl-6,7-dihydro-5H-cyclopenta[d]pyrimidin-4-yl)spiro[indoline-3,4'-piperidine] | m/z 433, 435 Rt: 2.80 min |
| 39 | 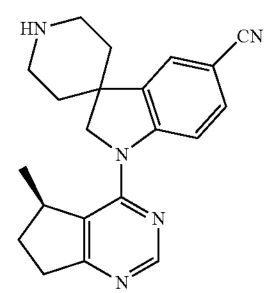 | (R)-1-(5-methyl-6,7-dihydro-5H-cyclopenta[d]pyrimidin-4-yl)spiro[indoline-3,4'-piperidine]-5-carbonitrile | m/z 346 Rt: 2.27 min |
| 40 | 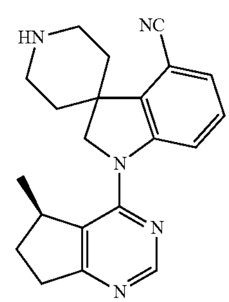 | (R)-1-(5-methyl-6,7-dihydro-5H-cyclopenta[d]pyrimidin-4-yl)spiro[indoline-3,4'-piperidine]-4-carbonitrile | m/z 346 Rt: 2.43 min |

TABLE 1-continued

| Example | Structure | Name | LCMS |
|---|---|---|---|
| 41 | 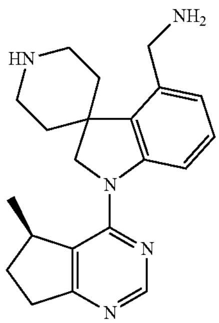 | (R)-1-(-(5-methyl-6,7-dihydro-5H-cyclopenta[d]pyrimidin-4-yl)spiro[indoline-3,4'-piperidine]-4-yl)methanamine | m/z 350 Rt: 2.45 min |
| 42 | 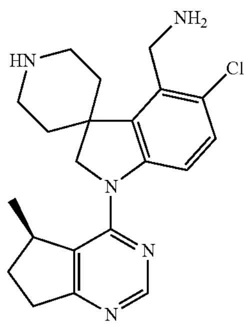 | (R)-(5-chloro-1-(5-methyl-6,7-dihydro-5H-cyclopenta[d]pyrimidin-4-yl)spiro[indoline-3,4'-piperidine]-4-yl)methanamine | m/z 384, 386 Rt: 2.11 min |
| 43 | 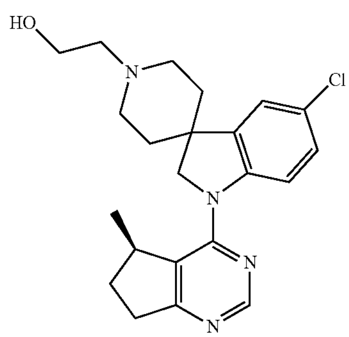 | (R)-2-(5-chloro-1-(5-methyl-6,7-dihydro-5H-cyclopenta[d]pyrimidin-4-yl)spiro[indoline-3,4'-piperidine]-1'-yl)ethanol | m/z 399, 401 Rt: 2.46 min |
| 44 | 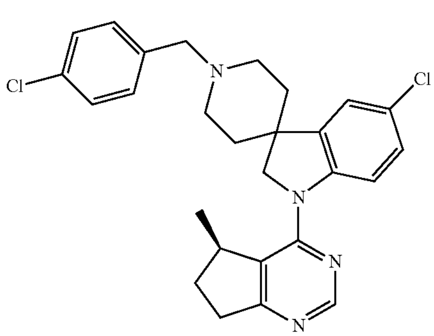 | (R)-5-chloro-1'-(4-chlorobenzyl)-1-(5-methyl-6,7-dihydro-5H-cyclopenta[d]pyrimidin-4-yl)spiro[indoline-3,4'-piperidine] | m/z 479, 481 Rt: 4.58 min |

TABLE 1-continued

| Example | Structure | Name | LCMS |
|---|---|---|---|
| 45 | 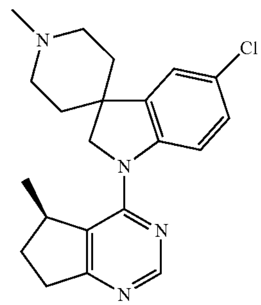 | (R)-5-chloro-1'-methyl-1-(5-methyl-6,7-dihydro-5H-cyclopenta[d]pyrimidin-4-yl)spiro[indoline-3,4'-piperidine] | m/z 369, 371 Rt: 2.56 min |
| 46 | 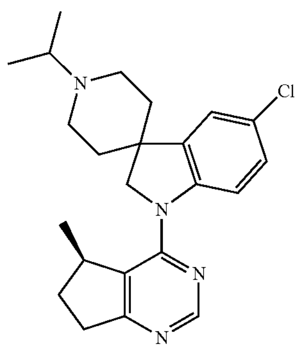 | (R)-5-chloro-1'-isopropyl-1-(5-methyl-6,7-dihydro-5H-cyclopenta[d]pyrimidin-4-yl)spiro[indoline-3,4'-piperidine] | m/z 397, 399 Rt: 2.71 min |
| 47 | 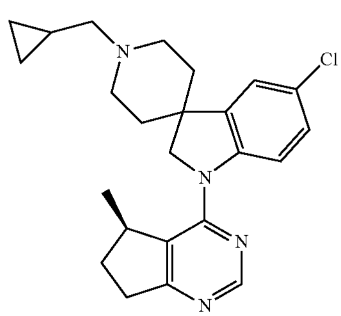 | (R)-5-chloro-1'-(cyclopropylmethyl)-1-(5-methyl-6,7-dihydro-5H-cyclopenta[d]pyrimidin-4-yl)spiro[indoline-3,4'-piperidine] | m/z 409, 411 Rt: 2.87 min |
| 48 | 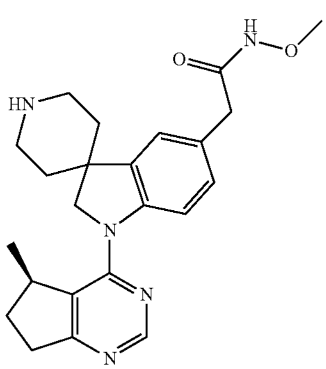 | (R)-N-methoxy-2-(1-(5-methyl-6,7-dihydro-5H-cyclopenta[d]pyrimidin-4-yl)spiro[indoline-3,4'-piperidine]-5-yl)acetamide | m/z 408 Rt: 1.82 min |

TABLE 1-continued

| Example | Structure | Name | LCMS |
|---|---|---|---|
| 49 | 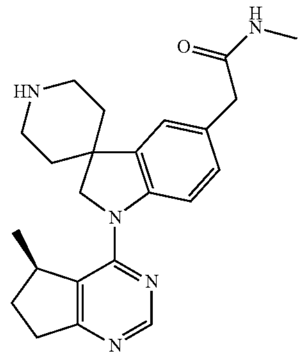 | (R)-N-methyl-2-(1-(5-methyl-6,7-dihydro-5H-cyclopenta[d]pyrimidin-4-yl)spiro[indoline-3,4'-piperidine]-5-yl)acetamide | m/z 392 Rt: 1.89 min |
| 50 | 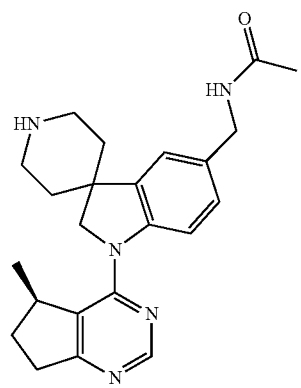 | (R)-N-((1-(5-methyl-6,7-dihydro-5H-cyclopenta[d]pyrimidin-4-yl)spiro[indoline-3,4'-piperidine]-5-yl)methyl)acetamide | m/z 392 Rt: 1.86 min |
| 51 | 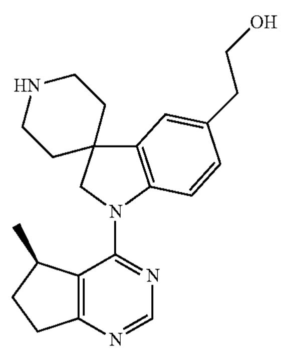 | (R)-2-(1-(5-methyl-6,7-dihydro-5H-cyclopenta[d]pyrimidin-4-yl)spiro[indoline-3,4'-piperidine]-5-yl)ethanol | m/z 365 Rt: 1.96 min |
| 52 | 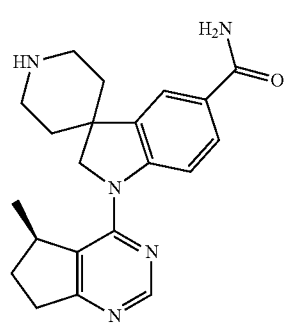 | (R)-1-(5-methyl-6,7-dihydro-5H-cyclopenta[d]pyrimidin-4-yl)spiro[indoline-3,4'-piperidine]-5-carboxamide | m/z 364 Rt: 1.78 min |

TABLE 1-continued

| Example | Structure | Name | LCMS |
|---|---|---|---|
| 53 | 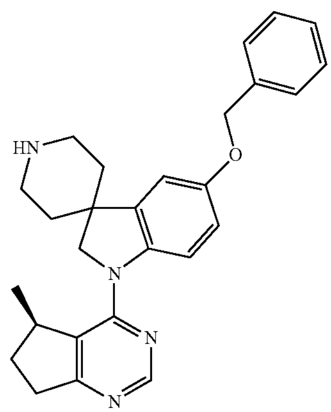 | (R)-5-(benzyloxy)-1-(5-methyl-6,7-dihydro-5H-cyclopenta[d]pyrimidin-4-yl)spiro[indoline-3,4'-piperidine] | m/z 427 Rt: 2.84 min |
| 54 | 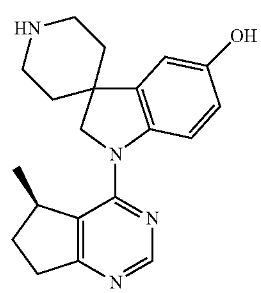 | (R)-1-(5-methyl-6,7-dihydro-5H-cyclopenta[d]pyrimidin-4-yl)spiro[indoline-3,4'-piperidin]-5-ol | m/z 337 Rt: 2.01 min |
| 55 | 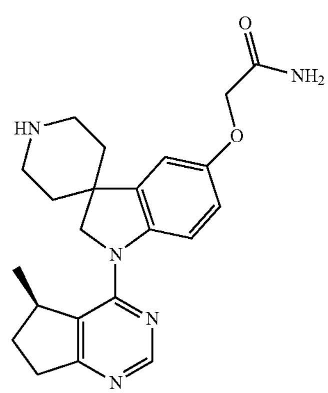 | (R)-2-(1-(5-methyl-6,7-dihydro-5H-cyclopenta[d]pyrimidin-4-yl)spiro[indoline-3,4'-piperidine]-5-yloxy)acetamide | m/z 394 Rt: 1.98 min |
| 56 | 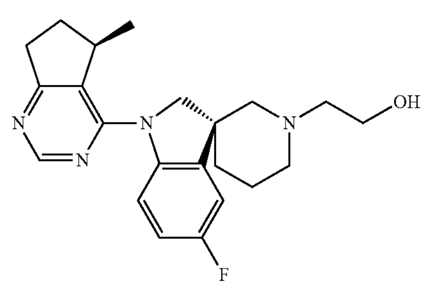 | 2-((R)-5-fluoro-1-((R)-5-methyl-6,7-dihydro-5H-cyclopenta[d]pyrimidin-4-yl)spiro[indoline-3,3'-piperidine]-1'-yl)ethanol | m/z 383 Rt: 3.81 min |

TABLE 1-continued

| Example | Structure | Name | LCMS |
|---|---|---|---|
| 57 | 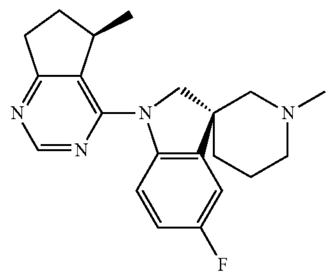 | (R)-4-((R)-5-fluoro-1'-methylspiro[indoline-3,3'-piperidine]-1-yl)-5-methyl-6,7-dihydro-5H-cyclopenta[d]pyrimidine | m/z 353 Rt: 3.04 min |
| 58 | 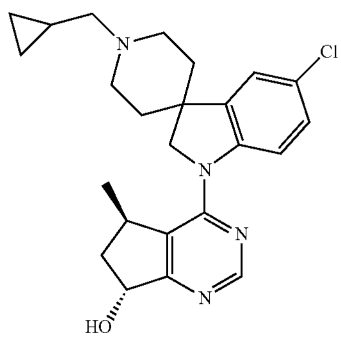 | (5R,7R)-4-(5-chloro-1'-(cyclopropylmethyl)spiro[indoline-3,4'-piperidine]-1-yl)-5-methyl-6,7-dihydro-5H-cyclopenta[d]pyrimidin-7-ol | m/z 425, 427 Rt: 2.48 min |
| 59 | 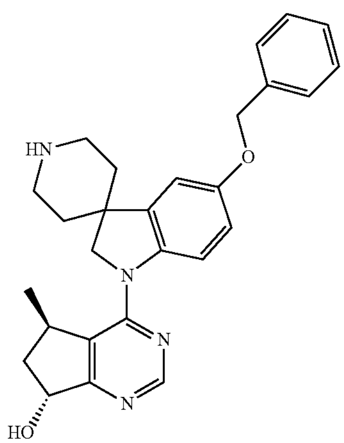 | (5R,7R)-4-(5-(benzyloxy)spiro[indoline-3,4'-piperidine]-1-yl)-5-methyl-6,7-dihydro-5H-cyclopenta[d]pyrimidin-7-ol | m/z 443 Rt: 2.51 min |
| 60 | 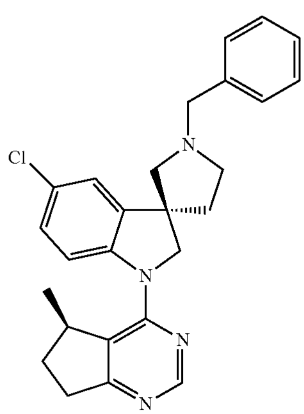 | (S)-1'-benzyl-5-chloro-1-((R)-5-methyl-6,7-dihydro-5H-cyclopenta[d]pyrimidin-4-yl)spiro[indoline-3,3'-pyrrolidine] | m/z 431, 433 Rt: 4.66 min |

TABLE 1-continued

| Example | Structure | Name | LCMS |
|---|---|---|---|
| 61 | 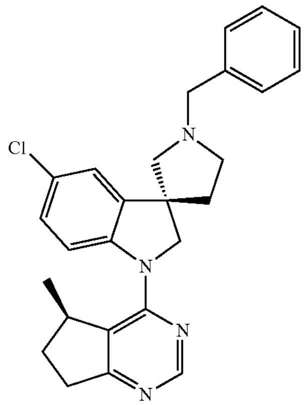 | (R)-1'-benzyl-5-chloro-1-((R)-5-methyl-6,7-dihydro-5H-cyclopenta[d]pyrimidin-4-yl)spiro[indoline-3,3'-pyrrolidine] | m/z 431, 433 Rt: 4.71 min |
| 62 | 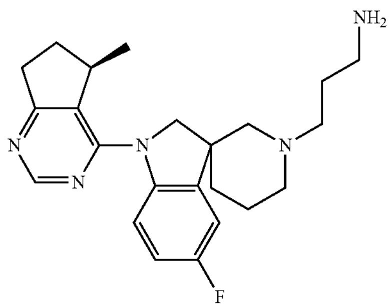 | 3-(5-fluoro-1-((R)-5-methyl-6,7-dihydro-5H-cylcopenta[d]pyrimidin-4-yl)spiro[indoline-3,3'-piperidine]-1'-yl)propan-1-amine | m/z 396 Rt: 2.63 min |
| 63 | 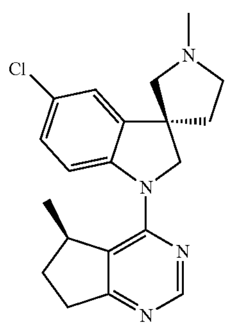 | (S)-5-chloro-1'-methyl-1-((R)-5-methyl-6,7-dihydro-5H-cyclopenta[d]pyrimidin-4-yl)spiro[indoline-3,3'-pyrrolidine] | m/z 355, 357 Rt: 3.89 min |
| 64 | 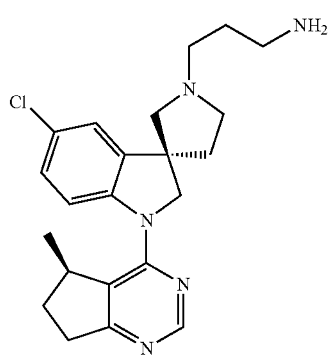 | 3-((S)-5-chloro-1-((R)-5-methyl-6,7-dihydro-5H-cyclopenta[d]pyrimidin-4-yl)spiro[indoline-3,3'-pyrrolidine]-1'-yl)propan-1-amine | m/z 398, 400 Rt: 3.03 min |

TABLE 1-continued

| Example | Structure | Name | LCMS |
|---|---|---|---|
| 65 | 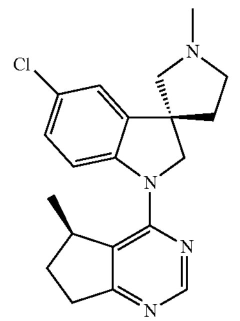 | (R)-5-chloro-1'-methyl-1-((R)-5-methyl-6,7-dihydro-5H-cyclopenta[d]pyrimidin-4-yl)spiro[indoline-3,3'-pyrrolidine] | m/z 355, 357 Rt: 2.69 min |
| 66 | 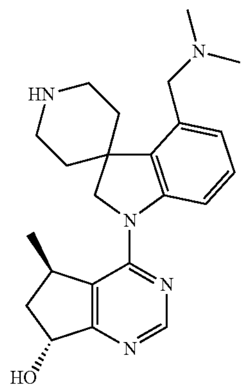 | (5R,7R)-4-(4-((dimethylamino)methyl)spiro[indoline-3,4'-piperidine]-1-yl)-5-methyl-6,7-dihydro-5H-cyclopenta[d]pyrimidin-7-ol | m/z 394 Rt: 1.79 min |

Example 67

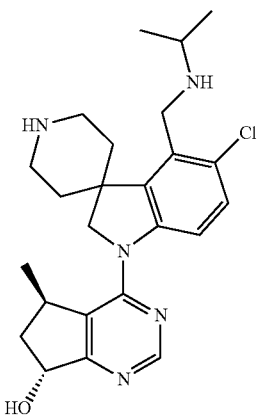

(5R,7R)-4-(5-chloro-4-((isopropylamino)methyl)spiro[indoline-3,4'-piperidine]-1-yl)-5-methyl-6,7-dihydro-5H-cyclopenta[d]pyrimidin-7-ol Step 1: (5R,7R)-4-(4-(aminomethyl)-1'-benzyl-5-chlorospiro[indoline-3,4'-piperidine]-1-yl)-5-methyl-6,7-dihydro-5H-cyclopenta[d]pyrimidin-7-yl 4-nitrobenzoate trihydrochloride (36 mg, 100%) was prepared by the procedures described in Example 1, Step 9, substituting (5R,7R)-4-(1'-benzyl-4-((tert-butoxycarbonylamino)methyl)-5-chlorospiro[indoline-3,4'-piperidine]-1-yl)-5-methyl-6,7-dihydro-5H-cyclopenta[d]pyrimidin-7-yl 4-nitrobenzoate for (R)-tert-butyl 5-chloro-1-(5-methyl-6,7-dihydro-5H-cyclopenta[d]pyrimidin-4-yl)spiro[indoline-3,4'-piperidine]-1'-carboxylate. LCMS (APCI+) m/z 639, 641 [M+H]+; Rt=3.61 min.

Step 2: (5R,7R)-4-(1'-benzyl-5-chloro-4-((isopropylamino)methyl)spiro[indoline-3,4'-piperidine]-1-yl)-5-methyl-6,7-dihydro-5H-cyclopenta[d]pyrimidin-7-yl 4-nitrobenzoate (17 mg, 44%) was prepared by the procedures described in Example 18, substituting (5R,7R)-4-(4-(aminomethyl)-1'-benzyl-5-chloro spiro[indoline-3,4'-piperidine]-1-yl)-5-methyl-6,7-dihydro-5H-cyclopenta[d]pyrimidin-7-yl 4-nitrobenzoate trihydrochloride for (5R,7R)-4-(5-chlorospiro[indoline-3,4'-piperidine]-1-yl)-5-methyl-6,7-dihydro-5H-cyclopenta[d]pyrimidin-7-ol dihydrochloride, and substituting acetone for formaldehyde. LCMS (APCI+) m/z 681, 683 [M+H]+; Rt=4.52 min.

Step 3: To a stirred solution of (5R,7R)-4-(1'-benzyl-5-chloro-4-((isopropylamino)methyl)spiro[indoline-3,4'-piperidine]-1-yl)-5-methyl-6,7-dihydro-5H-cyclopenta[d]pyrimidin-7-yl 4-nitrobenzoate (17 mg, 0.025 mmol) in dichloroethane (0.5 mL) was added 1-chloroethyl carbonochloridate (8.1 µL, 0.075 mmol) at 0° C. The reaction mixture was heated at reflux overnight. After cooling, the solvents were evaporated in vacuo. The residue was dissolved in MeOH (1 mL) and heated at reflux for 1 hour. After cooling, the solvent was evaporated in vacuo. The residue was taken up in DCM, washed with saturated aqueous NaHCO₃ solution and brine, dried, and concentrated. The residue was purified by column chromatography (4% 7N ammonia in MeOH/DCM) to give (5R,7R)-4-(5-chloro-4-((isopropylamino)methyl)spiro[indoline-3,4'-piperidine]-1-yl)-5-methyl-6,7-dihydro-5H-cyclopenta[d]pyrimidin-7-yl 4-nitrobenzoate (6 mg, 41%). LCMS (APCI+) m/z 591, 593 [M+H]+; Rt=2.78 min.

Step 4: A solution of (5R,7R)-4-(5-chloro-4-((isopropylamino)methyl)spiro[indoline-3,4'-piperidine]-1-yl)-5-methyl-6,7-dihydro-5H-cyclopenta[d]pyrimidin-7-yl 4-nitrobenzoate (6 mg, 0.01 mmol) in THF (0.2 mL) was cooled to 0° C. and treated with 1N LiOH—H$_2$O (0.020 mL, 0.020 mmol). The reaction was stirred at room temperature overnight. The reaction was partitioned between DCM and saturated aqueous NaHCO$_3$ solution. The aqueous layer was extracted with DCM. The combined organic layers were washed with brine, dried, and concentrated. The crude residue was purified by column chromatography (10% 7N ammonia in MeOH/DCM) to yield the free base, which was taken up in DCM and acidified with 2N HCl in Et$_2$O. The solvents were removed in vacuo. (5R,7R)-4-(5-chloro-4-((isopropylamino)methyl)spiro[indoline-3,4'-piperidine]-1-yl)-5-methyl-6,7-dihydro-5H-cyclopenta[d]pyrimidin-7-ol trihydrochloride (4 mg, 71%) was obtained as a solid. LCMS (APCI+) m/z 442, 444 [M+H]+; Rt=1.90 min.

Example 68

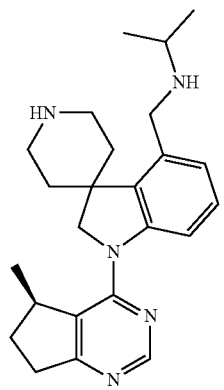

(R)-N-((1-(5-methyl-6,7-dihydro-5H-cyclopenta[d]pyrimidin-4-yl)spiro[indoline-3,4'-piperidine]-4-yl)methyl)propan-2-amine Step 1: (R)-tert-butyl (1'-benzyl-1-(5-methyl-6,7-dihydro-5H-cyclopenta[d]pyrimidin-4-yl)spiro[indoline-3,4'-piperidine]-4-yl)methylcarbamate (157 mg, 47%) was prepared by the procedures described in Example 1, Step 8, substituting tert-butyl (1'-benzylspiro[indoline-3,4'-piperidine]-4-yl)methylcarbamate for tert-butyl 5-chlorospiro[indoline-3,4'-piperidine]-1'-carboxylate. LCMS (APCI+) m/z 540 [M+H]+; Rt=3.30 min.

Step 2: (R)-(1'-benzyl-1-(5-methyl-6,7-dihydro-5H-cyclopenta[d]pyrimidin-4-yl)spiro[indoline-3,4'-piperidine]-4-yl)methanamine trihydrochloride (158 mg, 99%) was prepared by the procedures described in Example 1, Step 9, substituting (R)-tert-butyl (1'-benzyl-1-(5-methyl-6,7-dihydro-5H-cyclopenta[d]pyrimidin-4-yl)spiro[indoline-3,4'-piperidine]-4-yl)methylcarbamate for (R)-tert-butyl 5-chloro-1-(5-methyl-6,7-dihydro-5H-cyclopenta[d]pyrimidin-4-yl)spiro[indoline-3,4'-piperidine]-1'-carboxylate. LCMS (APCI+) m/z 440 [M+H]+; Rt=2.37 min.

Step 3: (R)-N-((1'-benzyl-1-(5-methyl-6,7-dihydro-5H-cyclopenta[d]pyrimidin-4-yl)spiro[indoline-3,4'-piperidine]-4-yl)methyl)propan-2-amine (33 mg, 60%) was prepared by the procedures described in Example 18, substituting (R)-(1'-benzyl-1-(5-methyl-6,7-dihydro-5H-cyclopenta[d]pyrimidin-4-yl)spiro[indoline-3,4'-piperidine]-4-yl)methanamine trihydrochloride trihydrochloride for (5R,7R)-4-(5-chlorospiro[indoline-3,4'-piperidine]-1-yl)-5-methyl-6,7-dihydro-5H-cyclopenta[d]pyrimidin-7-ol dihydrochloride, and substituting acetone for formaldehyde. LCMS (APCI+) m/z 482 [M+H]+; Rt=2.59 min.

Step 4: Ammonium formate (43 mg, 0.68 mmol) and 10% Pd/C (6 mg, 20% weight) was added to a solution of (R)-N-((1'-benzyl-1-(5-methyl-6,7-dihydro-5H-cyclopenta[d]pyrimidin-4-yl)spiro[indoline-3,4'-piperidine]-4-yl)methyl)propan-2-amine (33 mg, 0.069 mmol) in MeOH (0.8 mL). The mixture was allowed to stir at reflux for 4 hours. After cooling, the reaction mixture was filtered through Celite. The filtrate was evaporated in vacuo. The residue was taken up in DCM, washed with saturated aqueous NaHCO$_3$ solution and brine, dried and concentrated. The crude residue was purified by column chromatography (5% 7 N ammonia in MeOH/DCM) to yield the free base, which was taken up in DCM and acidified with 2N HCl in Et$_2$O. Evaporation of the solvents in vacuo gave (R)-N-((1-(5-methyl-6,7-dihydro-5H-cyclopenta[d]pyrimidin-4-yl)spiro[indoline-3,4'-piperidine]-4-yl)methyl)propan-2-amine trihydrochloride (24 mg, 89%) as a solid. LCMS (APCI+) m/z 392 [M+H]+; Rt=1.77 min.

Example 69

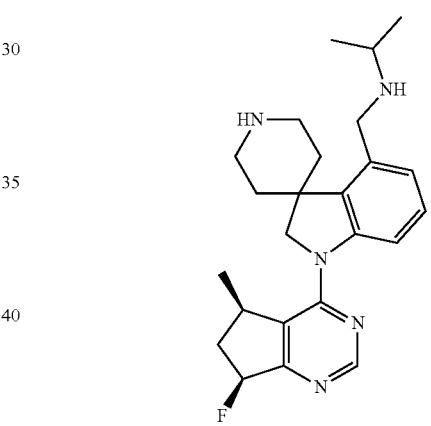

N-((1-((5R,7S)-7-fluoro-5-methyl-6,7-dihydro-5H-cyclopenta[d]pyrimidin-4-yl)spiro[indoline-3,4'-piperidine]-4-yl)methyl)propan-2-amine Step 1: Et$_3$N (0.039 mL, 0.28 mmol) was added to a stirred solution of (5R,7R)-4-(4-((isopropylamino)methyl)spiro[indoline-3,4'-piperidine]-1-yl)-5-methyl-6,7-dihydro-5H-cyclopenta[d]pyrimidin-7-o 1 (38 mg, 0.093 mmol) in DCM (1 mL). A solution of Boc$_2$O (45 mg, 0.20 mmol) in DCM (0.5 mL) was added. The reaction was stirred at room temperature for 3 days. The reaction was diluted with DCM, washed with saturated aqueous NaHCO$_3$ solution and brine, dried, and concentrated. The residue was purified by column chromatography (DCM:MeOH, 70:1 to 30:1) to give tert-butyl 4-((tert-butoxycarbonyl(isopropyl)amino)methyl)-1-((5R,7R)-7-hydroxy-5-methyl-6,7-dihydro-5H-cyclopenta[d]pyrimidin-4-yl)spiro[indoline-3,4'-piperidine]-1'-carboxylate (45 mg, 79%) as an oil. LCMS (APCI+) m/z 608 [M+H]+; Rt=4.20 min.

Step 2: tert-Butyl 4-((tert-butoxycarbonyl(isopropyl)amino)methyl)-1-((5R,7S)-7-fluoro-5-methyl-6,7-dihydro- 5H-cyclopenta[d]pyrimidin-4-yl)spiro[indoline-3,4'-piperidine]-1'-carboxylate (12 mg, 63%) was prepared by the procedures described in Example 3, Step 13, substituting tert-butyl 4-((tert-butoxycarbonyl(isopropyl)amino)methyl)-145R,7R)-7-hydroxy-5-methyl-6,7-dihydro-5H-cyclopenta[d]pyrimidin-4-yl)spiro[indoline-3,4'-piperidine]-1'-carboxylate for tert-butyl 5-chloro-1-((5R,7R)-7-hydroxy-5-methyl-6,7-dihydro-5H-cyclopenta[d]pyrimidin-4-yl)spiro[indoline-3,4'-piperidine]-1'-carboxylate. LCMS (APCI+) m/z 610 [M+H]+; Rt=4.35 min.

Step 3: 4N HCl in dioxane (0.1 mL) was added to a solution of tert-butyl 4-((tert-butoxycarbonyl(isopropyl)amino)methyl)-1-((5R,7 S)-7-fluoro-5-methyl-6,7-dihydro-5H-cyclopenta[d]pyrimidin-4-yl)spiro[indoline-3,4'-piperidine]-1'-carboxylate (12 mg, 0.020 mmol) in DCM (0.3 mL). The reaction mixture was stirred at room temperature overnight. The solvents were evaporated. The crude residue was taken up in MeOH and basified with 7N ammonia in MeOH. After evaporation of the solvent, the residue was purified by column chromatography (4% 7 N ammonia in MeOH/DCM) to yield the free base, which was taken up in DCM and acidified with 2N HCl in Et$_2$O. Removal of the solvents afforded N-((1-((5R,7S)-7-fluoro-5-methyl-6,7-dihydro-5H-cyclopenta[d]pyrimidin-4-yl)spiro[indoline-3,4'-piperidine]-4-yl)methyl)propan-2-amine trihydrochloride (9 mg, 88%) as a solid. LCMS (APCI+) m/z 410 [M+H]+; Rt=1.55 min.

Example 70

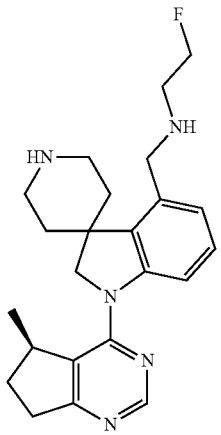

(R)-2-fluoro-N-((1-(5-methyl-6,7- dihydro-5H-cyclopenta[d]pyrimidin-4-yl)spiro[indoline-3,4'-piperidine]-4-yl)methyl)ethanamine Step 1: Ammonium formate (1.82 g, 28.9 mmol) and 10% Pd/C (0.31 g, 20% weight) was added to a solution of (R)-tert-butyl (1'-benzyl-1-(5-methyl-6,7-dihydro-5H-cyclopenta[d]pyrimidin-4-yl)spiro[indoline-3,4'-piperidine]-4-yl)methylcarbamate (1.56 g, 2.89 mmol) in MeOH (28 mL). The mixture was allowed to stir at reflux for 4 hours. After cooling, the reaction mixture was filtered through Celite. The filtrate was evaporated in vacuo. The crude product was taken up in DCM, washed with saturated aqueous NaHCO$_3$ solution and brine, dried and concentrated. The residue was puffed by column chromatography (5% 7N ammonia in MeOH/DCM) to give (R)-tert-butyl (1-(5-methyl-6,7-dihydro-5H-cyclopenta[d]pyrimidin-4-yl)spiro[indoline-3,4'-piperidine]-4-yl)methylcarbamate (1.01 g, 78%). LCMS (APCI+) m/z 450 [M+H]+; Rt=2.15 min.

Step 2: (R)-(1-(5-methyl-6,7-dihydro-5H-cyclopenta[d]pyrimidin-4-yl)spiro[indoline-3,4'-piperidine]-4-yl)methanamine trihydrochloride (1.03 g, 100%) was prepared by the procedures described in Example 1, Step 9, substituting (R)-tert-butyl (1-(5-methyl-6,7-dihydro-5H-cyclopenta[d]pyrimidin-4-yl)spiro[indoline-3,4'-piperidine]-4-yl)methylcarbamate for (R)-tert-butyl 5-chloro-1-(5-methyl-6,7-dihydro-5H-cyclopenta[d]pyrimidin-4-yl)spiro[indoline-3,4'-piperidine]-1'-carboxylate. LCMS (APCI+) m/z 350 [M+H]+; Rt=1.33 min.

Step 3: A solution of Boc$_2$O (0.49 g, 2.2 mmol) in DCM (10 mL) at 0° C. was added dropwise to a stirred solution of (R)-(1-(5-methyl-6,7-dihydro-5H-cyclopenta[d]pyrimidin-4-yl)spiro[indoline-3,4'-piperidine]-4-yl)methanamine trihydrochloride (1.03 g, 2.24 mmol) in DCM (15 mL) and Et$_3$N (1.41 mL, 10.1 mmol). After 30 minutes, the reaction mixture was diluted with DCM, washed with saturated aqueous NaHCO$_3$ solution and brine, dried and concentrated. The residue was purified by column chromatography (DCM:MeOH, 10:1) to give (R)-tert-butyl 4-(aminomethyl)-1-(5-methyl-6,7-dihydro-5H-cyclopenta[d]pyrimidin-4-yl)spiro[indoline-3,4'-piperidine]-1'-carboxylate (0.66 g, 65%) as a solid. LCMS (APCI+) m/z 450 [M+H]+; Rt=2.15 min.

Step 4: DIEA (0.015 mL, 0.093 mmol) and 1-bromo-2-fluoroethane (0.0067 mL, 0.075 mmol) was added to a stirred solution of (R)-tert-butyl 4-(aminomethyl)-1-(5-methyl-6,7-dihydro-5H-cyclopenta[d]pyrimidin-4-yl)spiro[indoline-3,4'-piperidine]-1'-carboxylate (28 mg, 0.062 mmol) in DMF (0.6 mL) The reaction mixture was stirred at 80° C. overnight. After cooling, the reaction mixture was partitioned between EtOAc and water. The aqueous layer was extracted with EtOAc. The combined organic layers were washed with brine, dried and concentrated. The residue was purified by column chromatography (DCM:MeOH, 60:1) to give (R)-tert-butyl 4-((2-fluoroethylamino)methyl)-1-(5-methyl-6,7-dihydro-5H-cyclopenta[d]pyrimidin-4-yl)spiro[indoline-3,4'-piperidine]-1'-carboxylate (12 mg, 39%) as an oil. LCMS (APCI+) m/z 496 [M+H]+; Rt=3.03 min.

Step 5: (R)-2-fluoro-N-((1-(5-methyl-6,7-dihydro-5H-cyclopenta[d]pyrimidin-4-yl)spiro[indoline-3,4'-piperidine]-4-yl)methyl)ethanamine trihydrochloride (8 mg, 65%) was prepared by the procedures described in Example 1, Step 9, substituting (R)-tert-butyl 4-((2-fluoroethylamino)methyl)-1-(5-methyl-6,7-dihydro-5H-cyclopenta[d]pyrimidin-4-yl)spiro[indoline-3,4'-piperidine]-1'-carboxylate for (R)-tert-butyl 5-chloro-1-(5-methyl-6,7-dihydro-5H-cyclopenta[d]pyrimidin-4-yl)spiro[indoline-3,4'-piperidine]-1'-carboxylate. LCMS (APCI+) m/z 396 [M+H]+; Rt=1.63 min.

Example 71

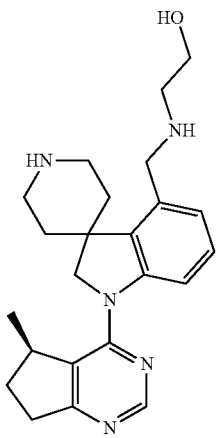

(R)-2-((1-(5-methyl-6,7-dihydro-5H-cyclopenta[d]
pyrimidin-4-yl)spiro[indoline-3,4'-piperidine]-4-yl)
methylamino)ethanol Step 1: (R)-tert-butyl 4-((2-hydroxyethylamino)methyl)-1-(5-methyl-6,7-dihydro-5H-cyclopenta[d]pyrimidin-4-yl)spiro[indoline-3,4'-piperidine]-1'-carboxylate (16 mg, 43%) was prepared by the procedures described in Example 70, Step 4, substituting 2-bromoethanol for 1-bromo-2-fluoroethane. LCMS (APCI+) m/z 494 [M+H]+; Rt=2.37 min.

Step 2: (R)-2-((1-(5-methyl-6,7-dihydro-5H-cyclopenta[d]pyrimidin-4-yl)spiro[indoline-3,4'-piperidine]-4-yl)methylamino)ethanol trihydrochloride (12 mg, 74%) was prepared by the procedures described in Example 1, Step 9, substituting (R)-tert-butyl 4-((2-hydroxyethylamino)methyl)-1-(5-methyl-6,7-dihydro-5H-cyclopenta[d]pyrimidin-4-yl)spiro[indoline-3,4'-piperidine]-1'-carboxylate for (R)-tert-butyl 5-chloro-1-(5-methyl-6,7-dihydro-5H-cyclopenta[d]pyrimidin-4-yl)spiro[indoline-3,4'-piperidine]-1'-carboxylate. LCMS (APCI+) m/z 394 [M+H]+; Rt=2.12 min.

Example 72

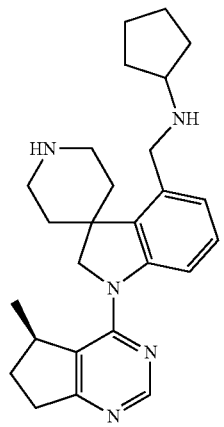

(R)-N-((1-(5-methyl-6,7-dihydro-5H-cyclopenta[d]
pyrimidin-4-yl)spiro[indoline-3,4'-piperidine]-4-yl)
methyl)cyclopentanamine Step 1: A solution of cyclopentone (0.036 mL, 0.40 mmol) in THF (0.15 mL) was added to a stirred solution of (R)-tert-butyl 4-(aminomethyl)-1-(5-methyl-6,7-dihydro-5H-cyclopenta[d]pyrimidin-4-yl)spiro[indoline-3,4'-piperidine]-1'-carboxylate (30 mg, 0.067 mmol) in DCE (0.6 mL) The reaction was allowed to stir at room temperature for 15 minutes, at which point Na(OAc)$_3$BH was added, and the reaction allowed to stir at room temperature for 2 hours. The reaction mixture was diluted with DCM, washed with saturated aqueous NaHCO$_3$ solution and brine, dried and concentrated. The residue was purified by column chromatography (DCM:MeOH, 20:1) to give (R)-N-((1'-benzyl-1-(5-methyl-6,7-dihydro-5H-cyclopenta[d]pyrimidin-4-yl)spiro[indoline-3,4'-piperidine]-4-yl)methyl)cyclopentanamine (34 mg, 98%) as an oil. LCMS (APCI+) m/z 518 [M+H]+; Rt=2.91 min.

Step 2: (R)-N-((1-(5-methyl-6,7-dihydro-5H-cyclopenta[d]pyrimidin-4-yl)spiro[indoline-3,4'-piperidine]-4-yl)methyl)cyclopentanamine trihydrochloride (32 mg, 92%) was prepared by the procedures described in Example 1, Step 9, substituting (R)-N-((1'-benzyl-1-(5-methyl-6,7-dihydro-5H-cyclopenta[d]pyrimidin-4-yl)spiro[indoline-3,4'-piperidine]-4-yl)methyl)cyclopentanamine for (R)-tert-butyl 5-chloro-1-(5-methyl-6,7-dihydro-5H-cyclopenta[d]pyrimidin-4-yl)spiro[indoline-3,4'-piperidine]-1'-carboxylate. LCMS (APCI+) m/z 418 [M+H]+; Rt=1.96 min.

Example 73

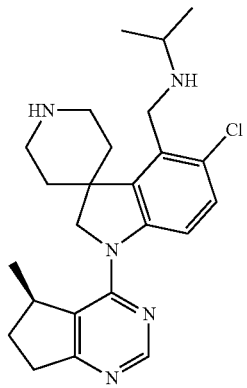

(R)-N-((5-chloro-1-(5-methyl-6,7-dihydro-5H-cyclopenta[d]pyrimidin-4-yl)spiro[indoline-3,4'-piperidine]-4-yl)methyl)propan-2-amine Step 1: A 1.0M THF solution of NaHMDS (158 mL, 158 mmol) at −78° C. was added dropwise to a stirred solution of 2-oxoindoline-4-carbonitrile (6.0 g, 37.3 mmol) in THF (100 mL) under N$_2$. After stirring at −78° C. for 30 minutes, N-benzylbis(2-chloroethyl)amine hydrochloride (10.9 g, 41.2 mmol) was added as a solid. The reaction mixture was stirred at −78° C. for 30 minutes and then allowed to warm to room temperature. The reaction mixture was then heated to reflux for 12 hours. After cooling to 0° C., the reaction was quenched by the addition of saturated aqueous NH$_4$Cl solution. The reaction mixture was partitioned between EtOAc and water. The aqueous layer was extracted with EtOAc (2×200 mL). The combined organics layers were washed with brine, dried with MgSO$_4$ and concentrated. The residue was purified by column chromatography (1:1 hexanes:EtOAc to EtOAc to give 1'-benzyl-2-oxospiro[indoline-3,4'-piperidine]-4-carbonitrile (4.90 g, 50%) as a solid. LCMS (APCI+) m/z 318 [M+H]+; Rt=2.41 min.

Step 2: To a stirred solution of 1'-benzyl-2-oxospiro[indoline-3,4'-piperidine]-4-carbonitrile (4.89 g, 15.4 mmol) in THF (100 mL) was added dropwise a solution of 1N LiAlH$_4$ in THF (46.2 mL, 46.2 mmol) under N$_2$ at 0° C. The reaction mixture was allowed to warm to room temperature and then refluxed overnight. The reaction mixture was cooled to 0° C. and quenched by the dropwise addition of water (5 mL), followed by 3N NaOH (3 mL). The mixture was diluted with ether (100 mL) and stirred for 10 minutes, at which point the reaction mixture was filtered through Celite. The filtrate was concentrated to give crude (1'-benzylspiro[indoline-3,4'-piperine]-4-yl)methanamine (4.74 g, 102%), which was carried forward in the next step without further purification. LCMS (APCI+) m/z 308 [M+H]+; Rt=1.95 min.

Step 3: A solution of Boc$_2$O (3.20 g, 14.6 mmol) in DCM (50 mL) was added dropwise to a stirred solution of (1'-benzylspiro[indoline-3,4'-piperine]-4-yl)methanamine (4.74 g, 15.4 mmol) in DCM (75 mL) cooled to 0° C. The reaction mixture was stirred for 4 hours, at which point a solution of 1M methyl amine in MeOH (10 mL, 10 mmol) was added. The reaction was allowed to stir for 1 hour. The organic layer was washed with saturated aqueous $NaHCO_3$ solution and brine, dried with $MgSO_4$ and concentrated. The crude residue was purified by column chromatography (30:1 DCM:MeOH) to give tert-butyl(1'-benzylspiro[indoline-3,4'-piperine]-4-yl)methylcarbamate (5.98 g, 95%) as a foam. LCMS (APCI+) m/z 408 [M+H]+; Rt=3.30 min.

Step 4: A round bottom flask was charged with $Pd(OAc)_2$ (24.8 mg, 0.110 mmol) and 9,9-dimethyl-4,5bis(diphenylphosphino)xanthene (95.8 mg, 0.166 mmol) in toluene (10 mL), and the solution purged with nitrogen. (R)-4-Chloro-5-methyl-6,7-dihydro-5H-cyclopenta[d]pyrimidine (186 mg, 1.10 mmol), tert-butyl (1'-benzylspiro[indoline-3,4'-piperine]-4-yl)methylcarbamate (450 mg, 1.10 mmol) and $Cs_2CO_3$ (540 mg, 1.66 mmol) were added to the flask. The mixture was heated at 100° C. for 4 hours. After cooling to room temperature, the reaction was diluted with EtOAc, filtered through Celite and concentrated. The crude product was purified by column chromatography (2:1 hexanes:EtOAc) to give (R)-tert-butyl(1' benzyl-1-(5-methyl-6,7-dihydro-5H-cyclopenta[d]pyrimidin-4-yl)spiro[indoline-3,4'-piperidine]-4-yl)methylcarbamate (451 mg, 75.7%) as a solid. LCMS (APCI+) m/z 540 [M+H+]; Rt=3.70 min.

Step 5: 10% Pd/C (110 mg, 0.92 mmol) and ammonium formate (585 mg, 9.25 mmol) were added to (R)-tert-butyl (1'benzyl-1-(5-methyl-6,7-dihydro-5H-cyclopenta[d]pyrimidin-4-yl)spiro[indoline-3,4'-piperidine]-4-yl)methylcarbamate (1.00 g, 1.85 mmol) in MeOH (20 mL) The reaction was heated to reflux for 6 hours, at which point the reaction was cooled to room temperature and filtered through Celite. The filtrate was concentrated to give (R)-tert-butyl(1-(5-methyl-6,7-dihydro-5H-cyclopenta[d]pyrimidin-4-yl)spiro[indoline-3,4'-piperidine]-4-yl)methylcarbamate (800 mg, 96%), which was used without further purification. $Boc_2O$ (462 mg, 2.12 mmol) was added to a solution of (R)-tert-butyl (1-(5-methyl-6,7-dihydro-5H-cyclopenta[d]pyrimidin-4-yl) spiro[indoline-3,4'-piperidine]-4-yl)methylcarbamate (800 mg, 1.77 mmol) in DCM (25 mL). The reaction mixture was stirred overnight. The organic layer was washed with saturated aqueous $NaHCO_3$ solution and brine, dried with $MgSO_4$ and concentrated. The crude residue was purified by column chromatography (4:1 hexane:EtOAc) to give (R)-tert-butyl 4-((tert-butoxycarbonylamine)methyl)-1-(5-methyl-6,7-dihydro-5H-cyclopenta[d]pyrimidin-4-yl)spiro[indoline-3,4'-piperidine]-1'-carboxylate (856 mg, 88%) as a foam. LCMS (APCI+) m/z 550 [M+H]+; Rt=4.36 min.

Step 6: NCS (131 mg, 0.98 mmol) was added to a stirred solution of (R)-tert-butyl 4-((tert-butoxycarbonylamine)methyl)-1-(5-methyl-6,7-dihydro-5H-cyclopenta[d]pyrimidin-4-yl)spiro[indoline-3,4'-piperidine]-1'-carboxylate (300 mg, 0.54 mmol) in DCM (5 mL) The reaction was stirred at room temperature for 48 hours. The reaction was diluted with DCM, washed with saturated aqueous $NaHCO_3$, brine, dried with $MgSO_4$ and concentrated. The crude material was purified by column chromatography (hexane:EtOAc, 1:1 to EtOAc:5% MeOH) to give (R)-tert-butyl 4-((tert-butoxycarbonylamine)methyl)-5-chloro-1-(5-methyl-6,7-dihydro-5H-cyclopenta[d]pyrimidin-4-yl)spiro[indoline-3,4'-piperidine]-1'-carboxylate (200 mg, 63%) as a solid. LCMS (APCI+) m/z 584/586 [M+H]+; Rt=4.72 min.

Step 7: 4N HCl in dioxane (3 mL) was added to a stirred solution of (R)-tert-butyl 4-((tert-butoxycarbonylamine)methyl)-5-chloro-1-(5-methyl-6,7-dihydro-5H-cyclopenta[d] pyrimidin-4-yl)spiro[indoline-3,4'-piperidine]-1'-carboxylate (200 mg, 0.34 mmol) in DCM (10 mL). The reaction was stirred at room temperature for 6 hours, at which point the reaction was concentrated to give (R)-(5-chloro-1-(5-methyl-6,7-dihydro-5H-cyclopenta[d]pyrimidine-4-yl)spiro[indoline-3,4'-piperidine]-4-yl)methanamine trihydrochloride salt (190 mg, 93%), which was used without further purification. A solution of $Boc_2O$ (90 mg, 0.41 mmol) in DMC (5 mL) was added to a solution of (R)-(5-chloro-1-(5-methyl-6,7-dihydro-5H-cyclopenta[d]pyrimidin-4-yl)spiro[indoline-3,4'-piperidine]-4-yl)methanamine trihydrochloride salt (190 mg, 0.41 mmol) and Huning's base (214 mg, 1.66 mmol) in DCM (10 mL) cooled to 0° C. After 3 hours, the reaction mixture was diluted with DCM (20 mL) and washed with aqueous $NaHCO_3$. The organic layer was washed with brine, dried with $MgSO_4$ and concentrated. The residue was purified by column:chromatography (4:1 hexanes:EtOAc to 3% MeOH in EtOAc) to give (R)-tert-butyl 4-((tert-butoxycarbonylamine)methyl)-1-(5-methyl-6,7-dihydro-5H-cyclopenta[d] pyrimidin-4-yl)spiro[indoline-3,4'-piperidine]-1'-carboxylate (57 mg, 25%) as a foam (LCMS (APCI+) m/z 550/552 [M+H]+; Rt=4.36 min) and (R)-tert-butyl 4-(aminomethyl)-5-chloro-1-(5-methyl-6,7-dihydro-5H-cyclopenta[d]pyrimidin-4-yl)spiro[indoline-3,4'-piperidine]-1'-carboxylate (133 mg, 71%) as a foam (LCMS (APCI+) m/z 450/452 [M+H]+; Rt=2.93 min).

Step 8: 2-Propanone (12 mg, 0.20 mmol) was added to a solution of (R)-tert-butyl 4-(aminomethyl)-5-chloro-1-(5-methyl-6,7-dihydro-5H-cyclopenta[d]pyrimidin-4-yl)spiro [indoline-3,4'-piperidine]-1'-carboxylate (20 mg, 0.041 mmol) in DCE (2 mL). The reaction was allowed to stir at room temperature for 15 minutes, at which point $Na(OAc)_3$ BH was added. The reaction was allowed to stir overnight. The reaction mixture was diluted with DCM, washed with saturated aqueous $NaHCO_3$ solution and brine, dried with $MgSO_4$ and concentrated. The residue was purified by column chromatography (15:1, DCM:MeOH) to give (R)-tert-butyl 5-chloro-4-((isopropylamino)methyl)-1-(5-methyl-6,7-dihydro-5H-cyclopenta[d]pyrimidin-4-yl)spiro[indoline-3,4'-piperidine]-1'-carboxylate (13 mg, 58%) as an oil. LCMS (APCI+) m/z 526/528 [M+H]+; Rt=4.72 min. This material was taken up into DCM (2 mL), and 2N HCl in ether was added (1 mL). The reaction was allowed to stir for 1 hour, at which point it was concentrated to give (R)-N-((5-chloro-1-(5-methyl-6,7-dihydro-5H-cyclopenta[d]pyrimidin-4-yl) spiro[indoline-3,4'-piperidine]-4-yl)methyl)propan-2-amine trihydrochloride salt (13 mg, 59%) as a solid. $^1$H NMR ($D_2O$, 400 MHz) δ 8.52 (s, 1H), 7.70 (d, J=8.8 Hz, 1H), 7.40 (d, J=8.8 Hz, 1H), 4.51-4.38 (m, 4H), 4.15 (d, J=9.6 Hz, 1H), 3.71-3.5 (m, 5H), 3.16-2.96 (m, 5H), 2.46-2.18 (m, 3H), 2.06-2.00 (m, 1H), 1.89-1.74 (m, 2H), 1.34-1.32 (m, 6H). LCMS (APCI+) m/z 426/428 [M+H]+; Rt=2.38 min.

Example 74

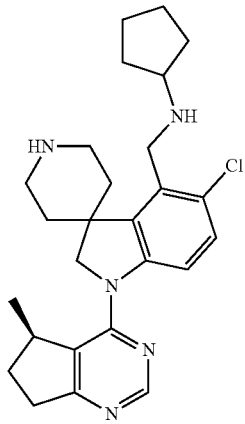

(R)-N-((5-chloro-1-(5-methyl-6,7-dihydro-5H-cyclopenta[d]pyrimidin-4-yl)spiro[indoline-3,4'-piperidine]-4-yl)methyl)cyclopentanamine Cyclopentanone (17.4 mg, 0.207 mmol) was added to a solution of (R)-tert-butyl 4-(aminomethyl)-5-chloro-1-(5-methyl-6,7-dihydro-5H-cyclopenta[d]pyrimidin-4-yl)spiro[indoline-3,4'-piperidine]-1'-carboxylate (20 mg, 0.041 mmol) in DCE (2 mL). The reaction was allowed to stir at room temperature for 15 minutes, at which point $Na(OAc)_3BH$ (22 mg, 0.103 mmol) was added. The reaction was allowed to stir overnight. The reaction mixture was diluted with DCM, washed with saturated aqueous $NaHCO_3$ solution and brine, dried with $MgSO_4$ and concentrated. The residue was purified by column chromatography (15:1, DCM:MeOH) to give (R)-tert-butyl 5-chloro-4-((cyclopentylamino)methyl)-1-(5-methyl-6,7-dihydro-5H-cyclopenta[d]pyrimidin-4-yl)spiro[indoline-3,4'-piperidine]-1'-carboxylate (13 mg, 54%) as an oil. LCMS (APCI+) m/z 552/554 [M+H]+; Rt=4.79 min This material was taken up into DCM (2 mL), and 2N HCl in ether was added (1 mL). The reaction was allowed to stir for 1 hour, at which point it was concentrated to give (R)-N-((5-chloro-1-(5-methyl-6,7-dihydro-5H-cyclopenta[d]pyrimidin-4-yl)spiro[indoline-3,4'-piperidine]-4-yl)methyl)propan-2-amine trihydrochloride salt (12 mg, 52%) as a solid. $^1$H NMR ($D_2O$, 400 MHz) δ 8.53 (s, 1H), 7.74 (d, J=8.8 Hz, 1H), 7.40 (d, J=8.8 Hz, 1H), 4.55-4.39 (m, 3H), 4.17-4.15 (m, 1H), 3.84-3.38 (m, 7H), 3.17-2.97 (m, 4H), 2.44-1.67 (m, 14H). LCMS (APCI+) m/z 452/454 [M+H]+; Rt=2.52 min.

Example 75

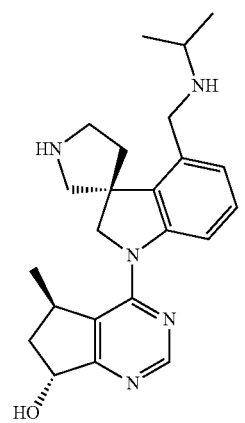

(5R,7R)-4-((S)-4-((isopropylamino)methyl)spiro[indoline-3,3'-pyrrolidine]-1-yl)-5-methyl-6,7-dihydro-5H-cyclopenta[d]pyrimidin-7-ol Step 1: 1-(Chloromethyl)-4-methoxybenzene (30.3 g, 193 mmol) was added to a slurry of 1H-indole-4-carbonitrile (25.0 g, 176 mmol) and NaH (7.74 g, 193 mmol) in DMF (586 mL, 176 mmol) at 0° C., and the resulting mixture was stirred at ambient temperature for 24 hours. The reaction mixture was poured into water and extracted with ethyl acetate (3×). The combined organic layers were washed with water and brine, dried ($Na_2SO_4$) and concentrated to afford a crude residue, which was purified by column chromatography eluting with an ethyl acetate/hexanes gradient to give 1-(4-methoxybenzyl)-1H-indole-4-carbonitrile (46.0 g, 175 mmol, 99%). $^1$H NMR (400 MHz, $CDCl_3$) δ 7.89 (d, J=8.2 Hz, 1H), 7.81 (d, J=3.1 Hz, 1H), 7.54 (d, J=7.4 Hz, 1H), 7.26 (t, J=7.8 Hz, 1H), 7.21 (d, J=8.6 Hz, 2H), 6.87 (d, J=8.6 Hz, 2H), 6.64 (d, J=2.7 Hz, 1H), 5.44 (s, 2H), 3.70 (s, 3H).

Step 2: Pyridinium bromide perbromide (196 g, 614 mmol) was slowly added to a solution of 1-(4-methoxybenzyl)-1H-indole-4-carbonitrile (46.0 g, 175 mmol) in t-BuOH (175 mL) and water (58.5 mL). The reaction mixture was partitioned between DCM and water. The organic layer was washed with water and brine, dried, and concentrated to give 3,3-dibromo-1-(4-methoxybenzyl)-2-oxoindoline-4-carbonitrile, which was combined with zinc dust (105 g, 1.61 mol) in acetic acid (803 mL) The mixture was stirred at 80° C. overnight. The hot reaction mixture was filtered, and the filter cake was washed with ethyl acetate. The filtrate was concentrated to give a solid that was further purified by column chromatography eluting with a hexanes/ethyl acetate gradient to give 1-(4-methoxybenzyl)-2-oxoindoline-4-carbonitrile (5.30 g, 19.0 mmol, 11%). LCMS (APCI+) M+H+277 (60%), 279 (60%); Rt=3.33 min.

Step 3: NaH (0.457 g, 19.0 mmol) was added to a solution of 1-(4-methoxybenzyl)-2-oxoindoline-4-carbonitrile (5.30 g, 19.0 mmol) in DMF (38 mL), and the resulting slurry was stirred at ambient temperature for 1 hour. Dibromoethane (3.94 g, 21.0 mmol) was then added to this mixture, and the mixture was stirred at room temperature for 1 hour. An additional equivalent of NaH (0.457 g, 19.0 mmol) was then added to the reaction mixture, and the reaction was stirred at 80° C. for 3 hours. The reaction mixture was concentrated and purified by column chromatography with a hexanes/ethyl acetate gradient+15% DCM. The mixed product fractions were recrystallized with DCM/hexanes to give 1'-(4-methoxybenzyl)-T-oxospiro[cyclopropane-1,3'-indoline]-4'-carbonitrile (5.00 g, 16.4 mmol, 86%). LCMS (APCI+) M+H+ 305 (100%); Rt=3.65 min.

Step 4: A solution of 1'-(4-methoxybenzyl)-T-oxospiro[cyclopropane-1,3'-indoline]-4'-carbonitrile (4.00 g, 13.1 mmol), $MgI_2$ (3.66 g, 13.1 mmol), N-benzyl-hexahydrotriazene (1.64 g, 4.60 mmol) in THF (65.7 mL, 13.1 mmol) was heated at 80° C. for 24 hours. The reaction mixture was diluted with ether and water. The organic layer was washed with brine, dried ($Na_2SO_4$) and concentrated to give the crude product. The crude material was purified by column chromatography eluting with a hexanes/ethyl acetate gradient to afford 1'-benzyl-1-(4-methoxybenzyl)-2-oxospiro[indoline-3,3'-pyrrolidine]-4-carbonitrile (5.02 g, 11.9 mmol, 90%). LCMS (APCI+) M+H+424 (100%); Rt=4.17 min.

Step 5: A solution of 1'-benzyl-1-(4-methoxybenzyl)-2-oxospiro[indoline-3,3'-pyrrolidine]-4-carbonitrile (3.00 g, 7.08 mmol) in LAH (1.0M in THF, 35.4 mL, 35.4 mmol) was heated at reflux for 12 hours. The reaction mixture was quenched with $Na_2SO_4 \cdot 10H_2O$, dried and filtered. The filter cake was washed with ethyl acetate, and the filtrate was concentrated. The residue was purified by chromatography (hexanes/ethyl acetate gradient) to give (1'-benzyl-1-(4-methoxybenzyl)spiro[indoline-3,3'-pyrrolidine]-4-yl)methanamine (500 mg, 1.21 mmol, 17%). LCMS (APCI+) M+H+414 (100%); Rt=3.23 min.

Step 6: A solution of (1'-benzyl-1-(4-methoxybenzyl)spiro[indoline-3,3'-pyrrolidine]-4-yl)methanamine (0.500 g, 1.21 mmol) in TFA (7.00 mL) was heated at 85° C. for 24 hours. The solvent was evaporated to give (1'-benzylspiro[indoline-3,3'-pyrrolidine]-4-yl)methanamine trifluoroacetic acid salt (0.355 g, 0.872 mmol, 72%). LCMS (APCI+) M+H+294 (100%); Rt=2.06 min.

Step 7: To a solution of (1'-benzylspiro[indoline-3,3'-pyrrolidine]-4-yl)methanamine (0.355 g, 0.772 mmol) and TEA (0.570 mL, 4.09 mmol) in DCM (6.82 mL) was slowly added $Boc_2O$ portionwise until the reaction was complete, as determined by LCMS. The residue was purified by chromatography (DCM/MeOH+1% $NH_4OH$ gradient) to give tert-butyl (1'-benzylspiro[indoline-3,3'-pyrrolidine]-4-yl)methylcarbamate (130 mg, 0.330 mmol, 24%). LCMS (APCI+) M+H+394 (100%); Rt=3.38 min.

Step 8: A solution of (5R,7R)-4-chloro-5-methyl-6,7-dihydro-5H-cyclopenta[d]pyrimidin-7-yl 4-nitrobenzoate (0.110 g, 0.330 mmol), tert-butyl (1'-benzylspiro[indoline-3,3'-pyrrolidine]-4-yl)methylcarbamate (0.130 g, 0.330 mmol), $Cs_2CO_3$ (0.162 g, 0.496 mmol), and Xantphos (28.7 mg, 0.050 mmol) in toluene (2.00 mL) was degassed by bubbling a stream of nitrogen through the solution. $Pd(OAc)_2$ (7.42 mg, 0.0330 mmol) was then added to this solution, and the resulting mixture was heated overnight at 100° C. The reaction mixture was concentrated and purified by Analogix chromatography (DCM/5% MeOH/1% $NH_4OH$) to give (5R,7R)-4-(1'-benzyl-4-((tert-butoxycarbonylamino)methyl)spiro[indoline-3,3'-pyrrolidine]-1-yl)-5-methyl-6,7-dihydro-5H-cyclopenta[d]pyrimidin-7-yl 4-nitrobenzoate (180 mg, 261 mmol, 79%). LCMS (APCI+) M+H+692 (100%); Rt=4.89 min.

Step 9: A solution of (5R,7R)-4-(1'-benzyl-4-((tert-butoxycarbonylamino)methyl)spiro[indoline-3,3'-pyrrolidine]-1-yl)-5-methyl-6,7-dihydro-5H-cyclopenta[d]pyrimidin-7-yl 4-nitrobenzoate (0.180 g, 0.261 mmol) and LiOH—$H_2O$ (0.219 g, 5.21 mmol) in THF (1.04 mL) and water (0.261 mL) was stirred at ambient temperature for 2 hours. The solvent was removed, and the residue was purified with a Gilson C18 prep HPLC system (5-95 ACN/$H_2O$+1% TFA) to give pure diastereomers (45 mg of each diastereomer, 0.083 mmol, 64%). The absolute configuration of diastereomers was assigned by NMR. tert-Butyl ((R)-1'-benzyl-1-((5R,7R)-7-hydroxy-5-methyl-6,7-dihydro-5H-cyclopenta[d]pyrimidin-4-yl)spiro[indoline-3,3'-pyrrolidine]-4-yl)methylcarbamate: LCMS (APCI+) M+H+542 (100%); Rt=3.52 min. tert-Butyl ((S)-1'-benzyl-1-((5R,7R)-7-hydroxy-5-methyl-6,7-dihydro-5H-cyclopenta[d]pyrimidin-4-yl)spiro[indoline-3,3'-pyrrolidine]-4-yl)methylcarbamate: LCMS (APCI+) M+H+542 (100%); Rt=3.90 min.

Step 10: HCl (0.50 mL; 4N in dioxane) was added to a solution of tert-butyl ((S)-1'-benzyl-1-((5R,7R)-7-hydroxy-5-methyl-6,7-dihydro-5H-cyclopenta[d]pyrimidin-4-yl)spiro[indoline-3,3'-pyrrolidine]-4-yl)methylcarbamate (45 mg, 0.083 mmol) in MeOH (4.2 mL). The solution was stirred at ambient temperature for 24 hours. The solvent was evaporated to give a film that was used without purification (38 mg, 95%, 0.079 mmol). LCMS (APCI+) M+H+442 (100%); Rt=2.18 min.

Step 11: $NaBH(OAc)_3$ (57.6 mg, 0.272 mmol) was added to a solution of (5R,7R)-4-(S)-4-(aminomethyl)-1'-benzylspiro[indoline-3,3'-pyrrolidine]-1-yl)-5-methyl-6,7-dihydro-5H-cyclopenta[d]pyrimidin-7-ol (40 mg, 0.091 mmol), acetone (52.6 mg, 0.906 mmol) in DCE (1.0 mL), and the resulting solution was stirred at ambient temperature for 8 hours. The reaction mixture was diluted with DCM and washed with 25% NaOH. The aqueous layer was separated and extracted with DCM (3×). The combined organic layers were dried ($Na_2SO_4$) and concentrated to give (5R,7R)-4-((S)-1'-benzyl-4-((isopropylamino)methyl)spiro[indoline-3,3'-pyrrolidine]-1-yl)-5-methyl-6,7-dihydro-5H-cyclopenta[d]pyrimidin-7-ol (40.0 mg, 0.083 mmol, 91%). LCMS (APCI+) M+H+484 (100%); Rt=2.64 min Step 12: Pd/C (35.2 mg, 0.017 mmol) and ammonium formate (52.2 mg, 0.827 mmol) was added to a solution of (5R,7R)-4-((S)-1'-benzyl-4-((isopropylamino)methyl)spiro[indoline-3,3'-pyrrolidine]-1-yl)-5-methyl-6,7-dihydro-5H-cyclopenta[d]pyrimidin-7-ol (40.0 mg, 0.083 mmol) in MeOH (3 mL). The resulting mixture was stirred at ambient temperature overnight. The reaction mixture was filtered, and the filtrate was concentrated and purified by Analogix chromatography (DCM/MeOH/1% $NH_4OH$ gradient) to give (5R,7R)-4-((S)-4-((isopropylamino)methyl)spiro[indoline-3,3'-pyrrolidine]-1-yl)-5-methyl-6,7-dihydro-5H-cyclopenta[d]pyrimidin-7-ol. This material was converted to the bis-HCl salt by dissolving the material in DCM and adding HCl (4N in dioxane) and concentrating the mixture (9.0 mg, 0.022 mmol, 27%). $^1$H NMR (400 MHz, $d_6$-DMSO) δ 10.05 (br s, 1H), 9.92 (br s, 1H), 9.58 (br s, 1H), 9.47 (br s, 1H), 8.89 (s, 1H), 8.10 (d, J=8.2 Hz, 1H), 7.66 (s, J=7.8 Hz, 1H), 7.46 (t, J=8.2 Hz, 1H), 5.30 (t, J=7.8 Hz, 1H), 4.83 (d, J=10.5 Hz, 1H), 4.35 (t, J=10.5 Hz, 1H), 4.20 (d, J=7.8 Hz, 1H), 4.14 (d, J=10.9 Hz, 1H), 3.96-3.85 (m, 1H), 3.71-3.67 (m, 4H), 3.43 (dd, J=10.9, 3.9 Hz, 2H), 3.41-3.31 (m, 2H), 2.63-2.58 (m, 1H), 2.35-2.33 (m, 1H), 2.18-2.13 (m, 2H), 1.41 (d, J=6.2 Hz, 6H), 1.18 (d, J=6.4 Hz, 2H), 1.12 (d, J=6.6 Hz, 3H). LCMS (APCI+) M+H+394 (100%); Rt=1.72 min. HPLC purity at 254 nm >99%, Rt=1.63 min.

Example 76

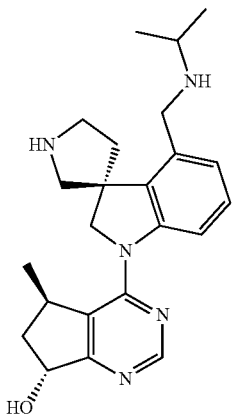

(5R,7R)-4-(R)-4-((isopropylamino)methyl)spiro[indoline-3,3'-pyrrolidine]-1-yl)-5-methyl-6,7-dihydro-5H-cyclopenta[d]pyrimidin-7-ol Step 1: (5R,7R)-4-((R)-4-(Aminomethyl)-1'-benzylspiro[indoline-3,3'-pyrrolidine]-1-yl)-5-methyl-6,7-dihydro-5H-cyclopenta[d]pyrimidin-7-ol hydrochloride salt (38.0 mg, 95%, 0.079 mmol) was prepared by the procedures described in Example 76, Step 10, substituting tert-butyl ((R)-1'-benzyl-1-((5R,7R)-7-hydroxy-5-methyl-6,7-dihydro-5H-cyclopenta[d]pyrimidin-4-yl)spiro[indoline-3,3'-pyrrolidine]-4-yl)methylcarbamate for tert-butyl ((S)-1'-benzyl-1-((5R,7R)-7-hydroxy-5-methyl-6,7-dihydro-5H-cyclopenta[d]pyrimidin-4-yl)spiro[indoline-3,3'-pyrrolidine]-4-yl)methylcarbamate. LCMS (APCI+) M+H+442 (100%); Rt=2.18 min.

Step 2: (5R,7R)-4-((R)-1'-Benzyl-4-((isopropylamino)methyl)spiro[indoline-3,3'-pyrrolidine]-yl)-5-methyl-6,7-dihydro-5H-cyclopenta[d]pyrimidin-7-ol (40.0 mg, 0.083 mmol, 91%) was prepared by the procedure described in Example 76, Step 11, substituting (5R,7R)-4-(R)-4-(aminomethyl)-1'-benzylspiro[indoline-3,3'-pyrrolidine]-1-yl)-5-methyl-6,7-dihydro-5H-cyclopenta[d]pyrimidin-7-ol for (5R,7R)-4-(S)-4-(aminomethyl)-1'-benzylspiro[indoline-3,3'-pyrrolidine]-1-yl)-5-methyl-6,7-dihydro-5H-cyclopenta[d]pyrimidin-7-ol. LCMS (APCI+) M+H+484 (100%); Rt=2.55 min.

Step 3: (5R,7R)-4-((R)-4-((isopropylamino)methyl)spiro[indoline-3,3'-pyrrolidine]-1-yl)-5-methyl-6,7-dihydro-5H-cyclopenta[d]pyrimidin-7-ol bis-hydrochloride salt (4.6 mg, 0.010 mmol, 13%) was prepared by the procedure described in Example 76, Step 12, substituting (5R,7R)-4-((R)-1'-benzyl-4-((isopropylamino)methyl)spiro[indoline-3,3'-pyrrolidine]-1-yl)-5-methyl-6,7-dihydro-5H-cyclopenta[d]pyrimidin-7-ol for (5R,7R)-4-((S)-1'-benzyl-4-((isopropylamino)methyl)spiro[indoline-3,3'-pyrrolidine]-1-yl)-5-methyl-6,7-dihydro-5H-cyclopenta[d]pyrimidin-7-ol. $^1$H NMR (400 MHz, d$_6$-DMSO) δ 10.25 (br s, 1H), 9.85 (br s, 1H), 9.52 (br s, 1H), 9.37 (br s, 1H), 8.87 (s, 1H), 7.95 (d, J=7.8 Hz, 1H), 7.59 (s, J=7.8 Hz, 1H), 7.43 (t, J=7.8 Hz, 1H), 5.25 (t, J=7.4 Hz, 1H), 4.83 (m, 2H), 4.35 (m 1H), 4.23 (m, 1H), 4.18 (m, 1H), 3.96-3.85 (m, 1H), 3.71-3.67 (m, 4H), 3.43 (dd, J=7.8, 4.3 Hz, 2H), 3.60-3.58 (m, 2H), 2.51-2.49 (m, 2H), 2.18-2.13 (m, 2H), 1.41 (t, J=5.5 Hz, 6H), 1.23 (m, 2H), 1.09 (d, J=7.0 Hz, 3H). LCMS (APCI+) M+H+394 (100%); Rt=1.56 min. HPLC purity at 254 nm 90%, Rt=1.64 min.

Example 77

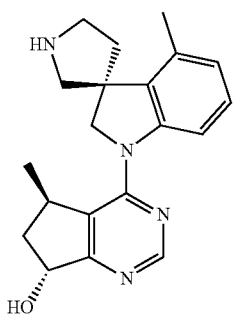

(5R,7R)-5-methyl-4-((R)-4-methylspiro[indoline-3,3'-pyrrolidine]-1-yl)-6,7-dihydro-5H-cyclopenta[d]pyrimidin-7-ol (5R,7R)-5-methyl-4-((R)-4-methylspiro[indoline-3,3'-pyrrolidine]-1-yl)-6,7-dihydro-5H-cyclopenta[d]pyrimidin-7-ol (3.8 mg, 0.011 mmol, 13%) was obtained as a result of over-reduction in the last step for the preparation of (5R,7R)-4-((R)-4-((isopropylamino)methyl)spiro[indoline-3,3'-pyrrolidine]-1-yl)-5-methyl-6,7-dihydro-5H-cyclopenta[d]pyrimidin-7-ol bis-hydrochloride salt (Example 76, Step 3). $^1$H NMR (400 MHz, d$_6$-DMSO) δ 9.84 (s, 1H), 9.60 (s, 1H), 8.86 (s, 1H), 7.91 (d, J=7.8 Hz, 1H), 7.25 (t, J=7.8 Hz, 1H), 6.97 (s, J=7.4 Hz, 1H), 5.76 (s, 1H), 5.26 (t, J=7.4 Hz, 1H), 4.65 (s, 1H), 4.41 (d, J=10.5 Hz, 1H), 4.28 (d, J=10.5 Hz, 1H), 3.90-3.80 (m, 2H), 3.71 (m, 4H), 3.68 (dd, J=12.0, 4.3 Hz, 2H), 3.67 (s, 6H), 3.59 (m, 3H), 2.43 (m, 3H), 2.20-2.10 (m, 2H), 1.10 (d, J=7.0 Hz, 2H). LCMS (APCI+) M+H+337 (100%); Rt=1.97 min. HPLC purity at 254 nm 97%, Rt=1.78 min.

Example 78

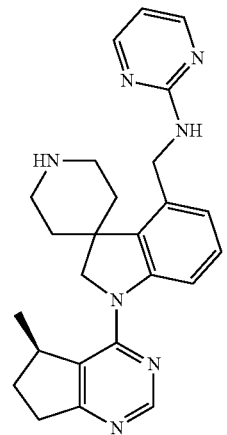

(R)-N-((1-(5-methyl-6,7-dihydro-5H-cyclopenta[d]pyrimidin-4-yl)spiro[indoline-3,4'-piperidine]-4-yl)methyl)pyrimidin-2-amine Step 1: A solution of (R)-tert-butyl 4-(aminomethyl)-1-(5-methyl-6,7-dihydro-5H-cyclopenta[d]pyrimidin-4-yl)spiro[indoline-3,4'-piperidine]-1'-carboxylate (15 mg, 0.033 mmol), 2-chloropyrimidine (3.8 mg, 0.033 mmol), and triethylamine (25 µL, 0.16 mmol) in DMF (0.50 mL) was heated at 100° C. for 24 hours. The material was diluted with MeOH and purified with a Gilson C18 prep HPLC system to give (R)-tert-butyl 1-(5-methyl-6,7-dihydro-5H-cyclopenta[d]pyrimidin-4-yl)-4-((pyrimidin-2-ylamino)methyl)spiro[indoline-3,4'-piperidine]-1'-carboxylate (7.0 mg, 0.013 mmol, 40%). LCMS (APCI+) M+H+528 (85%); Rt=3.89 min.

Step 2: A solution of (R)-tert-butyl 1-(5-methyl-6,7-dihydro-5H-cyclopenta[d]pyrimidin-4-yl)-4-((pyrimidin-2-ylamino)methyl)spiro[indoline-3,4'-piperidine]-1'-carboxylate (4 mg, 7.58 µmol) and HCl (50.0 µL; 4N in dioxane) was stirred at ambient temperature overnight. The solvent was removed to yield (R)-N-((1-(5-methyl-6,7-dihydro-5H-cyclopenta[d]pyrimidin-4-yl)spiro[indoline-3,4'-piperidine]-4-yl)methyl)pyrimidin-2-amine bishydrochloride as a solid (4.0 mg, 7.6 mmol, >99%). $^1$H NMR (400 MHz, CD$_3$OD) δ

8.77 (s, 1H), 8.59 (br s, 2H), 7.99 (br d, J=6.6 Hz, 1H), 7.35 (t, J=8.2 Hz, 1H), 7.27 (d, J=7.8 Hz, 1H), 6.98 (t, J=5.1 Hz, 1H), 4.95 (d, J=3.12 Hz, 2H), 4.69 (d, J=10.2 Hz, 1H), 4.26 (d, J=10.5 Hz, 1H), 3.96-3.91 (m, 1H), 3.74-3.71 (m, 1H), 3.64-3.58 (m, 4H), 3.60-3.52 (m, 2H), 3.46 (m, 2H), 3.14-3.10 (m, 2H), 2.95-2.85 (m, 1H), 2.65-2.55 (m, 2H), 1.92 (d, J=12.9 Hz, 114), 1.95-1.88 (m, 2H), 1.27 (m, 6H), 1.13 (d, J=5.9 Hz, 1H). LCMS (APCI+) M+H+428 (100%); Rt=2.49 min. HPLC purity at 254 nm>99%, Rt=1.84 min.

Example 79

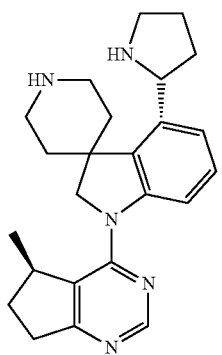

1-((R)-5-methyl-6,7-dihydro-5H-cyclopenta[d]pyrimidin-4-yl)-4-(R)-pyrrolidin-2-yl)spiro[indoline-3,4'-piperidine]

Step 1: sec-Butyl lithium (25.3 mL, 35.4 mmol) was added into a solution of tert-butyl 1-pyrrolidinecarboxylate (6.2 mL, 35.4 mmol) and (−)-spartiene (8.29 g, 35.4 mmol) in MTBE (100 mL) at −78° C. The mixture was stirred for 1 hour at −78° C. Zinc chloride solution (35.4 mL, 35.4 mmol) was added, and the reaction was stirred for 15 minutes at −78° C. The reaction was allowed to warm up to room temperature. 4-Bromoindolin-2-one (5.00 g, 23.6 mmol), palladium (II) acetate (0.53 g, 2.4 mmol) and tri-tert-butylphosphine tetrafluoroborate (0.68 g, 2.4 mmol) was added into the reaction mixture. The reaction was stirred for 12 hours at room temperature. The reaction mixture was poured into EtOAc (200 mL), and the suspension was filtered with a pad of celite. The filtrate was concentrated, and the residue was purified by flash chromatography (silica gel eluted with 4:1 hexanes:ethyl acetate) to give (R)-tert-butyl 2-(2-oxoindolin-4-yl)pyrrolidine-1-carboxylate (1.9 g, 27%) as a solid. $^1$H NMR (CDCl$_3$, 400 MHz) δ 7.80 (s, 1H), 7.10-7.20 (m, 1H), 6.75-6.82 (m, 1H), 6.62-6.78 (m, 1H), 4.65-4.93 (m, 1H), 3.34-3.73 (m, 4H), 2.20-2.40 (m, 1H), 1.84-2.00 (m, 2H), 1.68-1.83 (m, 1H), 1.45 (2, 4H), 1.14 (s, 5H). MS (APCI+) [M+H]+ 303.

Step 2: NaHMDS (5.0 mL, 5.0 mmol) was added into a solution of (R)-tert-butyl 2-(2-oxoindolin-4-yl)pyrrolidine-1-carboxylate (300 mg, 0.992 mmol) in THF (10 mL) at −78° C. The mixture was stirred for 20 minutes at that temperature. N-benzyl-2-chloro-N-(2-chloroethyl)ethanamine HCl salt (300 mg, 1.12 mmol) was added into the solution at −78° C. The reaction mixture was allowed to warm up to room temperature and was heated to reflux for 12 hours. The reaction was quenched by pouring the reaction mixture into water (10 mL) and was extracted with EtOAc (100 mL). The organic layer was washed with brine, dried with Na$_2$SO$_4$, filtered and concentrated. The residue was purified with flash chromatography to afford the product (R)-tert-butyl 2-(1'-benzyl-2-oxospiro[indoline-3,4'-piperidine]-4-yl)pyrrolidine-1-carboxylate (150 mg, 0.325 mmol, 32.8%) as a solid. $^1$H NMR (CDCl$_3$, 400 MHz) δ 7.20-7.45 (m, 6H), 7.10 (t, 1H), 6.80 (d, 1H), 6.60-6.70 (m, 1H), 5.40-5.80 (m, 1H), 3.50-3.80 (m, 4H), 3.00-3.20 (m, 2H), 2.90-3.00 (m, 2H), 2.75-2.85 (m, 2H), 2.60-2.70 (m, 1H), 2.20-2.50 (m, 2H), 1.90-2.00 (m, 1H), 1.80-1.90 (m, 1H), 1.70-1.80 (m, 1H), 1.60-1.70 (m, 1H), 1.50-1.60 (m, 1H), 1.00-1.50 (m, 9H). MS (APCI+) [M+H]+ 462.

Step 3: RED-AL (250 μL, 0.83 mmol) was added into a solution of (R)-tert-butyl 2-(1'-benzyl-2-oxospiro[indoline-3,4'-piperidine]-4-yl)pyrrolidine-1-carboxylate (120 mg, 0.26 mmol) in toluene (3 mL), and the resulting solution was heated to 70° C. for 30 minutes. The reaction was quenched by adding EtOAc (5 mL) into the reaction mixture. The resulting mixture was treated with 1M aqueous potassium sodium tartrate (2 mL) and was extracted with EtOAc (10 mL). The organic layer was washed with brine, dried with Na$_2$SO$_4$, filtered and concentrated. The residue was purified with flash chromatography to afford the product (R)-tert-butyl 2-(1'-benzylspiro[indoline-3,4'-piperidine]-4-yl)pyrrolidine-1-carboxylate (50 mg, 43.0%) as a solid. $^1$H NMR (CDCl$_3$, 400 MHz) δ 7.30-7.40 (m, 4H), 7.18-7.20 (m, 1H), 6.90-7.00 (m, 1H), 6.42-6.52 (m, 1H), 5.20-5.40 (m, 1H), 3.40-3.80 (m, 4H), 3.18-3.40 (m, 1H), 2.80-3.00 (m, 2H), 2.22-2.42 (m, 3H), 2.20 (s, 2H), 1.95-2.02 (m, 2H), 1.70-1.85 (m, 2H), 1.56 (s, 4H), 1.38-1.42 (m, 1H), 1.22-1.30 (m, 1H), 1.20 (s, 6H). MS (APCI+) [M+H]+ 448.

Step 4: A mixture of (R)-tert-butyl 2-(1'-benzylspiro[indoline-3,4'-piperidine]-4-yl)pyrrolidine-1-carboxylate (50 mg, 0.11 mmol), (R)-4-chloro-5-methyl-6,7-dihydro-5H-cyclopenta[d]pyrimidine (19 mg, 0.11 mmol), Cs$_2$CO$_3$ (40 mg, 0.12 mmol), Pd(OAc)$_2$ (3.0 mg, 0.01 mmol), Xantphos (7.0 mg, 0.01 mmol) in toluene (5 mL) was degassed by a nitrogen balloon, and the mixture was heated to 90° C. for 12 hours. The reaction mixture was filtered by a pad of celite and eluted with EtOAc. The filtrate was concentrated, and the residue was purified by flash chromatography to afford the product (R)-tert-butyl 2-(1'-benzyl-1-((R)-5-methyl-6,7-dihydro-5H-cyclopenta[d]pyrimidin-4-yl)spiro[indoline-3,4'-piperidine]-4-yl)pyrrolidine-1-carboxylate (15 mg, 23%) as a solid. $^1$H NMR (CDCl$_3$, 400 MHz) δ 8.68 (s, 1H), 7.20-7.40 (m, 5H), 7.09-7.12 (m, 1H), 6.84-6.90 (m, 1H), 6.70-6.74 (m, 1H), 5.25-5.32 (m, 1H), 4.10-4.20 (m, 1H), 3.80-3.90 (m, 1H), 3.70-3.80 (m, 1H), 3.50-3.60 (m, 2H), 3.30-3.40 (m, 1H), 2.95-3.00 (m, 2H), 2.85-2.95 (m, 2H), 2.20-2.60 (m, 4H), 1.95-2.05 (m, 2H), 1.80-1.95 (m, 2H), 1.60-1.80 (m, 4H), 1.30 (s, 4H), 1.20 (s, 511), 0.80-0.90 (m, 3H). MS (APCI+) [M+H]+ 580.

Step 5: A mixture of palladium on carbon (10% degussa typed, 10 mg), ammonium formate (50 mg, 0.80 mmol) and (R)-tert-butyl 2-(1'-benzyl-1-((R)-5-methyl-6,7-dihydro-5H-cyclopenta[d]pyrimidin-4-yl)spiro[indoline-3,4'-piperidine]-4-yl)pyrrolidine-1-carboxylate (15 mg, 0.026 mmol) in MeOH (5 mL) was heated to reflux for 5 hours. The reaction was filtered with a pad of celite and eluted with EtOAc (100 mL), and the filtrate was washed with water (10 mL). The organic layer was dried with Na$_2$SO$_4$, filtered and concentrated. The residue was purified with flash chromatography (eluted with 10% MeOH/ethyl acetate, 10% 7N NH$_3$ in MeOH/ethyl acetate) to afford the product (R)-tert-butyl 2-(1-((R)-5-methyl-6,7-dihydro-5H-cyclopenta[d]pyrimidin-4-yl)spiro[indoline-3,4'-piperidine]-4-yl)pyrrolidine-1-carboxylate (8 mg, 63%) as a solid. $^1$H NMR (CDCl$_3$, 400 MHz) δ 8.80 (s, 1H), 7.13 (t, 1H), 6.86-6.92 (m, 1H), 7.40 (d, 1H), 5.30-5.40 (m, 1H), 4.20-4.30 (m, 1H), 3.58-4.00 (m, 1H), 3.70-3.80 (m, 1H), 3.55-3.65 (m, 1H), 3.40-3.50 (m, 1H), 3.00-3.20 (m, 2H), 2.80-3.00 (m, 2H), 2.65-2.80 (m, 1H), 2.40-2.50 (m, 2H), 2.30-2.40 (m, 1H), 2.10-2.20 (m, 1H), 2.00-2.10 (m, 1H), 1.80-1.95 (m, 2H), 1.55-1.75 (m, 3H), 1.40-1.50 (m, 1H), 1.20 (s, 9H), 0.80-0.90 (m, 3H). MS (APCI+) [M+H]+ 490.

Step 6: 4M HCl in dioxane (2 mL) was added into a solution of (R)-tert-butyl 2-(1-((R)-5-methyl-6,7-dihydro-5H-cyclopenta[d]pyrimidin-4-yl)spiro[indoline-3,4'-piperidine]-4-yl)pyrrolidine-1-carboxylate (8 mg, 0.02 mmol) in CH$_2$Cl$_2$ (5 mL). The reaction was stirred at room temperature for 1 hour. The solvent was evaporated, and the crude material was recovered to afford the product 1-((R)-5-methyl-6,7-dihydro-5H-cyclopenta[d]pyrimidin-4-yl)-4-((R)-pyrrolidin-2-yl)spiro[indoline-3,4'-piperidine] (3 mg, 47% yield) as a solid. $^1$H NMR (d$_6$-DMSO, 400 MHz) δ 8.80 (s, 1H), 8.00-8.10 (m, 1H), 7.52 (t, 1H), 7.40 (d, 1H), 5.35-5.45 (m, 1H), 4.60-4.70 (m, 1H), 4.20-4.30 (m, 1H), 3.85-4.00 (m, 1H), 3.70-3.80 (m, 1H), 3.60-3.70 (m, 3H), 3.50-3.60 (m, 2H), 3.20-3.30 (m, 2H), 3.10-3.20 (m, 1H), 2.80-2.90 (m, 1H), 2.50-2.70 (m, 2H), 2.40-2.50 (m, 1H), 2.30-2.40 (m, 1H), 2.10-2.20 (m, 2H), 1.90-2.05 (m, 2H), 1.10 (d, 3H). MS (APCI+) [M+H]+ 390.

Example 80

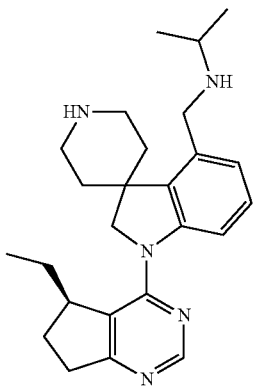

(R)-N-((1-(5-ethyl-6,7-dihydro-5H-cyclopenta[d]pyrimidin-4-yl)spiro[indoline-3,4'-piperidine]-4-yl)methyl)propan-2-amine Step 1: A round bottom flask was charged with copper(I) chloride (0.0575 g, 0.581 mmol) and purged with N$_2$. A solution of 1-Methylmagnesium bromide in THF (23.2 mL, 23.2 mmol) was injected and the mixture was cooled to 0° C. A solution of (E)-dimethyl hex-2-enedioate (2 g, 11.6 mmol) in anhydrous THF (10 mL) was injected over 15 minutes, and the reaction was stirred for 30 minutes at 0° C. (E)-Dimethyl hex-2-enedioate was prepared as described in Nugent, William A. and Frank W. Hobbs, Jr. "Conjugate Addition-Cyclization of a Cyanocuprate: 2-Carboethoxy-3-vinylcyclopentanone." *Organic Syntheses. Vol.* 66 (1988): pp. 52-59, using methyl acrylate (100.00 mL, 1110.5 mmol), anhydrous LiBF$_4$ (9.109 g, 97.17 mmol), and tetrakis(acetonitrile)palladium (II) tetrafluoroborate (1.332 g, 2.998 mmol). The reaction was warmed to room temperature and stirred at room temperature for 1 hour. TLC (5:1 EtOAc/Hexanes) showed disappearance of the UV-active starting material spot. The reaction was concentrated to a solid under vacuum and partitioned between DCM and saturated aqueous NH$_4$Cl. The organic was washed with brine and dried over anhydrous Na$_2$SO$_4$. The reaction produced methyl 2-ethyl-5-oxocyclopentanecarboxylate (1.88 g, 11.0 mmol, 95.1% yield) as an oil. $^1$H NMR (CDCl$_3$, 400 MHz) δ 3.76 (s, 3H), 2.84 (d, 1H), 2.2-2.6 (m, 4H), 1.62 (m, 1H), 1.41-1.52 (m, 2H), 0.96 (t, 3H). MS (APCI+) [M+H]: 171.0.

Step 2: Ammonium acetate (8.51 g, 110 mmol) was added to a solution of methyl 2-ethyl-5-oxocyclopentanecarboxylate (1.88 g, 11.0 mmol) in methanol (20 mL, 494 mmol). The reaction was heated to 65° C. for 2 hours. LCMS confirmed conversion to the desired product. The reaction was cooled, and the solvent removed under vacuum. The resulting oil was partitioned between DCM and half-saturated NaHCO$_3$. The organic layer was separated and dried over anhydrous Na$_2$SO$_4$. The crude oil was purified by silica gel chromatography (gradient: 5-50% EtOAc/Hexanes). Purification provided methyl 2-amino-5-ethylcyclopent-1-enecarboxylate (1.62 g, 9.57 mmol, 86.7% yield) as an oil that crystallized while sitting on the bench top. $^1$H NMR (d$_6$-DMSO, 400 MHz) δ 4.03 (s, 3H), 3.16 (m, 1H), 3.00 (m, 1H), 2.95 (t, 1H), 2.74-2.81 (m, 1H), 2.32 (m, 1H), 2.10 (m, 1H), 1.96 (m, 1H), 1.67 (m, 2H), 1.29 (t, 3H). MS (APCI+) [M+H]: 170.0.

Step 3: Methyl 2-amino-5-ethylcyclopent-1-enecarboxylate (1.62 g, 9.57 mmol) was combined with ammonium formate (3.02 g, 47.9 mmol) and formamide (3.80 mL, 95.7 mmol), and the reaction mixture was heated to 150° C. for 16 hours. Conversion was confirmed by LCMS. The reaction was cooled to room temperature and partitioned between a 5:1 DCM/i-PrOH solution and water. The aqueous layer was extracted multiple times with the same DCM/i-PrOH solution. The combined extracts were concentrated to dryness and partitioned between DCM and brine. The organic portion was concentrated to provide 5-ethyl-6,7-dihydro-5H-cyclopenta[d]pyrimidin-4-ol (1.13 g, 6.88 mmol, 71.9% yield) as an oil, which was taken to the next step without purification. MS (APCI+) [M+H]: 165.0.

Step 4: Phosphorous oxychloride (1.92 mL, 20.6 mmol) was added to a solution of 5-ethyl-6,7-dihydro-5H-cyclopenta[d]pyrimidin-4-ol (1.13 g, 6.88 mmol) in acetonitrile (40 mL, 766 mmol) and heated to 80° C. The reaction was stirred at 80° C. for 15 hours. LCMS confirmed consumption of the starting material peak and conversion to a new product peak. The reaction was cooled to room temperature and concentrated under vacuum. The residue was partitioned between DCM and saturated aqueous NaHCO$_3$. The organic layer was dried over anhydrous Na$_2$SO$_4$. The crude solution was concentrated under vacuum to an oil. The crude was purified by silica gel chromatography (gradient: 10-50% EtOAc/Hexanes). Purification provided 4-chloro-5-ethyl-6,7-dihydro-5H-cyclopenta[d]pyrimidine (334 mg, 1.83 mmol, 26.6% yield) as an oil. MS (APCI+) [M+H]: 183.0.

Step 5: A 3-neck round bottom flask was charged with tert-butyl (1'-benzylspiro[indoline-3,4'-piperidine]-4-yl)methylcarbamate (446 mg, 1.09 mmol; see Example 27, Step 3), Pd(OAc)$_2$ (24.6 mg, 0.109 mmol), Xantphos (95 mg, 0.164 mmol) and Cs$_2$CO$_3$ (536 mg, 1.64 mmol) and purged with N$_2$. Toluene (6 mL, 0.547 mmol; sparged with N$_2$ for 30 minutes) and 4-chloro-5-ethyl-6,7-dihydro-5H-cyclopenta[d]pyrimidine (200 mg, 1.09 mmol) were injected into the reaction, and the reaction was heated to 95° C. for 24 hours. LCMS showed most of the starting material had been consumed. The reaction was cooled, mixed with EtOAc and filtered through glass filter paper. The filtrate was concentrated to a residue and purified by silica gel chromatography (gradient: 5-50% (80 DCM: 19 MeOH: 1 NH$_4$OH)/DCM). Purification provided tert-butyl (1'-benzyl-1-(5-ethyl-6,7-dihydro-5H-cyclopenta

[d]pyrimidin-4-yl)spiro[indoline-3,4'-piperidine]-4-yl)methylcarbamate (422 mg, 0.762 mmol, 70% yield). $^1$H NMR (CDCl$_3$, 400 MHz) δ 8.62 (s, 1H), 7.29-7.35 (m, 5H), 7.25 (m, 1H), 7.16 (t, 1H), 6.91 (d, 1H), 4.54 (br.s, 1H), 4.20-4.30 (m, 3H), 3.97 (m, 2H), 3.53 (s, 2H), 3.27 (m, 1H), 2.85-2.97 (m, 4H), 2.51 (m, 1H), 2.26 (m, 1H), 2.11 (d, 2H), 2.04 (t, 1H), 1.85 (m, 1H), 1.75 (d, 1H), 1.59 (d, 1H), 1.46 (s, 9H), 1.18 (m, 1H), 0.77 (t, 311). MS (APCI+) [M+H]: 554.2.

Step 6: tert-Butyl (1'-benzyl-1-(5-ethyl-6,7-dihydro-5H-cyclopenta[d]pyrimidin-4-yl)spiro[indoline-3,4'-piperidine]-4-yl)methylcarbamate (422 mg, 0.762 mmol) was dissolved in a 1:1 TFA/DCM solution (10 mL). After 2 hours at room temperature, the LCMS suggested complete deprotection of the BOC amine. The reaction was concentrated to (1'-benzyl-1-(5-ethyl-6,7-dihydro-5H-cyclopenta[d]pyrimidin-4-yl)spiro[indoline-3,4'-piperidine]-4-yl)methanamine tris(2,2,2-trifluoroacetate) (606 mg, 0.762 mmol, 99.9% yield) as an oil. MS (APCI+) [M+H]: 454.2.

Step 7: (1'-Benzyl-1-(5-ethyl-6,7-dihydro-5H-cyclopenta[d]pyrimidin-4-yl)spiro[indoline-3,4'-piperidine]-4-yl)methanamine tris(2,2,2-trifluoroacetate) (606 mg, 0.762 mmol) was stirred in a solution of acetone (0.280 mL, 3.81 mmol) and DCE (5 mL) for 15 minutes. NaBH(OAc)$_3$ (323 mg, 1.52 mmol) was added in one portion and resulted in vigorous evolution of gas. After 1 hour at room temperature, LCMS suggested complete conversion to the desired isopropylamine. The reaction was concentrated and partitioned between EtOAc and 10% aqueous K$_2$CO$_3$. The organic was washed with brine, dried over Na$_2$SO$_4$ and concentrated to a crude residue. The racemic crude was purified by silica gel chromatography (gradient: 5-100% (80 DCM: 19 MeOH: 1 NH$_4$OH)/DCM). Purification provided N-((1'-benzyl-1-(5-ethyl-6,7-dihydro-5H-cyclopenta[d]pyrimidin-4-yl)spiro[indoline-3,4'-piperidine]-4-yl)methyl)propan-2-amine (68 mg, 0.137 mmol, 18.0% yield) as an oil. $^1$H NMR (CDCl$_3$, 400 MHz) δ 8.62 (s, 1H), 7.27-7.33 (m, 5H), 7.24 (m, 1H), 7.18 (t, 1H), 6.96 (d, 1H), 3.95 (m, 411), 3.54 (s, 2H), 3.27 (m, 1H), 2.84-2.99 (m, 5H), 2.63 (dt, 1H), 2.03-2.31 (m, 4H), 1.86 (m, 1H), 1.70 (dd, 2H), 1.42 (m, 2H), 1.15-1.119 (m, 7H), 0.78 (t, 3H). MS (APCI+) [M+H]: 496.3. Separation of isomers was conducted by preparative HPLC using a Chiralpak AD-H column (4.6×100 mm) The compound was eluted with 25% methanol/water (0.1% TEA additive) at 3 mL/min and 120 bars.

Step 8: Ammonium formate (21.5 mg, 0.341 mmol) was added to a mixture of (R)-N-((1'-benzyl-1-(5-ethyl-6,7-dihydro-5H-cyclopenta[d]pyrimidin-4-yl)spiro[indoline-3,4'-piperidine]-4-yl)methyl)propan-2-amine (16.9 mg, 0.0341 mmol) and 10% Pd/C (10 mg) in methanol (1 mL) and refluxed. LCMS suggested debenzylation was complete after 2 hours. The reaction was concentrated and partitioned between DCM and saturated NaHCO$_3$ solution. The aqueous portion was extracted a second time, and the combined organics were dried over Na$_2$SO$_4$. The DCM solution was decanted and concentrated under vacuum to provide the free-base product, (R)-N-((1-(5-ethyl-6,7-dihydro-5H-cyclopenta[d]pyrimidin-4-yl)spiro[indoline-3,4'-piperidine]-4-yl)methyl)propan-2-amine. $^1$H NMR (CDCl$_3$, 400 MHz) δ 8.62 (s, 1H), 7.31 (d, 1H), 7.14 (t, 1H), 6.93 (d, 1H), 3.85-4.01 (m, 4H), 3.29 (m, 1H), 3.08 (dd, 2H), 2.90-2.97 (m, 4H), 2.58 (m, 1H), 2.01-2.26 (m, 4H), 1.85 (m, 1H), 1.68 (dd, 2H), 1.46 (m, 2H), 1.03-1.11 (m, 7H), 0.78 (t, 3H). The product was dissolved in THF (1 mL) and converted to the hydrochloride salt by treatment with a 1M HCl solution in Et$_2$O (1 mL). The reaction was sonicated, and the solvent was removed under vacuum providing (R)-N-((1-(5-ethyl-6,7-dihydro-5H-cyclopenta[d]pyrimidin-4-yl)spiro[indoline-3,4'-piperidine]-4-yl)methyl) propan-2-amine trihydrochloride (11 mg, 0.021 mmol, 62% yield) as a powder. MS (APCI+) [M+H]: 406.3.

Example 81

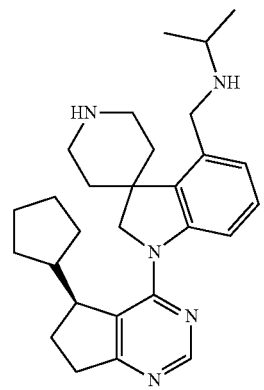

(S)-N-((1-(5-cyclopentyl-6,7-dihydro-5H-cyclopenta[d]pyrimidin-4-yl)spiro[indoline-3,4'-piperidine]-4-yl)methyl)propan-2-amine (S)-N-((1-(5-Cyclopentyl-6,7-dihydro-5H-cyclopenta[d]pyrimidin-4-yl)spiro[indoline-3,4'-piperidine]-4-yl)methyl)propan-2-amine was prepared as described in Example 80, substituting cyclopentylmagnesium bromide for ethylmagnesium bromide in Step 1. $^1$H NMR (CDCl$_3$, 400 MHz) δ 8.62 (s, 1H), 7.08-7.26 (m, 2H), 6.97 (d, 1H), 4.01 (s, 2H), 3.88-3.97 (m, 2H), 3.42 (m, 1H), 3.14 (dd, 2H), 2.96-2.98 (m, 3H), 2.80 (dt, 2H), 2.57-2.59 (m, 1H), 2.09-2.21 (m, 3H), 1.93 (m, 1H), 1.86 (m, 2H), 1.59 (d, 1H), 1.34-1.48 (m, 6H), 1.11 (s, 6H), 0.99 (m, 1H). (S)-N-((1-(5-cyclopentyl-6,7-dihydro-5H-cyclopenta[d]pyrimidin-4-yl)spiro[indoline-3,4'-piperidine]-4-yl)methyl)propan-2-amine trihydrochloride. MS (APCI+) [M+H]: 446.3.

Example 82

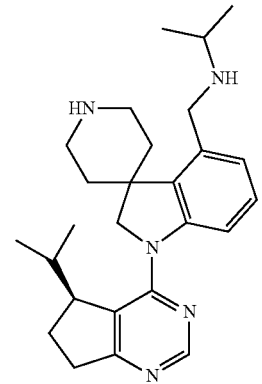

(S)-N-((1-(5-isopropyl-6,7-dihydro-5H-cyclopenta[d]pyrimidin-4-yl)spiro[indoline-3,4'-piperidine]-4-yl)methyl)propan-2-amine Step 1: An isopropylmagnesium bromide (58 mL, 58 mmol) solution (15% in THF, ~1 M) was treated with Cu(I)I (0.28 g, 1.5 mmol) and cooled to 0° C. A solution of (E)-dimethyl hex-2-enedioate (5.0 g, 29 mmol; See Example 80, Step 1) was added dropwise, and the solution was stirred at 0° C. for an additional 30 minutes and then at room temperature. The product was poured into saturated $NHCl_4$ (250 mL) with rapid stirring. The mixture was extracted into DCM. The combined organics were back extracted with $H_2O$, and dried with $MgSO_4$, filtered, and concentrated under reduced pressure to yield methyl 2-isopropyl-5-oxocyclopentanecarboxylate (5.4 g, 100%), which was used without further purification. $^1H$ NMR ($CDCl_3$, 400 MHz) δ 3.76-3.73 (m, 3H), 2.94-2.91 (m, 1H), 2.48-2.16 (m, 2H), 1.87-1.84 (m, 2H), 1.68-1.43 (m, 2H), 0.97-0.84 (m, 6H).

Step 2: A solution of methyl 2-isopropyl-5-oxocyclopentanecarboxylate (5.4 g, 29.31 mmol) in MeOH (145 mL) was treated with ammonium acetate (22.59 g, 293.1 mmol), and the mixture was heated to 50° C. for 2 hours and stirred at room temperature overnight. The solvents were removed under reduced pressure, and the crude residue was taken up in DCM and $H_2O$. The combined organics were washed with brine, dried $Na_2SO_4$, filtered, and concentrated. The crude residue was purified by column chromatography (5 then 15% EtOAc/Hexane) to yield pure methyl 2-amino-5-isopropyl-cyclopent-1-enecarboxylate (3.27 g, 61%). LCMS (APCI+) m/z 184.0 [M+H]+; Rt=3.51 min.

Step 3: A mixture of methyl 2-amino-5-isopropylcyclopent-1-enecarboxylate (3.272 g, 17.86 mmol), ammonium formate (5.630 g, 89.28 mmol), and formamide (7.092 mL, 178.6 mmol) was heated at 150° C. for 20 hours. The reaction was diluted with water, and extracted with 1:5 IPA:DCM, until no more product in aqueous by TLC. The combined organics were concentrated under reduced pressure, dissolved in DCM and dried $Na_2SO_4$. The reaction was filtered and concentrated to give 5-isopropyl-6,7-dihydro-5H-cyclopenta[d]pyrimidin-4-ol (4.29 g, 100%), which was used without further purification. LCMS (APCI+) m/z 179.0 [M+H]+; Rt=2.33 min.

Step 4: A solution of 5-isopropyl-6,7-dihydro-5H-cyclopenta[d]pyrimidin-4-ol (4.29 g, 24.09 mmol) in acetonitrile (94.75 mL, 1814 mmol) was treated with $POCl_3$ (6.62 mL, 72.28 mmol). The mixture was heated at 80° C. overnight. No reaction was observed by LC-MS or HPLC. An additional 3 equivalents of $POCl_3$ were added, and the reaction was heated at 80° C. for 4 hours. The reaction was charged with an additional 10 equivalents of $POCl_3$ and TEA (6.716 mL, 48.18 mmol) and heated at 80° C. overnight. The reaction was cooled to room temperature, and the solvent and $POCl_3$ were removed under reduced pressure. The residue was taken up in DCM and was carefully added to stirring saturated $NaHCO_3$. The mixture was stirred for 1 hour to confirm complete neutralization. The organics were combined and washed with brine, dried $Na_2SO_4$, filtered, and concentrated under reduced pressure. The crude material was purified by column chromatography (25% EtOAc/Hexane) to yield 4-chloro-5-isopropyl-6,7-dihydro-5H-cyclopenta[d]pyrimidine (1.23 g, 26%). LCMS (APCI+) m/z 196.9 [M+H]+; Rt=3.57 min Step 5: A flask was charged with $Pd_2 dba_3$ (0.233 g, 0.254 mmol) and Xantphos (0.221 g, 0.381 mmol) and purged with nitrogen. The flask was then charged with tert-butyl (1'-benzylspiro[indoline-3,4'-piperidine]-4-yl)methylcarbamate (1.04 g, 2.54 mmol), 4-chloro-5-isopropyl-6,7-dihydro-5H-cyclopenta[d]pyrimidine (0.500 g, 2.54 mmol), $Cs_2CO_3$ (1.24 g, 3.81 mmol) and toluene (12.7 mL) The reaction was purged with nitrogen and heated to 100° C. overnight. The reaction was cooled to room temperature and filtered through celite, then GFF, and concentrated under reduced pressure. The crude residue was purified by column chromatography (1-5% MeOH/DCM) to yield tert-butyl (1'-benzyl-1-(5-isopropyl-6,7-dihydro-5H-cyclopenta[d]pyrimidin-4-yl)spiro[indoline-3,4'-piperidine]-4-yl)methylcarbamate (1.0 g, 69%). LCMS (APCI+) m/z 568.3 [M+H]+; Rt=4.30 min.

Step 6: A solution of tert-butyl (1'-benzyl-1-(5-isopropyl-6,7-dihydro-5H-cyclopenta[d]pyrimidin-4-yl)spiro[indoline-3,4'-piperidine]-4-yl)methylcarbamate (1.00 g, 1.76 mmol) in DCM (8 mL) was treated with 4N HCl in dioxane (2 mL). The reaction was stirred at room temperature for 1 hour and concentrated under reduced pressure to yield (1'-benzyl-1-(5-isopropyl-6,7-dihydro-5H-cyclopenta[d]pyrimidin-4-yl)spiro[indoline-3,4'-piperidine]-4-yl)methanamine trihydrochloride. LCMS (APCI+) m/z 468.2 [M+H]+; Rt=3.42 min.

Step 7: A stirring solution of (1'-benzyl-1-(5-isopropyl-6,7-dihydro-5H-cyclopenta[d]pyrimidin-4-yl)spiro[indoline-3,4'-piperidine]-4-yl)methanamine (0.250 g, 0.43 mmol) in DCE (3 mL) was treated with acetone (0.159 mL, 2.17 mmol). The reaction was allowed to stir for 20 minutes, followed by the addition of $NaBH(OAc)_3$ (0.184 g, 0.87 mmol). The reaction was stirred at room temperature overnight. An additional 2.5 equivalents of acetone and 1.0 equivalent of $NaBH(OAc)_3$ were added to the reaction and stirred an additional 2 hours. The reaction was quenched by the addition of saturated $NaHCO_3$ and diluted with DCM. The combined organics were washed with brine, dried $Na_2SO_4$, filtered, and concentrated under reduced pressure to give N-((1'-benzyl-1-(5-isopropyl-6,7-dihydro-5H-cyclopenta[d]pyrimidin-4-yl)spiro[indoline-3,4'-piperidine]-4-yl)methyl)propan-2-amine (0.185 g, 84%), which was used without further purification. LCMS (APCI+) m/z 536.4 [M+H]+; Rt=3.61 min.

Step 8: A solution of N-((1'-benzyl-1-(5-isopropyl-6,7-dihydro-5H-cyclopenta[d]pyrimidin-4-yl)spiro[indoline-3,4'-piperidine]-4-yl)methyl)propan-2-amine (0.185 g, 0.363 mmol) in DCM (2 mL) was treated with TEA (0.0759 mL, 0.544 mmol) followed by $Boc_2O$ (0.0871 g, 0.399 mmol). The reaction was stirred at room temperature overnight. The reaction was diluted with saturated $NaHCO_3$ and DCM. The combined organics were washed with brine, dried $Na_2SO_4$, filtered, and concentrated under reduced pressure. The crude residue was purified by column chromatography (30-50% EtOAc/Hexane) to yield tert-butyl (1'-benzyl-1-(5-isopropyl-6,7-dihydro-5H-cyclopenta[d]pyrimidin-4-yl)spiro[indoline-3,4'-piperidine]-4-yl)methyl(isopropyl)carbamate (0.088 g, 40%). LCMS (APCI+) m/z 610.2 [M+H]+; Rt=4.35 min.

Step 9: A solution of tert-butyl (1'-benzyl-1-(5-isopropyl-6,7-dihydro-5H-cyclopenta[d]pyrimidin-4-yl)spiro[indoline-3,4'-piperidine]-4-yl)methyl(isopropyl)carbamate (0.088 g, 0.14 mmol) in MeOH (1 mL) was treated with ammonium formate (0.027 g, 0.43 mmol) and Pd/C (0.0077 g, 0.0072 mmol) and heated to reflux for 7 hours and stirred at room temperature overnight. The reaction was filtered through glass filter paper, and the solvent was removed under reduced pressure. The crude residue was purified by column chromatography (5% MeOH/DCM, then 5% 7N $NH_4$ in MeOH/DCM) to yield pure tert-butyl isopropyl((1-(5-isopropyl-6,7-dihydro-5H-cyclopenta[d]pyrimidin-4-yl)spiro[indoline-3,4'-piperidine]-4-yl)methyl)carbamate (0.57 g, 76%). LCMS (APCI+) m/z 520.2 [M+H]+; Rt=3.80 min.

Step 10: Chiral separation of tert-butyl isopropyl((1-(5-isopropyl-6,7-dihydro-5H-cyclopenta[d]pyrimidin-4-yl) spiro[indoline-3,4'-piperidine]-4-yl)methyl)carbamate was preformed using chiralpak 1A (21.2×250 mm) 25% IPA+ 0.1% TEA at 50 mL/min 254 nm to yield (S)-tert-butyl isopropyl((1-(5-isopropyl-6,7-dihydro-5H-cyclopenta[d]pyrimidin-4-yl)spiro[indoline-3,4'-piperidine]-4-yl)methyl)carbamate.

Step 11: A solution of (S)-tert-butyl isopropyl(0-(5-isopropyl-6,7-dihydro-5H-cyclopenta[d]pyrimidin-4-yl)spiro[indoline-3,4'-piperidine]-4-yl)methyl)carbamate (0.0189 g, 0.0364 mmol) in DCM (2 mL) was treated with 4N HCl in dioxane (0.5 mL). The reaction was stirred at room temperature for 1 hour and concentrated under reduced pressure to give (S)-N-((1-(5-isopropyl-6,7-dihydro-5H-cyclopenta[d]pyrimidin-4-yl)spiro[indoline-3,4'-piperidine]-4-yl)methyl)propan-2-amine trihydrochloride (0.020 g, 100%). LCMS (APCI+) m/z 420.3 [M+H]+; Rt=3.14 min.

Example 83

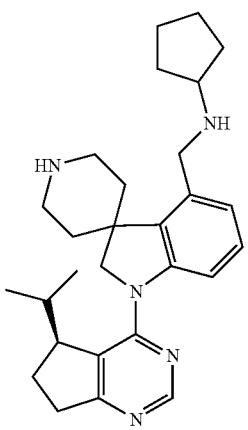

(S)-N-((1-(5-isopropyl-6,7-dihydro-5H-cyclopenta[d]pyrimidin-4-yl)spiro[indoline-3,4'-piperidine]-4-yl) methyl)cyclopentanamine Step 1: A stirring solution of (1'-benzyl-1-(5-isopropyl-6,7-dihydro-5H-cyclopenta[d]pyrimidin-4-yl)spiro[indoline-3,4'-piperidine]-4-yl)methanamine (0.250 g, 0.433 mmol) in DCE (3 mL) was treated with cyclopentanone (0.192 mL, 2.17 mmol). The reaction was allowed to stir for 20 minutes, followed by the addition of NaBH(OAc)₃ (0.184 g, 0.867 mmol). The reaction was stirred at room temperature overnight. An additional 2.5 equivalents of cyclopentanone and 1.0 eq of NaBH(OAc)₃ were added to the reaction and stirred an additional 2 hours. The reaction was quenched by the addition of saturated NaHCO₃ and diluted with DCM. The combined organics were washed with brine, dried Na₂SO₄, filtered, and concentrated under reduced pressure to yield N-((1'-benzyl-1-(5-isopropyl-6,7-dihydro-5H-cyclopenta[d]pyrimidin-4-yl)spiro[indoline-3,4'-piperidine]-4-yl)methyl)cyclopentanamine (0.211 g, 91%), which was used without further purification. LCMS (APCI+) m/z 536.4 [M+H]+; Rt=3.61 min.

Step 2: A solution of N-((1'-benzyl-1-(5-isopropyl-6,7-dihydro-5H-cyclopenta[d]pyrimidin-4-yl)spiro[indoline-3,4'-piperidine]-4-yl)methyl)cyclopentanamine (0.211 g, 0.39 mmol) in DCM (2 mL) was treated with TEA (0.082 mL, 0.59 mmol) followed by Boc₂O (0.095 g, 0.43 mmol). The reaction was stirred at room temperature overnight. The reaction was diluted with saturated NaHCO₃ and DCM. The combined organics were washed with brine, dried Na₂SO₄, filtered, and concentrated under reduced pressure. The crude residue was purified by column chromatography (30-50% EtOAc/Hexane) to yield tert-butyl (1'-benzyl-1-(5-isopropyl-6,7-dihydro-5H-cyclopenta[d]pyrimidin-4-yl)spiro[indoline-3,4'-piperidine]-4-yl)methyl(cyclopentyl)carbamate (0.095 g, 38%). LCMS (APCI+) m/z 636.4 [M+H]+; Rt=3.92 min.

Step 3: A solution of tert-butyl (1'-benzyl-1-(5-isopropyl-6,7-dihydro-5H-cyclopenta[d]pyrimidin-4-yl)spiro[indoline-3,4'-piperidine]-4-yl)methyl(cyclopentyl)carbamate (0.095 g, 0.15 mmol) in MeOH (1 mL) was treated with Pd/C (0.0079 g, 0.0075 mmol) and ammonium formate (0.028 g, 0.45 mmol) and heated to reflux for 7 hours then stirred at room temperature overnight. The reaction was filtered through glass filter paper, and the solvent was removed under reduced pressure. The crude residue was purified by column chromatography (5% MeOH/DCM then 5% 7N NH₄ in MeOH/DCM) to yield tert-butyl cyclopentyl((1-(5-isopropyl-6,7-dihydro-5H-cyclopenta[d]pyrimidin-4-yl)spiro[indoline-3,4'-piperidine]-4-yl)methyl)carbamate (0.066 g, 81%). LCMS (APCI+) m/z 546.1 [M+H]+; Rt=4.25 min.

Step 4: Chiral separation of tert-butyl cyclopentyl((1-(5-isopropyl-6,7-dihydro-5H-cyclopenta[d]pyrimidin-4-yl)spiro[indoline-3,4'-piperidine]-4-yl)methyl)carbamate was preformed using chiralpak 1A (21.2×250 mm) 25% IPA+0.1% TEA at 50 mL/min 254 nm to yield (5)-tert-butyl cyclopentyl((1-(5-isopropyl-6,7-dihydro-5H-cyclopenta[d]pyrimidin-4-yl)spiro[indoline-3,4'-piperidine]-4-yl)methyl)carbamate.

Step 5: A solution of (S)-tert-butyl cyclopentyl((1-(5-isopropyl-6,7-dihydro-5H-cyclopenta[d]pyrimidin-4-yl)spiro[indoline-3,4'-piperidine]-4-yl)methyl)carbamate (0.0156 g, 0.0286 mmol) in DCM (2 mL) was treated with 4N HCl in dioxane (0.5 mL). The reaction was stirred at room temperature for 1 hour and concentrated to yield (S)-N-((1-(5-isopropyl-6,7-dihydro-5H-cyclopenta[d]pyrimidin-4-yl)spiro[indoline-3,4'-piperidine]-4-yl)methyl)cyclopentanamine trihydrochloride as a solid. LCMS (APCI+) m/z 446.3 [M+H]+; Rt=3.28 min.

Example 84

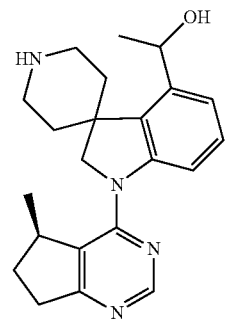

1-(1-((R)-5-methyl-6,7-dihydro-5H-cyclopenta[d]pyrimidin-4-yl)spiro[indoline-3,4'-piperidine]-4-yl)ethanol Step 1: A stirred solution of 4-bromoindolin-2-one (13.0 g, 61.3 mmol) in THF (500 mL) was treated by the dropwise addition of a 1.0M THF solution of NaHMDS (306 mL, 306 mmol) at −78° C. under nitrogen. After stirring at −78° C. for 30 minutes, N-benzylbis(2-chloroethyl)amine hydrochloride (18.05 g, 67.4 mmol) was added as a solid. The reaction mixture was stirred at −78° C. for 30 minutes and then allowed to warm to room temperature. The reaction mixture was then heated to reflux for 12 hours. After cooling to 0° C., the reaction was quenched by the addition of saturated aqueous NH$_4$Cl solution. The reaction mixture was partitioned between EtOAc and water. The aqueous layer was extracted with EtOAc (3×200 mL) The combined organics layers were washed with brine, dried with MgSO$_4$ and concentrated under reduced pressure. The resulting solid was triturated with DCM/EtOAc to give 1'-benzyl-4-bromospiro[indoline-3,4'-piperidin]-2-one (19.3 g, 85%) as a solid. LCMS (APCI+) m/z 371/373 [M+H]+; Rt=2.71 min.

Step 2: A solution of 1'-benzyl-4-bromospiro[indoline-3,4'-piperidin]-2-one (12.0 g, 32.3 mmol) in THF (300 mL) was carefully treated with the addition of BH$_3$-THF complex (97 mL, 97 mmol). The reaction was then heated at 80° C. for 24 hours. The reaction mixture was quenched by the addition of 1N HCl. The aqueous layer was extracted with EtOAc (3×100 mL). The aqueous layer was basified to a pH of 12 with NaOH pellets and extracted with EtOAc (3×200 mL) The organic layers were dried with MgSO$_4$ and concentrated under reduced pressure to give 1'-benzyl-4-bromospiro[indoline-3,4'-piperidine] (7.3 g, 63%) as an oil. LCMS (APCI+) m/z 357/359 [M+H]+; Rt=3.07 min.

Step 3: A solution of 1'-benzyl-4-bromospiro[indoline-3,4'-piperidine] (7.0 g, 19.6 mmol) in DCM (300 mL) was treated by the portion wise addition of Boc$_2$O (4.28 g, 19.6 mmol). The reaction was allowed to stir overnight, at which point the reaction was diluted with saturated aqueous NH$_4$Cl. The organic layer was separated, washed with brine, dried with MgSO$_4$ and concentrated under reduced pressure. The crude material was purified by column chromatography (10:1 Hexane:EtOAc to EtOAc) to give tert-butyl 1'-benzyl-4-bromospiro[indoline-3,4'-piperidine]-1-carboxylate (7.56 g, 84%) as a solid. LCMS (APCI+) m/z 457/459 [M+H]+; Rt=4.52 min.

Step 4: A solution of tert-butyl 1'-benzyl-4-bromospiro[indoline-3,4'-piperidine]-1-carboxylate (0.700 g, 1.53 mmol) in THF (10 mL) at −78° C. was treated by the dropwise addition of 1.6M in hexanes n-BuLi (0.673 ml, 1.68 mmol). The mixture was stirred at −78° C. for 30 minutes, and acetaldehyde (0.129 mL, 2.30 mmol) was added neat and stirring was continued an additional 30 minutes at −78° C. The reaction was then stirred at room temperature for 1.5 hours. The reaction was quenched by the addition of saturated NH$_4$Cl, and the reaction was extracted with EtOAc. The combined organics were washed with brine, dried with Na$_2$SO$_4$, filtered, and concentrated under reduced pressure. The residue was purified by column chromatography (20 then 50-70% EtOAc/Hexane) to yield pure tert-butyl 1'-benzyl-4-(1-hydroxyethyl)spiro[indoline-3,4'-piperidine]-1-carboxylate (0.491 g, 76%). LCMS (APCI+) m/z 423.2 [M+H]+; Rt=3.66 min Step 5: A solution of tert-butyl 1'-benzyl-4-(1-hydroxyethyl)spiro[indoline-3,4'-piperidine]-1-carboxylate (0.045 g, 0.11 mmol) in DCM (2 mL) was treated with 4N HCl in dioxane (0.5 mL). The reaction was stirred at room temperature for 4 hours and concentrated under reduced pressure to yield 1-(1'-benzylspiro[indoline-3,4'-piperidine]-4-yl)ethanol dihydrochloride (0.047 g, 100%), which was used without further purification. LCMS (APCI+) m/z 323.2 [M+H]+; Rt=2.38 min Step 6: A flask was charged with Pd(OAc)$_2$ (0.0027 g, 0.012 mmol) and Xantphos (0.010 g, 0.018 mmol) and purged with nitrogen. The flask was then charged with (R)-4-chloro-5-methyl-6,7-dihydro-5H-cyclopenta[d]pyrimidine (0.022 g, 0.13 mmol), 1-(1'-benzylspiro[indoline-3,4'-piperidine]-4-yl)ethanol (0.047 g, 0.12 mmol), Cs$_2$CO$_3$ (0.058 g, 0.18 mmol), and toluene (0.6 mL) The reaction was purged with nitrogen and heated to 100° C. for 3 hours. Additional (R)-4-chloro-5-methyl-6,7-dihydro-5H-cyclopenta[d]pyrimidine was added, and the reaction was heated at 100° C. for an additional 4 hours and then stirred at room temperature overnight. The reaction was filtered through GFF and concentrated under reduced pressure. The crude residue was purified by column chromatography (5% MeOH/DCM, then 5% 7N NH$_4$ in MeOH/DCM) to yield 1-(1'-benzyl-1-((R)-5-methyl-6,7-dihydro-5H-cyclopenta[d]pyrimidin-4-yl)spiro[indoline-3,4'-piperidine]-4-yl)ethanol (0.017 g, 31%). LCMS (APCI+) m/z 455.2 [M+H]+; Rt=3.18 min.

Step 7: A solution of 1-(1'-benzyl-1-((R)-5-methyl-6,7-dihydro-5H-cyclopenta[d]pyrimidin-4-yl)spiro[indoline-3,4'-piperidine]-4-yl)ethanol (0.17 g, 0.37 mmol) in MeOH (0.2 mL) and treated with ammonium formate (0.007 g, 0.11 mmol) and Pd/C (0.002 g, 0.002 mmol). The reaction was heated to reflux for 2.5 hours and then stirred at room temperature. The reaction was then heated to reflux for an addition 2 hours, at which time the reaction was complete. The reaction was then cooled to room temperature and filtered through glass filter paper. The solvents were removed under reduced pressure, and the crude residue was dissolved in DCM and treated with 1N HCl in ether. The solvents were removed under reduced pressure to yield 1-(1-((R)-5-methyl-6,7-dihydro-5H-cyclopenta[d]pyrimidin-4-yl)spiro[indoline-3,4'-piperidine]-4-yl)ethanol dihydrochloride (0.012 g, 73%). LCMS (APCI+) m/z 365.1 [M+H]+; Rt=2.56 min.

Examples 85-101 shown in Table 2 can also be made according to the above described methods.

TABLE 2

| Example | Structure | Name | LCMS |
|---|---|---|---|
| 85 | 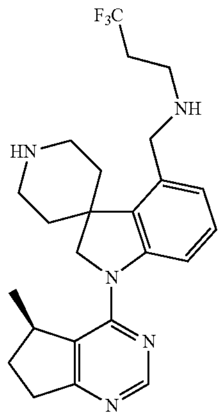 | (R)-3,3,3-trifluoro-N-((1-(5-methyl-6,7-dihydro-5H-cyclopenta[d]pyrimidin-4-yl)spiro[indoline-3,4'-piperidine]-4-yl)methyl)propan-1-amine | m/z 446 Rt: 2.08 min |
| 86 | 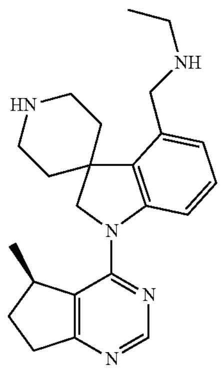 | (R)-N-((1-(5-methyl-6,7-dihydro-5H-cyclopenta[d]pyrimidin-4-yl)spiro[indoline-3,4'-piperidine]-4-yl)methyl)ethanamine | m/z 378 Rt: 2.17 min |
| 87 | 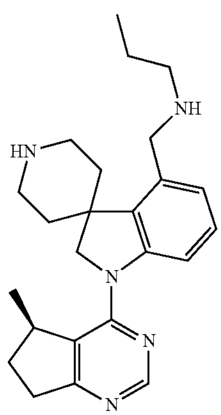 | (R)-N-((1-(5-methyl-6,7-dihydro-5H-cyclopenta[d]pyrimidin-4-yl)spiro[indoline-3,4'-piperidine]-4-yl)methyl)propan-1-amine | m/z 392 Rt: 1.90 min |
| 88 | 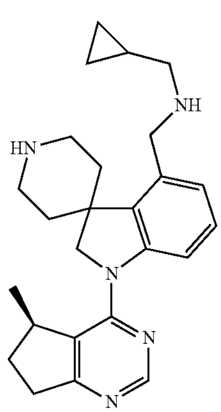 | (R)-1-cyclopropyl-N-((1-(5-methyl-6,7-dihydro-5H-cyclopenta[d]pyrimidin-4-yl)spiro[indoline-3,4'-piperidine]-4-yl)methyl)methanamine | m/z 404 Rt: 1.94 min |

TABLE 2-continued

| Example | Structure | Name | LCMS |
|---|---|---|---|
| 89 | 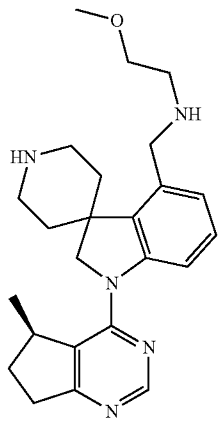 | (R)-2-methoxy-N-((1-(5-methyl-6,7-dihydro-5H-cyclopenta[d]pyrimidin-4-yl)spiro[indoline-3,4'-piperidine]-4-yl)methyl)ethanamine | m/z 408 Rt: 1.96 min |
| 90 | 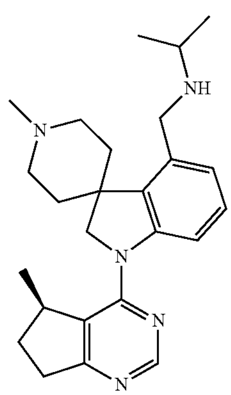 | (R)-N-((1'-methyl-1-(5-methyl-6,7-dihydro-5H-cyclopenta[d]pyrimidin-4-yl)spiro[indoline-3,4'-piperidine]-4-yl)methyl)propan-2-amine | m/z 406 Rt: 2.33 min |
| 91 | 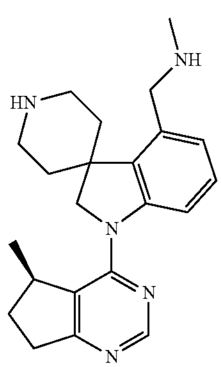 | (R)-N-methyl-1-(1-(5-methyl-6,7-dihydro-5H-cyclopenta[d]pyrimidin-4-yl)spiro[indoline-3,4'-piperidine]-4-yl)methanamine | m/z 364 Rt: 1.91 min |

TABLE 2-continued

| Example | Structure | Name | LCMS |
|---|---|---|---|
| 92 | 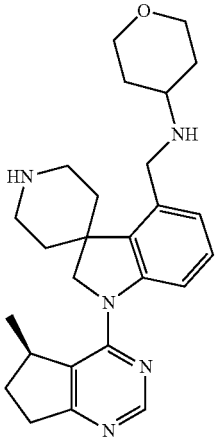 | (R)-N-((1-(5-methyl-6,7-dihydro-5H-cyclopenta[d]pyrimidin-4-yl)spiro[indoline-3,4'-piperidine]-4-yl)methyl)tetrahydro-2H-pyran-4-amine | m/z 434 Rt: 2.00 min |
| 93 | 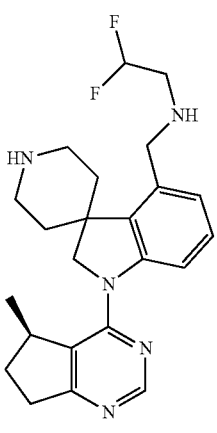 | (R)-2,2-difluoro-N-((1-(5-methyl-6,7-dihydro-5H-cyclopenta[d]pyrimidin-4-yl)spiro[indoline-3,4'-piperidine]-4-yl)methyl)ethanamine | m/z 414 Rt: 1.99 min |
| 94 | 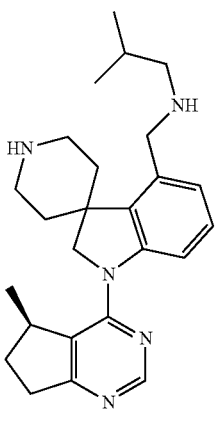 | (R)-2-methyl-N-((1-(5-methyl-6,7-dihydro-5H-cyclopenta[d]pyrimidin-4-yl)spiro[indoline-3,4'-piperidine]-4-yl)methyl)propan-1-amine | m/z 406 Rt: 1.69 min |

TABLE 2-continued

| Example | Structure | Name | LCMS |
|---|---|---|---|
| 95 | 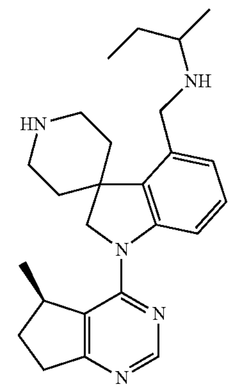 | N-((1-((R)-5-methyl-6,7-dihydro-5H-cyclopenta[d]pyrimidin-4-yl)spiro[indoline-3,4'-piperidine]-4-yl)methyl)butan-2-amine | m/z 406 Rt: 1.55 min |
| 96 | 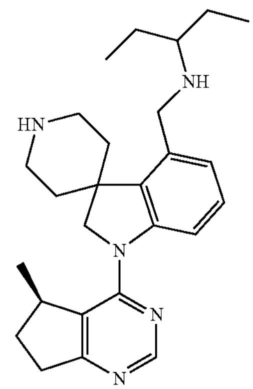 | (R)-N-((1-(5-methyl-6,7-dihydro-5H-cyclopenta[d]pyrimidin-4-yl)spiro[indoline-3,4'-piperidine]-4-yl)methyl)pentan-3-amine | m/z 420 Rt: 1.71 min |
| 97 | 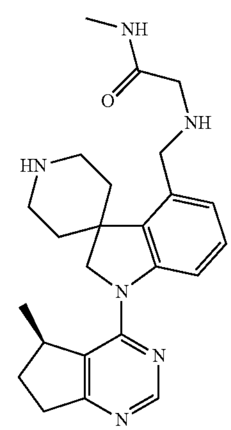 | (R)-N-methyl-2-((1-(5-methyl-6,7-dihydro-5H-cyclopenta[d]pyrimidin-4-yl)spiro[indoline-3,4'-piperidine]-4-yl)methylamino)acetamide | m/z 421 Rt: 1.68 min |
| 98 | 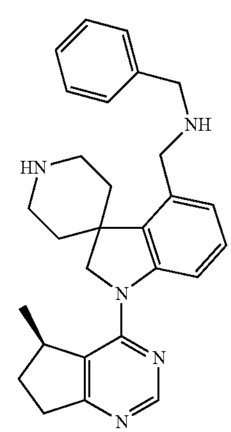 | (R)-N-benzyl-1-(1-(5-methyl-6,7-dihydro-5H-cyclopenta[d]pyrimidin-4-yl)spiro[indoline-3,4'-piperidine]-4-yl)methanamine | m/z 440 Rt: 1.79 min |

TABLE 2-continued

| Example | Structure | Name | LCMS |
|---|---|---|---|
| 99 | 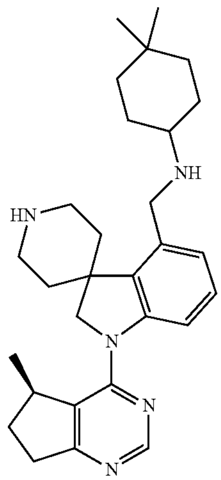 | (R)-4,4-dimethyl-N-((1-(5-methyl-6,7-dihydro-5H-cyclopenta[d]pyrimidin-4-yl)spiro[indoline-3,4'-piperidine]-4-yl)methyl)cyclohexanamine | m/z 460 Rt: 2.77 min |
| 100 | 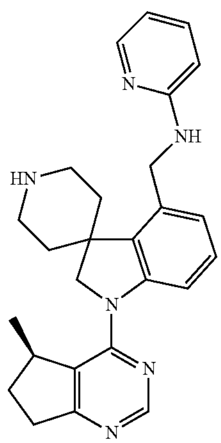 | (R)-N-((1-(5-methyl-6,7-dihydro-5H-cyclopenta[d]pyrimidin-4-yl)spiro[indoline-3,4'-piperidine]-4-yl)methyl)pyridin-2-amine | m/z 427 Rt: 2.77 min |
| 101 | 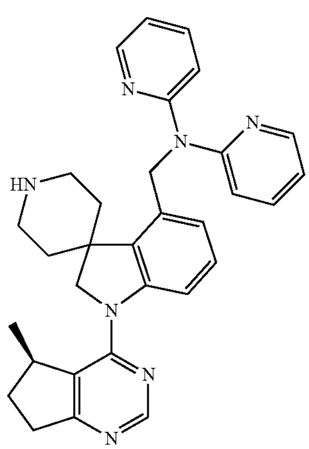 | (R)-N-((1-(5-methyl-6,7-dihydro-5H-cyclopenta[d]pyrimidin-4-yl)spiro[indoline-3,4'-piperidine]-4-yl)methyl)-N-(pyridin-2-yl)pyridin-2-amine | m/z 504 Rt: 2.91 min |

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups.

What is claimed is:

1. A compound of Formula I:

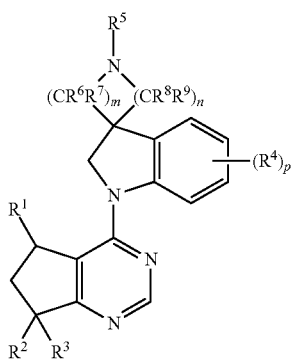

and tautomers, resolved enantiomers, resolved diastereomers, metabolites, salts and pharmaceutically acceptable prodrugs thereof, wherein:

$R^1$ is H, $CH_3$, $CH_2CH_3$, $CH(CH_3)_2$, $CH=CH_2$, $CH_2OH$, $CF_3$, $CHF_2$, $CH_2F$, or $C_3$-$C_6$ cycloalkyl;

$R^2$ is H, OH, $OCH_3$ or F;

$R^3$ is H, F or $CH_3$;

each $R^4$ is independently selected from H, F, Cl, Br, I, CN, $(CH_2)_tNR^{10}R^{10}$, $(CH_2)_tOR^{10}$, $(CH_2)_tC(O)R^{10}$, $(CH_2)_tC(O)OR^{10}$, $(CH_2)_tC(O)NR^{10}R^{10}$, $(CH_2)_tNR^{10}C(O)R^{10}$, $(CH_2)_tNR^{10}C(O)OR^{10}$, $(CH_2)_1NR^{10}C(O)NR^{10}R^{10}$, $C_1$-$C_6$ alkyl, $(CR^{10}R^{10})_tC_3$-$C_8$ cycloalkyl, $(CR^{10}R^{10})_tC_3$-$C_6$ heterocyclyl, $(CR^{10}R^{10})_tC_6$-$C_8$ aryl, $O(CR^{10}R^{10})_tC_6$-$C_8$ aryl, $(CR^{10}R^{10})_tC_3$-$C_6$ heteroaryl, wherein said alkyl, cycloalkyl, heterocyclyl, aryl and heteroaryl are optionally substituted by one or more F, Cl, Br, I, CN, $C_1$-$C_3$ alkyl, $CF_3$, OH or $O(C_1$-$C_3$ alkyl);

$R^5$ is H, $C_1$-$C_6$ alkyl, $(CR^{10}R^{10})_tOR^{10}$, $(CR^{10}R^{10})_tNR^{10}R^{10}$, $(CH_2)_tC_3$-$C_8$ cycloalkyl, $(CH_2)_tC_6$-$C_8$ aryl, wherein said aryl is optionally substituted by F, Cl, Br or I;

$R^6$, $R^7$, $R^8$ and $R^9$ are independently selected from H, $C_1$-$C_6$ alkyl, $(CR^{10}R^{10})_tOR^{10}$, $(CR^{10}R^{10})_tC_6$-$C_8$ aryl; wherein said aryl is optionally substituted by F, Cl, Br or I;

$R^{10}$ is independently selected from H, OH, $O(C_1$-$C_3$ alkyl), $(CH_2)_tNR^{11}R^{11}$, $(CH_2)_tC(O)NR^{11}R^{11}$, $(CH_2)_tS(O)NR^{11}R^{11}$, $(CH_2)_tS(O)_2NR^{11}R^{11}$, $C_1$-$C_6$ alkyl, $(CH_2)_tC_3$-$C_8$ cycloalkyl, $(CH_2)_tC_3$-$C_6$ heterocyclyl, $(CH_2)_tC_6$-$C_8$ aryl and $(CH_2)_tC_3$-$C_6$ heteroaryl, wherein said alkyl, cycloalkyl, heterocyclyl, aryl and heteroaryl are optionally substituted by one or more F, Cl, Br, I, CN, $C_1$-$C_3$ alkyl, $CF_3$, OH, $O(C_1$-$C_3$ alkyl); or two $R^{10}$ are taken together to form oxo or a $C_3$-$C_6$ heterocyclyl;

$R^{11}$ is independently selected from H, $C_1$-$C_3$ alkyl, OH, $OC_1$-$C_3$ alkyl, $NH_2$, $N(C_1$-$C_3$ alkyl)$_2$; or two $R^{11}$ are taken together to form a $C_3$-$C_6$ heterocyclyl, optionally substituted by methyl or ethyl;

m and n are independently 1, 2 or 3, provided that m and n taken together are 3, 4 or 5;

p is 0, 1, 2 or 3; and each t is independently 0, 1, 2, 3 or 4.

2. The compound of claim 1, wherein $R^1$ is H, $CH_3$, $CH_2CH_3$, $CH=CH_2$, $CH_2OH$, $CF_3$, $CHF_2$ or $CH_2F$.

3. The compound of claim 1, wherein m is 2 and n is 1.

4. The compound of claim 1, wherein m is 2 and n is 2.

5. The compound of claim 1, wherein m is 3 and n is 1.

6. The compound of claim 1, wherein m is 3 and n is 2.

7. The compound of claim 1, wherein m is 4 and n is 1.

8. The compound of claim 1, wherein m and n are independently 1 or 2, provided that m and n taken together are 3.

9. The compound of claim 1, wherein m and n are independently 1, 2 or 3, provided that m and n taken together are 4.

10. The compound according to claim 1, wherein p is 1 or 2 and $R^4$ is F, Cl, Br, I, CN, $(CH_2)_tNR^{10}R^{10}$ or $(CH_2)_tOR^{10}$.

11. The compound of claim 10, wherein the residue of Formula I having the structure

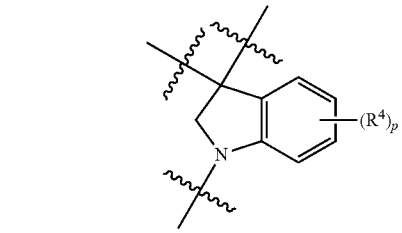

is selected from:

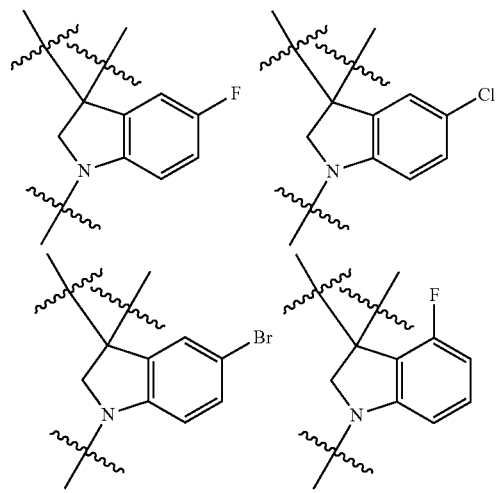

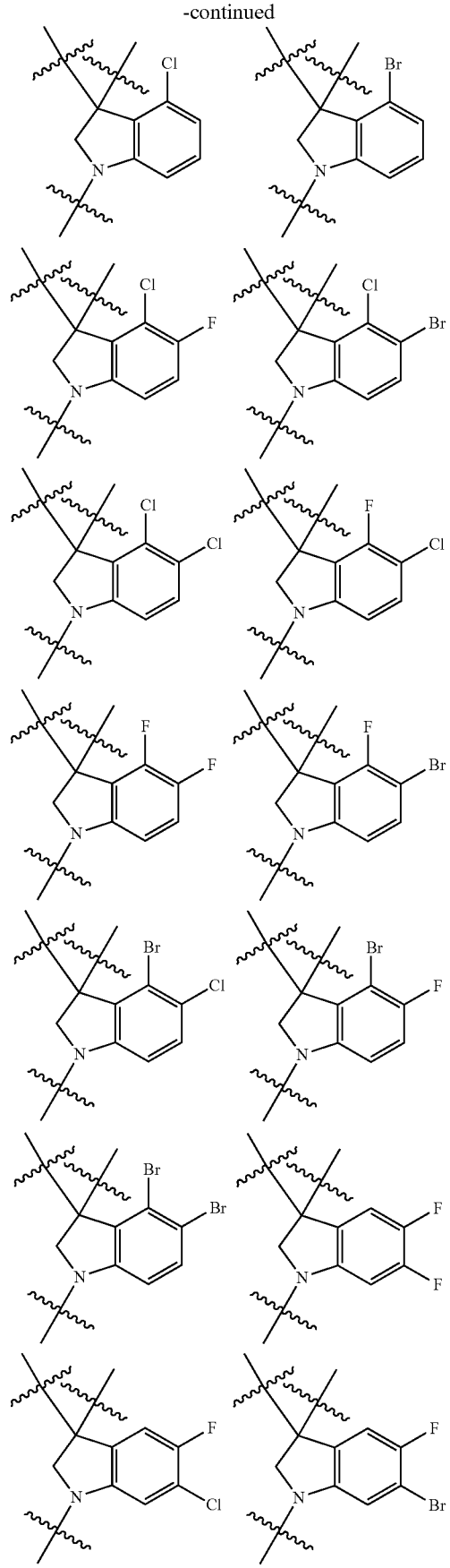
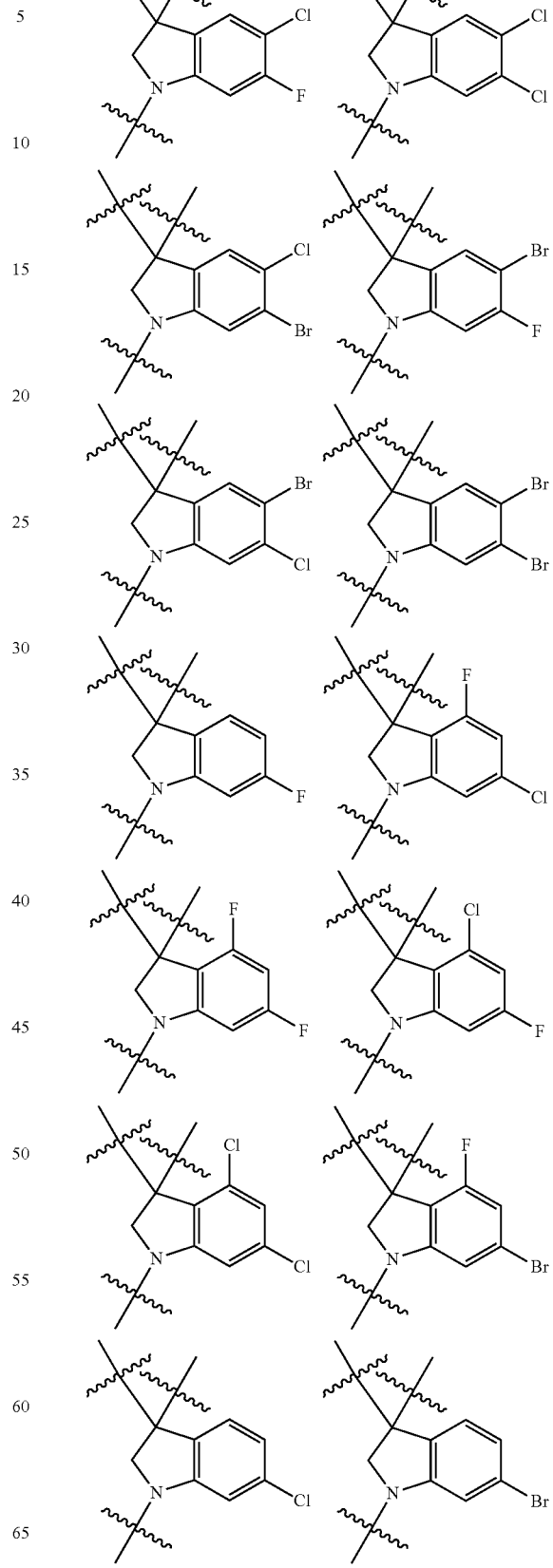

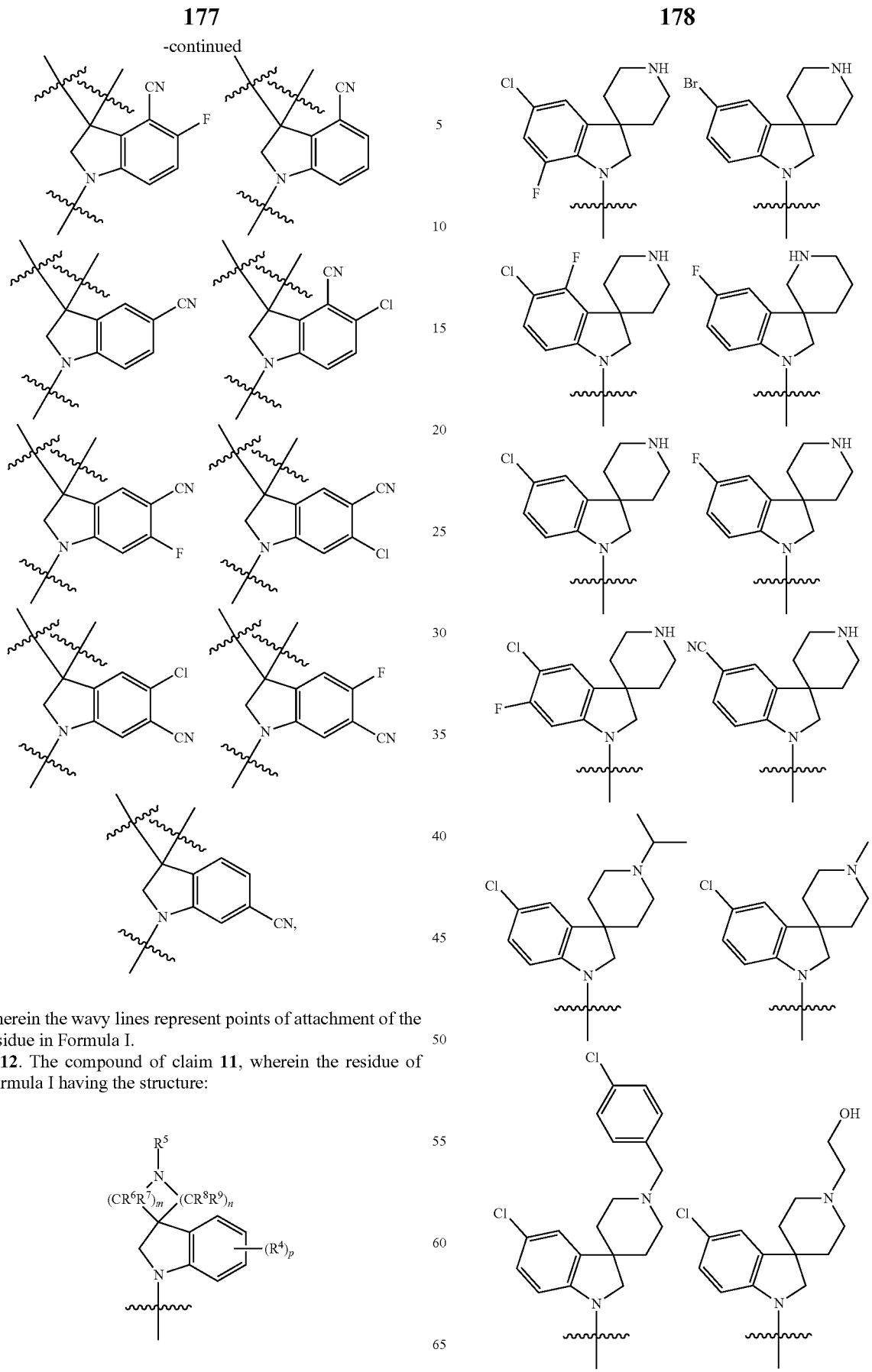
wherein the wavy lines represent points of attachment of the residue in Formula I.
12. The compound of claim 11, wherein the residue of Formula I having the structure:
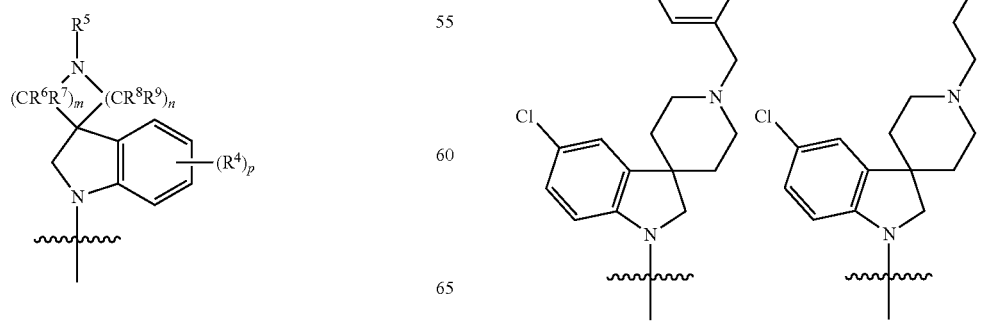
is selected from:

179
-continued
180
-continued
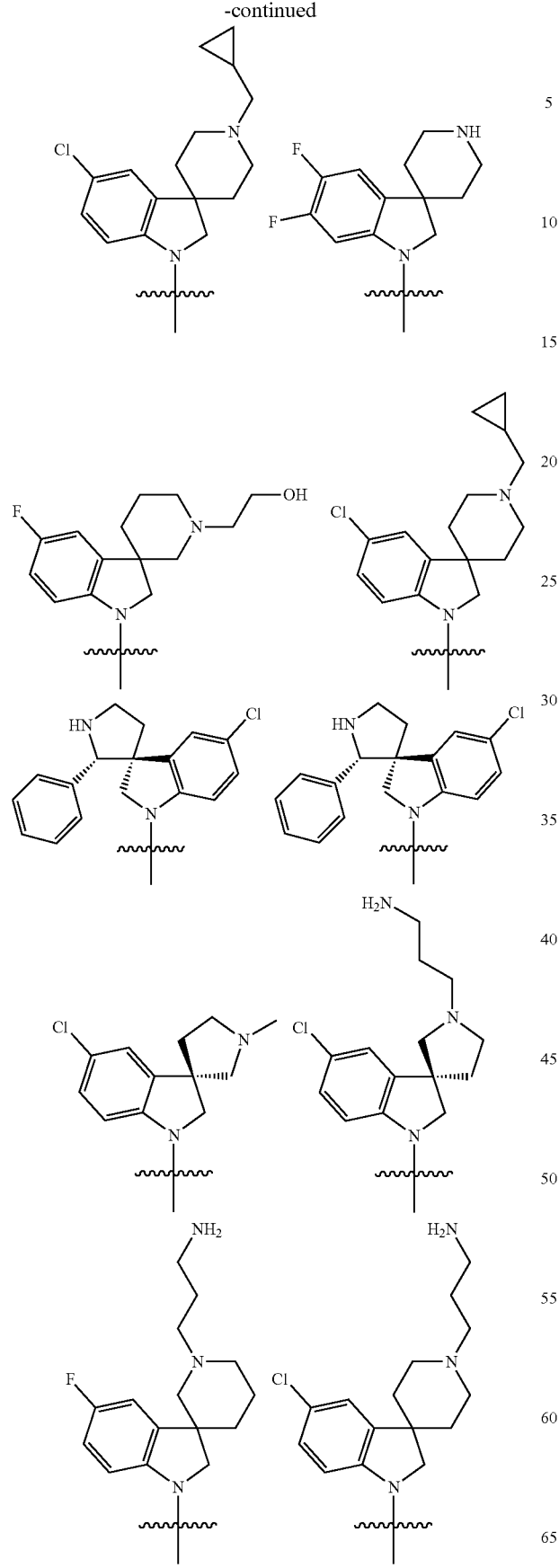
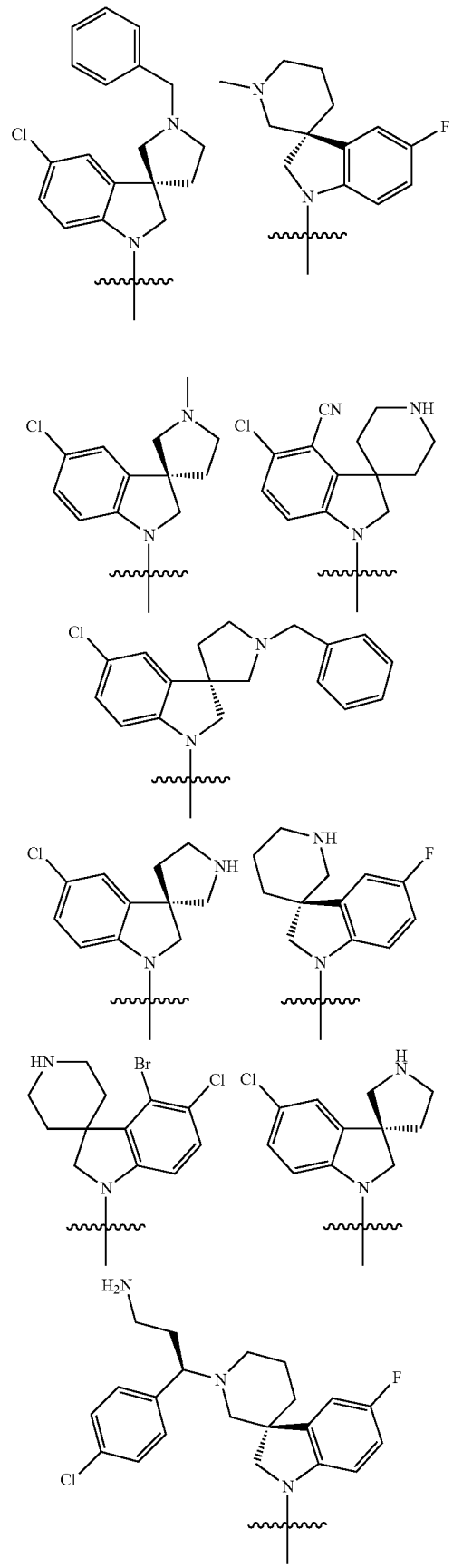

-continued
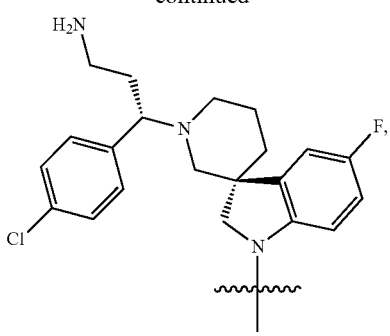
wherein the wavy line represents points of attachment for the residue in Formula I.
13. The compound of claim 10, wherein the residue of Formula I having the structure
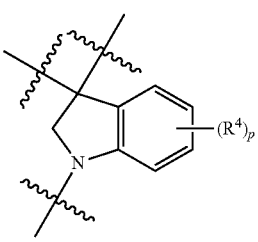
is selected from:
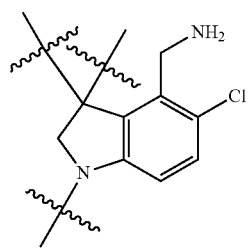 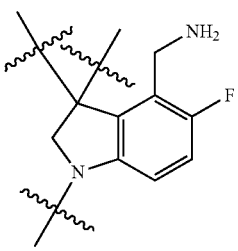
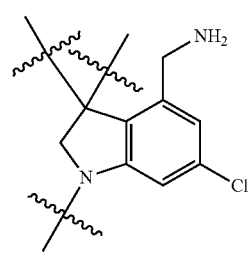 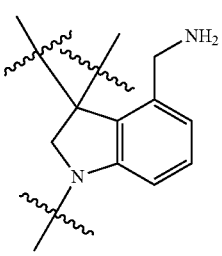
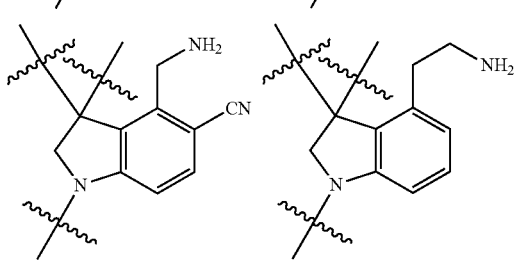
-continued
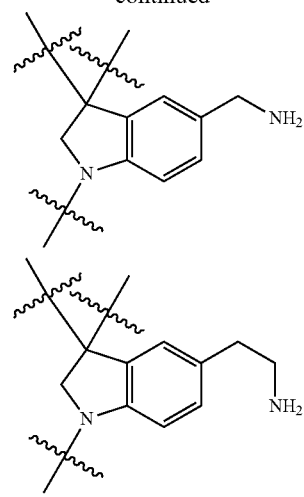
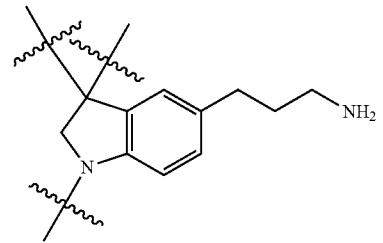
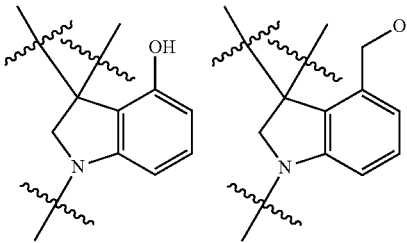
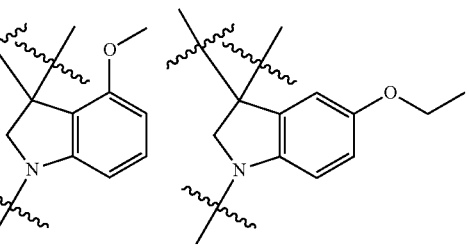
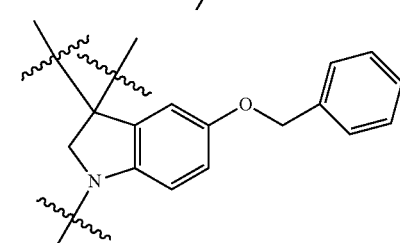
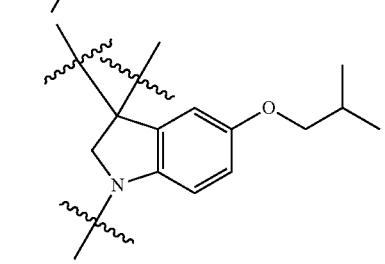

-continued
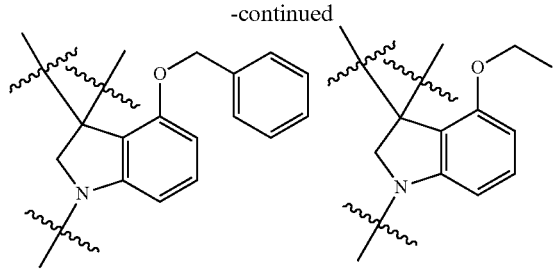
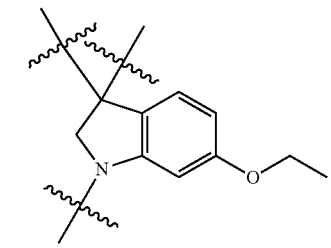
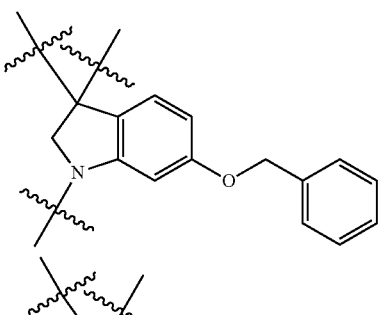
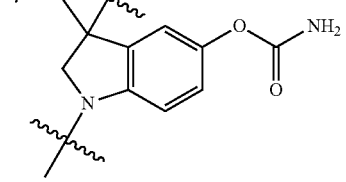
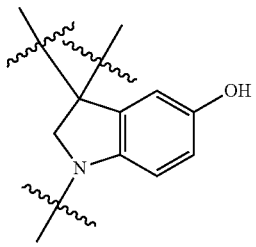
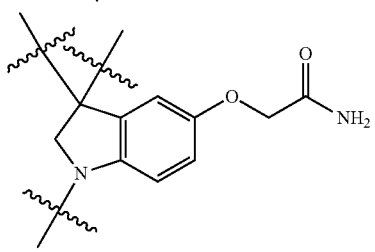
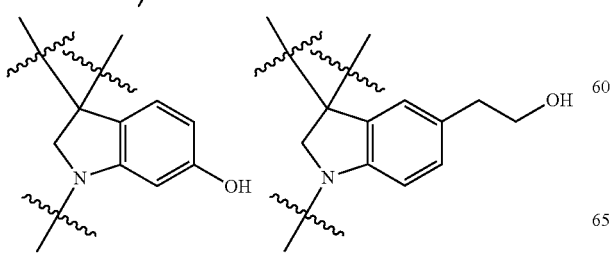
-continued
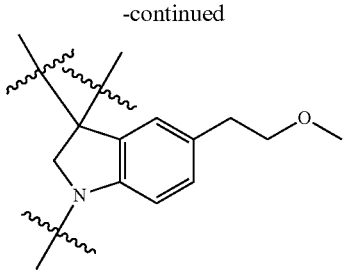
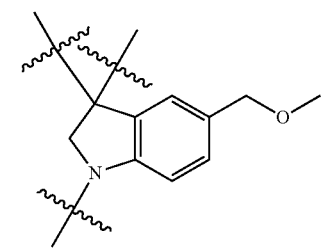
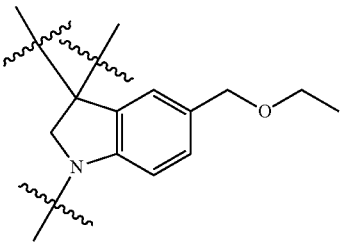
wherein the wavy lines represent points of attachment of the residue in Formula I.
14. The compound of claim 10, wherein the residue of Formula I having the structure
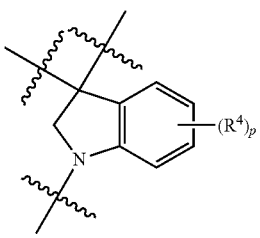
is selected from:
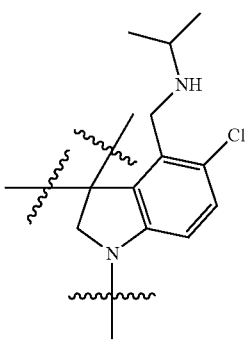 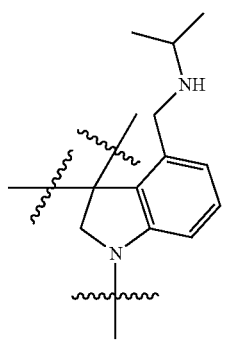

-continued
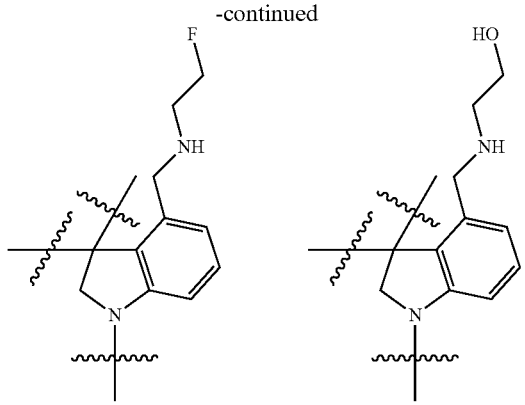
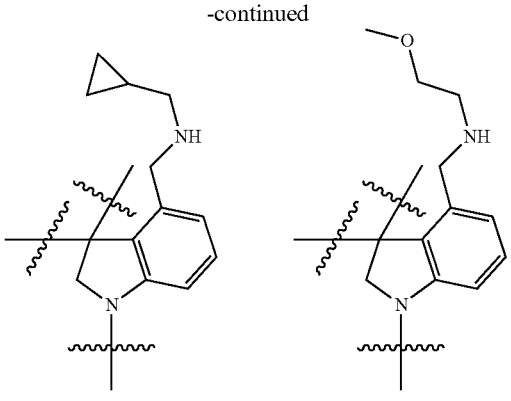
-continued
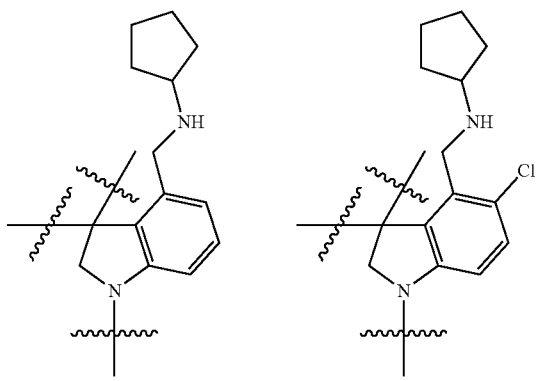
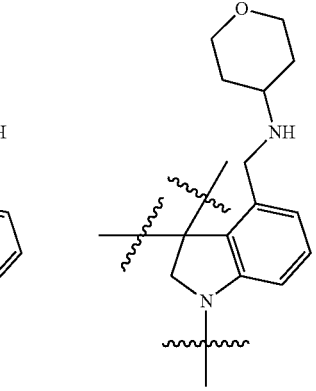
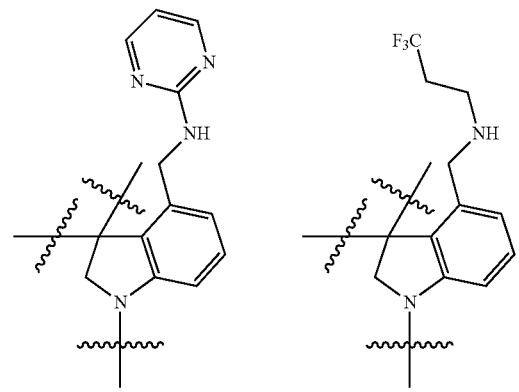
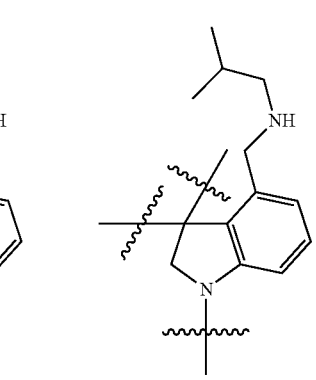
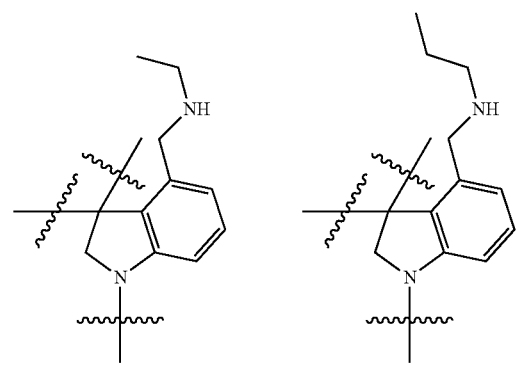
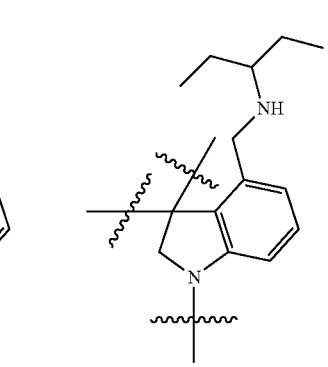

-continued

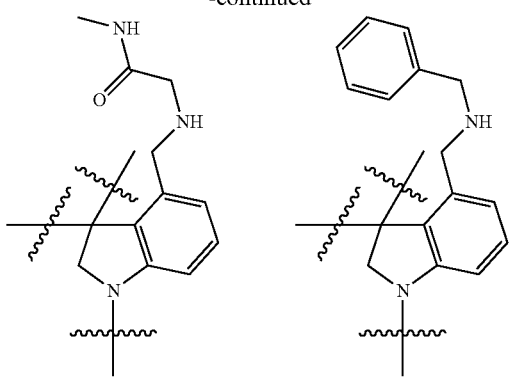

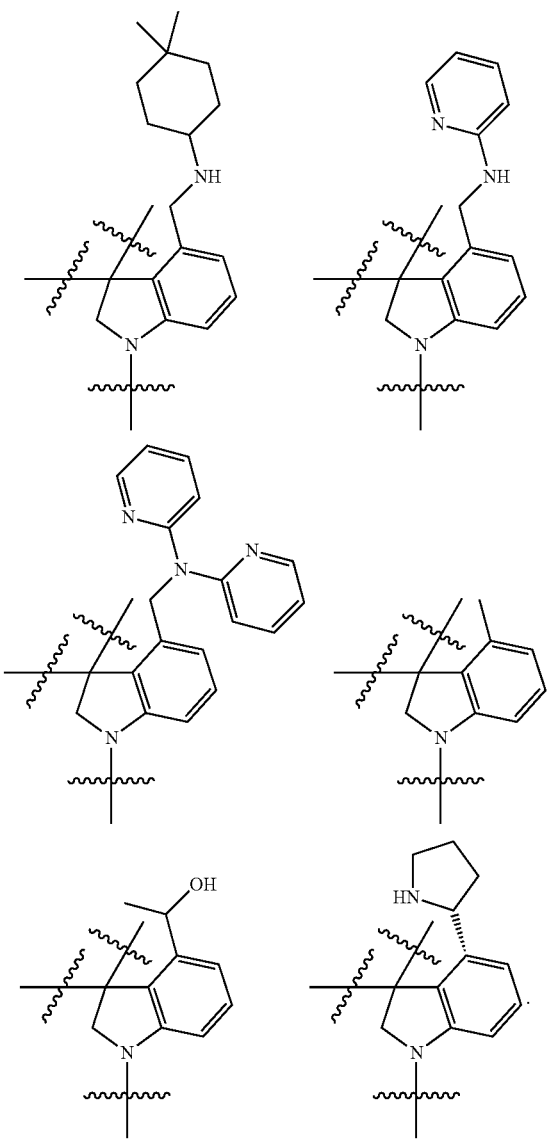

15. The compound of claim 1, wherein $R^4$ is $(CR^{10}R^{10})_tC_6$-$C_8$ aryl, wherein said aryl is optionally substituted by F, Cl, Br or I.

16. The compound of claim 15, wherein $R^4$ is selected from:

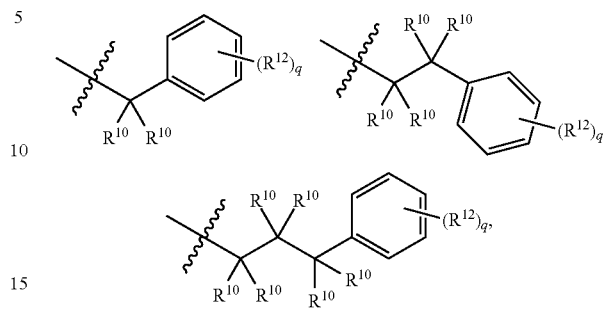

wherein the wavy line represents the point of attachment of $R^4$ in Formula I;

$R^{12}$ is F, Cl, Br or I;

q is 0, 1, 2, 3, 4 or 5; and $R^{10}$ is independently selected from H, OH, O($C_1$-$C_3$ alkyl), $(CH_2)_tNR^{11}R^{11}$, $C_1$-$C_6$ alkyl, $(CH_2)_tC_3$-$C_8$ cycloalkyl or $(CH_2)_tC_3$-$C_6$ heterocyclyl, wherein said cycloalkyl and heterocyclyl are optionally substituted by one or more $C_1$-$C_3$ alkyl; or two $R^{10}$ are taken together to form oxo.

17. The compound of claim 16, wherein $R^4$ is selected from

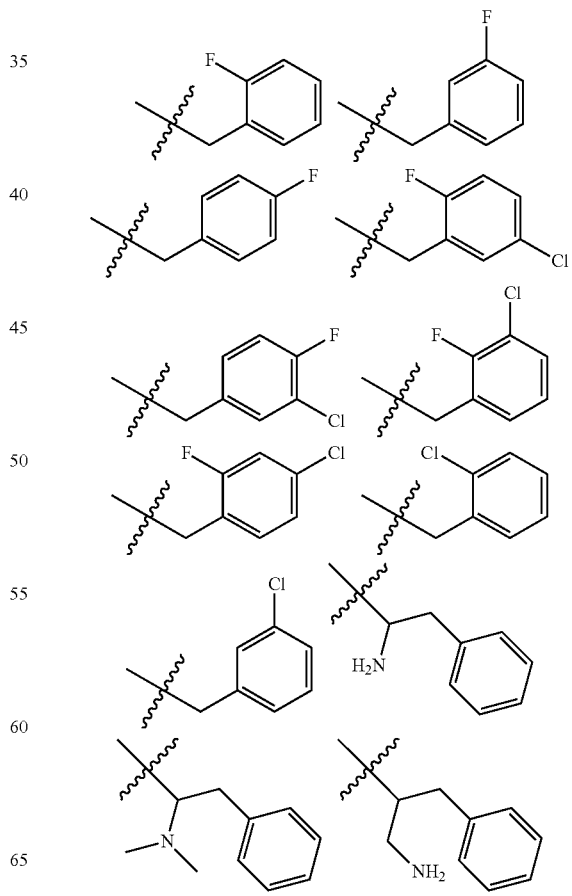

189

-continued

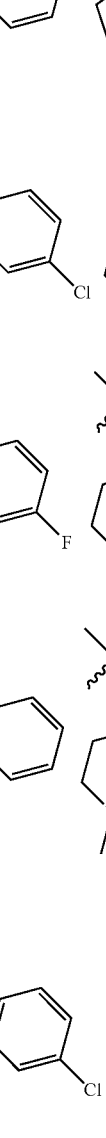

18. The compound of claim 1, wherein $R^4$ is $O(CR^{10}R^{10})_t$ $C_6$-$C_8$ aryl, wherein said aryl is optionally substituted by F, Cl, Br or I.

19. The compound of claim 18, wherein t is 0, 1, 2 or 3; $R^{10}$ is independently selected from H, OH, O($C_1$-$C_3$ alkyl) or $(CH_2)NR^{11}R^{11}$, or two $R^{10}$ are taken together to form oxo; and $R^{11}$ is independently selected from H or $C_1$-$C_3$ alkyl, or two $R^{11}$ are taken together to form a $C_3$-$C_6$ heterocyclyl, optionally substituted by methyl or ethyl.

190

20. The compound of claim 19, wherein $R^4$ is selected from:

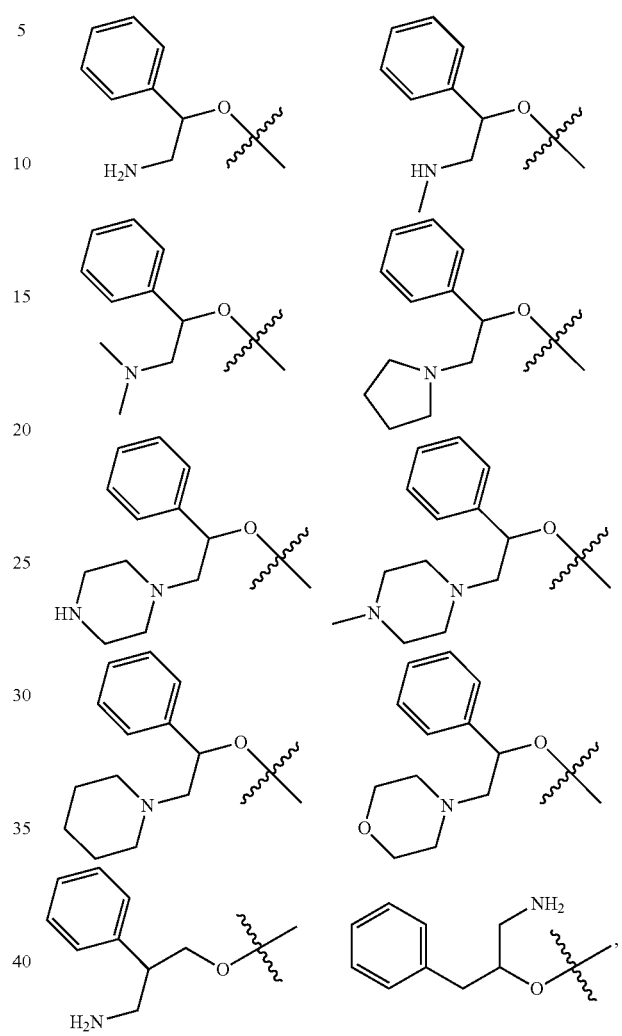

wherein the wavy line represents the point of attachment of $R^4$ in Formula I.

21. The compound of claim 1, wherein $R^4$ is $C_1$-$C_6$ alkyl or $(CR^{10}R^{10})_tC_3$-$C_8$ cycloalkyl, wherein said alkyl and cycloalkyl are optionally substituted by F.

22. The compound of claim 21, wherein $R^4$ is methyl, ethyl, n-propyl, isopropyl, cyclopropyl, cyclobutyl, cyclopentyl, methylcyclopropyl or ethylcyclopropyl.

23. The compound of claim 1, wherein $R^4$ is $(CH_2)_tC(O)NR^{10}R^{10}$ or $(CH_2)NR^{10}C(O)R^{10}$.

24. The compound of claim 23, wherein $R^4$ is selected from:

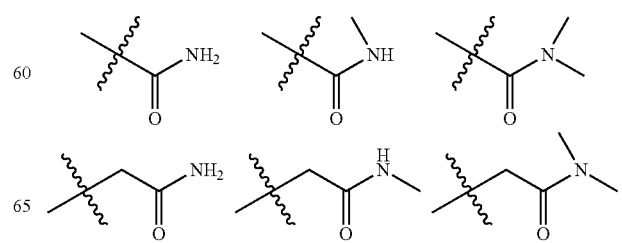

191

-continued

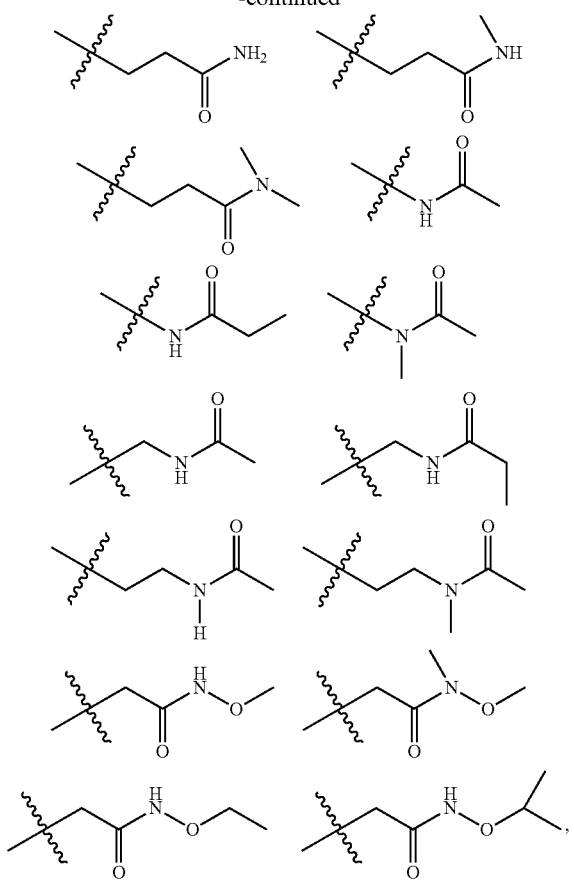

wherein the wavy line represents the point of attachment of R[4] in Formula I.

25. The compound of claim 1, wherein R[4] is selected from:

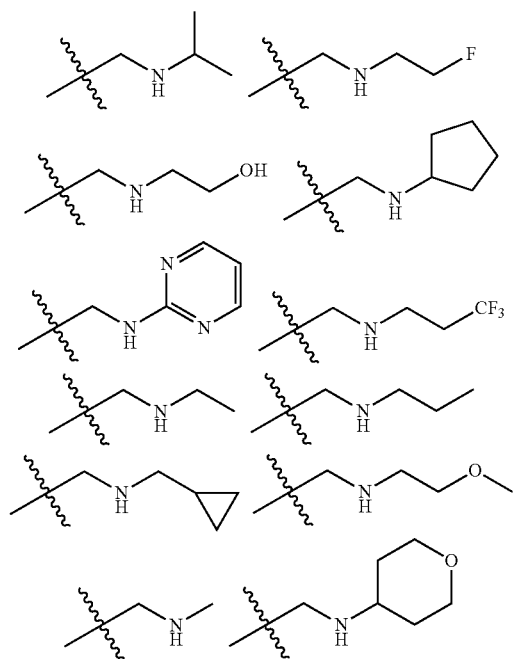

192

-continued

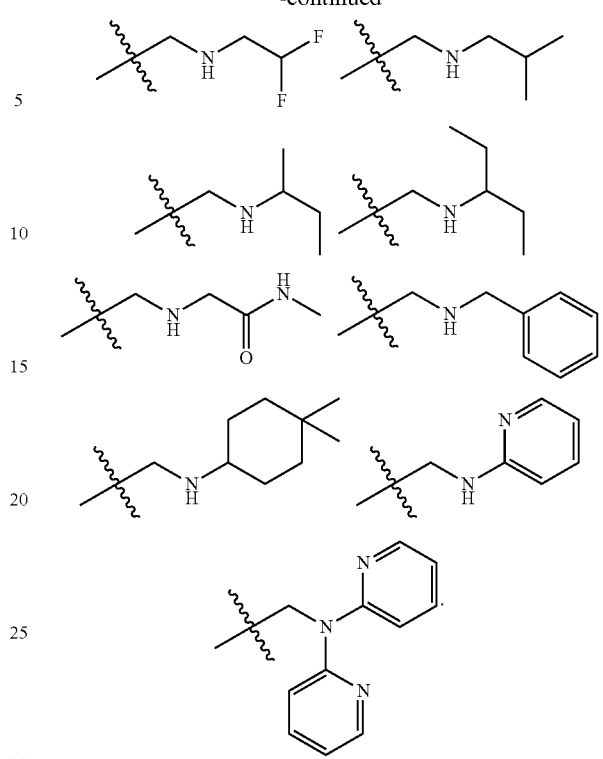

26. The compound of claim 1, wherein $R^1$ is H, $CH_3$, $CH_2CH_3$ or $CF_3$; $R^2$ is H, F, OH, or $OCH_3$; and $R^3$ is H, $CH_3$ or F.

27. The compound of claim 26, wherein $R^1$ is H or $CH_3$.

28. The compound of claim 26, wherein $R^2$ is H, F or OH.

29. The compound of claim 26, wherein $R^3$ is H or F.

30. The compound of claim 26, wherein the residue of Formula I having the structure:

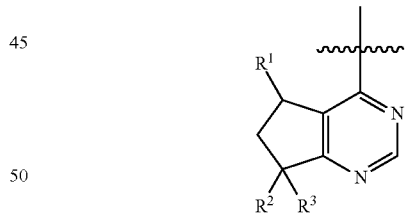

is selected from:

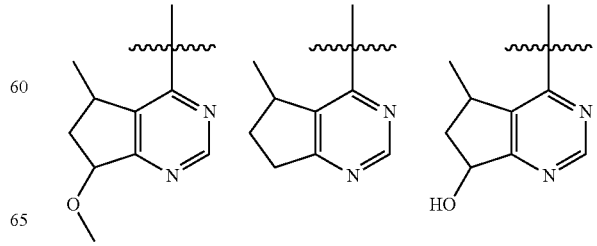

-continued

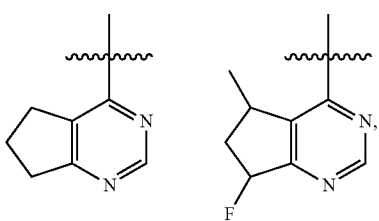

and wherein the wavy line represents the point of attachment of the residue in Formula I.

31. The compound of claim 30, wherein said residue of Formula I is selected from:

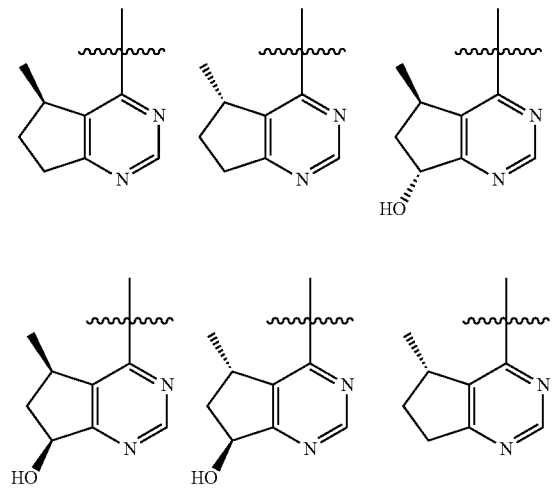

32. The compound of claim 1, wherein $R^1$ is H, $CH_3$, $CH_2CH_3$, $CH(CH_3)_2$, $CH=CH_2$, $CH_2OH$, $CF_3$, $CHF_2$, $CH_2F$, or $C_3$-$C_6$ cycloalkyl.

33. The compound of claim 32, wherein the residue of Formula I having the structure:

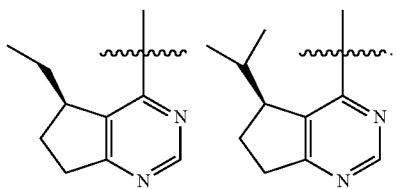

is selected from:

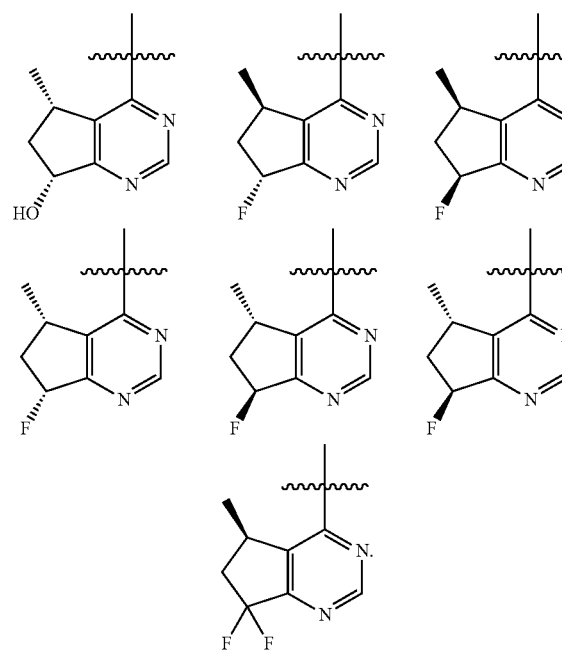

34. The compound of claim 1, wherein $R^5$ is H.

35. The compound of claim 1, wherein $R^5$ is methyl, ethyl, n-propyl, iso-propyl.

36. The compound of claim 1, wherein $R^5$ is $(CR^{10}R^{10})_t OR^{10}$ or $(CR^{10}R^{10})_t NR^{10}R^{10}$.

37. The compound of claim 36, wherein $(CR^{10}R^{10})_t OR^{10}$ is $(CR^{10}R^{10})_t OH$; and $(CR^{10}R^{10})_t NR^{10}R^{10}$ is $(CR^{10}R^{10})_t NH_2$ or $(CR^{10}R^{10})_t NHR^{10}$.

38. The compound of claim 37, wherein $R^5$ is selected from:

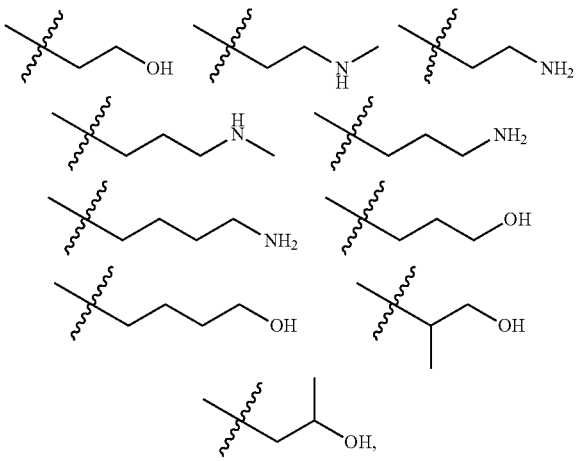

wherein the wavy line represents the point of attachment of $R^5$ in Formula I.

39. The compound of claim 36, wherein $R^5$ is selected from:

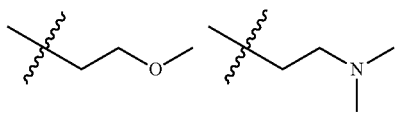

-continued

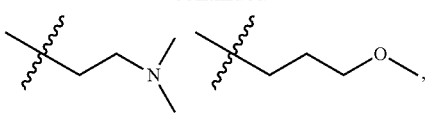

wherein the wavy line represents the point of attachment of $R^5$ in Formula I.

40. The compound of claim 1, wherein $R^5$ is $(CH_2)_t C_3$-$C_8$ cycloalkyl or $(CH_2)_t C_6$-$C_8$ aryl, wherein said aryl is optionally substituted by F or Cl.

41. The compound of claim 40, wherein $R^5$ is selected from:

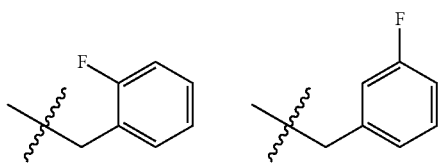

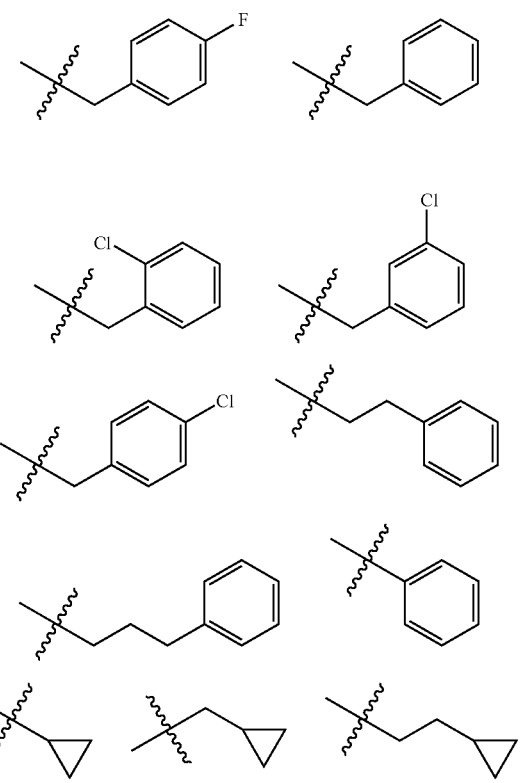

wherein the wavy line represents the point of attachment of $R^5$ in Formula I.

42. The compound of claim 1, wherein one of $R^6$, $R^7$, $R^8$ and $R^9$ is $(CR^{10}R^{10})_t C_6$-$C_8$ aryl, wherein said aryl is optionally substituted by F, Cl, Br or I.

43. The compound of claim 42, wherein $(CR^{10}R^{10})_t C_6$-$C_8$ aryl is $(CR^{10}R^{10})_t$phenyl optionally substituted by F, Cl, Br or I.

44. The compound of claim 43, wherein t is 0.

45. The compound of claim 42, wherein one of $R^6$, $R^7$, $R^8$ and $R^9$ is selected from:

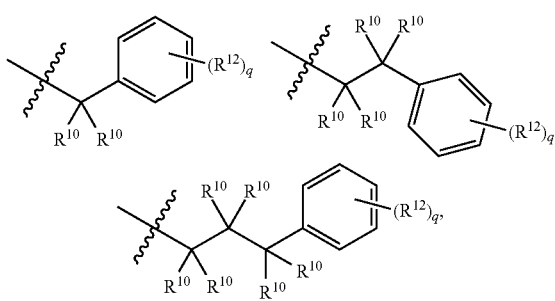

and the remaining $R^6$, $R^7$, $R^8$ and $R^9$ are H, wherein the wavy line represents the point of attachment in Formula I;
$R^{12}$ is F, Cl, Br or I;
q is 0, 1, 2, 3, 4 or 5; and
$R^{10}$ is independently selected from H, OH, O($C_1$-$C_3$ alkyl), $(CH_2)NR^{11}R^{11}$, $C_1$-$C_6$ alkyl, $(CH_2)_t C_3$-$C_8$ cycloalkyl, $(CH_2)_t C_3$-$C_6$ heterocyclyl.

46. The compound of claim 45, wherein one of $R^6$, $R^7$, $R^8$ and $R^9$ is selected from:

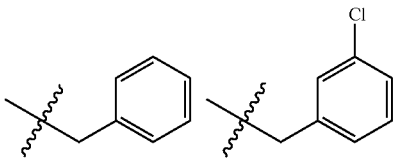

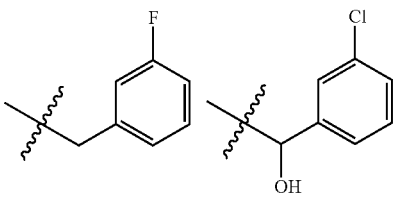

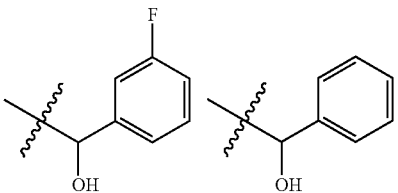

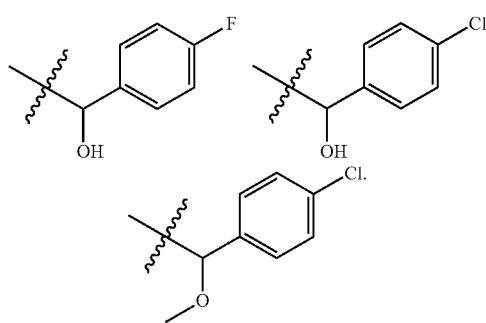

47. The compound of claim 45, wherein one of $R^6$, $R^7$, $R^8$ and $R^9$ is selected from:

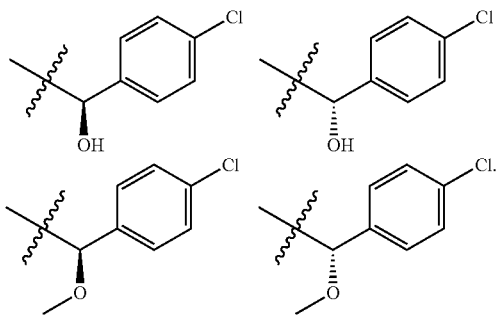

48. The compound of claim 1, wherein one of $R^6$, $R^7$, $R^8$ and $R^9$ is $(CR^{10}R^{10})_tOR^{10}$, and the remaining $R^6$, $R^7$, $R^8$ and $R^9$ are H.

49. The compound of claim 48, wherein $(CR^{10}R^{10})_tOR^{10}$ is $(CR^{10}R^{10})_tOH$.

50. The compound of claim 49, wherein $(CR^{10}R^{10})_tOH$ is selected from:

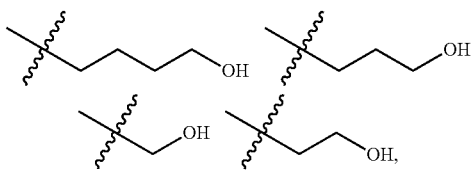

wherein the wavy line represents the point of attachment in Formula I.

51. A compound selected from:
(R)-5-chloro-1-(5-methyl-6,7-dihydro-5H-cyclopenta[d]pyrimidin-4-yl)spiro[indoline-3,4'-piperidine];
(R)-5-bromo-1-(5-methyl-6,7-dihydro-5H-cyclopenta[d]pyrimidin-4-yl)spiro[indoline-3,4'-piperidine];
5-chloro-1-((5R,7S)-7-fluoro-5-methyl-6,7-dihydro-51'-cyclopenta[d]pyrimidin-4-yl)spiro[indoline-3,4'-piperidine];
5-chloro-1-45R,7R)-7-fluoro-5-methyl-6,7-dihydro-5H-cyclopenta[d]pyrimidin-4-yl)spiro[indoline-3,4'-piperidine];
(5R,7R)-4-(5-chlorospiro[indoline-3,4'-piperidine]-1-yl)-5-methyl-6,7-dihydro-5H-cyclopenta[d]pyrimidin-7-ol;
(5R,7S)-4-(5-chlorospiro[indoline-3,4'-piperidine]-1-yl)-5-methyl-6,7-dihydro-5H-cyclopenta[d]pyrimidin-7-ol;
(R)-5-cyclopropyl-1-(5-methyl-6,7-dihydro-5H-cyclopenta[d]pyrimidin-4-yl)spiro[indoline-3,4'-piperidine];
(R)-5-chloro-1-(5-methyl-6,7-dihydro-5H-cyclopenta[d]pyrimidin-4-yl)spiro[indoline-3,4'-piperidine]-4-carbonitrile;
(R)-N-(3-chlorophenyl)-1-(5-methyl-6,7-dihydro-5H-cyclopenta[d]pyrimidin-4-yl)spiro[indoline-3,4'-piperidin]-5-amine;
(R)-2-(1-(5-methyl-6,7-dihydro-5H-cyclopenta[d]pyrimidin-4-yl)spiro[indoline-3,4'-piperidine]-5-yl)acetamide;
(R)-5-(3-fluorobenzyl)-1-(5-methyl-6,7-dihydro-5H-cyclopenta[d]pyrimidin-4-yl)spiro[indoline-3,4'-piperidine];
2-(1-((R)-5-methyl-6,7-dihydro-5H-cyclopenta[d]pyrimidin-4-yl)spiro[indoline-3,4'-piperidine]-5-yloxy)-2-phenylethanamine;
(R)-(1-(5-methyl-6,7-dihydro-5H-cyclopenta[d]pyrimidin-4-yl)spiro[indoline-3,4'-piperidine]-5-yl)methanamine;
(R)-2-(1-(5-methyl-6,7-dihydro-5H-cyclopenta[d]pyrimidin-4-yl)spiro[indoline-3,4'-piperidine]-5-yl)ethanamine;
(S)-5-chloro-1-((R)-5-methyl-6,7-dihydro-5H-cyclopenta[d]pyrimidin-4-yl)spiro[indoline-3,3'-pyrrolidine];
(R)-5-chloro-1-((R)-5-methyl-6,7-dihydro-5H-cyclopenta[d]pyrimidin-4-yl)spiro[indoline-3,3'-pyrrolidine];
(R)-4-((R)-5-fluorospiro[indoline-3,3'-piperidine]-1-yl)-5-methyl-6,7-dihydro-5H-cyclopenta[d]pyrimidine;
(R)-4-(S)-5-fluorospiro[indoline-3,3'-piperidine]-1-yl)-5-methyl-6,7-dihydro-5H-cyclopenta[d]pyrimidine;
(5R,7R)-4-(5-chloro-1'-methylspiro[indoline-3,4'-piperidine]-1-yl)-5-methyl-6,7-dihydro-5H-cyclopenta[d]pyrimidin-7-ol;
(R)-3-(4-chlorophenyl)-3-((R)-5-fluoro-1-((R)-5-methyl-6,7-dihydro-5H-cyclopenta[d]pyrimidin-4-yl)spiro[indoline-3,3'-piperidine]-1'-yl)propan-1-amine;
(S)-3-(4-chlorophenyl)-3-((R)-5-fluoro-1-((R)-5-methyl-6,7-dihydro-5H-cyclopenta[d]pyrimidin-4-yl)spiro[indoline-3,3'-piperidine]-1'-yl)propan-1-amine;
(R)-3-(5-chloro-1-(5-methyl-6,7-dihydro-5H-cyclopenta[d]pyrimidin-4-yl)spiro[indoline-3,4'-piperidine]-1'-yl)propan-1-amine;
(5R,7R)-4-(5-chlorospiro[indoline-3,3'-pyrrolidine]-1-yl)-5-methyl-6,7-dihydro-5H-cyclopenta[d]pyrimidin-7-ol;
(2'R,3S)-5-chloro-1-((R)-5-methyl-6,7-dihydro-5H-cyclopenta[d]pyrimidin-4-yl)-2'-phenylspiro[indoline-3,3'-pyrrolidine];
(2'S,3S)-5-chloro-1-((R)-5-methyl-6,7-dihydro-5H-cyclopenta[d]pyrimidin-4-yl)-2'-phenylspiro[indoline-3,3'-pyrrolidine];
(5R,7R)-4-((3S,5'S)-5'-(hydroxymethyl)spiro[indoline-3,3'-pyrrolidine]-1-yl)-5-methyl-6,7-dihydro-5H-cyclopenta[d]pyrimidin-7-ol;
(5R,7R)-4-((3S,5'S)-5'-((R)-(4-chlorophenyl)(hydroxy)methyl)spiro[indoline-3,3'-pyrrolidine]-1-yl)-5-methyl-6,7-dihydro-5H-cyclopenta[d]pyrimidin-7-ol;
(5R,7R)-4-((3S,5'S)-5'-((S)-(4-chlorophenyl)(hydroxy)methyl)spiro[indoline-3,3'-pyrrolidine]-1-yl)-5-methyl-6,7-dihydro-5H-cyclopenta[d]pyrimidin-7-ol;
(5R,7R)-4-(2'-benzyl-5-chlorospiro[indoline-3,4'-piperidine]-1-yl)-5-methyl-6,7-dihydro-5H-cyclopenta[d]pyrimidin-7-ol;
N-((1-((5R,7R)-7-hydroxy-5-methyl-6,7-dihydro-5H-cyclopenta[d]pyrimidin-4-yl)spiro[indoline-3,4'-piperidine]-4-yl)methyl)acetamide;
(5R,7R)-4-(4-((isopropylamino)methyl)spiro[indoline-3,4'-piperidine]-1-yl)-5-methyl-6,7-dihydro-5H-cyclopenta[d]pyrimidin-7-ol;
(5R,7R)-4-(4-(aminomethyl)-5-chlorospiro[indoline-3,4'-piperidine]-1-yl)-5-methyl-6,7-dihydro-5H-cyclopenta[d]pyrimidin-7-ol;
5-chloro-1-(6,7-dihydro-5H-cyclopenta[d]pyrimidin-4-yl)spiro[indoline-3,4'-piperidine];
(R)-5-ethoxy-1-(5-methyl-6,7-dihydro-5H-cyclopenta[d]pyrimidin-4-yl)spiro[indoline-3,4'-piperidine];
(R)-5-fluoro-1-(5-methyl-6,7-dihydro-5H-cyclopenta[d]pyrimidin-4-yl)spiro[indoline-3,4'-piperidine];

(R)-5-chloro-7-fluoro-1-(5-methyl-6,7-dihydro-5H-cyclopenta[d]pyrimidin-4-yl)spiro[indoline-3,4'-piperidine];
(R)-5-chloro-6-fluoro-1-(5-methyl-6,7-dihydro-5H-cyclopenta[d]pyrimidin-4-yl)spiro[indoline-3,4'-piperidine];
(R)-5-chloro-4-fluoro-1-(5-methyl-6,7-dihydro-5H-cyclopenta[d]pyrimidin-4-yl)spiro[indoline-3,4'-piperidine];
(R)-4,5-difluoro-1-(5-methyl-6,7-dihydro-51'-cyclopenta[d]pyrimidin-4-yl)spiro[indoline-3,4'-piperidine];
(R)-5,6-difluoro-1-(5-methyl-6,7-dihydro-5H-cyclopenta[d]pyrimidin-4-yl)spiro[indoline-3,4'-piperidine];
(R)-4-bromo-5-chloro-1-(5-methyl-6,7-dihydro-5H-cyclopenta[d]pyrimidin-4-yl)spiro[indoline-3,4'-piperidine];
(R)-1-(5-methyl-6,7-dihydro-5H-cyclopenta[d]pyrimidin-4-yl)spiro[indoline-3,4'-piperidine]-5-carbonitrile;
(R)-1-(5-methyl-6,7-dihydro-5H-cyclopenta[d]pyrimidin-4-yl)spiro[indoline-3,4'-piperidine]-4-carbonitrile;
(R)-(1-(5-methyl-6,7-dihydro-5H-cyclopenta[d]pyrimidin-4-yl)spiro[indoline-3,4'-piperidine]-4-yl)methanamine;
(R)-(5-chloro-1-(5-methyl-6,7-dihydro-5H-cyclopenta[d]pyrimidin-4-yl)spiro[indoline-3,4'-piperidine]-4-yl)methanamine;
(R)-2-(5-chloro-1-(5-methyl-6,7-dihydro-5H-cyclopenta[d]pyrimidin-4-yl)spiro[indoline-3,4'-piperidine]-1'-yl)ethanol;
(R)-5-chloro-1'-(4-chlorobenzyl)-1-(5-methyl-6,7-dihydro-5H-cyclopenta[d]pyrimidin-4-yl)spiro[indoline-3,4'-piperidine];
(R)-5-chloro-1'-methyl-1-(5-methyl-6,7-dihydro-5H-cyclopenta[d]pyrimidin-4-yl)spiro[indoline-3,4'-piperidine];
(R)-5-chloro-1'-isopropyl-1-(5-methyl-6,7-dihydro-5H-cyclopenta[d]pyrimidin-4-yl)spiro[indoline-3,4'-piperidine];
(R)-5-chloro-1'-(cyclopropylmethyl)-1-(5-methyl-6,7-dihydro-5H-cyclopenta[d]pyrimidin-4-yl)spiro[indoline-3,4'-piperidine];
(R)-N-methoxy-2-(1-(5-methyl-6,7-dihydro-5H-cyclopenta[d]pyrimidin-4-yl)spiro[indoline-3,4'-piperidine]-5-yl)acetamide;
(R)-N-methyl-2-(1-(5-methyl-6,7-dihydro-5H-cyclopenta[d]pyrimidin-4-yl)spiro[indoline-3,4'-piperidine]-5-yl)acetamide;
(R)-N-((1-(5-methyl-6,7-dihydro-5H-cyclopenta[d]pyrimidin-4-yl)spiro[indoline-3,4'-piperidine]-5-yl)methyl)acetamide;
(R)-2-(1-(5-methyl-6,7-dihydro-5H-cyclopenta[d]pyrimidin-4-yl)spiro[indoline-3,4'-piperidine]-5-yl)ethanol;
(R)-1-(5-methyl-6,7-dihydro-5H-cyclopenta[d]pyrimidin-4-yl)spiro[indoline-3,4'-piperidine]-5-carboxamide;
(R)-5-(benzyloxy)-1-(5-methyl-6,7-dihydro-5H-cyclopenta[d]pyrimidin-4-yl)spiro[indoline-3,4'-piperidine];
(R)-1-(5-methyl-6,7-dihydro-5H-cyclopenta[d]pyrimidin-4-yl)spiro[indoline-3,4'-piperidin]-5-ol;
(R)-2-(1-(5-methyl-6,7-dihydro-5H-cyclopenta[d]pyrimidin-4-yl)spiro[indoline-3,4'-piperidine]-5-yloxy)acetamide;
2-((R)-5-fluoro-1-((R)-5-methyl-6,7-dihydro-5H-cyclopenta[d]pyrimidin-4-yl)spiro[indoline-3,3'-piperidine]-1'-yl)ethanol;
(R)-4-((R)-5-fluoro-1'-methylspiro[indoline-3,3'-piperidine]-1-yl)-5-methyl-6,7-dihydro-5H-cyclopenta[d]pyrimidine;
(5R,7R)-4-(5-chloro-1'-(cyclopropylmethyl)spiro[indoline-3,4'-piperidine]-1-yl)-5-methyl-6,7-dihydro-5H-cyclopenta[d]pyrimidin-7-ol;
(5R,7R)-4-(5-(benzyloxy)spiro[indoline-3,4'-piperidine]-1-yl)-5-methyl-6,7-dihydro-5H-cyclopenta[d]pyrimidin-7-ol;
(S)-1'-benzyl-5-chloro-1-((R)-5-methyl-6,7-dihydro-5H-cyclopenta[d]pyrimidin-4-yl)spiro[indoline-3,3'-pyrrolidine];
(R)-1'-benzyl-5-chloro-1-((R)-5-methyl-6,7-dihydro-5H-cyclopenta[d]pyrimidin-4-yl)spiro[indoline-3,3'-pyrrolidine];
3-(5-fluoro-1-((R)-5-methyl-6,7-dihydro-5H-cyclopenta[d]pyrimidin-4-yl)spiro[indoline-3,3'-piperidine]-1'-yl)propan-1-amine;
(S)-5-chloro-1'-methyl-1-((R)-5-methyl-6,7-dihydro-5H-cyclopenta[d]pyrimidin-4-yl)spiro[indoline-3,3'-pyrrolidine];
3-((S)-5-chloro-1-((R)-5-methyl-6,7-dihydro-5H-cyclopenta[d]pyrimidin-4-yl)spiro[indoline-3,3'-pyrrolidine]-1'-yl)propan-1-amine;
(R)-5-chloro-1'-methyl-1-((R)-5-methyl-6,7-dihydro-5H-cyclopenta[d]pyrimidin-4-Y$_1$)spiro[indoline-3,3'-pyrrolidine]; and
(5R,7R)-4-(4-((dimethylamino)methyl)spiro[indoline-3,4'-piperidine]-1-yl)-5-methyl-6,7-dihydro-5H-cyclopenta[d]pyrimidin-7-ol;
and pharmaceutically acceptable salts thereof.

52. A compound selected from:
(5R,7R)-4-(5-chloro-4-((isopropylamino)methyl)spiro[indoline-3,4'-piperidine]-1-yl)-5-methyl-6,7-dihydro-5H-cyclopenta[d]pyrimidin-7-ol;
(R)-N-((1-(5-methyl-6,7-dihydro-5H-cyclopenta[d]pyrimidin-4-yl)spiro[indoline-3,4'-piperidine]-4-yl)methyl)propan-2-amine;
N-((1-((5R,7S)-7-fluoro-5-methyl-6,7-dihydro-5H-cyclopenta[d]pyrimidin-4-yl)spiro[indoline-3,4'-piperidine]-4-yl)methyl)propan-2-amine;
(R)-2-fluoro-N-((1-(5-methyl-6,7-dihydro-5H-cyclopenta[d]pyrimidin-4-yl)spiro[indoline-3,4'-piperidine]-4-yl)methyl)ethanamine;
(R)-2-((1-(5-methyl-6,7-dihydro-5H-cyclopenta[d]pyrimidin-4-yl)spiro[indoline-3,4'-piperidine]-4-yl)methylamino)ethanol;
(R)-N-((1-(5-methyl-6,7-dihydro-5H-cyclopenta[d]pyrimidin-4-yl)spiro[indoline-3,4'-piperidine]-4-yl)methyl)cyclopentanamine;
(R)-N-((5-chloro-1-(5-methyl-6,7-dihydro-5H-cyclopenta[d]pyrimidin-4-yl)spiro[indoline-3,4'-piperidine]-4-yl)methyl)propan-2-amine;
(R)-N-((5-chloro-1-(5-methyl-6,7-dihydro-5H-cyclopenta[d]pyrimidin-4-yl)spiro[indoline-3,4'-piperidine]-4-yl)methyl)cyclopentanamine;
(5R,7R)-4-((S)-4-((isopropylamino)methyl)spiro[indoline-3,3'-pyrrolidine]-1-yl)-5-methyl-6,7-dihydro-5H-cyclopenta[d]pyrimidin-7-ol;
(5R,7R)-4-((R)-4-((isopropylamino)methyl)spiro[indoline-3,3'-pyrrolidine]-1-yl)-5-methyl-6,7-dihydro-5H-cyclopenta[d]pyrimidin-7-ol;
(5R,7R)-5-methyl-4-((R)-4-methyl)spiro[indoline-3,3'-pyrrolidine]-1-yl)-6,7-dihydro-5H-cyclopenta[d]pyrimidin-7-ol;

(R)-N-((1-(5-methyl-6,7-dihydro-5H-cyclopenta[d]pyrimidin-4-yl)spiro[indoline-3,4'-piperidine]-4-yl)methyl)pyrimidin-2-amine;

1-((R)-5-methyl-6,7-dihydro-5H-cyclopenta[d]pyrimidin-4-yl)-4-((R)-pyrrolidin-2-yl)spiro[indoline-3,4'-piperidine];

(R)-N-((1-(5-ethyl-6,7-dihydro-5H-cyclopenta[d]pyrimidin-4-yl)spiro[indoline-3,4'-piperidine]-4-yl)methyl)propan-2-amine;

(S)-N-((1-(5-cyclopentyl-6,7-dihydro-5H-cyclopenta[d]pyrimidin-4-yl)spiro[indoline-3,4'-piperidine]-4-yl)methyl)propan-2-amine;

(S)-N-((1-(5-isopropyl-6,7-dihydro-5H-cyclopenta[d]pyrimidin-4-yl)spiro[indoline-3,4'-piperidine]-4-yl)methyl)propan-2-amine;

(S)-N-((1-(5-isopropyl-6,7-dihydro-5H-cyclopenta[d]pyrimidin-4-yl)spiro[indoline-3,4'-piperidine]-4-yl)methyl)cyclopentanamine;

1-(1-((R)-5-methyl-6,7-dihydro-5H-cyclopenta[d]pyrimidin-4-yl)spiro[indoline-3,4'-piperidine]-4-yl)ethanol;

(5R,7R)-4-(4-((isopropylamino)methyl)spiro[indoline-3,4'-piperidine]-1-yl)-5-methyl-6,7-dihydro-5H-cyclopenta[d]pyrimidin-7-ol;

(R)-3,3,3-trifluoro-N-((1-(5-methyl-6,7-dihydro-5H-cyclopenta[d]pyrimidin-4-yl)spiro[indoline-3,4'-piperidine]-4-yl)methyl)propan-1-amine;

(R)-N-((1-(5-methyl-6,7-dihydro-5H-cyclopenta[d]pyrimidin-4-yl)spiro[indoline-3,4'-piperidine]-4-yl)methyl)ethanamine;

(R)-N-((1-(5-methyl-6,7-dihydro-5H-cyclopenta[d]pyrimidin-4-yl)spiro[indoline-3,4'-piperidine]-4-yl)methyl)propan-1-amine;

(R)-1-cyclopropyl-N-((1-(5-methyl-6,7-dihydro-5H-cyclopenta[d]pyrimidin-4-yl)spiro[indoline-3,4'-piperidine]-4-yl)methyl)methanamine;

(R)-2-methoxy-N-((1-(5-methyl-6,7-dihydro-5H-cyclopenta[d]pyrimidin-4-yl)spiro[indoline-3,4'-piperidine]-4-yl)methyl)ethanamine;

(R)-N-((1'-methyl-1-(5-methyl-6,7-dihydro-5H-cyclopenta[d]pyrimidin-4-yl)spiro[indoline-3,4'-piperidine]-4-yl)methyl)propan-2-amine;

(R)-N-methyl-1-(1-(5-methyl-6,7-dihydro-5H-cyclopenta[d]pyrimidin-4-yl)spiro[indoline-3,4'-piperidine]-4-yl)methanamine;

(R)-N-((1-(5-methyl-6,7-dihydro-5H-cyclopenta[d]pyrimidin-4-yl)spiro[indoline-3,4'-piperidine]-4-yl)methyl)tetrahydro-2H-pyran-4-amine;

(R)-2,2-difluoro-N-((1-(5-methyl-6,7-dihydro-5H-cyclopenta[d]pyrimidin-4-yl)spiro[indoline-3,4'-piperidine]-4-yl)methyl)ethanamine;

(R)-2-methyl-N-((1-(5-methyl-6,7-dihydro-5H-cyclopenta[d]pyrimidin-4-yl)spiro[indoline-3,4'-piperidine]-4-yl)methyl)propan-1-amine;

N-((1-((R)-5-methyl-6,7-dihydro-5H-cyclopenta[d]pyrimidin-4-yl)spiro[indoline-3,4'-piperidine]-4-yl)methyl)butan-2-amine;

(R)-N-((1-(5-methyl-6,7-dihydro-5H-cyclopenta[d]pyrimidin-4-yl)spiro[indoline-3,4'-piperidine]-4-yl)methyl)pentan-3-amine;

(R)-N-methyl-2-((1-(5-methyl-6,7-dihydro-5H-cyclopenta[d]pyrimidin-4-yl)spiro[indoline-3,4'-piperidine]-4-yl)methylamino)acetamide;

(R)-N-benzyl-1-(1-(5-methyl-6,7-dihydro-5H-cyclopenta[d]pyrimidin-4-yl)spiro[indoline-3,4'-piperidine]-4-yl)methanamine;

(R)-4,4-dimethyl-N-((1-(5-methyl-6,7-dihydro-5H-cyclopenta[d]pyrimidin-4-yl)spiro[indoline-3,4'-piperidine]-4-yl)methyl)cyclohexanamine;

(R)-N-((1-(5-methyl-6,7-dihydro-5H-cyclopenta[d]pyrimidin-4-yl)spiro[indoline-3,4'-piperidine]-4-yl)methyl)pyridin-2-amine; and (R)-N-((1-(5-methyl-6,7-dihydro-5H-cyclopenta[d]pyrimidin-4-yl)spiro[indoline-3,4'-piperidine]-4-yl)methyl)-N-(pyridin-2-yl)pyridin-2-amine;

and pharmaceutically acceptable salts thereof.

53. A pharmaceutical composition comprising a compound of claim 1 and a pharmaceutically acceptable carrier, adjuvant or vehicle.

54. The composition of claim 53, further comprising an additional therapeutic agent selected from an anti-proliferative agent, an anti-inflammatory agent, an immunomodulatory agent, a neurotropic factor, an agent for treating cardiovascular disease, an agent for treating liver disease, an antiviral agent, an agent for treating blood disorders, an agent for treating diabetes, or an agent for treating immunodeficiency disorders.

55. A pharmaceutical composition comprising a compound of claim 1 in an amount to detectably inhibit Akt kinase activity and a pharmaceutically acceptable carrier, adjuvant or vehicle.

56. A kit for treating a hyperproliferative disorder, comprising:
(a) a first pharmaceutical composition comprising a compound of claim 1; and
(b) instructions for use.

57. The kit of claim 56, further comprising:
(c) a second pharmaceutical composition, comprising a second compound having anti-hyperproliferative activity.

58. The kit of claim 57, wherein said instructions comprise instructions for the simultaneous, sequential or separate administration of said first and second pharmaceutical compositions to a patient in need thereof.

59. The kit of claim 58, wherein said first and second compositions are contained in separate containers.

60. The kit of claim 58, wherein said first and second compositions are contained in the same container.

* * * * *